US010105429B2

(12) United States Patent
Serino et al.

(10) Patent No.: US 10,105,429 B2
(45) Date of Patent: Oct. 23, 2018

(54) ESCHERICHIA COLI VACCINE COMBINATION

(71) Applicant: GlaxoSmithKline Biologicals SA, Rixensart (BE)

(72) Inventors: Laura Serino, Siena (IT); Mariagrazia Pizza, Siena (IT)

(73) Assignee: GLAXOSMITHKLINE BIOLOGICALS SA, Rixensart (BE)

(*) Notice: Subject to any disclaimer, the term of this patent is extended or adjusted under 35 U.S.C. 154(b) by 0 days.

(21) Appl. No.: 15/369,405

(22) Filed: Dec. 5, 2016

(65) Prior Publication Data

US 2017/0296643 A1 Oct. 19, 2017

Related U.S. Application Data

(62) Division of application No. 14/344,892, filed as application No. PCT/IB2012/054825 on Sep. 14, 2012, now Pat. No. 9,511,130.

(30) Foreign Application Priority Data

Sep. 14, 2011 (GB) .................................. 1115906.8
Jul. 25, 2012 (GB) .................................. 1213251.0

(51) Int. Cl.
*A61K 39/108* (2006.01)
*C07K 14/245* (2006.01)
*A61K 39/00* (2006.01)

(52) U.S. Cl.
CPC ........ *A61K 39/0258* (2013.01); *C07K 14/245* (2013.01); *A61K 2039/54* (2013.01); *A61K 2039/541* (2013.01); *A61K 2039/552* (2013.01); *A61K 2039/55516* (2013.01); *A61K 2039/55544* (2013.01); *A61K 2039/70* (2013.01)

(58) Field of Classification Search
CPC ............ A61K 39/0258; A61K 2039/54; A61K 2039/55544; A61K 2039/542; A61K 2039/543; A61K 2039/55516; A61K 2039/541; C07K 14/245
See application file for complete search history.

(56) References Cited

U.S. PATENT DOCUMENTS

| | | | |
|---|---|---|---|
| 5,057,540 | A | 10/1991 | Kensil et al. |
| 5,916,588 | A | 6/1999 | Popescu et al. |
| 6,090,406 | A | 7/2000 | Popescu et al. |
| 6,207,646 | B1 | 3/2001 | Krieg et al. |
| 6,239,116 | B1 | 5/2001 | Krieg et al. |
| 6,429,199 | B1 | 8/2002 | Krieg et al. |

FOREIGN PATENT DOCUMENTS

| | | |
|---|---|---|
| EP | 0626169 A2 | 11/1994 |
| EP | 0735898 A1 | 10/1996 |
| EP | 0761231 A1 | 3/1997 |
| EP | 0835318 A2 | 4/1998 |
| WO | 1990/014837 A1 | 12/1990 |
| WO | 1994/000153 A1 | 1/1994 |
| WO | 1995/017211 A1 | 6/1995 |
| WO | 1998/040100 A1 | 9/1998 |
| WO | 1998/042375 A1 | 10/1998 |
| WO | 1998/057659 A1 | 12/1998 |
| WO | 1999/011241 A1 | 3/1999 |
| WO | 1999/027960 A1 | 6/1999 |
| WO | 1999/040936 A2 | 8/1999 |
| WO | 1999/044636 A2 | 9/1999 |
| WO | 1999/052549 A1 | 10/1999 |
| WO | 2002/081653 A2 | 10/2002 |
| WO | 2003/024480 A2 | 3/2003 |
| WO | 2003/024481 A2 | 3/2003 |
| WO | 2005/103073 A2 | 11/2005 |
| WO | 2006/089264 A2 | 8/2006 |
| WO | 2006/091517 A2 | 8/2006 |
| WO | 2009/104092 A2 | 8/2009 |
| WO | 2011/004263 A2 | 1/2011 |
| WO | 2011/007257 A1 | 1/2011 |
| WO | 2011/080595 A2 | 7/2011 |

OTHER PUBLICATIONS

Houghten et al. (Vaccines, 1986, Edited by Fred Brown: Cold Spring Harbor Laboratory).*
Search Report received for Great Britain Patent Application No. 1115906.8, dated Jan. 11, 2012, 2 pages.
International Preliminary Report on Patentability received for PCT Patent Application No. PCT/IB2012/054825, dated Mar. 27, 2014, 13 pages.
International Search Report and Written Opinion received for PCT Patent Application No. PCT/IB2012/054825, dated Apr. 5, 2013, 18 pages.
Advisory Action received for U.S. Appl. No. 14/344,892, dated May 26, 2016, 3 pages.
Andrianov et al., "Preparation of Hydrogel Microspheres by Coacervation of Aqueous Polyphosphazene Solutions", Biomaterials, vol. 19, No. 1-3, Jan. 1998, pp. 109-115.
Andrianov et al., "Protein Release from Polyphosphazene Matrices", Advanced Drug Delivery Reviews, vol. 31, No. 3, May 1998, pp. 185-196.
Beignon et al., "The LTR72 Mutant of Heat-Labile Enterotoxin of *Escherichia coli* Enhances the Ability of Peptide Antigens to Elicit CD4+ T Cells and Secrete Gamma Interferon after Coapplication onto Bare Skin", Infection and Immunity, vol. 70, No. 6, Jun. 2002, pp. 3012-3019.
Durant et al., "Identification of Candidates for a Subunit Vaccine against Extraintestinal Pathogenic *Escherichia coli*", Infection and Immunity, vol. 75, No. 4, Apr. 2007, pp. 1916-1925.

(Continued)

*Primary Examiner* — Padmavathi Baskar
(74) *Attorney, Agent, or Firm* — Birch, Stewart, Kolasch & Birch, LLP

(57) ABSTRACT

The invention provides an immunogenic composition comprising a combination of (i) bacterial Ig-like domain protein fragment (orf405B) having the amino acid sequence set forth in SEQ ID NO:2 or a protein having at least 80% similarity thereto, and (ii) putative Lipoprotein (orf3526) having the amino acid sequence set forth in SEQ ID NO:8 or a protein having at least 80% similarity thereto.

6 Claims, 19 Drawing Sheets

Specification includes a Sequence Listing.

(56) References Cited

OTHER PUBLICATIONS

Evans et al., "Enhancement of Antigen-Specific Immunity via the TLR4 Ligands MPL™ Adjuvant and Ribi.529", Expert Review of Vaccines, vol. 2, No. 2, Apr. 2003, pp. 219-229.
Final Office Action received for U.S. Appl. No. 14/344,892, dated Mar. 11, 2016, 4 pages.
Gerber et al., "Human Papillomavirus Virus-Like Particles are Efficient Oral Immunogens when Coadministered with *Escherichia coli* Heat-Labile Enterotoxin Mutant R192G or CpG DNA", Journal of Virology, vol. 75, No. 10, May 2001, pp. 4752-4760.
Glück et al., "New Technology Platforms in the Development of Vaccines for the Future", Vaccine, vol. 20, Suppl. 5, Dec. 20, 2002, pp. B10-B16.
Ibba, Michael, "Strategies for in Vitro and in Vivo Translation with Non-natural Amino Acids", Biotechnology and Genetic Engineering Reviews, vol. 13, Dec. 1995, pp. 197-216.
Johnson et al., "Synthesis and Biological Evaluation of a New Class of Vaccine Adjuvants: Aminoalkyl Glucosaminide 4-Phosphates (AGPs)", Bioorganic & Medicinal Chemistry Letters, vol. 9, No. 15, Aug. 1999, pp. 2273-2278.
Jones, Taff, "Resiquimod 3M (PMID:12669385)", Current Opinion in Investigational Drugs, vol. 4, No. 2, Feb. 2003, pp. 214-218.
Krieg, Arthur M., "CpG Motifs: The Active Ingredient in Bacterial Extracts?", Nature Medicine, vol. 9, 2003, pp. 831-835.
Lenz et al., "Papillomavirus-Like Particles Induce Acute Activation of Dendritic Cells", The Journal of Immunology, vol. 166, No. 9, 2001, pp. 5346-5355.
Male et al., "Introduction to the Immune System", Immunology, Seventh Edition, 2006, 4 pages.
McCluskie et al., "Parenteral and Mucosal Prime-Boost Immunization Strategies in Mice with Hepatitis B Surface Antigen and CpG DNA", FEMS Immunology and Medical Microbiology, vol. 32,, 2002, pp. 179-185.
Mellmann et al., "Prospective Genomic Characterization of the German Enterohemorrhagic *Escherichia coli* O104:H4 Outbreak by Rapid Next Generation Sequencing Technology", PLoS One, vol. 6, No. 7, e22751, Jul. 2011, pp. 1-9.
Meraldi et al., "OM-174, a New Adjuvant with a Potential for Human Use, Induces a Protective Response when Administered with the Synthetic C-Terminal Fragment 242-310 from the Circumsporozoite Protein of Plasmodium Berghei", Vaccine, vol. 21, No. 19-20, Jun. 2, 2003, pp. 2485-2491.
Moriel et al., "Identification of Protective and Broadly Conserved Vaccine Antigens from the Genome of Extraintestinal Pathogenic *Escherichia coli*", Proceedings of the National Academy of Sciences of the United States of America, vol. 107, No. 20, May 18, 2010, pp. 9072-9077.
Niikura et al., "Chimeric Recombinant Hepatitis E Virus-like Particles as an Oral Vaccine Vehicle Presenting Foreign Epitopes", Virology, vol. 293, 2002, pp. 273-280.
Notice of Allowance received for U.S. Appl. No. 14/344,892, dated Aug. 1, 2016, 8 pages.
Non-Final Office Action received for U.S. Appl. No. 14/344,892, dated Sep. 23, 2015, 8 Pages.
O'Hagan, Derek T., "Vaccine Adjuvants: Preparation Methods and Research Protocols", Methods in Molecular Medicine, vol. 42, 2000, 353 pages.
Pajak et al., "The Adjuvant OM-174 Induces both the Migration and Maturation of Murine Dendritic Cells in Vivo", Vaccine, vol. 21, No. 9-10, Feb. 14, 2003, pp. 836-842.
Partidos et al., "Heat-Labile Enterotoxin of *Escherichia coli* and Its Site-Directed Mutant LTK63 Enhance the Proliferative and Cytotoxic T-Cell Responses to Intranasally Co-Immunized Synthetic Peptides", Immunology Letters, vol. 67, No. 3, Apr. 1999, pp. 209-216.
Peppoloni et al., "Mutants of the *Escherichia coli* Heat-Labile Enterotoxin as Safe and Strong Adjuvants for Intranasal Delivery of Vaccines", Expert Review of Vaccines, vol. 2, No. 2, Apr. 2003, pp. 285-293.
Pine et al., "Intranasal Immunization with Influenza Vaccine and a Detoxified Mutant of Heat Labile Enterotoxin from *Escherichia coli* (LTK63)", Journal of Controlled Release, vol. 85, No. 1, Dec. 2002, pp. 263-270.
Pinto et al., "Cellular Immune Responses to Human Papillomavirus (HPV)-16 L1 in Healthy Volunteers Immunized with Recombinant HPV-16 L1 Virus-Like Particles", The Journal of Infectious Diseases, vol. 188, No. 2, Jul. 15, 2003, pp. 327-338.
Pizza et al., "LTK63 and LTR72, Two Mucosal Adjuvants Ready for Clinical Trials", International Journal of Medical Microbiology, vol. 295, No. 4-5, Oct. 2000, pp. 455-461.
Pizza et al., "Mucosal Vaccines: Non Toxic Derivatives of LT and CT as Mucosal Adjuvants", Vaccine, vol. 19, No. 17-19,, Mar. 2001, pp. 2534-2541.
Podda et al., "MF59-Adjuvanted Vaccines: Increased Immunogenicity with an Optimal Safety Profile", Expert Review of Vaccines, vol. 2, No. 2, Apr. 2003, pp. 197-204.
Podda, Audino, "The Adjuvanted Influenza Vaccines with Novel Adjuvants: 36. Experience with the MF59-Adjuvanted Vaccine", Vaccine, vol. 19, 2001, pp. 2673-2680.
Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells", Infection and Immunity, vol. 67, No. 12, Dec. 1999, pp. 6270-6280.
Scharton-Kersten et al., "Transcutaneous Immunization with Bacterial ADP-Ribosylating Exotoxins, Subunits, and Unrelated Adjuvants", Infection and Immunity, vol. 68, No. 9, Sep. 2000, pp. 5306-5313.
Schellack et al., "IC31, a Novel Adjuvant Signaling via TLR9, Induces Potent Cellular and Humoral Immune Responses", Vaccine, vol. 24, No. 26, Jun. 2006, pp. 5461-5472.
Singh et al., "A Novel Bioadhesive Intranasal Delivery System for Inactivated Influenza Vaccines", Journal of Controlled Release, vol. 70, No. 3, Feb. 2001, pp. 267-276.
Stanley, M. A., "Imiquimod and the Imidazoquinolones: Mechanism of Action and Therapeutic Potential", Clinical and Experimental Dermatology, vol. 27, No. 7, Oct. 2002, pp. 571-577.
Welch et al., "Extensive Mosaic Structure Revealed by the Complete Genome Sequence of Uropathogenic *Escherichia coli*", PNAS, vol. 99, No. 26, 2002, pp. 17020-17024.

\* cited by examiner

| Candidate | NMEC | APEC | UPEC | EHEC | EAEC | EIEC | EPEC | ETEC | AIEC |
|---|---|---|---|---|---|---|---|---|---|
| Orf3526 | | | | | | | | | |
| Upec1232 | | | | | | | | | |
| orf405B | | | | | | | | | |
| orf3515 | | | | | | | | | |

FIG. 1A

| Candidate | ExPEC | EHEC | EPEC | ETEC | AIEC |
|---|---|---|---|---|---|
| Orf3526 | 51/59 | 6/25 | 5/6 | 9/9 | 4/4 |
| orf405B | 54/59 | 24/25 | 6/6 | 8/9 | 3/4 |
| Upec1232 | 46/59 | 4/25 | 2/4 | 8/9 | 1/4 |

FIG. 1B

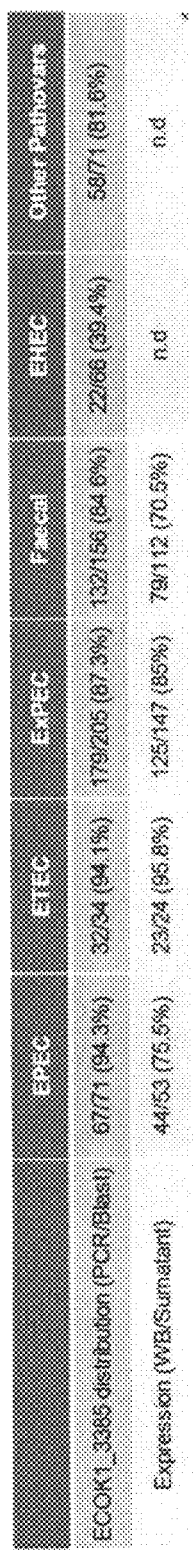
FIG. 2A
FIG. 2B
FIG. 2C

| Sample | MW(KDa) | Conc(µM) | Buffer | Batch | Zinc content (mol %) |
|---|---|---|---|---|---|
| ΔG3526TL | 164 | 4.3 | 10mM KH₂PO₄, 150mM NaCl | ExPEC_102 | 70 |
| ΔG3526 his | 165 | 3 | PBS+ 40% glycerol | ExPEC_115 | 68 |
| 3526 A his | 81 | 4.9 | PBS | ExPEC_092 | 33 |
| 3526 B his | 86 | 4.4 | PBS+ 40% glycerol | ExPEC_086 | 5 |
| ΔG3526 C his | 140 | 3.2 | PBS | ExPEC_112 | 18 |
| ΔG3526E1305-his | 165 | 3.3 | PBS+ 40% glycerol | ExPEC_099 | 43 |
| ΔG3526TL3M | 164 | 3.1 | 10mM KH₂PO₄, 150mM NaCl | ExPEC_117 | 8 |

ESCHERICHIA COLI VACCINE COMBINATION

TECHNICAL FIELD

The present invention relates generally to the field of immunisation against *E. coli* and *E. coli* vaccines. More specifically, the invention relates to combinations of polypeptides useful in the preparation of prophylactic and therapeutic vaccine combinations for use in immunisation against pathogenic *E. coli* pathotypes. In particular, it relates to a vaccine useful in protecting humans against a broad spectrum of *E. coli* strains.

BACKGROUND TO THE INVENTION

Several publications and patent documents are referenced in this application in order to describe more fully the state of the art to which this invention pertains. The disclosure of each of these publications is incorporated herein by reference.

*Escherichia coli* is a common colonizer of the human gastrointestinal tract and although *E. coli* strains are largely regarded as commensal, some isolates have the potential to cause diseases. Two distinct pathogenic categories of *E. coli* are recognized depending on whether they cause intestinal or extraintestinal infections. The extraintestinal pathogenic *E. coli* (ExPEC) group includes human pathogenic strains causing urinary tract infections (UPEC), neonatal meningitis (NMEC) and septicemia. Other ExPEC strains are instead pathogenic for avian species (APEC). The intestinal pathogenic *E. coli* (InPEC) group includes many pathotypes such as enterotoxigenic (ETEC), enteropathogenic (EPEC), enterohemorrhagic (EHEC), enteroinvasive, adherent invasive, and diffusely adherent *E. coli*, all causing infections to the human intestinal tract. These pathogenic strains of *Escherichia coli* are the most common cause of bacterial infections presenting a recurrent global threat that kills over two million of people in the world every year.

Vaccination would undoubtedly be the most cost-effective preventive measure against morbidity and death from pathogenic *E. coli* strains. However, primary studies have focused attention on the identification of candidates for use in vaccines protective against individual pathogenic categories, for example against UPEC alone or NMEC alone. In an earlier publication based on a comparative genome analysis and using the complete genome sequences of three ExPEC strains (IHE3034, CFT073 and 536), the Inventors identified nine potential vaccine candidates able to confer protection from sepsis (PNAS 2010; 107:20, p 9072-9077).

Whilst vaccines for use against individual diseases or illnesses are useful, it would be desirable to provide broad spectrum vaccines that provide protective immunity in animals, particularly humans, against all, or a large number, of infections caused by *E. coli*. For example, once vaccinated an individual could be covered or protected against all, or a high percentage, of the different diseases that *E. coli* can cause. A broadly protective vaccine would be of further benefit due to the spread of antibiotic resistant bacteria (CTX-M β-lactamase and carbepenemases) in hospitals and communities as a whole. However, the development of such a 'universal' or 'pan *E. coli*' vaccine is challenging because of the need to selectively prevent against subtypes of *E. coli* strains that are not normally part of the commensal flora. There is thus a need for improved *E. coli* vaccines, including a need to move away from crude cell lysates and towards better-defined molecules, and a need to identify antigens that are suitable for inclusion in a 'universal' vaccine, particularly antigens that are prevalent among clinically relevant strains without also being found in commensal strains.

In addition, a needle-free or mucosally administered vaccine would be preferable for reasons of improved patient comfort and ease of administration, as well as reducing the risk of contamination and other adverse effects while promoting patient compliance and increasing the safety of vaccination.

The present Inventors have discovered a combination of antigens suitable for use in the preparation of a broad spectrum vaccine against pathogenic *E. coli*. Surprisingly, the vaccine combination provides protection against disease/illness caused by pathogenic strains of *E. coli* from both ExPEC and InPEC groups.

BRIEF DESCRIPTION OF THE INVENTION

In a first aspect, the invention provides an immunogenic composition comprising a combination of (i) bacterial Ig-like domain protein fragment (orf405B) having the amino acid sequence set forth in SEQ ID NO:2 or a protein having at least 80% similarity thereto, and (ii) putative Lipoprotein (orf3526) having the amino acid sequence set forth in SEQ ID NO:8 or a protein having at least 80% similarity thereto.

In certain embodiments the immunogenic compositions further comprise (iii) upec1232 having the amino acid sequence set forth in SEQ ID NO:4 or a protein having at least 80% similarity thereto.

In further embodiments the immunogenic compositions further comprise (iv) gspK (orf3515) having the amino acid sequence set forth in SEQ ID NO:30 or a protein having at least 80% similarity thereto.

In other embodiments the immunogenic compositions further comprise at least one bacterial toxin. Particularly, the bacterial toxin is an *Escherichia coli* toxin. More particularly, the bacterial toxin is modified heat-labile toxin of *Escherichia coli* (LTK63), yet more particularly detoxified heat-labile toxin of *Escherichia coli* (LTK63).

Protein components of the compositions of the invention may be fragments of the proteins or amino acid sequences mentioned herein.

In certain embodiments, the putative Lipoprotein (orf3526) utilised in the immunogenic compositions is a mutant protein wherein at least one amino acid (e.g., 1, 2, 3, 4 or 5 amino acids) at positions 1304, 1305, 1306, 1307 and/or 1308 with reference to SEQ ID 8 is/are substituted by another amino acid. In certain embodiments, the putative Lipoprotein (orf3526) is a mutant orf3526 protein wherein the zinc binding activity is reduced by at least 50% relative to wild-type orf3526. In certain embodiments, the mutant has a zinc content which is at least 50% lower than the content of an equivalent amount of wild-type orf3526. The mutant polypeptides may be lipidated e.g. at an N-terminal cysteine. The mutant polypeptides may be prepared having a reduced zinc ion content or substantially free from zinc ions, relative to other variants of orf3526 polypeptide or fragments thereof, for example relative to wild-type orf3526 polypeptide. A mutant orf3526 protein having such reduced the zinc binding activity may have one or more (e.g., 2, 3, 4 or 5) of the aforementioned amino acid substitutions at positions 1304, 1305, 1306, 1307 and/or 1308. Particular mutant orf3526 proteins comprise the amino acid sequence of SEQ ID: 31, or immunogenic fragments thereof, which include mutations at positions 1304, 1305 and 1308. One such fragment includes mutations at positions 1304, 1305 and 1308 and comprises amino acid residues 24-1520, or residues 34-1520, of SEQ ID 31. The mutant polypeptides, or immunogenic fragments thereof, may be prepared having a reduced zinc ion content or substantially free from zinc ions, relative to other variants of orf3526 polypeptide or fragments thereof, for example relative to wild-type orf3526 polypeptide.

In certain embodiments, isoform B (corresponding to peak B in FIG. 9A) of orf3526, or an immunogenic fragment thereof, is preferred. One such exemplary immunogenic fragments is isoform B of a polypeptide that includes mutations at positions 1304, 1305 and 1308 and comprises amino acid residues 24-1520, or residues 34-1520, of SEQ ID 31.

In other embodiments, isoform A (corresponding to peak A in FIG. 9A) of orf3526, or an immunogenic fragment thereof, is preferred. One such exemplary immunogenic fragments is isoform A of a polypeptide that includes mutations at positions 1304, 1305 and 1308 and comprises amino acid residues 24-1520, or residues 34-1520, of SEQ ID 31.

In other embodiments, isoform C (corresponding to peak C in FIG. 9A) of orf3526, or an immunogenic fragment thereof, is preferred.

In further embodiments, a combination of at least two of isoforms A, B and C of orf3526, or immunogenic fragments thereof, is preferred. In particular, a combination of isoform A and B of orf3526, or immunogenic fragments thereof, is preferred. For example, a combination of isoforms A and B of a polypeptide that includes mutations at positions 1304, 1305 and 1308 and comprises amino acid residues 24-1520, or residues 34-1520, of SEQ ID 31, is preferred.

The immunogenic compositions of the invention may comprise one or more pharmaceutically acceptable carriers, diluents and/or adjuvants. The immunogenic compositions of the invention may comprise propane-1,2,3-triol (glycerol). The immunogenic compositions of the invention may be vaccines, or vaccine compositions.

In other aspects there is provided a method for treating or preventing *E. coli* infection in a mammal, which comprises administering to said mammal an effective amount of an immunogenic composition according to the invention. In certain embodiments the immunogenic composition will be administered to a mucosal surface such as nasal epithelium, oral mucosa or luminal surface of a gastrointestinal organ selected from the group consisting of: stomach, small intestine, large intestine, and rectum. Preferably, immunogenic compositions of the present invention are administered by parenteral administration.

In other aspects there is provided the use of immunogenic compositions of the invention in medicine, e.g. for treating or preventing *E. coli* infections in a mammal, in particular for providing broad protection against pathogenic *E. coli*, e.g. extraintestinal or intraintestinal pathogenic *E. coli*, in particular for treating or preventing infections by more than one *E. coli* pathotype, e.g. infections by both extraintestinal and intraintestinal pathogenic *E. coli*, i.e. both ExPEC and InPEC pathotypes, such as NMEC, APEC, UPEC, EHEC, AIEC, EPEC, EAEC, EIEC, ETEC and DAEC pathotypes. Thus the subject may be protected against diseases including, but not limited to peritonitis, pyelonephritis, cystitis, endocarditis, prostatitis, urinary tract infections (UTIs), meningitis (particularly neonatal meningitis), sepsis (or SIRS), dehydration, pneumonia, diarrhea (infantile, travellers', acute, persistent, etc.), bacillary dysentery, hemolytic uremic syndrome (HUS), pericarditis, bacteriuria, etc. Thus, the invention provides the use of immunogenic compositions of the invention for the manufacture of a medicament for treating or preventing *E. coli* infections, e.g. extraintestinal or intraintestinal pathogenic *E. coli*, in particular infections by more than one *E. coli* pathotype, e.g. infections by both extraintestinal and intraintestinal pathogenic *E. coli*, i.e. both ExPEC and InPEC pathotypes, such as NMEC, APEC, UPEC, EHEC, AIEC, EPEC, EAEC, EIEC, ETEC and DAEC pathotypes, or any of the aforementioned diseases.

The invention also provides orf3526 mutant polypeptides wherein at least one amino acid (e.g., 1, 2, 3, 4 or 5 amino acids) at positions 1304, 1305, 1306, 1307 and/or 1308 (numbered with reference to SEQ ID: 8) is/are substituted by another amino acid. In certain embodiments, the mutant has a zinc content which is at least 50% lower than the content of an equivalent amount of wild-type orf3526. Particular mutant orf3526 polypeptides comprise the amino acid sequence of SEQ ID: 31, or immunogenic fragments thereof which include said amino acid positions 1304, 1305 and 1308. One such fragment comprises amino acid residues 24-1520, or residues 34-1520, of SEQ ID 31. The mutant polypeptides may be lipidated e.g. at an N-terminal cysteine. The mutant polypeptides may be prepared having a reduced zinc ion content or substantially free from zinc ions, relative to other variants of orf3526 polypeptide or fragments thereof, for example relative to wild-type orf3526 polypeptide.

The invention also provides isoform B of the 3526 polypeptide (corresponding to peak B in FIG. 9A), or an immunogenic fragment thereof, obtainable by purification using size exclusion chromatography (e.g. CaptoQ and/or butyl sepharose chromatography) from a composition comprising recombinant 3526 polypeptide(s) of a fraction that elutes at around 17 mins, or that elutes after isoform A and/or before isoform C. In further embodiments, isoform B is of a 3526 polypeptide that includes mutations at positions 1304, 1305 and 1308 and, optionally, lacks amino acid residues 1-23, or residues 1-33, of SEQ ID 31.

The invention also provides isoform A of the 3526 polypeptide (corresponding to peak A in FIG. 9A), or an immunogenic fragment thereof, obtainable by purification using size exclusion chromatography (e.g. CaptoQ and/or butyl sepharose chromatography) from a composition comprising recombinant 3526 polypeptide(s) of a fraction that elutes at around 16 mins, or of a fraction that elutes before isoform B and/or before isoform C. In further embodiments, isoform A is of a 3526 polypeptide that includes mutations at positions 1304, 1305 and 1308 and, optionally, lacks amino acid residues 1-23, or residues 1-33, of SEQ ID 31.

The invention also provides isoform C of the 3526 polypeptide (corresponding to peak C in FIG. 9A), or an immunogenic fragment thereof, obtainable by purification using size exclusion chromatography (e.g. CaptoQ and/or butyl sepharose chromatography) from a composition comprising recombinant 3526 polypeptide(s) of a fraction that elutes at around 19 mins, or that elutes after isoform A and/or after isoform B. In further embodiments, isoform C is of a 3526 polypeptide that includes mutations at positions 1304, 1305 and 1308 and, optionally, lacks amino acid residues 1-23, or residues 1-33, of SEQ ID 31.

In further embodiments, the invention provides a combination of at least two of isoforms A, B and C of orf3526, or immunogenic fragments thereof, obtainable by purification using size exclusion chromatography (e.g. CaptoQ and/or butyl sepharose chromatography) from a composition comprising recombinant 3526 polypeptide(s) of a fraction that elutes at around 16 mins for isoform A, at around 17 mins for isoform B, and around 19 mins for isoform C; or of a fraction that elutes before isoform B and/or before isoform C for isoform A, or that elutes after isoform A and/or before isoform C for isoform B, or that elutes after isoform A and/or after isoform B for isoform C. For example, a combination of isoform A and B of orf3526, or immunogenic fragments thereof, such as a combination of isoforms A and B of a polypeptide that includes mutations at positions 1304, 1305 and 1308 and comprises amino acid residues 24-1520, or residues 34-1520, of SEQ ID 31.

"Isoform C" is used as a synonym for "fragment C".

The invention also provides a protein which binds to an antibody which antibody does bind to isoform B of the 3526 polypeptide obtainable by purification using size exclusion chromatography (e.g. CaptoQ and/or butyl sepharose chromatography) from a composition comprising recombinant 3526 polypeptide(s) of a fraction that elutes at around 17 mins, or that elutes after isoform A and/or before isoform C, but which antibody does not bind to isoform A of the 3526 polypeptide obtainable by purification using size exclusion chromatography (e.g. CaptoQ and/or butyl sepharose chromatography) from a composition comprising recombinant 3526 polypeptide(s) of a fraction that elutes at around 16 mins, or of a fraction that elutes before isoform B and/or before isoform C, or to isoform C of the 3526 polypeptide, obtainable by purification using size exclusion chromatography (e.g. CaptoQ and/or butyl sepharose chromatography) from a composition comprising recombinant 3526 polypeptide(s) of a fraction that elutes at around 19 mins, or that elutes after isoform A and/or after isoform B. In further embodiments, isoform B is of a 3526 polypeptide that includes mutations at positions 1304, 1305 and 1308 and, optionally, lacks amino acid residues 1-23, or residues 1-33, of SEQ ID 31.

The invention also provides a protein which binds to an antibody which antibody does bind to isoform A of the 3526 polypeptide obtainable by purification using size exclusion chromatography (e.g. CaptoQ and/or butyl sepharose chromatography) from a composition comprising recombinant 3526 polypeptide(s) of a fraction that elutes at around 16 mins, or of a fraction that elutes before isoform B and/or before isoform C, but which antibody does not bind to isoform B of the 3526 polypeptide obtainable by purification using size exclusion chromatography (e.g. CaptoQ and/or butyl sepharose chromatography) from a composition comprising recombinant 3526 polypeptide(s) of a fraction that elutes at around 17 mins, or that elutes after isoform A and/or before isoform C, or to isoform C of the 3526 polypeptide obtainable by purification using size exclusion chromatography (e.g. CaptoQ and/or butyl sepharose chromatography) from a composition comprising recombinant 3526 polypeptide(s) of a fraction that elutes at around 19 mins, or that elutes after isoform A and/or after isoform B. In further embodiments, isoform B is of a 3526 polypeptide that includes mutations at positions 1304, 1305 and 1308 and, optionally, lacks amino acid residues 1-23, or residues 1-33, of SEQ ID 31.

The invention also provides a protein which binds to an antibody which antibody does bind to isoform C of the 3526 polypeptide obtainable by purification using size exclusion chromatography (e.g. CaptoQ and/or butyl sepharose chromatography) from a composition comprising recombinant 3526 polypeptide(s) of a fraction that elutes at around 19 mins, or that elutes after isoform A and/or after isoform B, but which antibody does not bind to isoform A of the 3526 polypeptide obtainable by purification using size exclusion chromatography (e.g. CaptoQ and/or butyl sepharose chromatography) from a composition comprising recombinant 3526 polypeptide(s) of a fraction that elutes at around 16 mins, or of a fraction that elutes before isoform B and/or before isoform C, or to obtainable by purification using size exclusion chromatography (e.g. CaptoQ and/or butyl sepharose chromatography) from a composition comprising recombinant 3526 polypeptide(s) of a fraction that elutes at around 17 mins, or that elutes after isoform A and/or before isoform C. In further embodiments, isoform B is of a 3526 polypeptide that includes mutations at positions 1304, 1305 and 1308 and, optionally, lacks amino acid residues 1-23, or residues 1-33, of SEQ ID 31.

Such antibodies can be prepared by screening methods known in the art (e.g. chromatography using isoforms for positive and negative selection; phage display).

The invention also provides immunogenic compositions comprising one or more of these isoforms, and their use in a method for treating or preventing *E. coli* infection, for example in a mammal.

BRIEF DESCRIPTION OF FIGURES

FIGS. 1A-B: Presence of each of the antigens utilised in compositions of the present invention were determined in most pathogenic strains, specifically NMEC, APEC, UPEC, EHEC, EAEC, EIEC, EPEC, ETEC and AIEC (FIG. 1A); Gene presence of protective candidates was evaluated in sequenced genomes (based on >85% sequence homology) and in clinical isolates (by PCR amplification) (FIG. 1B).

FIGS. 2A-C: Gene distribution analysis—Gene presence of best protective candidates was evaluated in 603 *E. coli* strains by PCR amplification and blast searches on sequenced genomes. ExPEC: APEC=Avian, UPEC=Uropathogenic, NMEC=Newborn meningitic, SEPEC=Septicaemia, pathogenic *E. coli*. EPEC=Enteropathogenic *E. coli*. ETEC=Enterotoxigenic *E. coli*. EHEC=Enterohaemorrhagic *E. coli* Faecal *E. coli* and Other Pathovars=Lab.Strains, STEC=Toxinproducing *E. coli*, EIEC=enteroinvasive *E. coli*, AIEC=adhesive invasive *E. coli*, EAEC=enteroagregative *E. coli*. AREC=ampicillin resistent *E. coli* orf3526 (ECOK1_3385) expression was assessed by immunoblotting analysis on supernatant fractions using polyclonal rabbit serum.

FIG. 11: Zinc content of various orf3526 derivatives was determined by atomic absorption spectroscopy. Results suggest the presence of a single zinc ion per protein molecule. The unexpected low zinc content of 3526 B his, actually containing the zinc binding motif, could be explained by misfolding of this truncated derivative, while the single amino acid exchange in the E1305 mutant apparently is not sufficient to completely abolish zinc binding (red boxes). In contrast, zinc affinity is completely lost in the TL3M triple mutant.

Figure 12:
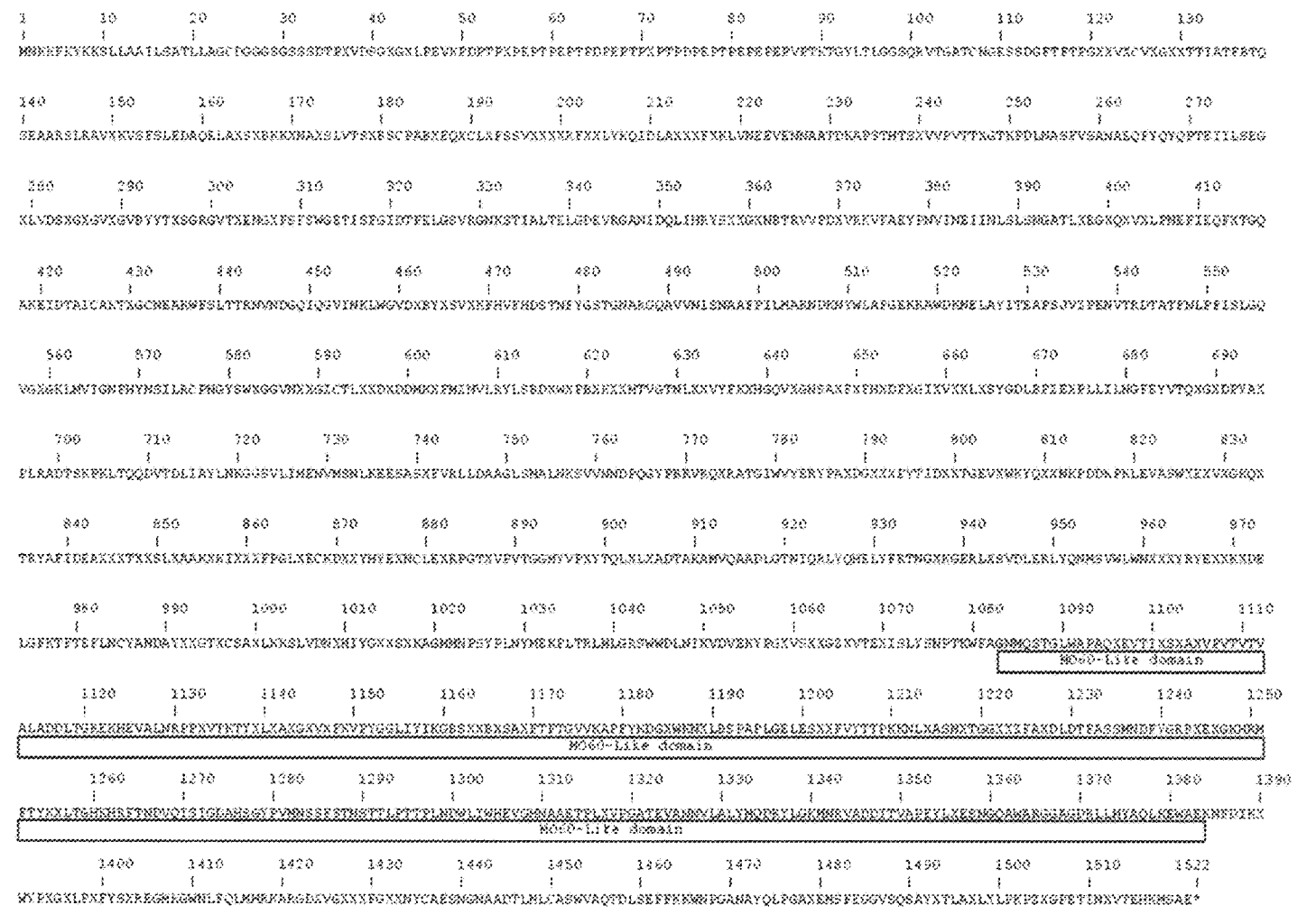

FIG. 12: orf3526 75% consensus sequence. Each specified residue is found at that position in at least 75% of the orf3526 sequences used to generate the consensus sequence. X represents any amino acid. The MO60-Like domain is highlighted.

Figure 13:
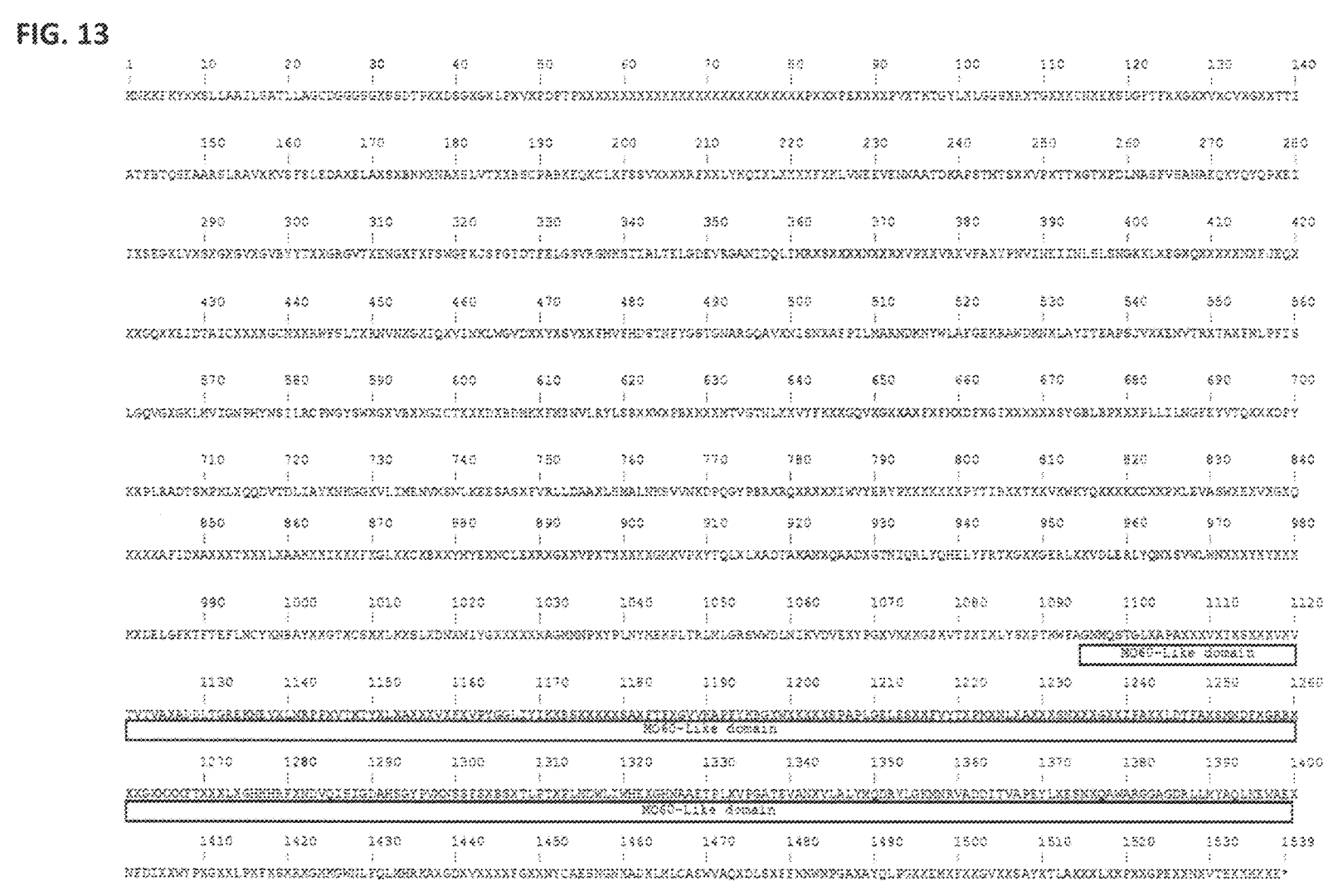

FIG. 13: orf3526 100% consensus sequence. Each specified residue is found at that position in all of the orf3526 sequences used to generate the consensus sequence. X represents any amino acid. The MO60-Like domain is highlighted.

DETAILED DESCRIPTION OF THE INVENTION

Figure 3A:
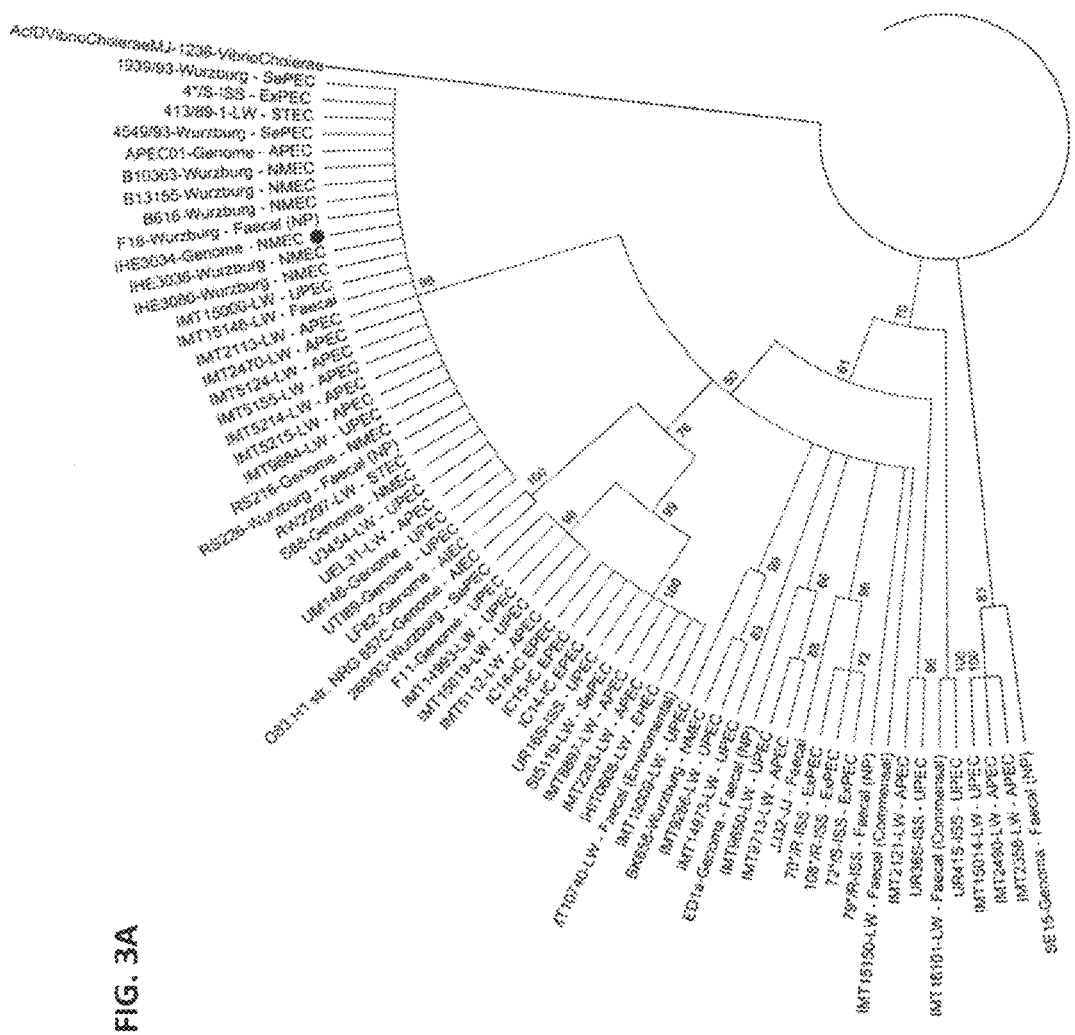
FIGS. 3A-D: Study of molecular diversity of orf3526: sequence alignment analysis of 217 sequences of orf3526 protein revealed a sequence identity ranging from 86% to 100%; the derived phylogenetic tree revealed the presence of 6 major variants. The phylogenetic tree was inferred using the Maximum likelihood method implemented in MEGA5 package.
Figure 3B:
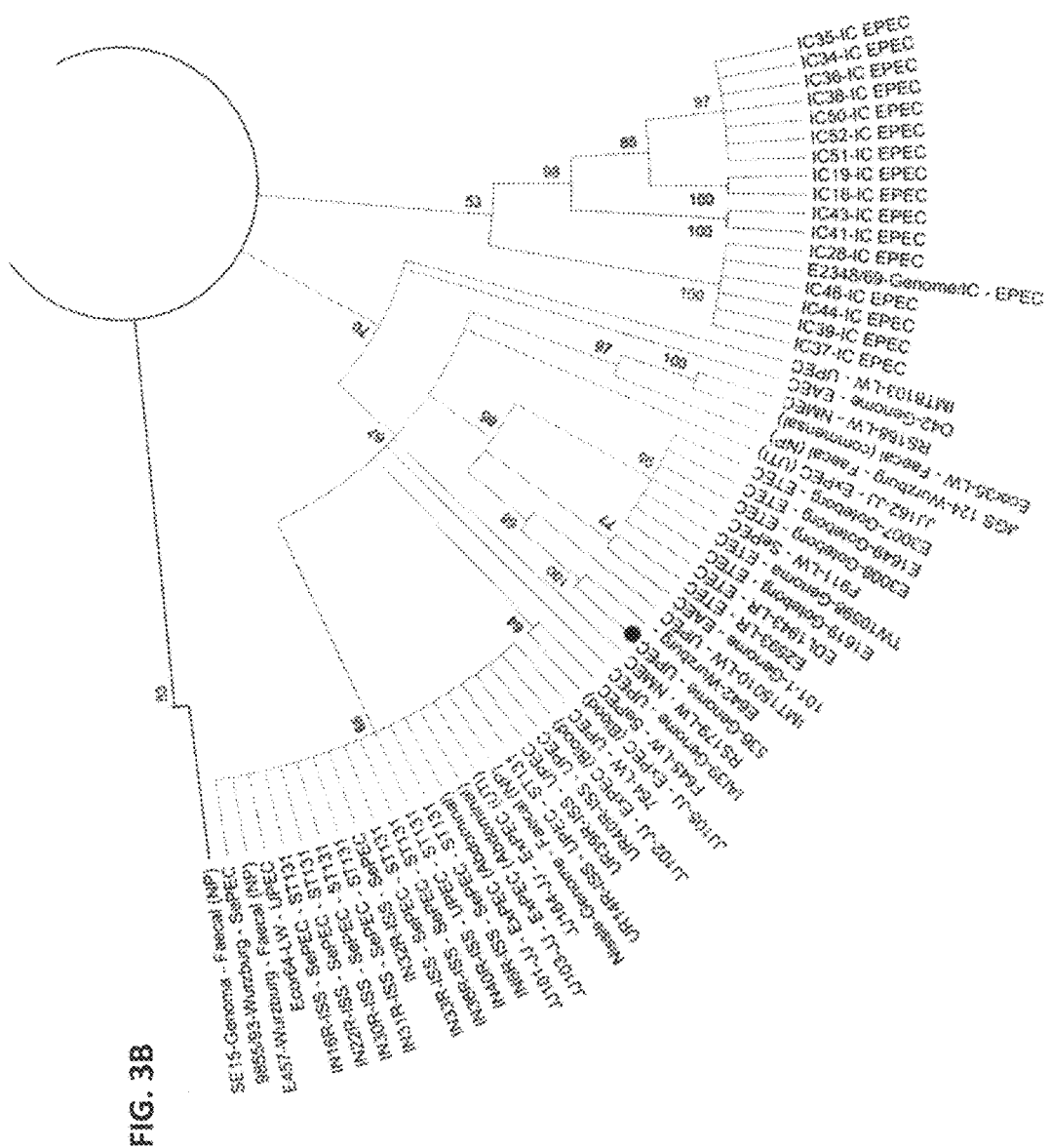
Figure 3C:
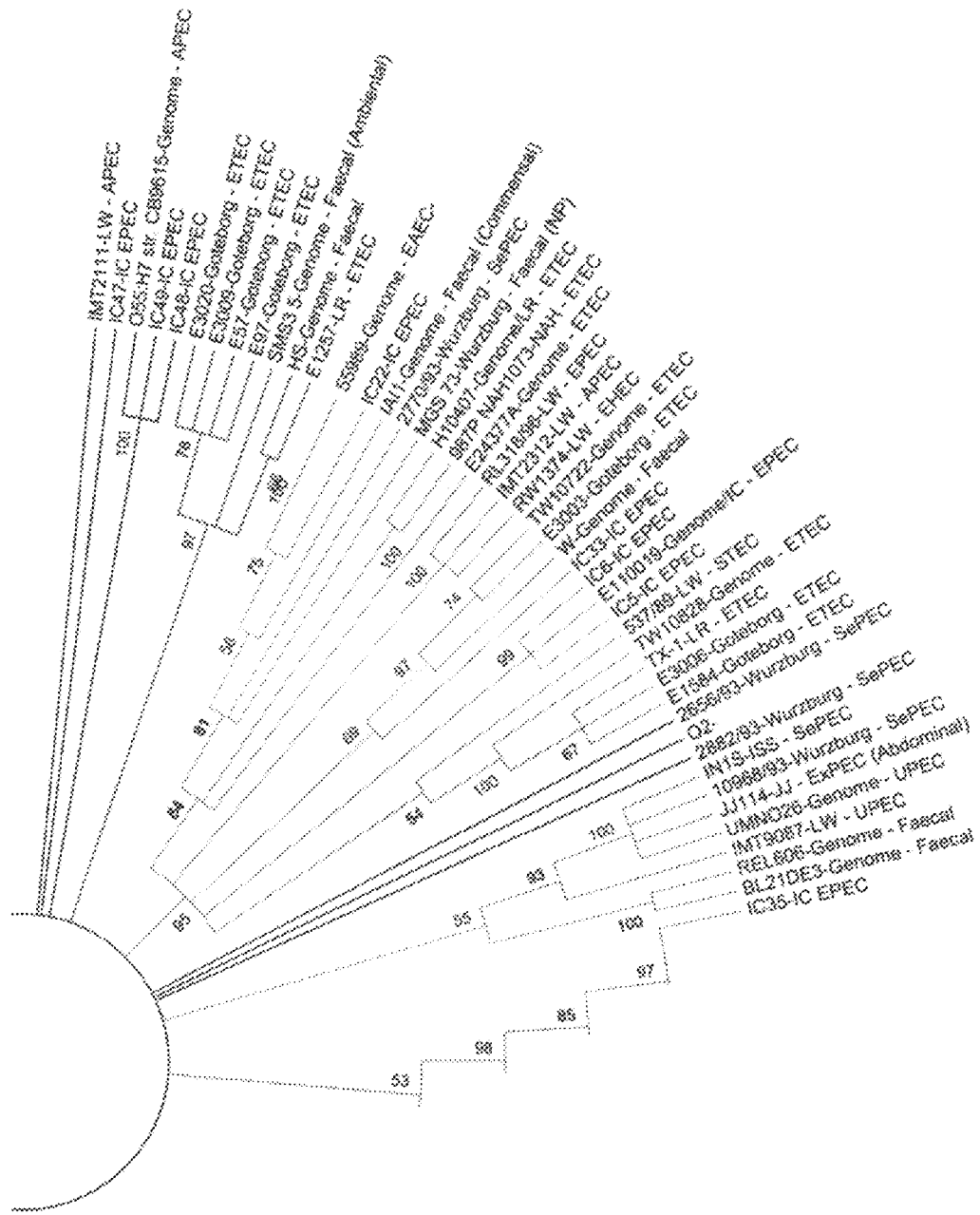
Figure 3D:
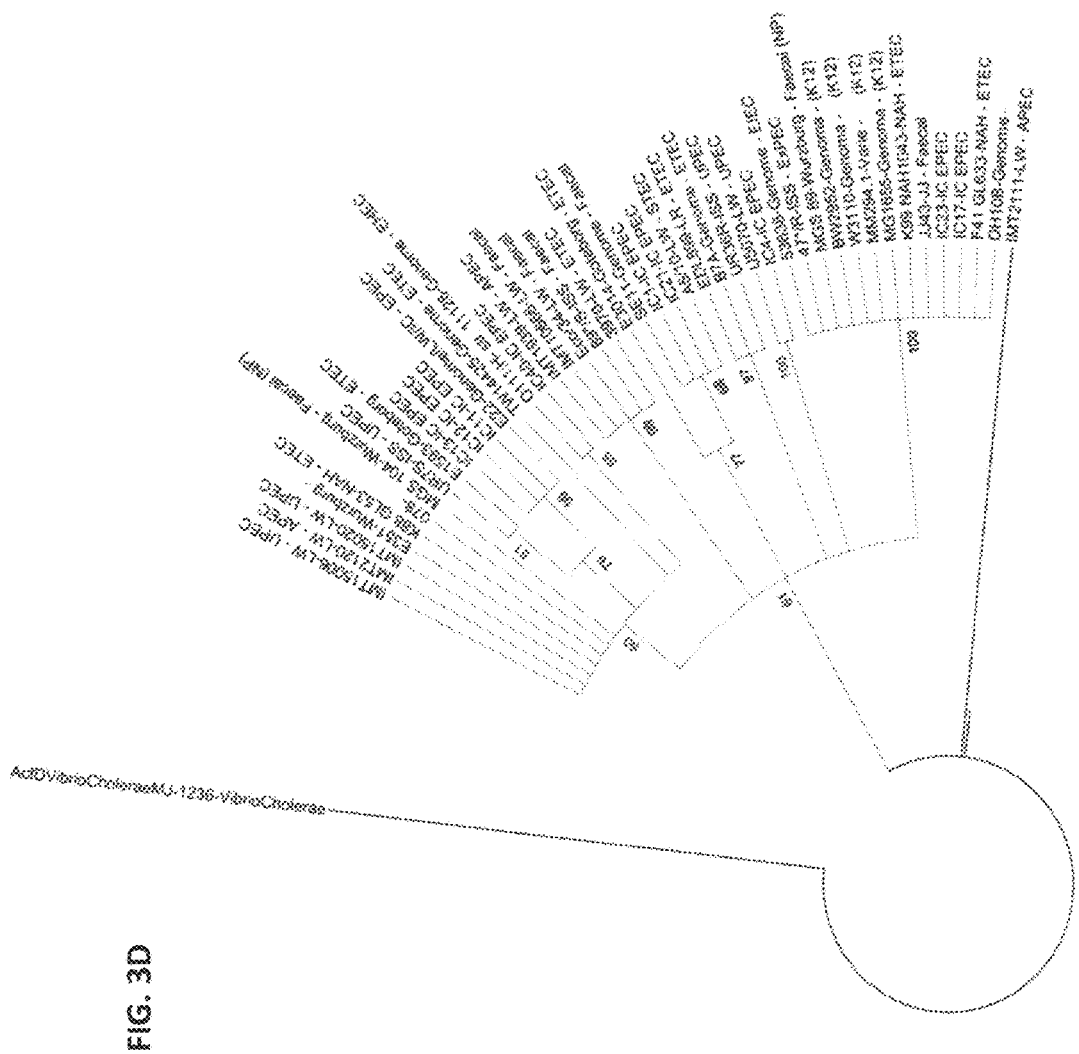

The invention provides immunogenic compositions comprising an immunogenic component of *Escherichia coli* wherein the immunogenic component is selected from the group consisting of bacterial Ig-like domain protein fragment (orf405B) having the amino acid sequence set forth in SEQ ID NO:2 or a protein having at least 80% similarity thereto, upec1232 having the amino acid sequence set forth in SEQ ID NO:4 or a protein having at least 80% similarity thereto, putative Lipoprotein (orf3526) having the amino acid sequence set forth in SEQ ID NO:8 or a protein having at least 80% similarity thereto and gspK (orf3515) having the amino acid sequence set forth in SEQ ID NO:30 or a protein having at least 80% similarity thereto. A composition of the invention may comprise e.g. one, two, three or four of the aforementioned components, e.g.

orf405B and upec1232; orf405B and orf3526; orf405B and orf3515;
upec1232 and orf3526; upec1232 and orf3515;
orf3526 and orf3515;
orf405B, upec1232 and orf3526; orf405B, orf3526 and orf3515; or upec1232, orf3526s and orf3515;
or proteins having at least 80% similarity to any thereof.

Preferably, an immunogenic composition of the invention comprises one, two or three components selected from orf405B, upec1232, orf3526, or proteins having at least 80% similarity to any thereof. For example, an immunogenic composition of the invention may comprise the three components orf405B, upec1232 and orf3526, or proteins having at least 80% similarity to any thereof. More preferably, an immunogenic composition of the invention comprises one or two components selected from orf405B and orf3526, or proteins having at least 80% similarity to any thereof. For example, an immunogenic composition of the invention may comprise the two components orf405B and orf3526, or proteins having at least 80% similarity to any thereof. Alternatively, an immunogenic composition of the invention may comprise orf405B, upec1232, orf3526, and orf3515, or proteins having at least 80% similarity to any thereof.

Components of compositions of the invention may be isolated or purified.

As used herein, the term "immunogenic" means that, for example the polypeptide(s), composition and the like, is/are capable of eliciting a humoral or cellular immune response, and preferably both. For example, the term "immunogenic composition" refers to any composition able, once it has been administered to a subject, such as an animal for example a human, to induce or stimulate an immune response against *E. coli*.

An immunogenic polypeptide is also antigenic. A molecule is "antigenic" when it is capable of specifically interacting with an antigen recognition molecule of the immune system, such as an immunoglobulin (antibody) or T cell antigen receptor. An antigenic polypeptide contains an epitope of at least about five, and particularly at least about 10, at least 15, at least 20 or at least 50 amino acids. An antigenic portion of a polypeptide, also referred to as an epitope, can be that portion that is immunodominant for antibody or T cell receptor recognition, or it can be a portion used to generate an antibody to the molecule by conjugating the antigenic portion to a carrier polypeptide for immunization. The skilled person will recognise that a molecule that is antigenic need not be itself immunogenic, for example, some antigens require the presence of an adjuvant or carrier to render them capable of eliciting an immune response.

The term "antigen" refers to a molecule against which a subject can initiate a humoral and/or cellular immune response. An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the subject will display either a therapeutic or protective immunological response such that resistance to new infection will be enhanced and/or the clinical severity of the disease reduced. Such protection will be demonstrated by either a reduction or lack of symptoms normally displayed by an infected subject, a quicker recovery time and/or a lowered viral titre in the infected host. The term "immunogenic" protein or polypeptide as used herein also refers to an amino acid sequence which elicits an immunological response as described above.

When said immunogenic compositions prevent, ameliorate, palliate or eliminate disease from an animal then the immunogenic composition may optionally be referred to as a vaccine.

The term "vaccine" as used herein refers to a vaccine composition that comprises either purified antigenic determinants, nucleic acids encoding the purified antigenic determinants or fragments thereof, in the absence of the disease-causing organism. Such vaccines may also be referred to as a "sub-unit vaccine". The terms are not intended to encompass "whole-cell vaccines", for example those derived from whole bacterial cells that have been killed and which may contain the antigenic determinants in un-purified form as part of a complex and uncharacterised composition.

As used herein, the term "multivalent", means that the vaccine contains structurally similar or 'related' antigenic determinants from at least two strains or isolates, the antigenic determinants being homologues having minor differences between their amino acid sequences.

The terms "variant", "homologue", "derivative" or "fragment" in relation to polypeptides or antigens include any substitution of, variation of, modification of, replacement of, deletion of or addition of one (or more) amino acid or nucleotide from or to a sequence. Unless the context admits otherwise, references to particular antigens includes references to such variants, homologues, derivatives and fragments.

Preferred variants of an antigen can elicit antibodies which bind to that antigen. In particular, the antibodies bind to wild-type antigens as present in an *E. coli* cell.

In particular, the term "homologue" covers identity with respect to structure and/or function providing the resultant amino acid sequence has antigenic or immunogenic activity. With respect to sequence identity (i.e. similarity), there may be at least 70%, at least 75%, at least 80%, at least 85%, at least 90% sequence identity. There may be, e.g., at least 91%, 92%, 93%, or 94%, sequence identity. There may also be at least 95%, 96%, 97%, 98%, 99%, or 99.5% sequence identity. These terms also encompass polypeptides derived from amino acids which are allelic variations of nucleic acid or amino acid sequence(s). Percentage sequence identity and similarity between a sequence A and a sequence B is calculated as $(x/y)*100$, wherein x is the number of amino acids that are identical between A and B and y is the number of amino acids of the longest sequence selected from A and B. For example, in the case of 10 identical residues between a first sequence A consisting of 50 amino acids and a second sequence B consisting of 200 amino acids, the sequence identity between the two sequences is 5%.

Where reference is made to the "activity" or "biological activity" of a polypeptide, these terms are intended to refer to the antigenic and immunogenic activities of the polypeptide. Examples of such activities, and methods of assaying and quantifying these activities, are known in the art, and are described in detail elsewhere in this document.

As used herein a "deletion" is defined as a change in either nucleotide or amino acid sequence in which one or more nucleotides or amino acid residues, respectively, are absent. As used herein an "insertion" or "addition" is that change in a nucleotide or amino acid sequence which has resulted in the addition of one or more nucleotides or amino acid residues, respectively, as compared to the naturally occurring substance. As used herein "substitution" results from the replacement of one or more nucleotides or amino acids by different nucleotides or amino acids, respectively.

The terms "antigen" and "amino acid sequence", as they are used in this document, should be taken to include reference to each of the above sequences, as well as to their fragments, homologues, derivatives and variants.

The term "fragment" as used herein refers to partial nucleotide or amino acid sequences according to the present invention. In certain embodiments amino acid sequence or polypeptide fragments may include polypeptides comprising an amino acid sequence of at least 'n' consecutive amino acids derived from the listed sequence identifiers, for example at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino residues, at least 70 amino acid residues, at least 80 amino acid residues, at least 90 amino acid residues, at least 100, at least 150, at least 200 or at least 250 amino acid residues of the amino acid sequence. In certain embodiments amino acid fragments may include polypeptides comprising an amino acid sequence of no more than 50, no more than 60, no more than 75, no more than 100, no more than 150, no more than 200, no more than 250, no more than 300, no more than 350, no more than 400 amino acid residues. Preferred fragments comprise an epitope or are immunogenic fragments. Preferred fragments lack an amino-terminal portion of the polypeptides of the invention, such as residues 1-23 or residues 1-33 of SEQ ID NO: 8 or SEQ ID NO:31, or corresponding residues in other orf3526 polypeptides of the invention. Sequence identity and similarity between a fragment and a longer sequence is calculated according to the same method as described above, i.e. based on identical residues relative to the longest sequence.

As used herein, the term "purified" or "to purify" refers to the removal of contaminants from a sample. For example, antigens are purified by removal of contaminating proteins. The removal of contaminants results in an increase in the percent of antigen (e.g., antigen of the present invention) in the sample.

"Isolated" and "purified" as used herein describe certain molecules, proteins, polysaccharides, lipids, antigens, and the like, and refers to a state beyond that in which the molecules, proteins, polysaccharides, lipids, or antigens exist naturally in cells. Particularly the term as used herein means removed from its naturally occurring environment such as a cell, for example. In preferred embodiments, the isolated molecules, proteins, polysaccharides, lipids, antigens, and the like, are separated from greater than 20%, 30%, 40%, 50%, 60%, 70%, 80%, 90%, 95% or 99% of the proteins and/or the lipids with which the molecules, proteins, polysaccharides, lipids, antigens, and the like are normally associated naturally in cells. If the isolated molecules, proteins, polysaccharides, lipids, antigens, and the like are synthesized, they are contaminated with less than 50%, 40%, 30%, 20%, 10%, 5%, 1% or 0.1% of the chemical precursors or synthesis reagents used to synthesize the lipid antigen. In preferred embodiments, the molecules, proteins, polysaccharides, lipids or antigens are at least 1% pure, 5% pure, 10% pure, 20% pure, 30% pure, 40% pure, 50% pure, 60% pure, 70% pure, 80% pure, 90% pure, 95% pure, 99% pure, or 100% pure. As used herein, the term "% pure" indicates the percentage of a composition that is made up of the molecule of interest, by weight. Thus, a composition of 100 grams containing 50 grams of a molecule of interest is 50% pure with respect to the molecule of interest.

The term "treating" includes both therapeutic treatment and prophylactic or preventative treatment, wherein the object is to prevent or lessen infection. For example, treating may include directly affecting or curing, suppressing, inhibiting, preventing, reducing the severity of, delaying the onset of, reducing symptoms associated with, for example, infection, or a combination thereof. "Preventing" may refer, inter alia, to delaying the onset of symptoms, preventing relapse to a disease, and the like. Treating may also include "suppressing" or "inhibiting" an infection or illness, for example reducing severity, number, incidence or latency of symptoms, ameliorating symptoms, reducing secondary symptoms, reducing secondary infections, prolonging patient survival, or combinations thereof.

Polypeptides used in the invention can be prepared in many ways e.g. by chemical synthesis (in whole or in part), by digesting longer polypeptides using proteases, by translation from RNA, by purification from cell culture (e.g. from recombinant expression), from the organism itself (e.g. after bacterial culture, or direct from patients), etc. A preferred method for production of peptides <40 amino acids long involves in vitro chemical synthesis [1,2]. Solid-phase peptide synthesis is particularly preferred, such as methods based on tBoc or Fmoc [3] chemistry. Enzymatic synthesis [4] may also be used in part or in full. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non natural amino acids, such as iodotyrosine or methylphenylalanine, azidohomoalanine, etc.) [5]. Where D-amino acids are included, however, it is preferred to use chemical synthesis. Polypeptides may have covalent modifications at the C-terminus and/or N-terminus.

Polypeptides can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Polypeptides are preferably provided in purified or substantially purified form. Polypeptides may be attached to a solid support. Polypeptides may comprise a detectable label (e.g. a radioactive or fluorescent label, or a biotin label).

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains. Polypeptides can be naturally or non-naturally glycosylated (i.e. the polypeptide has a glycosylation pattern that differs from the glycosylation pattern found in the corresponding naturally occurring polypeptide).

Polypeptides used in the present invention may be produced by culturing a host cell under conditions which induce polypeptide expression. Expression of the polypeptide may take place in a heterologous host for expression. The heterologous host may be prokaryotic (e.g. a bacterium) or eukaryotic. Suitable hosts include *Bacillus subtilis*, *Vibrio cholerae*, *Salmonella typhi*, *Salmonella typhimurium*, *Neisseria lactamica*, *Neisseria cinerea*, Mycobacteria (e.g. *M. tuberculosis*), yeasts, etc.

Particular polypeptides used in combinations of the invention may comprise an amino acid sequence that is derived from bacterial Ig-like domain (group 1) protein fragment (orf405B), gspK (orf3515), upec-1232 and putative Lipoprotein (orf3526) each as more fully described herein.

Bacterial Ig-Like Domain Protein Fragment 'Orf405B'

Bacterial Ig-like domain (group 1) protein, from *E. coli* NMEC, is disclosed in WO2006/089264 (SEQ IDs 809 and 810) and is referred to therein as 'orf405', the protein is also referred to as 'orf284' from *E. coli* NMEC strain IHE3034, 'c0415' from CFT073 and 'ecp_0367' from 536. Fragments of this orf405 protein were first disclosed in WO2011/004263 (for example in SEQ IDs 641 and 642). Compositions according to the present invention preferably comprise bacterial Ig-like domain protein fragment 'orf405B'. The nucleotide and amino acid sequences of this protein fragment, referred to herein, as SEQ IDs 1 and 2 are:

>orf405B (SEQ ID 1)
GTTGCTGATGGTCAGCAAGCCTACACGCTGACACTGACAGCGGTGGACTC

CGAGGGTAATCCGGTGACGGGAGAAGCCAGCCGCCTGCGACTTGTTCCGC

AAGACACTAATGGTGTAACCGTTGGTGCCATTTCGGAAATAAAACCAGGG

GTTTACAGCGCCACGGTTTCTTCGACCCGTGCCGGAAACGTTGTTGTGCG

TGCCTTCAGCGAGCAGTATCAGCTGGGCACATTACAACAAACGCTGAAGT

TTGTTGCCGGGCCGCTTGATGCAGCACATTCGTCCATCACACTGAATCCT

GATAAACCGGTGGTTGGCGGTACAGTTACGGCAATCTGGACGGCAAAAGA

TGCTAATGACAACCCTGTAACTGGCCTCAATCCGGATGCACCGTCATTAT

CGGGCGCAGCTGCTGCTGGTTCTACGGCATCAGGCTGGACGGATAATGGC

GACGGGACCTGGACTGCGCAGATTTCTCTCGGCACTACGGCGGGTGAATT

AGACGTTATGCCGAAGCTCAATGGGCAGGACGCGGCAGCAAATGCGGCAA

AAGTAACCGTGGTGGCTGATGCATTATCTTCAAACCAGTCGAAAGTCTCT

GTCGCAGAAGATCACGTAAAAGCCGGTGAAAGCACAACCGTAACGCTGGT

GGCGAAAGATGCGCATGGCAACGCTATCAGTGGTCTTTCGTTGTCGGCAA

GTTTGACGGGGACCGCCTCTGAAGGGGCGACCGTTTCCAGTTGGACCGAA

AAAGGTGACGGTTCCTATGTTGCTACGTTAACTACAGGCGGAAAGACGGG

CGAGCTTCGTGTCATGCCGCTCTTCAACGGCCAGCCTGCAGCCACCGAAG

CCGCGCAGCTGACTGTTATTGCCGGAGAGATGTCATCAGCGAACTCTACG

CTTGTTGCGGACAATAAAACTCCAACGGTTAAAACGACGACGGAACTCAC

CTTCACCATGAAGGATGCGTACGGGAATCCGGTCACCGGGCTGAAGCCAG

ATGCACCAGTGTTTAGTGGTGCCGCCAGCACGGGGAGTGAGCGTCCTTCA

GCAGGAAACTGGACAGAGAAAGGTAATGGGGTCTACGTGTCGACCTTAAC

GCTGGGATCTGCCGCGGGTCAGTTGTCTGTGATGCCGCGAGTGAACGGCC

AAAATGCCGTTGCTCAGCCACTGGTGCTGAATGTTGCAGGTGACGCATCT

AAGGCTGAGATTCGTGATATGACAGTGAAGGTTAATAACCAA

>orf405B (SEQ ID 2)
VADGQQAYTLTLTAVDSEGNPVTGEASRLRLVPQDTNGVTVGAISEIKPG

VYSATVSSTRAGNVVVRAFSEQYQLGTLQQTLKFVAGPLDAAHSSITLNP

DKPVVGGTVTAIWTAKDANDNPVTGLNPDAPSLSGAAAAGSTASGWTDNG

DGTWTAQISLGTTAGELDVMPKLNGQDAAANAAKVTVVADALSSNQSKVS

VAEDHVKAGESTTVTLVAKDAHGNAISGLSLSASLTGTASEGATVSSWTE

KGDGSYVATLTTGGKTGELRVMPLFNGQPAATEAAQLTVIAGEMSSANST

LVADNKTPTVKTTTELTFTMKDAYGNPVTGLKPDAPVFSGAASTGSERPS

AGNWTEKGNGVYVSTLTLGSAAGQLSVMPRVNGQNAVAQPLVLNVAGDAS

KAEIRDMTVKVNNQ

When used according to the present invention, orf405B protein may take various forms. Particular orf405B sequences have 80% or more identity (e.g. 80%, 85%, 90%, 95%, 96%, 97%, 98%, 99% or more) to SEQ ID NOs 1 and/or 2. This includes variants (e.g. allelic variants, homologs, orthologs, paralogs, mutants etc).

Upec1232 Protein

'Upec1232' protein from *E. coli* UPEC is disclosed in WO2006/091517 (SEQ ID 138) and is also known as: 'c1275' from CFT073. When used according to the present invention, upec1232 protein may take various forms. Preferred upec1232 sequences have 80% or more identity (e.g. 80%, 85%, 90%, 95%, 96%, 97%, 98%, 99% or more) to SEQ ID NOs 3, 4, 5 or 6. This includes variants (e.g. allelic variants, homologs, orthologs, paralogs, mutants etc).

>upec-1232

(SEQ ID 3)
ATGATTCACCTGTTCAAAACCTGCATGATTACCGCCTTCATTCTGGGGTT

AACGTGGTCTGCCCCACTCCGGGCACAGGATCAACGTTACATCAGTATAC

GCAATACAGATACGATATGGCTCCCGGGAAATATTTGTGCTTACCAGTTC

CGGCTGGATAATGGCGGAAACGATGAAGGATTTGGCCCCCTCACCATCAC

TCTGCAACTCAAAGACAAATATGGTCAGACGCTGGTGACCAGAAAAATGG

AAACGGAAGCCTTTGGTGACAGTAATGCCACGCGAACCACAGACGCATTT

CTGGAAACGGAGTGCGTGGAAAATGTCGCCACAACCGAAATCATTAAAGC

AACTGAAGAAAGTAACGGCCATCGTGTCAGTCTGCCGTTATCGGTTTTCG

ATCCCCAGGACTACCATCCACTGCTGATTACCGTTTCCGGAAAAAACGTT

AAC

>upec-1232

(SEQ ID 4)
MIHLFKTCMITAFILGLTWSAPLRAQDQRYISIRNTDTIWLPGNICAYQF

RLDNGGNDEGFGPLTITLQLKDKYGQTLVTRKMETEAFGDSNATRTTDAF

LETECVENVATTEIIKATEESNGHRVSLPLSVFDPQDYHPLLITVSGKNV

N

>pCFT-1232

(SEQ ID 5)
CAGGATCAACGTTACATCAGTATACGCAATACAGATACGATATGGCTCCC

GGGAAATATTTGTGCTTACCAGTTCCGGCTGGATAATGGCGGAAACGATG

AAGGATTTGGCCCCCTCACCATCACTCTGCAACTCAAAGACAAATATGGT

CAGACGCTGGTGACCAGAAAAATGGAAACGGAAGCCTTTGGTGACAGTAA

TGCCACGCGAACCACAGACGCATTTCTGGAAACGGAGTGCGTGGAAAATG

TCGCCACAACCGAAATCATTAAAGCAACTGAAGAAAGTAACGGCCATCGT

GTCAGTCTGCCGTTATCGGTTTTCGATCCCCAGGACTACCATCCACTGCT

GATTACCGTTTCCGGAAAAAACGTTAAC

>pCFT-1232

(SEQ ID 6)
QDQRYISIRNTDTIWLPGNICAYQFRLDNGGNDEGFGPLTITLQLKDKYG

QTLVTRKMETEAFGDSNATRTTDAFLETECVENVATTEIIKATEESNGHR

VSLPLSVFDPQDYHPLLITVSGKNVN

Putative Lipoprotein Orf3526

Accessory colonization factor D (AcfD) precursor, also known as 'ECOK1_3385', also known as 'putative lipoprotein orf3526', also referred to as 'orf3526' protein from *E. coli* NMEC strain IHE3034 is disclosed in WO2006/089264. When used according to the present invention, orf3526 protein may take various forms. Preferred orf3526 sequences have 80% or more identity (e.g. 80%, 85%, 90%, 95%, 96%, 97%, 98%, 99% or more) to SEQ ID NOs 7-28. This includes variants (e.g. allelic variants, homologs, orthologs, paralogs, mutants etc).

>orf03526

(SEQ ID 7)
ATGAATAAGAAATTTAAATATAAGAAATCGCTTTTAGCGGCTATTTTAAGCGCAACCCTG

TTAGCCGGTTGTGATGGTGGTGGTTCAGGATCGTCCTCCGATACGCCGTCTGTAGATTCT

GGATCAGGGACTTTGCCGGAAGTGAAACCCGATCCAACACCAACCCCGGAGCCGACACCT

GAGCCGACGCCGGACCCAGAACCTACGCCGGATCCAACACCTGATCCTGAGCCGACACCA

GAACCGGAGCCAGAACCTGTTCCTACGAAAACGGGTTATCTGACCCTGGGCGGAAGCCAG

CGGGTAACTGGTGCTACCTGTAATGGTGAATCCAGCGATGGCTTTACCTTTACGCCAGGC

AATACCGTGAGTTGTGTGGTGGGCAGTACGACCATTGCAACATTCAACACCCAGTCAGAA

GCTGCGCGTAGCCTGCGTGCGGTTGACAAAGTGTCGTTTAGCCTGGAGGACGCGCAGGAG

CTGGCGAATTCTGAAAATAAGAAAACCAACGCCATCTCTCTGGTGACGTCCAGCGACAGT

TGCCCCGCAGATGCAGAACAGCTTTGTCTTACTTTCTCGTCAGTGGTTGATCGCGCGCGA

TTTGAAAAACTGTATAAGCAAATTGATCTGGCAACAGACAATTTCAGCAAGCTGGTCAAT

GAAGAGGTGGAAAACAATGCTGCGACTGATAAAGCGCCGTCCACCCATACCTCAACGGTA

GTGCCAGTCACGACAGAGGGAACAAAACCGGATCTGAACGCGTCCTTCGTGTCGGCTAAC

GCGGAACAGTTTTATCAGTATCAACCCACTGAAATCATTCTTTCCGAAGGCCAACTGGTG

-continued

```
GATAGCCTGGGGAACGGTGTTGCTGGCGTTGACTACTACACCAATTCAGGCCGTGGCGTA

ACTGACGAAAACGGTAAATTTTCCTTTAGCTGGGGCGAAACCATCTCCTTTGGTATCGAT

ACCTTTGAACTGGGCTCAGTACGTGGCAATAAGTCGACCATTGCGCTGACTGAATTGGGT

GATGAAGTTCGCGGGGCAAATATCGATCAGCTCATTCATCGTTATTCGACGACTGGTCAA

AATAATACTCGTGTTGTTCCGGACGATGTACGCAAGGTCTTTGCCGAATATCCCAACGTG

ATCAACGAGATAATCAATCTTTCGTTATCCAACGGTGCGACGCTGGATGAAGGCGATCAA

AACGTTGTGCTGCCTAACGAATTTATCGAGCAGTTTAAGACGGGTCAGGCCAAAGAGATC

GATACCGCGATTTGTGCGAAAACCGACGGTTGTAACGAGGCTCGCTGGTTCTCGCTGACA

ACGCGCAATGTTAATGACGGCCAGATTCAGGGCGTTATTAACAAGCTGTGGGCGTGGAT

ACGAACTATCAGTCTGTCAGCAAGTTCCACGTCTTCCATGACTCTACCAACTTCTATGGC

AGCACCGGTAACGCGCGCGGTCAGGCGGTGGTAAATATCTCCAACTCGGCATTCCCGATT

CTGATGGCGCGTAATGATAAAAACTACTGGCTGGCGTTTGGCGAAAAACGCGCCTGGGAT

AAAAATGAGCTGGCGTACATTACGGAAGCGCCTTCCATTGTGCAGCCAGAGAACGTTACG

CGCGATACTGCGACTTTCAACCTGCCGTTTATTTCGCTGGGGCAAGTCGGTGAAGGCAAA

CTGATGGTTATCGGTAACCCGCACTACAACAGCATCCTGCGTTGCCCGAACGGTTACAGT

TGGGGCGGTGGTGTTAATAGTAAAGGTGAGTGTACGCTCAGCGGTGATTCTGATGACATG

AAGCACTTTATGCAGAACGTACTGCGCTACTTGTCAAATGACATCTGGCAGCCAAATACC

AAGAGCATCATGACTGTCGGCACCAACCTGGAGAACGTTTATTTCAAAAAAGCGGGCCAG

GTATTGGGAAATAGTGCACCATTTGCTTTCCATGAGGATTTCACTGGTATCACGGTTAAA

CAGTTGACCAGCTATGGCGATCTGAATCCGGAAGAGATTCCGTTGCTGATCCTCAACGGC

TTTGAATATGTGACTCAGTGGTCTGGCGATCCCTATGCTGTGCCTCTGCGTGCAGATACC

AGCAAACCGAAGCTGACTCAGCAGGATGTGACCGATCTGATCGCTTATCTGAACAAAGGT

GGCTCGGTGCTGATCATGGAAAACGTGATGAGCAATCTTAAGGAAGAGAGCGCGTCCAGT

TTTGTGCGTCTGCTGGATGCCGCGGGTCTGTCAATGGCTCTGAACAAATCGGTGGTGAAC

AACGATCCGCAAGGGTATCCGGATCGCGTTCGTCAGCGTCGCGCGACTGGCATTTGGGTT

TATGAACGTTATCCTGCTGCAGACGGCGCGCAACCGCCGTACACCATCGACCCAAATACA

GGGGAAGTGACCTGGAAATACCAGCAAGACAACAAGCCTGATGACAAGCCGAAACTGGAA

GTTGCGAGCTGGCAGGAGGAAGTTGAGGGCAAACAGGTAACGCGTTATGCCTTTATTGAT

GAAGCGGAATACACAACAGAAGAATCTCTGGAAGCGGCAAAGGCAAAATCTTTGAGAAG

TTTCCTGGGTTACAGGAGTGTAAGGACTCGACTTACCATTACGAGATTAACTGTTTGGAG

CGCCGCCCAGGCACGGATGTTCCGGTAACAGGTGGCATGTATGTTCCGCGCTATACGCAA

CTGAATCTTGACGCCGACACCGCGAAAGCGATGGTGCAGGCGGCGGATTTAGGCACCAAC

ATTCAGCGCCTGTATCAGCATGAGCTTTATTTCCGTACCAAAGGCAGTAAAGGTGAGCGT

CTGAACAGTGTTGATCTGGAACGTCTGTACCAGAACATGTCGGTCTGGCTGTGGAACGAT

ACGAAATATCGTTACGAAGAGGGCAAGGAAGATGAGCTGGGCTTTAAAACGTTCACCGAG

TTCCTGAACTGCTACGCCAATGATGCCTATGCAGGCGGCACCAAGTGCTCCGCAGATCTG

AAAAAATCGCTGGTCGATAACAACATGATCTACGGTGACGGTAGCAGCAAAGCGGGCATG

ATGAACCCAAGCTATCCGCTCAACTATATGGAAAAACCGCTGACGCGTCTGATGCTGGGC

CGTTCCTGGTGGGATCTGAACATTAAGGTTGATGTGGAGAAGTACCCAGGATCCGTATCG

GCAAAGGGTGAGAGCGTTACGGAAAACATCAGCCTGTACTCGAATCCGACCAAATGGTTT
```

```
GCGGGTAACATGCAGTCAACCGGCCTGTGGGCACCGGCCCAGCAGGACGTCACCATTAAG

TCTTCGGCGTCAGTCCCAGTGACTGTTACCGTGGCGCTGGCTGACGACCTGACTGGACGT

GAGAAGCATGAAGTTGCGCTGAACCGTCCGCCAAGAGTGACTAAAACGTATACTCTGGAG

GCTAACGGTGAAGTGACCTTCAAGGTGCCTTATGGTGGTCTGATTTATATCAAGGGCGAC

AGTAAGGATGATGTTTCTGCTAACTTCACCTTTACCGGTGTAGTAAAAGCGCCGTTCTAT

AAAGACGGCGAATGGAAAAACGATCTGGACTCACCGGCGCCGCTGGGCGAGCTGGAGTCT

GCGTCGTTCGTCTATACCACGCCGAAGAAGAACCTTGAGGCCAGCAATTTCACTGGTGGT

GTAGCAGAATTCGCTAAAGATCTGGATACCTTTGCCAGCTCGATGAATGACTTCTACGGT

CGTAATGATGAAGACGGTAAGCACCGGATGTTTACCTATAAAAACTTGACGGGGCACAAG

CATCGTTTCACCAACGATGTGCAGATCTCCATCGGTGATGCGCACTCGGGTTATCCGGTA

ATGAACAGCAGCTTCTCGACGAACAGCACCACGCTGCCGACGACGCCGCTGAACGACTGG

CTGATTTGGCACGAAGTCGGTCATAACGCTGCAGAAACACCGCTGAACGTACCGGGTGCA

ACTGAAGTGGCGAACAACGTGCTGGCGCTGTACATGCAGGATCGCTATCTCGGTAAGATG

AACCGTGTCGCTGACGACATTACCGTCGCGCCGGAATATCTGGACGAGAGCAACGGTCAG

GCCTGGGCGCGCGGCGGTGCGGGTGACCGTCTGCTGATGTACGCACAGTTGAAGGAGTGG

GCAGAGGAAAACTTTGATATCAAACAGTGGTATCCAGATGGTGAGCTGCCTAAGTTCTAC

AGCGATCGTAAAGGGATGAAGGGCTGGAACCTGTTCCAGTTGATGCACCGTAAAGCGCGC

GGCGATGATGTTGGTAACAGCACCTTTGGTGGCAAGAATTACTGTGCTGAATCCAATGGT

AACGCTGCCGACACGCTGATGCTGTGTGCATCCTGGGTCGCTCAGGCGGATCTTTCGGAA

TTCTTTAAGAAATGGAATCCGGGTGCAAGTGCTTACCAGTTGCCGGGAGCAACGGAGATG

AGTTTCCAGGGCGGTGTGAGCTCTTCGGCTTACAGCACGCTGGCGTCACTCAAGCTGCCG

AAACCGGAAAAAGGGCCGGAAACCATTAACAAGGTTACCGAGCATAAGATGTCTGCCGAG

>orf03526
                                                         (SEQ ID 8)
MNKKFKYKKSLLAAILSATLLAGCDGGGSGSSSDTPSVDSGSGTLPEVKPDPTPTPEPTP

EPTPDPEPTPDPTPDPEPTPEPEPEPVPTKTGYLTLGGSQRVTGATCNGESSDGFTFTPG

NTVSCVVGSTTIATFNTQSEAARSLRAVDKVSFSLEDAQELANSENKKTNAISLVTSSDS

CPADAEQLCLTFSSVVDRARFEKLYKQIDLATDNFSKLVNEEVENNAATDKAPSTHTSTV

VPVTTEGTKPDLNASFVSANAEQFYQYQPTEIILSEGQLVDSLGNGVAGVDYYTNSGRGV

TDENGKFSFSWGETISFGIDTFELGSVRGNKSTIALTELGDEVRGANIDQLIHRYSTTGQ

NNTRVVPDDVRKVFAEYPNVINEIINLSLSNGATLDEGDQNVVLPNEFIEQFKTGQAKEI

DTAICAKTDGCNEARWFSLTTRNVNDGQIQGVINKLWGVDTNYQSVSKFHVFHDSTNFYG

STGNARGQAVVNISNSAFPILMARNDKNYWLAFGEKRAWDKNELAYITEAPSIVQPENVT

RDTATFNLPFISLGQVGEGKLMVIGNPHYNSILRCPNGYSWGGGVNSKGECTLSGDSDDM

KHFMQNVLRYLSNDIWQPNTKSIMTVGTNLENVYFKKAGQVLGNSAPFAFHEDFTGITVK

QLTSYGDLNPEEIPLLILNGFEYVTQWSGDPYAVPLRADTSKPKLTQQDVTDLIAYLNKG

GSVLIMENVMSNLKEESASSFVRLLDAAGLSMALNKSVVNNDPQGYPDRVRQRRATGIWV

YERYPAADGAQPPYTIDPNTGEVTWKYQQDNKPDDKPKLEVASWQEEVEGKQVTRYAFID

EAEYTTEESLEAAKAKIFEKFPGLQECKDSTYHYEINCLERRPGTDVPVTGGMYVPRYTQ

LNLDADTAKAMVQAADLGTNIQRLYQHELYFRTKGSKGERLNSVDLERLYQNMSVWLWND

TKYRYEEGKEDELGFKTFTEFLNCYANDAYAGGTKCSADLKKSLVDNNMIYGDGSSKAGM

MNPSYPLNYMEKPLTRLMLGRSWWDLNIKVDVEKYPGSVSAKGESVTENISLYSNPTKWF
```

-continued

AGNMQSTGLWAPAQQDVTIKSSASVPVTVTVALADDLTGREKHEVALNRPPRVTKTYTLE

ANGEVTFKVPYGGLIYIKGDSKDDVSANFTFTGVVKAPFYKDGEWKNDLDSPAPLGELES

ASFVYTTPKKNLEASNFTGGVAEFAKDLDTFASSMNDFYGRNDEDGKHRMFTYKNLTGHK

HRFTNDVQISIGDAHSGYPVMNSSFSTNSTTLPTTPLNDWLIW<u>HEVGH</u>NAAETPLNVPGA

TEVANNVLALYMQDRYLGKMNRVADDITVAPEYLDESNGQAWARGGAGDRLLMYAQLKEW

AEENFDIKQWYPDGELPKFYSDRKGMKGWNLFQLMHRKARGDDVGNSTFGGKNYCAESNG

NAADTLMLCASWVAQADLSEFFKKWNPGASAYQLPGATEMSFQGGVSSSAYSTLASLKLP

KPEKGPETINKVTEHKMSAE

>pK1-3526A (SEQ ID 9)

TGTGATGGTGGTGGTTCAGGATCGTCCTCCGATACGCCGTCTGTAGATTCTGGATCAGGG

ACTTTGCCGGAAGTGAAACCCGATCCAACACCAACCCCGGAGCCGACACCTGAGCCGACG

CCGGACCCAGAACCTACGCCGGATCCAACACCTGATCCTGAGCCGACACCAGAACCGGAG

CCAGAACCTGTTCCTACGAAAACGGGTTATCTGACCCTGGGCGGAAGCCAGCGGGTAACT

GGTGCTACCTGTAATGGTGAATCCAGCGATGGCTTTACCTTTACGCCAGGCAATACCGTG

AGTTGTGTGGTGGGCAGTACGACCATTGCAACATTCAACACCCAGTCAGAAGCTGCGCGT

AGCCTGCGTGCGGTTGACAAAGTGTCGTTTAGCCTGGAGGACGCGCAGGAGCTGGCGAAT

TCTGAAAATAAGAAAACCAACGCCATCTCTCTGGTGACGTCCAGCGACAGTTGCCCCGCA

GATGCAGAACAGCTTTGTCTTACTTTCTCGTCAGTGGTTGATCGCGCGCGATTTGAAAAA

CTGTATAAGCAAATTGATCTGGCAACAGACAATTTCAGCAAGCTGGTCAATGAAGAGGTG

GAAAACAATGCTGCGACTGATAAAGCGCCGTCCACCCATACCTCAACGGTAGTGCCAGTC

ACGACAGAGGGAACAAAACCGGATCTGAACGCGTCCTTCGTGTCGGCTAACGCGGAACAG

TTTTATCAGTATCAACCCACTGAAATCATTCTTTCCGAAGGCCAACTGGTGGATAGCCTG

GGGAACGGTGTTGCTGGCGTTGACTACTACACCAATTCAGGCCGTGGCGTAACTGACGAA

AACGGTAAATTTTCCTTTAGCTGGGGCGAAACCATCTCCTTTGGTATCGATACCTTTGAA

CTGGGCTCAGTACGTGGCAATAAGTCGACCATTGCGCTGACTGAATTGGGTGATGAAGTT

CGCGGGGCAAATATCGATCAGCTCATTCATCGTTATTCGACGACTGGTCAAAATAATACT

CGTGTTGTTCCGGACGATGTACGCAAGGTCTTTGCCGAATATCCCAACGTGATCAACGAG

ATAATCAATCTTTCGTTATCCAACGGTGCGACGCTGGATGAAGGCGATCAAAACGTTGTG

CTGCCTAACGAATTTATCGAGCAGTTTAAGACGGGTCAGGCCAAAGAGATCGATACCGCG

ATTTGTGCGAAAACCGACGGTTGTAACGAGGCTCGCTGGTTCTCGCTGACAACGCGCAAT

GTTAATGACGGCCAGATTCAGGGCGTTATTAACAAGCTGTGGGGCGTGGATACGAACTAT

CAGTCTGTCAGCAAGTTCCACGTCTTCCATGACTCTACCAACTTCTATGGCAGCACCGGT

AACGCGCGCGGTCAGGCGGTGGTAAATATCTCCAACTCGGCATTCCCGATTCTGATGGCG

CGTAATGATAAAAACTACTGGCTGGCGTTTGGCGAAAAACGCGCCTGGGATAAAAATGAG

CTGGCGTACATTACGGAAGCGCCTTCCATTGTGCAGCCAGAGAACGTTACGCGCGATACT

GCGACTTTCAACCTGCCGTTTATTTCGCTGGGGCAAGTCGGTGAAGGCAAACTGATGGTT

ATCGGTAACCCGCACTACAACAGCATCCTGCGTTGCCCCGAACGGTTACAGTTGGGGCGGT

GGTGTTAATAGTAAAGGTGAGTGTACGCTCAGCGGTGATTCTGATGACATGAAGCACTTT

ATGCAGAACGTACTGCGCTACTTGTCAAATGACATCTGGCAGCCAAATACCAAGAGCATC

ATGACTGTCGGCACCAACCTGGAGAACGTTTATTTCAAAAAAGCGGGCCAGGTATTGGGA

-continued

```
AATAGTGCACCATTTGCTTTCCATGAGGATTTCACTGGTATCACGGTTAAACAGTTGACC

AGCTATGGCGATCTGAATCCGGAAGAGATTCCGTTGCTGATCCTCAACGGCTTTGAATAT

GTGACTCAGTGGICTGGCGATCCCTATGCTGTGCCTCTGCGTGCAGATACCAGCAAACCG

AAGCTGACTCAGCAGGATGTGACCGATCTGATCGCTTATCTGAACAAAGGTGGCTCGGTG

CTGATCATGGAAAACGTGATGAGCAATCTTAAGGAAGAGAGCGCGTCCAGTTTTGTGCGT

CTGCTGGATGCCGCGGGTCTGTCAATGGCTCTGAACAAATCGGTGGTGAACAAC
```

>pK1-3526A
(SEQ ID 10)
```
CDGGGSGSSSDTPSVDSGSGTLPEVKPDPTPTPEPTPEPTPDPEPTPDPTPDPEPTPEPE

PEPVPTKTGYLTLGGSQRVTGATCNGESSDGFTFTPGNTVSCVVGSTTIATFNTQSEAAR

SLRAVDKVSFSLEDAQELANSENKKTNAISLVTSSDSCPADAEQLCLTFSSVVDRARFEK

LYKQIDLATDNFSKLVNEEVENNAATDKAPSTHTSTVVPVTTEGTKPDLNASFVSANAEQ

FYQYQPTEIILSEGQLVDSLGNGVAGVDYYTNSGRGVTDENGKFSFSWGETISFGIDTFE

LGSVRGNKSTIALTELGDEVRGANIDQLIHRYSTTGQNNTRVVPDDVRKVFAEYPNVINE

IINLSLSNGATLDEGDQNVVLPNEFIEQFKTGQAKEIDTAICAKTDGCNEARWFSLTTRN

VNDGQIQGVINKLWGVDTNYQSVSKFHVFHDSTNFYGSTGNARGQAVVNISNSAFPILMA

RNDKNYWLAFGEKRAWDKNELAYITEAPSIVQPENVTRDTATFNLPFISLGQVGEGKLMV

IGNPHYNSILRCPNGYSWGGGVNSKGECTLSGDSDDMKHFMQNVLRYLSNDIWQPNTKSI

MTVGTNLENVYFKKAGQVLGNSAPFAFHEDFTGITVKQLTSYGDLNPEEIPLLILNGFEY

VTQWSGDPYAVPLRADTSKPKLTQQDVTDLIAYLNKGGSVLIMENVMSNLKEESASSFVR

LLDAAGLSMALNKSVVNN
```

>pK1-3526B
(SEQ ID 11)
```
GATCCGCAAGGGTATCCGGATCGCGTTCGTCAGCGTCGCGCGACTGGCATTTGGGTTTAT

GAACGTTATCCTGCTGCAGACGGCGCGCAACCGCCGTACACCATCGACCCAAATACAGGG

GAAGTGACCTGGAAATACCAGCAAGACAACAAGCCTGATGACAAGCCGAAACTGGAAGTT

GCGAGCTGGCAGGAGGAAGTTGAGGGCAAACAGGTAACGCGTTATGCCTTTATTGATGAA

GCGGAATACACAACAGAAGAATCTCTGGAAGCGGCAAAGGCAAAAATCTTTGAGAAGTTT

CCTGGGTTACAGGAGTGTAAGGACTCGACTTACCATTACGAGATTAACTGTTTGGAGCGC

CGCCCAGGCACGGATGTTCCGGTAACAGGTGGCATGTATGITCCGCGCTATACGCAACTG

AATCTTGACGCCGACACCGCGAAAGCGATGGTGCAGGCGGCGGATTTAGGCACCAACATT

CAGCGCCTGTATCAGCATGAGCTTTATTTCCGTACCAAAGGCAGTAAAGGTGAGCGTCTG

AACAGTGTTGATCTGGAACGTCTGTACCAGAACATGTCGGTCTGGCTGTGGAACGATACG

AAATATCGITACGAAGAGGGCAAGGAAGATGAGCTGGGCTTTAAAACGTTCACCGAGTTC

CTGAACTGCTACGCCAATGATGCCTATGCAGGCGGCACCAAGTGCTCCGCAGATCTGAAA

AAATCGCTGGTCGATAACAACATGATCTACGGTGACGGTAGCAGCAAAGCGGGCATGATG

AACCCAAGCTATCCGCTCAACTATATGGAAAAACCGCTGACGCGTCTGATGCTGGGCCGT

TCCTGGTGGGATCTGAACATTAAGGTTGATGTGGAGAAGTACCCAGGATCCGTATCGGCA

AAGGGTGAGAGCGTTACGGAAAACATCAGCCTGTACTCGAATCCGACCAAATGGTTTGCG

GGTAACATGCAGTCAACCGGCCTGTGGGCACCGGCCCAGCAGGACGTCACCATTAAGTCT

TCGGCGTCAGTCCCAGTGACTGTTACCGTGGCGCTGGCTGACGACCTGACTGGACGTGAG

AAGCATGAAGTTGCGCTGAACCGTCCGCCAAGAGTGACTAAAACGTATACTCTGGAGGCT

AACGGTGAAGTGACCTTCAAGGTGCCTTATGGTGGTCTGATTTATATCAAGGGCGACAGT
```

-continued

```
AAGGATGATGTTTCTGCTAACTTCACCTTTACCGGTGTAGTAAAAGCGCCGTTCTATAAA

GACGGCGAATGGAAAAACGATCTGGACTCACCGGCGCCGCTGGGCGAGCTGGAGTCTGCG

TCGTTCGTCTATACCACGCCGAAGAAGAACCTTGAGGCCAGCAATTTCACTGGTGGTGTA

GCAGAATTCGCTAAAGATCTGGATACCTTTGCCAGCTCGATGAATGACTTCTACGGTCGT

AATGATGAAGACGGTAAGCACCGGATGTTTACCTATAAAAACTTGACGGGGCACAAGCAT

CGTTTCACCAACGATGTGCAGATCTCCATCGGTGATGCGCACTCGGGTTATCCGGTAATG

AACAGCAGCTTCTCGACGAACAGCACCACGCTGCCGACGACGCCGCTGAACGACTGGCTG

ATTTGGCACGAAGTCGGTCATAACGCTGCAGAAACACCGCTGAACGTACCGGGTGCAACT

GAAGTGGCGAACAACGTGCTGGCGCTGTACATGCAGGATCGCTATCTCGGTAAGATGAAC

CGTGTCGCTGACGACATTACCGTCGCGCCGGAATATCTGGACGAGAGCAACGGTCAGGCC

TGGGCGCGCGGCGGTGCGGGTGACCGTCTGCTGATGTACGCACAGTTGAAGGAGTGGGCA

GAGGAAAACTTTGATATCAAACAGTGGTATCCAGATGGTGAGCTGCCTAAGTTCTACAGC

GATCGTAAAGGGATGAAGGGCTGGAACCTGTTCCAGTTGATGCACCGTAAAGCGCGCGGC

GATGATGTTGGTAACAGCACCTTTGGTGGCAAGAATTACTGTGCTGAATCCAATGGTAAC

GCTGCCGACACGCTGATGCTGTGTGCATCCTGGGTCGCTCAGGCGGATCTTTCGGAATTC

TTTAAGAAATGGAATCCGGGTGCAAGTGCTTACCAGTTGCCGGGAGCAACGGAGATGAGT

TTCCAGGGCGGTGTGAGCTCTTCGGCTTACAGCACGCTGGCGTCACTCAAGCTGCCGAAA

CCGGAAAAAGGGCCGGAAACCATTAACAAGGTTACCGAGCATAAGATGTCTGCCGAG

>pK1-3526B                                                 (SEQ ID 12)
DPQGYPDRVRQRRATGIWVYERYPAADGAQPPYTIDPNTGEVTWKYQQDNKPDDKPKLEV

ASWQEEVEGKQVTRYAFIDEAEYTTEESLEAAKAKIFEKFPGLQECKDSTYHYEINCLER

RPGTDVPVTGGMYVPRYTQLNLDADTAKAMVQAADLGTNIQRLYQHELYFRTKGSKGERL

NSVDLERLYQNMSVWLWNDTKYRYEEGKEDELGFKTFTEFLNCYANDAYAGGTKCSADLK

KSLVDNNMIYGDGSSKAGMMNPSYPLNYMEKPLTRLMLGRSWWDLNIKVDVEKYPGSVSA

KGESVTENISLYSNPTKWFAGNMQSTGLWAPAQQDVTIKSSASVPVTVTVALADDLTGRE

KHEVALNRPPRVTKTYTLEANGEVTFKVPYGGLIYIKGDSKDDVSANFTFTGVVKAPFYK

DGEWKNDLDSPAPLGELESASFVYTTPKKNLEASNFTGGVAEFAKDLDTFASSMNDFYGR

NDEDGKHRMFTYKNLTGHKHRFTNDVQISIGDAHSGYPVMNSSFSTNSTTLPTTPLNDWL

IWHEVGHNAAETPLNVPGATEVANNVLALYMQDRYLGKMNRVADDITVAPEYLDESNGQA

WARGGAGDRLLMYAQLKEWAEENFDIKQWYPDGELPKFYSDRKGMKGWNLFQLMHRKARG

DDVGNSTFGGKNYCAESNGNAADTLMLCASWVAQADLSEFFKKWNPGASAYQLPGATEMS

FQGGVSSSAYSTLASLKLPKPEKGPETINKVTEHKMSAE

>pK1-3526dG                                                (SEQ ID 13)
GATACGCCGTCTGTAGATTCTGGATCAGGGACTTTGCCGGAAGTGAAACCCGATCCAACA

CCAACCCCGGAGCCGACACCTGAGCCGACGCCGGACCCAGAACCTACGCCGGATCCAACA

CCTGATCCTGAGCCGACACCAGAACCGGAGCCAGAACCTGTTCCTACGAAAACGGGTTAT

CTGACCCTGGGCGGAAGCCAGCGGGTAACTGGTGCTACCTGTAATGGTGAATCCAGCGAT

GGCTTTACCTTTACGCCAGGCAATACCGTGAGTTGTGTGGTGGGCAGTACGACCATTGCA

ACATTCAACACCCAGTCAGAAGCTGCGCGTAGCCTGCGTGCGGTTGACAAAGTGTCGTTT

AGCCTGGAGGACGCGCAGGAGCTGGCGAATTCTGAAAATAAGAAAACCAACGCCATCTCT
```

-continued
```
CTGGTGACGTCCAGCGACAGTTGCCCCGCAGATGCAGAACAGCTTTGTCTTACTTTCTCG

TCAGTGGTTGATCGCGCGCGATTTGAAAAACTGTATAAGCAAATTGATCTGGCAACAGAC

AATTTCAGCAAGCTGGTCAATGAAGAGGTGGAAAACAATGCTGCGACTGATAAAGCGCCG

TCCACCCATACCTCAACGGTAGTGCCAGTCACGACAGAGGGAACAAAACCGGATCTGAAC

GCGTCCTTCGTGTCGGCTAACGCGGAACAGTTTTATCAGTATCAACCCACTGAAATCATT

CTTTCCGAAGGCCAACTGGTGGATAGCCTGGGGAACGGTGTTGCTGGCGTTGACTACTAC

ACCAATTCAGGCCGTGGCGTAACTGACGAAAACGGTAAATTTTCCTTTAGCTGGGGCGAA

ACCATCTCCTTTGGTATCGATACCTTTGAACTGGGCTCAGTACGTGGCAATAAGTCGACC

ATTGCGCTGACTGAATTGGGTGATGAAGTTCGCGGGGCAAATATCGATCAGCTCATTCAT

CGTTATTCGACGACTGGTCAAAATAATACTCGTGTTGTTCCGGACGATGTACGCAAGGTC

TTTGCCGAATATCCCAACGTGATCAACGAGATAATCAATCTTTCGTTATCCAACGGTGCG

ACGCTGGATGAAGGCGATCAAAACGTTGTGCTGCCTAACGAATTTATCGAGCAGTTTAAG

ACGGGTCAGGCCAAAGAGATCGATACCGCGATTTGTGCGAAAACCGACGGTTGTAACGAG

GCTCGCTGGTTCTCGCTGACAACGCGCAATGTTAATGACGGCCAGATTCAGGGCGTTATT

AACAAGCTGTGGGGCGTGGATACGAACTATCAGTCTGTCAGCAAGTTCCACGTCTTCCAT

GACTCTACCAACTTCTATGGCAGCACCGGTAACGCGCGCGGTCAGGCGGTGGTAAATATC

TCCAACTCGGCATTCCCGATTCTGATGGCGCGTAATGATAAAAACTACTGGCTGGCGTTT

GGCGAAAAACGCGCCTGGGATAAAAATGAGCTGGCGTACATTACGGAAGCGCCTTCCATT

GTGCAGCCAGAGAACGTTACGCGCGATACTGCGACTTTCAACCTGCCGTTTATTTCGCTG

GGGCAAGTCGGTGAAGGCAAACTGATGGTTATCGGTAACCCGCACTACAACAGCATCCTG

CGTTGCCCGAACGGTTACAGTTGGGGCGGTGGTGTTAATAGTAAAGGTGAGTGTACGCTC

AGCGGTGATTCTGATGACATGAAGCACTTTATGCAGAACGTACTGCGCTACTTGTCAAAT

GACATCTGGCAGCCAAATACCAAGAGCATCATGACTGTCGGCACCAACCTGGAGAACGTT

TATTTCAAAAAAGCGGGCCAGGTATTGGGAAATAGTGCACCATTTGCTTTCCATGAGGAT

TTCACTGGTATCACGGTTAAACAGTTGACCAGCTATGGCGATCTGAATCCGGAAGAGATT

CCGTTGCTGATCCTCAACGGCTTTGAATATGTGACTCAGTGGTCTGGCGATCCCTATGCT

GTGCCTCTGCGTGCAGATACCAGCAAACCGAAGCTGACTCAGCAGGATGTGACCGATCTG

ATCGCTTATCTGAACAAAGGTGGCTCGGTGCTGATCATGGAAAACGTGATGAGCAATCTT

AAGGAAGAGAGCGCGTCCAGTTTTGTGCGTCTGCTGGATGCCGCGGGTCTGTCAATGGCT

CTGAACAAATCGGTGGTGAACAACGATCCGCAAGGGTATCCGGATCGCGTTCGTCAGCGT

CGCGCGACTGGCATTTGGGTTTATGAACGTTATCCTGCTGCAGACGGCGCGCAACCGCCG

TACACCATCGACCCAAATACAGGGGAAGTGACCTGGAAATACCAGCAAGACAACAAGCCT

GATGACAAGCCGAAACTGGAAGTTGCGAGCTGGCAGGAGGAAGTTGAGGGCAAACAGGTA

ACGCGTTATGCCTTTATTGATGAAGCGGAATACACAACAGAAGAATCTCTGGAAGCGGCA

AAGGCAAAAATCTTTGAGAAGTTTCCTGGGTTACAGGAGTGTAAGGACTCGACTTACCAT

TACGAGATTAACTGTTTGGAGCGCCGCCCAGGCACGGATGTTCCGGTAACAGGTGGCATG

TATGTTCCGCGCTATACGCAACTGAATCTTGACGCCGACACCGCGAAAGCGATGGTGCAG

GCGGCGGATTTAGGCACCAACATTCAGCGCCTGTATCAGCATGAGCTTTATTTCCGTACC

AAAGGCAGTAAAGGTGAGCGTCTGAACAGTGTTGATCTGGAACGTCTGTACCAGAACATG

TCGGTCTGGCTGTGGAACGATACGAAATATCGTTACGAAGAGGGCAAGGAAGATGAGCTG

GGCTTTAAAACGTTCACCGAGTTCCTGAACTGCTACGCCAATGATGCCTATGCAGGCGGC
```

-continued

```
ACCAAGTGCTCCGCAGATCTGAAAAAATCGCTGGTCGATAACAACATGATCTACGGTGAC
GGTAGCAGCAAAGCGGGCATGATGAACCCAAGCTATCCGCTCAACTATATGGAAAAACCG
CTGACGCGTCTGATGCTGGGCCGTTCCTGGTGGGATCTGAACATTAAGGTTGATGTGGAG
AAGTACCCAGGATCCGTATCGGCAAAGGGTGAGAGCGTTACGGAAAACATCAGCCTGTAC
TCGAATCCGACCAAATGGTTTGCGGGTAACATGCAGTCAACCGGCCTGTGGGCACCGGCC
CAGCAGGACGTCACCATTAAGTCTTCGGCGTCAGTCCCAGTGACTGTTACCGTGGCGCTG
GCTGACGACCTGACTGGACGTGAGAAGCATGAAGTTGCGCTGAACCGTCCGCCAAGAGTG
ACTAAAACGTATACTCTGGAGGCTAACGGTGAAGTGACCTTCAAGGTGCCTTATGGTGGT
CTGATTTATATCAAGGGCGACAGTAAGGATGATGTTTCTGCTAACTTCACCTTTACCGGT
GTAGTAAAAGCGCCGTTCTATAAAGACGGCGAATGGAAAAACGATCTGGACTCACCGGCG
CCGCTGGGCGAGCTGGAGTCTGCGTCGTTCGTCTATACCACGCCGAAGAAGAACCTTGAG
GCCAGCAATTTCACTGGTGGTGTAGCAGAATTCGCTAAAGATCTGGATACCTTTGCCAGC
TCGATGAATGACTTCTACGGTCGTAATGATGAAGACGGTAAGCACCGGATGTTTACCTAT
AAAAACTTGACGGGGCACAAGCATCGTTTCACCAACGATGTGCAGATCTCCATCGGTGAT
GCGCACTCGGGTTATCCGGTAATGAACAGCAGCTTCTCGACGAACAGCACCACGCTGCCG
ACGACGCCGCTGAACGACTGGCTGATTTGGCACGAAGTCGGTCATAACGCTGCAGAAACA
CCGCTGAACGTACCGGGTGCAACTGAAGTGGCGAACAACGTGCTGGCGCTGTACATGCAG
GATCGCTATCTCGGTAAGATGAACCGTGTCGCTGACGACATTACCGTCGCGCCGGAATAT
CTGGACGAGAGCAACGGTCAGGCCTGGGCGCGCGGCGGTGCGGGTGACCGTCTGCTGATG
TACGCACAGTTGAAGGAGTGGGCAGAGGAAAACTTTGATATCAAACAGTGGTATCCAGAT
GGTGAGCTGCCTAAGTTCTACAGCGATCGTAAAGGGATGAAGGGCTGGAACCTGTTCCAG
TTGATGCACCGTAAAGCGCGCGGCGATGATGTTGGTAACAGCACCTTTGGTGGCAAGAAT
TACTGTGCTGAATCCAATGGTAACGCTGCCGACACGCTGATGCTGTGTGCATCCTGGGTC
GCTCAGGCGGATCTTTCGGAATTCTTTAAGAAATGGAATCCGGGTGCAAGTGCTTACCAG
TTGCCGGGAGCAACGGAGATGAGTTTCCAGGGCGGTGTGAGCTCTTCGGCTTACAGCACG
CTGGCGTCACTCAAGCTGCCGAAACCGGAAAAAGGGCCGGAAACCATTAACAAGGTTACC
GAGCATAAGATGTCTGCCGAG
```

>pK1-3526dG                                                    (SEQ ID 14)

DTPSVDSGSGTLPEVKPDPTPTPEPTPEPTPDPEPTPDPTPDPEPTPEPEPEPVPTKTGY
LTLGGSQRVTGATCNGESSDGFTFTPGNTVSCVVGSTTIATENTQSEAARSLRAVDKVSF
SLEDAQELANSENKKTNAISLVTSSDSCPADAEQLCLTESSVVDRARFEKLYKQIDLATD
NFSKLVNEEVENNAATDKAPSTHTSTVVPVTTEGTKPDLNASEVSANAEQFYQYQPTE11
LSEGQLVDSLGNGVAGVDYYTNSGRGVTDENGKESFSWGETISFGIDTFELGSVRGNKST
IALTELGDEVRGANIDQLIHRYSTTGQNNTRVVPDDVRKVFAEYPNVINEIINLSLSNGA
TLDEGDQNVVLPNEFIEQFKTGQAKEIDTAICAKTDGCNEARWFSLTTRNVNDGQIQGVI
NKLWGVDTNYQSVSKFHVEHDSTNFYGSTGNARGQAVVNISNSAFPILMARNDKNYWLAF
GEKRAWDKNELAYITEAPSIVQPENVTRDTATENLPFISLGQVGEGKLMVIGNPHYNSIL
RCPNGYSWGGGVNSKGECTLSGDSDDMKHFMQNVLRYLSNDIWQPNTKSIMTVGTNLENV
YEKKAGQVLGNSAPFAFHEDFTGITVKQLTSYGDLNPEEIPLLILNGFEYVTQWSGDPYA
VPLRADTSKPKLTQQDVTDLIAYLNKGGSVLIMENVMSNLKEESASSFVRLLDAAGLSMA

LNKSVVNNDPQGYPDRVRQRRATGIWVYERYPAADGAQPPYTIDPNTGEVTWKYQQDNKP
DDKPKLEVASWQEEVEGKQVTRYAFIDEAEYTTEESLEAAKAKIFEKFPGLQECKDSTYH
YEINCLERRPGTDVPVTGGMYVPRYTQLNLDADTAKAMVQAADLGTNIQRLYQHELYERT
KGSKGERLNSVDLERLYQNMSVWLWNDTKYRYEEGKEDELGEKTFTEFLNCYANDAYAGG
TKCSADLKKSLVDNNMIYGDGSSKAGMMNPSYPLNYMEKPLTRLMLGRSWWDLNIKVDVE
KYPGSVSAKGESVTENISLYSNPTKWFAGNMQSTGLWAPAQQDVTIKSSASVPVTVTVAL
ADDLTGREKHEVALNRPPRVTKTYTLEANGEVTEKVPYGGLIYIKGDSKDDVSANFTFTG
VVKAPFYKDGEWKNDLDSPAPLGELESASFVYTTPKKNLEASNFTGGVAEFAKDLDTFAS
SMNDFYGRNDEDGKHRMFTYKNLTGHKHRFTNDVQISIGDAHSGYPVMNSSFSTNSTTLP
TTPLNDWLIWHEVGHNAAETPLNVPGATEVANNVLALYMQDRYLGKMNRVADDITVAPEY
LDESNGQAWARGGAGDRLLMYAQLKEWAEENFDIKQWYPDGELPKEYSDRKGMKGWNLFQ
LMHRKARGDDVGNSTEGGKNYCAESNGNAADTLMLCASWVAQADLSEFFKKWNPGASAYQ
LPGATEMSFQGGVSSSAYSTLASLKLPKPEKGPETINKVTEHKMSAE

>pK1-3526dP
(SEQ ID 15)
AAAACGGGTTATCTGACCCTGGGCGGAAGCCAGCGGGTAACTGGTGCTACCTGTAATGGT
GAATCCAGCGATGGCTTTACCTTTACGCCAGGCAATACCGTGAGTTGTGTGGTGGGCAGT
ACGACCATTGCAACATTCAACACCCAGTCAGAAGCTGCGCGTAGCCTGCGTGCGGTTGAC
AAAGTGTCGTTTAGCCTGGAGGACGCGCAGGAGCTGGCGAATTCTGAAAATAAGAAAACC
AACGCCATCTCTCTGGTGACGTCCAGCGACAGTTGCCCCGCAGATGCAGAACAGCTTTGT
CTTACTTTCTCGTCAGTGGTTGATCGCGCGCGATTTGAAAAACTGTATAAGCAAATTGAT
CTGGCAACAGACAATTTCAGCAAGCTGGTCAATGAAGAGGTGGAAAACAATGCTGCGACT
GATAAAGCGCCGTCCACCCATACCTCAACGGTAGTGCCAGTCACGACAGAGGGAACAAAA
CCGGATCTGAACGCGTCCTTCGTGTCGGCTAACGCGGAACAGTTTTATCAGTATCAACCC
ACTGAAATCATTCTTTCCGAAGGCCAACTGGTGGATAGCCTGGGGAACGGTGTTGCTGGC
GTTGACTACTACACCAATTCAGGCCGTGGCGTAACTGACGAAAACGGTAAATTTTCCTTT
AGCTGGGGCGAAACCATCTCCTTTGGTATCGATACCTTTGAACTGGGCTCAGTACGTGGC
AATAAGTCGACCATTGCGCTGACTGAATTGGGTGATGAAGTTCGCGGGGCAAATATCGAT
CAGCTCATTCATCGTTATTCGACGACTGGTCAAAATAATACTCGTGTTGTTCCGGACGAT
GTACGCAAGGTCTTTGCCGAATATCCCAACGTGATCAACGAGATAATCAATCTTTCGTTA
TCCAACGGTGCGACGCTGGATGAAGGCGATCAAAACGTTGTGCTGCCTAACGAATTTATC
GAGCAGTTTAAGACGGGTCAGGCCAAAGAGATCGATACCGCGATTTGTGCGAAAACCGAC
GGTTGTAACGAGGCTCGCTGGTTCTCGCTGACAACGCGCAATGTTAATGACGGCCAGATT
CAGGGCGTTATTAACAAGCTGTGGGGCGTGGATACGAACTATCAGTCTGTCAGCAAGTTC
CACGTCTTCCATGACTCTACCAACTTCTATGGCAGCACCGGTAACGCGCGCGGTCAGGCG
GTGGTAAATATCTCCAACTCGGCATTCCCGATTCTGATGGCGCGTAATGATAAAAACTAC
TGGCTGGCGTTTGGCGAAAAACGCGCCTGGGATAAAAATGAGCTGGCGTACATTACGGAA
GCGCCTTCCATTGTGCAGCCAGAGAACGTTACGCGCGATACTGCGACTTTCAACCTGCCG
TTTATTTCGCTGGGGCAAGTCGGTGAAGGCAAACTGATGGTTATCGGTAACCCGCACTAC
AACAGCATCCTGCGTTGCCCGAACGGTTACAGTTGGGGCGGTGGTGTTAATAGTAAAGGT
GAGTGTACGCTCAGCGGTGATTCTGATGACATGAAGCACTTTATGCAGAACGTACTGCGC
TACTTGTCAAATGACATCTGGCAGCCAAATACCAAGAGCATCATGACTGTCGGCACCAAC

-continued

```
CTGGAGAACGTTTATTTCAAAAAAGCGGGCCAGGTATTGGGAAATAGTGCACCATTTGCT

TTCCATGAGGATTTCACTGGTATCACGGTTAAACAGTTGACCAGCTATGGCGATCTGAAT

CCGGAAGAGATTCCGTTGCTGATCCTCAACGGCTTTGAATATGTGACTCAGTGGTCTGGC

GATCCCTATGCTGTGCCTCTGCGTGCAGATACCAGCAAACCGAAGCTGACTCAGCAGGAT

GTGACCGATCTGATCGCTTATCTGAACAAAGGTGGCTCGGTGCTGATCATGGAAAACGTG

ATGAGCAATCTTAAGGAAGAGAGCGCGTCCAGTTTTGTGCGTCTGCTGGATGCCGCGGGT

CTGTCAATGGCTCTGAACAAATCGGTGGTGAACAACGATCCGCAAGGGTATCCGGATCGC

GTTCGTCAGCGTCGCGCGACTGGCATTTGGGTTTATGAACGTTATCCTGCTGCAGACGGC

GCGCAACCGCCGTACACCATCGACCCAAATACAGGGGAAGTGACCTGGAAATACCAGCAA

GACAACAAGCCTGATGACAAGCCGAAACTGGAAGTTGCGAGCTGGCAGGAGGAAGTTGAG

GGCAAACAGGTAACGCGTTATGCCTTTATTGATGAAGCGGAATACACAACAGAAGAATCT

CTGGAAGCGGCAAAGGCAAAAATCTTTGAGAAGTTTCCTGGGTTACAGGAGTGTAAGGAC

TCGACTTACCATTACGAGATTAACTGTTTGGAGCGCCGCCCAGGCACGGATGTTCCGGTA

ACAGGTGGCATGTATGTTCCGCGCTATACGCAACTGAATCTTGACGCCGACACCGCGAAA

GCGATGGTGCAGGCGGCGGATTTAGGCACCAACATTCAGCGCCTGTATCAGCATGAGCTT

TATTTCCGTACCAAAGGCAGTAAAGGTGAGCGTCTGAACAGTGTTGATCTGGAACGTCTG

TACCAGAACATGTCGGTCTGGCTGTGGAACGATACGAAATATCGTTACGAAGAGGGCAAG

GAAGATGAGCTGGGCTTTAAAACGTTCACCGAGTTCCTGAACTGCTACGCCAATGATGCC

TATGCAGGCGGCACCAAGTGCTCCGCAGATCTGAAAAAATCGCTGGTCGATAACAACATG

ATCTACGGTGACGGTAGCAGCAAAGCGGGCATGATGAACCCAAGCTATCCGCTCAACTAT

ATGGAAAAACCGCTGACGCGTCTGATGCTGGGCCGTTCCTGGTGGGATCTGAACATTAAG

GTTGATGTGGAGAAGTACCCAGGATCCGTATCGGCAAAGGGTGAGAGCGTTACGGAAAAC

ATCAGCCTGTACTCGAATCCGACCAAATGGTTTGCGGGTAACATGCAGTCAACCGGCCTG

TGGGCACCGGCCCAGCAGGACGTCACCATTAAGTCTTCGGCGTCAGTCCCAGTGACTGTT

ACCGTGGCGCTGGCTGACGACCTGACTGGACGTGAGAAGCATGAAGTTGCGCTGAACCGT

CCGCCAAGAGTGACTAAAACGTATACTCTGGAGGCTAACGGTGAAGTGACCTTCAAGGTG

CCTTATGGTGGTCTGATTTATATCAAGGGCGACAGTAAGGATGATGTTTCTGCTAACTTC

ACCTTTACCGGTGTAGTAAAAGCGCCGTTCTATAAAGACGGCGAATGGAAAAACGATCTG

GACTCACCGGCGCCGCTGGGCGAGCTGGAGTCTGCGTCGTTCGTCTATACCACGCCGAAG

AAGAACCTTGAGGCCAGCAATTTCACTGGTGGTGTAGCAGAATTCGCTAAAGATCTGGAT

ACCTTTGCCAGCTCGATGAATGACTTCTACGGTCGTAATGATGAAGACGGTAAGCACCGG

ATGTTTACCTATAAAAACTTGACGGGGCACAAGCATCGTTTCACCAACGATGTGCAGATC

TCCATCGGTGATGCGCACTCGGGTTATCCGGTAATGAACAGCAGCTTCTCGACGAACAGC

ACCACGCTGCCGACGACGCCGCTGAACGACTGGCTGATTTGGCACGAAGTCGGTCATAAC

GCTGCAGAAACACCGCTGAACGTACCGGGTGCAACTGAAGTGGCGAACAACGTGCTGGCG

CTGTACATGCAGGATCGCTATCTCGGTAAGATGAACCGTGTCGCTGACGACATTACCGTC

GCGCCGGAATATCTGGACGAGAGCAACGGTCAGGCCTGGGCGCGCGGCGGTGCGGGTGAC

CGTCTGCTGATGTACGCACAGTTGAAGGAGTGGGCAGAGGAAAACTTTGATATCAAACAG

TGGTATCCAGATGGTGAGCTGCCTAAGTTCTACAGCGATCGTAAAGGGATGAAGGGCTGG

AACCTGTTCCAGTTGATGCACCGTAAAGCGCGCGGCGATGATGTTGGTAACAGCACCTTT
```

-continued

```
GGTGGCAAGAATTACTGTGCTGAATCCAATGGTAACGCTGCCGACACGCTGATGCTGTGT

GCATCCTGGGTCGCTCAGGCGGATCTTTCGGAATTCTTTAAGAAATGGAATCCGGGTGCA

AGTGCTTACCAGTTGCCGGGAGCAACGGAGATGAGTTTCCAGGGCGGTGTGAGCTCTTCG

GCTTACAGCACGCTGGCGTCACTCAAGCTGCCGAAACCGGAAAAAGGGCCGGAAACCATT

AACAAGGTTACCGAGCATAAGATGTCTGCCGAG
```

>pK1-3526dP (SEQ ID 16)

```
KTGYLTLGGSQRVTGATCNGESSDGFTFTPGNTVSCVVGSTTIATENTQSEAARSLRAVD

KVSFSLEDAQELANSENKKTNAISLVTSSDSCPADAEQLCLTESSVVDRARFEKLYKQID

LATDNESKLVNEEVENNAATDKAPSTHTSTVVPVTTEGTKPDLNASFVSANAEQFYQYQP

TEIILSEGQLVDSLGNGVAGVDYYTNSGRGVTDENGKESFSWGETISEGIDTFELGSVRG

NKSTIALTELGDEVRGANIDQLIHRYSTTGQNNTRVVPDDVRKVFAEYPNVINEIINLSL

SNGATLDEGDQNVVLPNEFIEQFKTGQAKEIDTAICAKTDGCNEARWFSLTTRNVNDGQI

QGVINKLWGVDTNYQSVSKFHVEHDSTNEYGSTGNARGQAVVNISNSAFPILMARNDKNY

WLAFGEKRAWDKNELAYITEAPSIVQPENVTRDTATENLPFISLGQVGEGKLMVIGNPHY

NSILRCPNGYSWGGGVNSKGECTLSGDSDDMKHFMQNVLRYLSNDIWQPNTKSIMTVGTN

LENVYFKKAGQVLGNSAPFAFHEDFTGITVKQLTSYGDLNPEEIPLLILNGFEYVTQWSG

DPYAVPLRADTSKPKLTQQDVTDLIAYLNKGGSVLIMENVMSNLKEESASSEVRLLDAAG

LSMALNKSVVNNDPQGYPDRVRQRRATGIWVYERYPAADGAQPPYTIDPNTGEVTWKYQQ

DNKPDDKPKLEVASWQEEVEGKQVTRYAFIDEAEYTTEESLEAAKAKIFEKFPGLQECKD

STYHYEINCLERRPGTDVPVTGGMYVPRYTQLNLDADTAKAMVQAADLGTNIQRLYQHEL

YERTKGSKGERLNSVDLERLYQNMSVWLWNDTKYRYEEGKEDELGEKTFTEFLNCYANDA

YAGGTKCSADLKKSLVDNNMIYGDGSSKAGMMNPSYPLNYMEKPLTRLMLGRSWWDLNIK

VDVEKYPGSVSAKGESVTENISLYSNPTKWFAGNMQSTGLWAPAQQDVTIKSSASVPVTV

TVALADDLTGREKHEVALNRPPRVTKTYTLEANGEVTEKVPYGGLIYIKGDSKDDVSANF

TFTGVVKAPFYKDGEWKNDLDSPAPLGELESASFVYTTPKKNLEASNFTGGVAEFAKDLD

TFASSMNDFYGRNDEDGKHRMFTYKNLTGHKHRFTNDVQISIGDAHSGYPVMNSSFSTNS

TTLPTTPLNDWLIWHEVGHNAAETPLNVPGATEVANNVLALYMQDRYLGKMNRVADDITV

APEYLDESNGQAWARGGAGDRLLMYAQLKEWAEENFDIKQWYPDGELPKEYSDRKGMKGW

NLFQLMHRKARGDDVGNSTEGGKNYCAESNGNAADTLMLCASWVAQADLSEFFKKWNPGA

SAYQLPGATEMSFQGGVSSSAYSTLASLKLPKPEKGPETINKVTEHKMSAE
```

>pKI-3526 (SEQ ID 17)

```
TGTGATGGTGGTGGTTCAGGATCGTCCTCCGATACGCCGTCTGTAGATTCTGGATCAGGG

ACTTTGCCGGAAGTGAAACCCGATCCAACACCAACCCCGGAGCCGACACCTGAGCCGACG

CCGGACCCAGAACCTACGCCGGATCCAACACCTGATCCTGAGCCGACACCAGAACCGGAG

CCAGAACCTGTTCCTACGAAAACGGGTTATCTGACCCTGGGCGGAAGCCAGCGGGTAACT

GGTGCTACCTGTAATGGTGAATCCAGCGATGGCTTTACCTTTACGCCAGGCAATACCGTG

AGTTGTGTGGTGGGCAGTACGACCATTGCAACATTCAACACCCAGTCAGAAGCTGCGCGT

AGCCTGCGTGCGGTTGACAAAGTGTCGTTTAGCCTGGAGGACGCGCAGGAGCTGGCGAAT

TCTGAAAATAAGAAAACCAACGCCATCTCTCTGGTGACGTCCAGCGACAGTTGCCCCGCA

GATGCAGAACAGCTTTGTCTTACTTTCTCGTCAGTGGTTGATCGCGCGCGATTTGAAAAA

CTGTATAAGCAAATTGATCTGGCAACAGACAATTTCAGCAAGCTGGTCAATGAAGAGGTG
```

-continued

```
GAAAACAATGCTGCGACTGATAAAGCGCCGTCCACCCATACCTCAACGGTAGTGCCAGTC
ACGACAGAGGGAACAAAACCGGATCTGAACGCGTCCTTCGTGTCGGCTAACGCGGAACAG
TTTTATCAGTATCAACCCACTGAAATCATTCTTTCCGAAGGCCAACTGGTGGATAGCCTG
GGGAACGGTGTTGCTGGCGTTGACTACTACACCAATTCAGGCCGTGGCGTAACTGACGAA
AACGGTAAATTTTCCTTTAGCTGGGGCGAAACCATCTCCTTTGGTATCGATACCTTTGAA
CTGGGCTCAGTACGTGGCAATAAGTCGACCATTGCGCTGACTGAATTGGGTGATGAAGTT
CGCGGGGCAAATATCGATCAGCTCATTCATCGTTATTCGACGACTGGTCAAAATAATACT
CGTGTTGTTCCGGACGATGTACGCAAGGTCTTTGCCGAATATCCCAACGTGATCAACGAG
ATAATCAATCTTTCGTTATCCAACGGTGCGACGCTGGATGAAGGCGATCAAAACGTTGTG
CTGCCTAACGAATTTATCGAGCAGTTTAAGACGGGTCAGGCCAAAGAGATCGATACCGCG
ATTTGTGCGAAAACCGACGGTTGTAACGAGGCTCGCTGGTTCTCGCTGACAACGCGCAAT
GTTAATGACGGCCAGATTCAGGGCGTTATTAACAAGCTGTGGGCGTGGATACGAACTAT
CAGTCTGTCAGCAAGTTCCACGTCTTCCATGACTCTACCAACTTCTATGGCAGCACCGGT
AACGCGCGCGGTCAGGCGGTGGTAAATATCTCCAACTCGGCATTCCCGATTCTGATGGCG
CGTAATGATAAAAACTACTGGCTGGCGTTTGGCGAAAAACGCGCCTGGGATAAAAATGAG
CTGGCGTACATTACGGAAGCGCCTTCCATTGTGCAGCCAGAGAACGTTACGCGCGATACT
GCGACTTTCAACCTGCCGTTTATTTCGCTGGGGCAAGTCGGTGAAGGCAAACTGATGGTT
ATCGGTAACCCGCACTACAACAGCATCCTGCGTTGCCCGAACGGTTACAGTTGGGGCGGT
GGTGTTAATAGTAAAGGTGAGTGTACGCTCAGCGGTGATTCTGATGACATGAAGCACTTT
ATGCAGAACGTACTGCGCTACTTGTCAAATGACATCTGGCAGCCAAATACCAAGAGCATC
ATGACTGTCGGCACCAACCTGGAGAACGTTTATTTCAAAAAAGCGGGCCAGGTATTGGGA
AATAGTGCACCATTTGCTTTCCATGAGGATTTCACTGGTATCACGGTTAAACAGTTGACC
AGCTATGGCGATCTGAATCCGGAAGAGATTCCGTTGCTGATCCTCAACGGCTTTGAATAT
GTGACTCAGTGGTCTGGCGATCCCTATGCTGTGCCTCTGCGTGCAGATACCAGCAAACCG
AAGCTGACTCAGCAGGATGTGACCGATCTGATCGCTTATCTGAACAAAGGTGGCTCGGTG
CTGATCATGGAAAACGTGATGAGCAATCTTAAGGAAGAGAGCGCGTCCAGTTTTGTGCGT
CTGCTGGATGCCGCGGGTCTGTCAATGGCTCTGAACAAATCGGTGGTGAACAACGATCCG
CAAGGGTATCCGGATCGCGTTCGTCAGCGTCGCGCGACTGGCATTTGGGTTTATGAACGT
TATCCTGCTGCAGACGCGCGCAACCGCCGTACACCATCGACCCAAATACAGGGGAAGTG
ACCTGGAAATACCAGCAAGACAACAAGCCTGATGACAAGCCGAAACTGGAAGTTGCGAGC
TGGCAGGAGGAAGTTGAGGGCAAACAGGTAACGCGTTATGCCTTTATTGATGAAGCGGAA
TACACAACAGAAGAATCTCTGGAAGCGGCAAAGGCAAAATCTTTGAGAAGTTTCCTGGG
TTACAGGAGTGTAAGGACTCGACTTACCATTACGAGATTAACTGTTTGGAGCGCCGCCCA
GGCACGGATGTTCCGGTAACAGGTGGCATGTATGTTCCGCGCTATACGCAACTGAATCTT
GACGCCGACACCGCGAAAGCGATGGTGCAGGCGGCGGATTTAGGCACCAACATTCAGCGC
CTGTATCAGCATGAGCTTTATTTCCGTACCAAAGGCAGTAAAGGTGAGCGTCTGAACAGT
GTTGATCTGGAACGTCTGTACCAGAACATGTCGGTCTGGCTGTGGAACGATACGAAATAT
CGTTACGAAGAGGGCAAGGAAGATGAGCTGGGCTTTAAAACGTTCACCGAGTTCCTGAAC
TGCTACGCCAATGATGCCTATGCAGGCGGCACCAAGTGCTCCGCAGATCTGAAAAAATCG
CTGGTCGATAACAACATGATCTACGGTGACGGTAGCAGCAAAGCGGGCATGATGAACCCA
```

-continued

```
AGCTATCCGCTCAACTATATGGAAAAACCGCTGACGCGTCTGATGCTGGGCCGTTCCTGG

TGGGATCTGAACATTAAGGTTGATGTGGAGAAGTACCCAGGATCCGTATCGGCAAAGGGT

GAGAGCGTTACGGAAAACATCAGCCTGTACTCGAATCCGACCAAATGGTTTGCGGGTAAC

ATGCAGTCAACCGGCCTGTGGGCACCGGCCCAGCAGGACGTCACCATTAAGTCTTCGGCG

TCAGTCCCAGTGACTGTTACCGTGGCGCTGGCTGACGACCTGACTGGACGTGAGAAGCAT

GAAGTTGCGCTGAACCGTCCGCCAAGAGTGACTAAAACGTATACTCTGGAGGCTAACGGT

GAAGTGACCTTCAAGGTGCCTTATGGTGGTCTGATTTATATCAAGGGCGACAGTAAGGAT

GATGTTTCTGCTAACTTCACCTTTACCGGTGTAGTAAAAGCGCCGTTCTATAAAGACGGC

GAATGGAAAAACGATCTGGACTCACCGGCGCCGCTGGGCGAGCTGGAGTCTGCGTCGTTC

GTCTATACCACGCCGAAGAAGAACCTTGAGGCCAGCAATTTCACTGGTGGTGTAGCAGAA

TTCGCTAAAGATCTGGATACCTTTGCCAGCTCGATGAATGACTTCTACGGTCGTAATGAT

GAAGACGGTAAGCACCGGATGTTTACCTATAAAAACTTGACGGGGCACAAGCATCGTTTC

ACCAACGATGTGCAGATCTCCATCGGTGATGCGCACTCGGGTTATCCGGTAATGAACAGC

AGCTTCTCGACGAACAGCACCACGCTGCCGACGACGCCGCTGAACGACTGGCTGATTTGG

CACGAAGTCGGTCATAACGCTGCAGAAACACCGCTGAACGTACCGGGTGCAACTGAAGTG

GCGAACAACGTGCTGGCGCTGTACATGCAGGATCGCTATCTCGGTAAGATGAACCGTGTC

GCTGACGACATTACCGTCGCGCCGGAATATCTGGACGAGAGCAACGGTCAGGCCTGGGCG

CGCGGCGGTGCGGGTGACCGTCTGCTGATGTACGCACAGTTGAAGGAGTGGGCAGAGGAA

AACTTTGATATCAAACAGTGGTATCCAGATGGTGAGCTGCCTAAGTTCTACAGCGATCGT

AAAGGGATGAAGGGCTGGAACCTGTTCCAGTTGATGCACCGTAAAGCGCGCGGCGATGAT

GTTGGTAACAGCACCTTTGGTGGCAAGAATTACTGTGCTGAATCCAATGGTAACGCTGCC

GACACGCTGATGCTGTGTGCATCCTGGGTCGCTCAGGCGGATCTTTCGGAATTCTTTAAG

AAATGGAATCCGGGTGCAAGTGCTTACCAGTTGCCGGGAGCAACGGAGATGAGTTTCCAG

GGCGGTGTGAGCTCTTCGGCTTACAGCACGCTGGCGTCACTCAAGCTGCCGAAACCGGAA

AAAGGGCCGGAAACCATTAACAAGGTTACCGAGCATAAGATGTCTGCCGAG
```

>pK1-3526

(SEQ ID 18)

```
CDGGGSGSSSDTPSVDSGSGTLPEVKPDPTPTPEPTPEPTPDPEPTPDPTPDPEPTPEPE

PEPVPTKTGYLTLGGSQRVTGATCNGESSDGFTFTPGNTVSCVVGSTTIATFNTQSEAAR

SLRAVDKVSFSLEDAQELANSENKKTNAISLVTSSDSCPADAEQLCLTESSVVDRARFEK

LYKQIDLATDNESKLVNEEVENNAATDKAPSTHTSTVVPVTTEGTKPDLNASEVSANAEQ

FYQYQPTEIILSEGQLVDSLGNGVAGVDYYTNSGRGVTDENGKESFSWGETISEGIDTFE

LGSVRGNKSTIALTELGDEVRGANIDQLIHRYSTTGQNNTRVVPDDVRKVFAEYPNVINE

IINLSLSNGATLDEGDQNVVLPNEFIEQFKTGQAKEIDTAICAKTDGCNEARWFSLTTRN

VNDGQIQGVINKLWGVDTNYQSVSKFHVEHDSTNEYGSTGNARGQAVVNISNSAFPILMA

RNDKNYWLAFGEKRAWDKNELAYITEAPSIVQPENVTRDTATENLPFISLGQVGEGKLMV

IGNPHYNSILRCPNGYSWGGGVNSKGECTLSGDSDDMKHEMQNVLRYLSNDIWQPNTKSI

MTVGTNLENVYFKKAGQVLGNSAPFAFHEDFTGITVKQLTSYGDLNPEEIPLLILNGFEY

VTQWSGDPYAVPLRADTSKPKLTQQDVTDLIAYLNKGGSVLIMENVMSNLKEESASSEVR

LLDAAGLSMALNKSVVNNDPQGYPDRVRQRRATGIWVYERYPAADGAQPPYTIDPNTGEV

TWKYQQDNKPDDKPKLEVASWQEEVEGKQVTRYAFIDEAEYTTEESLEAAKAKIFEKFPG

LQECKDSTYHYEINCLERRPGTDVPVTGGMYVPRYTQLNLDADTAKAMVQAADLGTNIQR
```

LYQHELYFRTKGSKGERLNSVDLERLYQNMSVWLWNDTKYRYEEGKEDELGFKTFTEFLN

CYANDAYAGGTKCSADLKKSLVDNNMIYGDGSSKAGMMNPSYPLNYMEKPLTRLMLGRSW

WDLNIKVDVEKYPGSVSAKGESVTENISLYSNPTKWFAGNMQSTGLWAPAQQDVTIKSSA

SVPVTVTVALADDLTGREKHEVALNRPPRVTKTYTLEANGEVTEKVPYGGLIYIKGDSKD

DVSANFTFTGVVKAPFYKDGEWKNDLDSPAPLGELESASFVYTTPKKNLEASNFTGGVAE

FAKDLDTFASSMNDFYGRNDEDGKHRMFTYKNLTGHKHRFTNDVQISIGDAHSGYPVMNS

SFSTNSTTLPTTPLNDWLIWHEVGHNAAETPLNVPGATEVANNVLALYMQDRYLGKMNRV

ADDITVAPEYLDESNGQAWARGGAGDRLLMYAQLKEWAEENFDIKQWYPDGELPKEYSDR

KGMKGWNLFQLMHRKARGDDVGNSTEGGKNYCAESNGNAADTLMLCASWVAQADLSEFFK

KWNPGASAYQLPGATEMSFQGGVSSSAYSTLASLKLPKPEKGPETINKVTEHKMSAE

>pK1-3526E1305A
(SEQ ID 19)
TGTGATGGTGGTGGTTCAGGATCGTCCTCCGATACGCCGTCTGTAGATTCTGGATCAGGG

ACTTTGCCGGAAGTGAAACCCGATCCAACACCAACCCCGGAGCCGACACCTGAGCCGACG

CCCGGACCCAGAACCTACGCCGGATCCAACACCTGATCCTGAGCCGACACCAGAACCGGAG

CCAGAACCTGTTCCTACGAAAACGGGTTATCTGACCCTGGGCGGAAGCCAGCGGGTAACT

GGTGCTACCTGTAATGGTGAATCCAGCGATGGCTTTACCTTTACGCCAGGCAATACCGTG

AGTTGTGTGGTGGGCAGTACGACCATTGCAACATTCAACACCCAGTCAGAAGCTGCGCGT

AGCCTGCGTGCGGTTGACAAAGTGTCGTTTAGCCTGGAGGACGCGCAGGAGCTGGCGAAT

TCTGAAAATAAGAAAACCAACGCCATCTCTCTGGTGACGTCCAGCGACAGTTGCCCCGCA

GATGCAGAACAGCTTTGTCTTACTTTCTCGTCAGTGGTTGATCGCGCGCGATTTGAAAAA

CTGTATAAGCAAATTGATCTGGCAACAGACAATTTCAGCAAGCTGGTCAATGAAGAGGTG

GAAAACAATGCTGCGACTGATAAAGCGCCGTCCACCCATACCTAACGGTAGTGCCAGTC

ACGACAGAGGGAACAAAACCGGATCTGAACGCGTCCTTCGTGTCGGCTAACGCGGAACAG

TTTTATCAGTATCAACCCACTGAAATCATTCTTTCCGAAGGCCAACTGGTGGATAGCCTG

GGGAACGGTGTTGCTGGCGTTGACTACTACACCAATTCAGGCCGTGGCGTAACTGACGAA

AACGGTAAATTTTCCTTTAGCTGGGGCGAAACCATCTCCTTTGGTATCGATACCTTTGAA

CTGGGCTCAGTACGTGGCAATAAGTCGACCATTGCGCTGACTGAATTGGGTGATGAAGTT

CGCGGGGCAAATATCGATCAGCTCATTCATCGTTATTCGACGACTGGTCAAAATAATACT

CGTGTTGTTCCGGACGATGTACGCAAGGTCTTTGCCGAATATCCCAACGTGATCAACGAG

ATAATCAATCTTTCGTTATCCAACGGTGCGACGCTGGATGAAGGCGATCAAAACGTTGTG

CTGCCTAACGAATTTATCGAGCAGTTTAAGACGGGTCAGGCCAAAGAGATCGATACCGCG

ATTTGTGCGAAAACCGACGGTTGTAACGAGGCTCGCTGGTTCTCGCTGACAACGCGCAAT

GTTAATGACGGCCAGATTCAGGGCGTTATTAACAAGCTGTGGGGCGTGGATACGAACTAT

CAGTCTGTCAGCAAGTTCCACGTCTTCCATGACTCTACCAACTTCTATGGCAGCACCGGT

AACGCGCGCGGTCAGGCGGTGGTAAATATCTCCAACTCGGCATTCCCGATTCTGATGGCG

CGTAATGATAAAAACTACTGGCTGGCGTTTGGCGAAAAACGCGCCTGGGATAAAAATGAG

CTGGCGTACATTACGGAAGCGCCTTCCATTGTGCAGCCAGAGAACGTTACGCGCGATACT

GCGACTTTCAACCTGCCGTTTATTTCGCTGGGGCAAGTCGGTGAAGGCAAACTGATGGTT

ATCGGTAACCCGCACTACAACAGCATCCTGCGTTGCCCGAACGGTTACAGTTGGGGCGGT

GGTGTTAATAGTAAAGGTGAGTGTACGCTCAGCGGTGATTCTGATGACATGAAGCACTTT

-continued

```
ATGCAGAACGTACTGCGCTACTTGTCAAATGACATCTGGCAGCCAAATACCAAGAGCATC
ATGACTGTCGGCACCAACCTGGAGAACGTTTATTTCAAAAAAGCGGGCCAGGTATTGGGA
AATAGTGCACCATTTGCTTTCCATGAGGATTTCACTGGTATCACGGTTAAACAGTTGACC
AGCTATGGCGATCTGAATCCGGAAGAGATTCCGTTGCTGATCCTCAACGGCTTTGAATAT
GTGACTCAGTGGTCTGGCGATCCCTATGCTGTGCCTCTGCGTGCAGATACCAGCAAACCG
AAGCTGACTCAGCAGGATGTGACCGATCTGATCGCTTATCTGAACAAAGGTGGCTCGGTG
CTGATCATGGAAAACGTGATGAGCAATCTTAAGGAAGAGAGCGCGTCCAGTITTGTGCGT
CTGCTGGATGCCGCGGGTCTGTCAATGGCTCTGAACAAATCGGTGGTGAACAACGATCCG
CAAGGGTATCCGGATCGCGTTCGTCAGCGTCGCGCGACTGGCATTTGGGTTTATGAACGT
TATCCTGCTGCAGACGGCGCGCAACCGCCGTACACCATCGACCCAAATACAGGGGAAGTG
ACCTGGAAATACCAGCAAGACAACAAGCCTGATGACAAGCCGAAACTGGAAGTTGCGAGC
TGGCAGGAGGAAGTTGAGGGCAAACAGGTAACGCGTTATGCCTTTATTGATGAAGCGGAA
TACACAACAGAAGAATCTCTGGAAGCGGCAAAGGCAAAAATCTTTGAGAAGTTTCCTGGG
TTACAGGAGTGTAAGGACTCGACTTACCATTACGAGATTAACTGTTTGGAGCGCCGCCCA
GGCACGGATGTTCCGGTAACAGGTGGCATGTATGTTCCGCGCTATACGCAACTGAATCTT
GACGCCGACACCGCGAAAGCGATGGTGCAGGCGGCGGATTTAGGCACCAACATTCAGCGC
CTGTATCAGCATGAGCTITATTTCCGTACCAAAGGCAGTAAAGGTGAGCGTCTGAACAGT
GTTGATCTGGAACGTCTGTACCAGAACATGTCGGTCTGGCTGTGAACGATACGAAATAT
CGTTACGAAGAGGGCAAGGAAGATGAGCTGGGCTTTAAAACGTTCACCGAGTTCCTGAAC
TGCTACGCCAATGATGCCTATGCAGGCGGCACCAAGTGCTCCGCAGATCTGAAAAAATCG
CTGGTCGATAACAACATGATCTACGGTGACGGTAGCAGCAAAGCGGGCATGATGAACCCA
AGCTATCCGCTCAACTATATGGAAAAACCGCTGACGCGTCTGATGCTGGGCCGTTCCTGG
TGGGATCTGAACATTAAGGTTGATGTGGAGAAGTACCCAGGATCCGTATCGGCAAAGGGT
GAGAGCGTTACGGAAAACATCAGCCTGTACTCGAATCCGACCAAATGGTTTGCGGGTAAC
ATGCAGTCAACCGGCCTGTGGGCACCGGCCCAGCAGGACGTCACCATTAAGTCTTCGGCG
TCAGTCCCAGTGACTGTTACCGTGGCGCTGGCTGACGACCTGACTGGACGTGAGAAGCAT
GAAGTTGCGCTGAACCGTCCGCCAAGAGTGACTAAAACGTATACTCTGGAGGCTAACGGT
GAAGTGACCTTCAAGGTGCCTTATGGTGGTCTGATTTATATCAAGGGCGACAGTAAGGAT
GATGTTTCTGCTAACTTCACCTTTACCGGTGTAGTAAAAGCGCCGTTCTATAAAGACGGC
GAATGGAAAAACGATCTGGACTCACCGGCGCCGCTGGGCGAGCTGGAGTCTGCGTCGTTC
GTCTATACCACGCCGAAGAAGAACCTTGAGGCCAGCAATTICACTGGTGGTGTAGCAGAA
TTCGCTAAAGATCTGGATACCTTTGCCAGCTCGATGAATGACTTCTACGGTCGTAATGAT
GAAGACGGTAAGCACCGGATGTTTACCTATAAAAACTTGACGGGGCACAAGCATCGTTTC
ACCAACGATGTGCAGATCTCCATCGGTGATGCGCACTCGGGTTATCCGGTAATGAACAGC
AGCTTCTCGACGAACAGCACCACGCTGCCGACGACGCCGCTGAACGACTGGCTGATTTGG
CACGCAGTCGGTCATAACGCTGCAGAAACACCGCTGAACGTACCGGGTGCAACTGAAGTG
GCGAACAACGTGCTGGCGCTGTACATGCAGGATCGCTATCTCGGTAAGATGAACCGTGTC
GCTGACGACATTACCGTCGCGCCGGAATATCTGGACGAGAGCAACGGTCAGGCCTGGGCG
CGCGGCGGTGCGGGTGACCGTCTGCTGATGTACGCACAGTTGAAGGAGTGGGCAGAGGAA
AACTTTGATATCAAACAGTGGTATCCAGATGGTGAGCTGCCTAAGTTCTACAGCGATCGT
AAAGGGATGAAGGGCTGGAACCTGTTCCAGTTGATGCACCGTAAAGCGCGCGGCGATGAT
```

-continued

```
GTTGGTAACAGCACCTTTGGTGGCAAGAATTACTGTGCTGAATCCAATGGTAACGCTGCC

GACACGCTGATGCTGTGTGCATCCTGGGTCGCTCAGGCGGATCTTTCGGAATTCTTTAAG

AAATGGAATCCGGGTGCAAGTGCTTACCAGTTGCCGGGAGCAACGGAGATGAGTTTCCAG

GGCGGTGTGAGCTCTTCGGCTTACAGCACGCTGGCGTCACTCAAGCTGCCGAAACCGGAA

AAAGGGCCGGAAACCATTAACAAGGTTACCGAGCATAAGATGTCTGCCGAG
```

>pK1-3526E1305A (SEQ ID 20)

```
CDGGGSGSSSDTPSVDSGSGTLPEVKPDPTPTPEPTPEPTPDPEPTPDPTPDPEPTPEPE

PEPVPTKTGYLTEGGSQRVTGATCNGESSDGFTFTPGNTVSCVVGSTTIATENTQSEAAR

SLRAVDKVSFSLEDAQELANSENKKTNAISLVTSSDSCPADAEQLCLTFSSVVDRARFEK

LYKQIDLATDNFSKLVNEEVENNAATDKAPSTHTSTVVPVTTEGTKPDLNASFVSANAEQ

FYQYQPTEIILSEGQLVDSLGNGVAGVDYYTNSGRGVTDENGKESFSWGETISEGIDTFE

LGSVRGNKSTIALTELGDEVRGANIDQLIHRYSTTGQNNTRVVPDDVRKVFAEYPNVINE

IINESESNGATEDEGDQNVVLPNEFIEQFKTGQAKEIDTAICAKTDGCNEARWFSLTTRN

VNDGQIQGVINKLWGVDTNYQSVSKPHVFHDSTNEYGSTGNARGQAVVNISNSAFPILMA

RNDKNYWLAFGEKRAWDKNELAYITEAPSIVQPENVTRDTATFNLPFISLGQVGEGKLMV

IGNPHYNSILRCPNGYSWGGGVNSKGECTLSGDSDDMKHFMQNVLRYLSNDIWQPNTKSI

MTVGTNLENVYFKKAGQVLGNSAPFAFHEDFTGITVKQLTSYGDLNPEEIPLLILNGFEY

VTQWSGDPYAVPLRADTSKPKLTQQDVTDLIAYLNKGGSVLIMENVMSNLKEESASSFVR

LLDAAGLSMALNKSVVNNDPQGYPDRVRQRRATGIWVYERYPAADGAQPPYTIDPNTGEV

TWKYQQDNKPDDKPKLEVASWQEEVEGKQVTRYAFIDEAEYTTEESLEAAKAKIFEKFPG

LQECKDSTYHYEINCLERRPGTDVPVTGGMYVPRYTQLNLDADTAKAMVQAADLGTNIQR

LYQHELYFRTKGSKGERLNSVDLERLYQNMSVWLWNDTKYRYEEGKEDELGFKTFTEFLN

CYANDAYAGGTKCSADLKKSLVDNNMIYGDGSSKAGMMNPSYPLNYMEKPLTRLMLGRSW

WDLNIKVDVEKYPGSVSAKGESVTENISLYSNPTKWFAGNMQSTGLWAPAQQDVTIKSSA

SVPVTVTVALADDLTGREKHEVALNRPPRVTKTYTLEANGEVTFKVPYGGLIYIKGDSKD

DVSANFTFTGVVKAPFYKDGEWKNDLDSPAPLGELESASFVYTTPKKNLEASNFTGGVAE

FAKDLDTFASSMNDFYGRNDEDGKHRMFTYKNLTGHKHRFTNDVQISIGDAHSGYPVMNS

SFSTNSTTLPTTPLNDWLIWHAVGHNAAETPLNVPGATEVANNVLALYMQDRYLGKMNRV

ADDITVAPEYLDESNGQAWARGGAGDRLLMYAQLKEWAEENFDIKQWYPDGELPKFYSDR

KGMKGWNLFQLMHRKARGDDVGNSTFGGKNYCAESNGNAADTLMLCASWVAQADLSEFFK

KWNPGASAYQLPGATEMSFQGGVSSSAYSTLASLKLPKPEKGPETINKVTEHKMSAE
```

>pK1-3526D1422A (SEQ ID 21)

```
TGTGATGGIGGTGGTTCAGGATCGTCCTCCGATACGCCGTCTGTAGATTCTGGATCAGGG

ACTTTGCCGGAAGTGAAACCCGATCCAACACCAACCCCGGAGCCGACACCTGAGCCGACG

CCGGACCCAGAACCTACGCCGGATCCAACACCTGATCCTGAGCCGACACCAGAACCGGAG

CCAGAACCTGTTCCTACGAAAACGGGTTATCTGACCCTGGGCGGAAGCCAGCGGGTAACT

GGTGCTACCTGTAATGGTGAATCCAGCGATGGCTTTACCTTTACGCCAGGCAATACCGTG

AGTTGTGTGGTGGGCAGTACGACCATTGCAACATTCAACACCCAGTCAGAAGCTGCGCGT

AGCCTGCGTGCGGTTGACAAAGTGTCGTTTAGCCTGGAGGACGCGCAGGAGCTGGCGAAT

TCTGAAAATAAGAAAACCAACGCCATCTCTCTGGTGACGTCCAGCGACAGTTGCCCCGCA
```

-continued

```
GATGCAGAACAGCTTTGTCTTACTTTCTCGTCAGTGGTTGATCGCGCGCGATTTGAAAAA

CTGTATAAGCAAATTGATCTGGCAACAGACAATTTCAGCAAGCTGGTCAATGAAGAGGTG

GAAAACAATGCTGCGACTGATAAAGCGCCGTCCACCCATACCTCAACGGTAGTGCCAGTC

ACGACAGAGGGAACAAAACCGGATCTGAACGCGTCCTTCGTGTCGGCTAACGCGGAACAG

TTTTATCAGTATCAACCCACTGAAATCATTCTTTCCGAAGGCCAACTGGTGGATAGCCTG

GGGAACGGTGTTGCTGGCGTTGACTACTACACCAATTCAGGCCGTGGCGTAACTGACGAA

AACGGTAAATFITCCTTTAGCTGGGGCGAAACCATCTCCTTTGGTATCGATACCTTTGAA

CTGGGCTCAGTACGTGGCAATAAGTCGACCATTGCGCTGACTGAATTGGGTGATGAAGTT

CGCGGGGCAAATATCGATCAGCTCATTCATCGTTATTCGACGACTGGTCAAAATAATACT

CGTGTTGTTCCGGACGATGTACGCAAGGTCTTTGCCGAATATCCCAACGTGATCAACGAG

ATAATCAATCTTTCGTTATCCAACGGTGCGACGCTGGATGAAGGCGATCAAAACGTTGTG

CTGCCTAACGAATTTATCGAGCAGTTTAAGACGGGTCAGGCCAAAGAGATCGATACCGCG

ATTTGTGCGAAAACCGACGGTTGTAACGAGGCTCGCTGGTTCTCGCTGACAACGCGCAAT

GTTAATGACGGCCAGATTCAGGGCGTTATTAACAAGCTGTGGGGCGTGGATACGAACTAT

CAGTCTGTCAGCAAGTTCCACGTCTTCCATGACTCTACCAACTTCTATGGCAGCACCGGT

AACGCGCGCGGTCAGGCGGTGGTAAATATCTCCAACTCGGCATTCCCGATTCTGATGGCG

CGTAATGATAAAAACTACTGGCTGGCGTTTGGCGAAAAACGCGCCTGGGATAAAAATGAG

CTGGCGTACATTACGGAAGCGCCTTCCATTGTGCAGCCAGAGAACGTTACGCGCGATACT

GCGACTTTCAACCTGCCGTTTATTTCGCTGGGGCAAGTCGGTGAAGGCAAACTGATGGTT

ATCGGTAACCCGCACTACAACAGCATCCTGCGTTGCCCGAACGGTTACAGTTGGGGCGGT

GGIGTTAATAGTAAAGGTGAGTGTACGCTCAGCGGTGATTCTGATGACATGAAGCACTTT

ATGCAGAACGTACTGCGCTACTTGTCAAATGACATCTGGCAGCCAAATACCAAGAGCATC

ATGACTGTCGGCACCAACCTGGAGAACGTTTATTTCAAAAAAGCGGGCCAGGTATTGGGA

AATAGTGCACCATTTGCTTTCCATGAGGATTTCACTGGTATCACGGTTAAACAGTTGACC

AGCTATGGCGATCTGAATCCGGAAGAGATTCCGTTGCTGATCCTCAACGGCTTTGAATAT

GTGACTCAGTGGTCTGGCGATCCCTATGCTGTGCCTCTGCGTGCAGATACCAGCAAACCG

AAGCTGACTCAGCAGGATGTGACCGATCTGATCGCTTATCTGAACAAAGGTGGCTCGGTG

CTGATCATGGAAAACGTGATGAGCAATCTTAAGGAAGAGAGCGCGTCCAGTTTTGTGCGT

CTGCTGGATGCCGCGGGTCTGICAATGGCTCTGAACAAATCGGTGGTGAACAACGATCCG

CAAGGGTATCCGGATCGCGTTCGTCAGCGTCGCGCGACTGGCATTTGGGTTTATGAACGT

TATCCTGCTGCAGACGGCGCGCAACCGCCGTACACCATCGACCCAAATACAGGGGAAGTG

ACCTGGAAATACCAGCAAGACAACAAGCCTGATGACAAGCCGAAACTGGAAGTTGCGAGC

TGGCAGGAGGAAGTTGAGGGCAAACAGGTAACGCGTTATGCCTTTATTGATGAAGCGGAA

TACACAACAGAAGAATCTCTGGAAGCGGCAAAGGCAAAAATCTTTGAGAAGTTTCCTGGG

TTACAGGAGTGTAAGGACTCGACTTACCATTACGAGATTAACTGTTTGGAGCGCCGCCCA

GGCACGGATGTTCCGGTAACAGGTGGCATGTATGTTCCGCGCTATACGCAACTGAATCTT

GACGCCGACACCGCGAAAGCGATGGTGCAGGCGGCGGATTTAGGCACCAACATTCAGCGC

CTGTATCAGCATGAGCTTTATTTCCGTACCAAAGGCAGTAAAGGTGAGCGTCTGAACAGT

GTTGATCTGGAACGTCTGTACCAGAACATGTCGGTCTGGCTGTGGAACGATACGAAATAT

CGTTACGAAGAGGGCAAGGAAGATGAGCTGGGCTTTAAAACGTTCACCGAGTTCCTGAAC

TGCTACGCCAATGATGCCTATGCAGGCGGCACCAAGTGCTCCGCAGATCTGAAAAAATCG
```

-continued

```
CTGGTCGATAACAACATGATCTACGGTGACGGTAGCAGCAAAGCGGGCATGATGAACCCA
AGCTATCCGCTCAACTATATGGAAAAACCGCTGACGCGTCTGATGCTGGGCCGTTCCTGG
TGGGATCTGAACATTAAGGTTGATGTGGAGAAGTACCCAGGATCCGTATCGGCAAAGGGT
GAGAGCGTTACGGAAAACATCAGCCTGTACTCGAATCCGACCAAATGGTTTGCGGGTAAC
ATGCAGTCAACCGGCCTGTGGGCACCGGCCCAGCAGGACGTCACCATTAAGTCTTCGGCG
TCAGTCCCAGTGACTGTTACCGTGGCGCTGGCTGACGACCTGACTGGACGTGAGAAGCAT
GAAGTTGCGCTGAACCGTCCGCCAAGAGTGACTAAAACGTATACTCTGGAGGCTAACGGT
GAAGTGACCTTCAAGGTGCCTTATGGTGGTCTGATTTATATCAAGGGCGACAGTAAGGAT
GATGTTTCTGCTAACTTCACCTTTACCGGTGTAGTAAAAGCGCCGTTCTATAAAGACGGC
GAATGGAAAAACGATCTGGACTCACCGGCGCCGCTGGGCGAGCTGGAGTCTGCGTCGTTC
GTCTATACCACGCCGAAGAAGAACCTTGAGGCCAGCAATTTCACTGGTGGTGTAGCAGAA
TTCGCTAAAGATCTGGATACCTTTGCCAGCTCGATGAATGACTTCTACGGTCGTAATGAT
GAAGACGGTAAGCACCGGATGTTTACCTATAAAAACTTGACGGGGCACAAGCATCGTTTC
ACCAACGATGTGCAGATCTCCATCGGTGATGCGCACTCGGGTTATCCGGTAATGAACAGC
AGCTTCTCGACGAACAGCACCACGCTGCCGACGACGCCGCTGAACGACTGGCTGATTTGG
CACGAAGTCGGTCATAACGCTGCAGAAACACCGCTGAACGTACCGGGTGCAACTGAAGTG
GCGAACAACGTGCTGGCGCTGTACATGCAGGATCGCTATCTCGGTAAGATGAACCGTGTC
GCTGACGACATTACCGTCGCGCCGGAATATCTGGACGAGAGCAACGGTCAGGCCTGGGCG
CGCGGCGGTGCGGGTGACCGTCTGCTGATGTACGCACAGTTGAAGGAGTGGGCAGAGGAA
AACTTTGATATCAAACAGTGGTATCCAGATGGTGAGCTGCCTAAGTTCTACAGCGATCGT
AAAGGGATGAAGGGCTGGAACCTGTTCCAGTTGATGCACCGTAAAGCGCGCGGCGCTGAT
GTTGGTAACAGCACCTTTGGTGGCAAGAATTACTGTGCTGAATCCAATGGTAACGCTGCC
GACACGCTGATGCTGTGTGCATCCTGGGTCGCTCAGGCGGATCTTTCGGAATTCTTTAAG
AAATGGAATCCGGGTGCAAGTGCTTACCAGTTGCCGGGAGCAACGGAGATGAGTTTCCAG
GGCGGTGTGAGCTCTTCGGCTTACAGCACGCTGGCGTCACTCAAGCTGCCGAAACCGGAA
AAAGGGCCGGAAACCATTAACAAGGTTACCGAGCATAAGATGTCTGCCGAG
```

>pK1-3526D1422A
(SEQ ID 22)

```
CDGGGSGSSSDTPSVDSGSGTLPEVKPDPTPTPEPTPEPTPDPEPTPDPTPDPEPTPEPE
PEPVPTKTGYLTLGGSQRVTGATCNGESSDGFTFTPGNTVSCVVGSTTIATFNTQSEAAR
SLRAVDKVSFSLEDAQELANSENKKTNAISLVTSSDSCPADAEQLCLTFSSVVDRARFEK
LYKQIDLATDNESKLVNEEVENNAATDKAPSTHTSTVVPVTTEGTKPDLNASFVSANAEQ
FYQYQPTEIILSEGQLVDSLGNGVAGVDYYTNSGRGVTDENGKESFSWGETISFGIDTFE
LGSVRGNKSTIALTELGDEVRGANIDQLIHRYSTTGQNNTRVVPDDVRKVFAEYPNVINE
IINLSLSNGATLDEGDQNVVLPNEFIEQFKTGQAKEIDTAICAKTDGCNEARWFSLTTRN
VNDGQIQGVINKLWGVDTNYQSVSKFHVFHDSTNFYGSTGNARGQAVVNISNSAFPILMA
RNDKNYWLAFGEKRAWDKNELAYITEAPSIVQPENVTRDTATFNLPFISLGQVGEGKLMV
IGNPHYNSILRCPNGYSWGGGVNSKGECTLSGDSDDMKHFMQNVLRYLSNDIWQPNTKSI
MTVGTNLENVYFKKAGQVLGNSAPFAFHEDFTGITVKQLTSYGDLNPEEIPLLILNGFEY
VTQWSGDPYAVPLRADTSKPKLTQQDVTDLIAYLNKGGSVLIMENVMSNLKEESASSFVR
LLDAAGLSMALNKSVVNNDPQGYPDRVRQRRATGIWVYERYPAADGAQPPYTIDPNTGEV
```

```
TWKYQQDNKPDDKPKLEVASWQEEVEGKQVTRYAFIDEAEYTTEESLEAAKAKIFEKFPG

LQECKDSTYHYEINCLERRPGTDVPVTGGMYVPRYTQLNLDADTAKAMVQAADLGTNIQR

LYQHELYERTKGSKGERLNSVDLERLYQNMSVWLWNDTKYRYEEGKEDELGFKTFTEFLN

CYANDAYAGGTKCSADLKKSLVDNNMIYGDGSSKAGMMNPSYPLNYMEKPLTRLMLGRSW

WDLNIKVDVEKYPGSVSAKGESVTENISLYSNPTKWFAGNMQSTGLWAPAQQDVTIKSSA

SVPVTVTVALADDLTGREKHEVALNRPPRVTKTYTLEANGEVTFKVPYGGLIYIKGDSKD

DVSANFTFTGVVKAPFYKDGEWKNDLDSPAPLGELESASFVYTTPKKNLEASNFTGGVAE

FAKDLDTFASSMNDFYGRNDEDGKHRMFTYKNLTGHKHRFTNDVQISIGDAHSGYPVMNS

SFSTNSTTLPTTPLNDWLIWHEVGHNAAETPLNVPGATEVANNVLALYMQDRYLGKMNRV

ADDITVAPEYLDESNGQAWARGGAGDRLLMYAQLKEWAEENFDIKQWYPDGELPKEYSDR

KGMKGWNLFQLMHRKARGADVGNSTFGGKNYCAESNGNAADTLMLCASWVAQADLSEFFK

KWNPGASAYQLPGATEMSFQGGVSSSAYSTLASLKLPKPEKGPETINKVTEHKMSAE
```

>pK1-3526AdG (SEQ ID 23)
```
GATACGCCGTCTGTAGATTCTGGATCAGGGACTTTGCCGGAAGTGAAACCCGATCCAACA

CCAACCCCGGAGCCGACACCTGAGCCGACGCCGGACCCAGAACCTACGCCGGATCCAACA

CCTGATCCTGAGCCGACACCAGAACCGGAGCCAGAACCTGTTCCTACGAAAACGGGTTAT

CTGACCCTGGGCGGAAGCCAGCGGGTAACTGGTGCTACCTGTAATGGTGAATCCAGCGAT

GGCTTTACCTTTACGCCAGGCAATACCGTGAGTTGTGTGGTGGGCAGTACGACCATTGCA

ACATTCAACACCCAGTCAGAAGCTGCGCGTAGCCTGCGTGCGGTTGACAAAGTGTCGTTT

AGCCTGGAGGACGCGCAGGAGCTGGCGAATTCTGAAAATAAGAAAACCAACGCCATCTCT

CTGGTGACGTCCAGCGACAGTTGCCCCGCAGATGCAGAACAGCTTTGTCTTACTTTCTCG

TCAGTGGTTGATCGCGCGCGATTTGAAAAACTGTATAAGCAAATTGATCTGGCAACAGAC

AATTTCAGCAAGCTGGTCAATGAAGAGGTGGAAAACAATGCTGCGACTGATAAAGCGCCG

TCCACCCATACCTCAACGGTAGTGCCAGTCACGACAGAGGGAACAAAACCGGATCTGAAC

GCGTCCTTCGTGTCGGCTAACGCGGAACAGTTTTATCAGTATCAACCCACTGAAATCATT

CTTTCCGAAGGCCAACTGGTGGATAGCCTGGGGAACGGTGTTGCTGGCGTTGACTACTAC

ACCAATTCAGGCCGTGGCGTAACTGACGAAAACGGTAAATTTTCCTTTAGCTGGGGCGAA

ACCATCTCCTTTGGTATCGATACCTTTGAACTGGGCTCAGTACGTGGCAATAAGTCGACC

ATTGCGCTGACTGAATTGGGTGATGAAGTTCGCGGGGCAAATATCGATCAGCTCATTCAT

CGTTATTCGACGACTGGTCAAAATAATACTCGTGTTGTTCCGGACGATGTACGCAAGGTC

TTTGCCGAATATCCCAACGTGATCAACGAGATAATCAATCTTTCGTTATCCAACGGTGCG

ACGCTGGATGAAGGCGATCAAAACGTTGTGCTGCCTAACGAATTTATCGAGCAGTTTAAG

ACGGGTCAGGCCAAAGAGATCGATACCGCGATTTGTGCGAAAACCGACGGTTGTAACGAG

GCTCGCTGGTTCTCGCTGACAACGCGCAATGTTAATGACGGCCAGATTCAGGGCGTTATT

AACAAGCTGTGGGGCGTGGATACGAACTATCAGTCTGTCAGCAAGTTCCACGTCTTCCAT

GACTCTACCAACTTCTATGGCAGCACCGGTAACGCGCGCGGTCAGGCGGTGGTAAATATC

TCCAACTCGGCATTCCCGATTCTGATGGCGCGTAATGATAAAAACTACTGGCTGGCGTTT

GGCGAAAAACGCGCCTGGGATAAAAATGAGCTGGCGTACATTACGGAAGCGCCTTCCATT

GTGCAGCCAGAGAACGTTACGCGCGATACTGCGACTTTCAACCTGCCGTTTATTTCGCTG

GGGCAAGTCGGTGAAGGCAAACTGATGGTTATCGGTAACCCGCACTACAACAGCATCCTG

CGTTGCCCGAACGGTTACAGTTGGGGCGGTGGTGTTAATAGTAAAGGTGAGTGTACGCTC
```

-continued

```
AGCGGTGATTCTGATGACATGAAGCACTTTATGCAGAACGTACTGCGCTACTTGTCAAAT

GACATCTGGCAGCCAAATACCAAGAGCATCATGACTGTCGGCACCAACCTGGAGAACGTT

TATTTCAAAAAAGCGGGCCAGGTATTGGGAAATAGTGCACCATTTGCTTTCCATGAGGAT

TTCACTGGTATCACGGTTAAACAGTTGACCAGCTATGGCGATCTGAATCCGGAAGAGATT

CCGTTGCTGATCCTCAACGGCTTTGAATATGTGACTCAGTGGTCTGGCGATCCCTATGCT

GTGCCTCTGCGTGCAGATACCAGCAAACCGAAGCTGACTCAGCAGGATGTGACCGATCTG

ATCGCTTATCTGAACAAAGGTGGCTCGGTGCTGATCATGGAAAACGTGATGAGCAATCTT

AAGGAAGAGAGCGCGTCCAGTTTTGTGCGTCTGCTGGATGCCGCGGGTCTGTCAATGGCT

CTGAACAAATCGGTGGTGAACAAC
```

>pK1-3526AdG                                                 (SEQ ID 24)
```
DTPSVDSGSGTLPEVKPDPTPTPEPTPEPTPDPEPTPDPTPDPEPTPEPEPEPVPTKTGY

LTLGGSQRVTGATCNGESSDGFTFTPGNTVSCVVGSTTIATENTQSEAARSLRAVDKVSF

SLEDAQELANSENKKTNAISLVTSSDSCPADAEQLCLTFSSVVDRARFEKLYKQIDLATD

NESKLVNEEVENNAATDKAPSTHTSTVVPVTTEGTKPDLNASEVSANAEQFYQYQPTEII

LSEGQLVDSLGNGVAGVDYYTNSGRGVTDENGKFSFSWGETISFGIDTFELGSVRGNKST

IALTELGDEVRGANIDQLIHRYSTTGQNNTRVVPDDVRKVFAEYPNVINEIINLSLSNGA

TLDEGDQNVVLPNEFIEQFKTGQAKEIDTAICAKTDGCNEARWFSLTTRNVNDGQIQGVI

NKLWGVDTNYQSVSKFHVFHDSTNFYGSTGNARGQAVVNISNSAFPILMARNDKNYWLAF

GEKRAWDKNELAYITEAPSIVQPENVTRDTATFNLPFISLGQVGEGKLMVIGNPHYNSIL

RCPNGYSWGGGVNSKGECTLSGDSDDMKHEMQNVLRYLSNDIWQPNTKSIMTVGTNLENV

YFKKAGQVLGNSAPFAFHEDFTGITVKQLTSYGDLNPEEIPLLILNGFEYVTQWSGDPYA

VPLRADTSKPKLTQQDVTDLIAYLNKGGSVLIMENVMSNLKEESASSFVRLLDAAGLSMA

LNKSVVNN
```

>pK1-3526CdG                                                 (SEQ ID 25)
```
GATACGCCGTCTGTAGATTCTGGATCAGGGACTTTGCCGGAAGTGAAACCCGATCCAACA

CCAACCCCGGAGCCGACACCTGAGCCGACGCCGGACCCAGAACCTACGCCGGATCCAACA

CCTGATCCTGAGCCGACACCAGAACCGGAGCCAGAACCTGTTCCTACGAAAACGGGTTAT

CTGACCCTGGGCGGAAGCCAGCGGGTAACTGGTGCTACCTGTAATGGTGAATCCAGCGAT

GGCTTTACCTTTACGCCAGGCAATACCGTGAGTTGTGTGGTGGGCAGTACGACCATTGCA

ACATTCAACACCCAGTCAGAAGCTGCGCGTAGCCTGCGTGCGGTTGACAAAGTGTCGTTT

AGCCTGGAGGACGCGCAGGAGCTGGCGAATTCTGAAAATAAGAAAACCAACGCCATCTCT

CTGGTGACGTCCAGCGACAGTTGCCCCGCAGATGCAGAACAGCTTTGTCTTACTTTCTCG

TCAGTGGTTGATCGCGCGCGATTTGAAAAACTGTATAAGCAAATTGATCTGGCAACAGAC

AATTTCAGCAAGCTGGTCAATGAAGAGGTGGAAAACAATGCTGCGACTGATAAAGCGCCG

TCCACCCATACCTCAACGGTAGTGCCAGTCACGACAGAGGGAACAAAACCGGATCTGAAC

GCGTCCTTCGTGTCGGCTAACGCGGAACAGTTTTATCAGTATCAACCCACTGAAATCATT

CTTTCCGAAGGCCAACTGGTGGATAGCCTGGGGAACGGTGTTGCTGGCGTTGACTACTAC

ACCAATTCAGGCCGTGGCGTAACTGACGAAAACGGTAAATTTTCCTTTAGCTGGGGCGAA

ACCATCTCCTTTGGTATCGATACCTTTGAACTGGGCTCAGTACGTGGCAATAAGTCGACC

ATTGCGCTGACTGAATTGGGTGATGAAGTTCGCGGGGCAAATATCGATCAGCTCATTCAT
```

-continued

```
CGTTATTCGACGACTGGTCAAAATAATACTCGTGTTGTTCCGGACGATGTACGCAAGGTC
TTTGCCGAATATCCCAACGTGATCAACGAGATAATCAATCTTTCGTTATCCAACGGTGCG
ACGCTGGATGAAGGCGATCAAAACGTTGTGCTGCCTAACGAATTTATCGAGCAGTTTAAG
ACGGGTCAGGCCAAAGAGATCGATACCGCGATTTGTGCGAAAACCGACGGTTGTAACGAG
GCTCGCTGGTTCTCGCTGACAACGCGCAATGTTAATGACGGCCAGATTCAGGGCGTTATT
AACAAGCTGTGGGGCGTGGATACGAACTATCAGTCTGTCAGCAAGTTCCACGTCTTCCAT
GACTCTACCAACTTCTATGGCAGCACCGGTAACGCGCGCGGTCAGGCGGTGGTAAATATC
TCCAACTCGGCATTCCCGATTCTGATGGCGCGTAATGATAAAAACTACTGGCTGGCGTTT
GGCGAAAAACGCGCCTGGGATAAAAATGAGCTGGCGTACATTACGGAAGCGCCTTCCATT
GTGCAGCCAGAGAACGTTACGCGCGATACTGCGACTTTCAACCTGCCGTTTATTTCGCTG
GGGCAAGTCGGTGAAGGCAAACTGATGGTTATCGGTAACCCGCACTACAACAGCATCCTG
CGTTGCCCGAACGGTTACAGTTGGGGCGGTGGTGTTAATAGTAAAGGTGAGTGTACGCTC
AGCGGTGATTCTGATGACATGAAGCACTTTATGCAGAACGTACTGCGCTACTTGTCAAAT
GACATCTGGCAGCCAAATACCAAGAGCATCATGACTGTCGGCACCAACCTGGAGAACGTT
TATTTCAAAAAAGCGGGCCAGGTATTGGGAAATAGTGCACCATTTGCTTTCCATGAGGAT
TTCACTGGTATCACGGTTAAACAGTTGACCAGCTATGGCGATCTGAATCCGGAAGAGATT
CCGTTGCTGATCCTCAACGGCTTTGAATATGTGACTCAGTGGTCTGGCGATCCCTATGCT
GTGCCTCTGCGTGCAGATACCAGCAAACCGAAGCTGACTCAGCAGGATGTGACCGATCTG
ATCGCTTATCTGAACAAAGGTGGCTCGGTGCTGATCATGGAAAACGTGATGAGCAATCTT
AAGGAAGAGAGCGCGTCCAGTTTTGTGCGTCTGCTGGATGCCGCGGGTCTGTCAATGGCT
CTGAACAAATCGGTGGTGAACAACGATCCGCAAGGGTATCCGGATCGCGTTCGTCAGCGT
CGCGCGACTGGCATTTGGGTTTATGAACGTTATCCTGCTGCAGACGGCGCGCAACCGCCG
TACACCATCGACCCAAATACAGGGGAAGTGACCTGGAAATACCAGCAAGACAACAAGCCT
GATGACAAGCCGAAACTGGAAGTTGCGAGCTGGCAGGAGGAAGTTGAGGGCAAACAGGTA
ACGCGTTATGCCTTTATTGATGAAGCGGAATACACAACAGAAGAATCTCTGGAAGCGGCA
AAGGCAAAAATCTTTGAGAAGTTCCTGGGTTACAGGAGTGTAAGGACTCGACTTACCAT
TACGAGATTAACTGTTTGGAGCGCCGCCCAGGCACGGATGTTCCGGTAACAGGTGGCATG
TATGTTCCGCGCTATACGCAACTGAATCTTGACGCCGACACCGCGAAAGCGATGGTGCAG
GCGGCGGATTTAGGCACCAACATTCAGCGCCTGTATCAGCATGAGCTTTATTTCCGTACC
AAAGGCAGTAAAGGTGAGCGTCTGAACAGTGTTGATCTGGAACGTCTGTACCAGAACATG
TCGGTCTGGCTGTGGAACGATACGAAATATCGTTACGAAGAGGGCAAGGAAGATGAGCTG
GGCTTTAAAACGTTCACCGAGTTCCTGAACTGCTACGCCAATGATGCCTATGCAGGCGGC
ACCAAGTGCTCCGCAGATCTGAAAAAATCGCTGGTCGATAACAACATGATCTACGGTGAC
GGTAGCAGCAAAGCGGGCATGATGAACCCAAGCTATCCGCTCAACTATATGGAAAAACCG
CTGACGCGTCTGATGCTGGGCCGTTCCTGGTGGGATCTGAACATTAAGGTTGATGTGGAG
AAGTACCCAGGATCCGTATCGGCAAAGGGTGAGAGCGTTACGGAAAACATCAGCCTGTAC
TCGAATCCGACCAAATGGTTTGCGGGTAACATGCAGTCAACCGGCCTGTGGGCACCGGCC
CAGCAGGACGTCACCATTAAGTCTTCGGCGTCAGTCCCAGTGACTGTTACCGTGGCGCTG
GCTGACGACCTGACTGGACGTGAGAAGCATGAAGTTGCGCTGAACCGTCCGCCAAGAGTG
ACTAAAACGTATACTCTGGAGGCTAACGGTGAAGTGACCTTCAAGGTGCCTTATGGTGGT
CTGATTTATATCAAGGGCGACAGTAAGGATGATGTTTCTGCTAACTTCACCTTTACCGGT
```

```
GTAGTAAAAGCGCCGTTCTATAAAGACGGCGAATGGAAAAACGATCTGGACTCACCGGCG

CCGCTGGGCGAGCTGGAGTCTGCGTCGTTCGTCTATACCACGCCGAAGAAGAACCTTGAG

GCCAGCAATTTCACTGGTGGTGTAGCAGAATTCGCTAAAGATCTGGATACCTTTGCCAGC

TCGATGAATGACTTCTACGGICGTAATGATGAAGACGGTAAGCACCGGATGTTTACCTAT

AAAAACTTGACGGGGCACAAGCATCGTTTCACCAACGATGTGCAGATCTCCATCGGTGAT

GCGCACTCGGGTTATCCGGTAATGAACAGCAGCTTCTCGACGAACAGCACCACGCTGCCG

ACGACGCCGCTGAACGACTGGCTGATTTGG
``` pK1-3526CdG (SEQ ID 26)

```
DTPSVDSGSGTLPEVKPDPTPTPEPTPEPTPDPEPTPDPTPDPEPTPEPEPEPVPTKTGY

LTLGGSQRVTGATCNGESSDGFTFTPGNTVSCVVGSTTIATFNTQSEAARSLRAVDKVSF

SLEDAQELANSENKKTNAISLVTSSDSCPADAEQLCLTESSVVDRARFEKLYKQIDLATD

NFSKLVNEEVENNAATDKAPSTHTSTVVPVTTEGTKPDLNASFVSANAEQFYQYQPTEII

LSEGQLVDSLGNGVAGVDYYTNSGRGVTDENGKFSFSWGETISFGIDTFELGSVRGNKST

IALTELGDEVRGANIDQLIHRYSTTGQNNTRVVPDDVRKVFAEYPNVINEIINLSLSNGA

TLDEGDQNVVLPNEFIEQFKTGQAKEIDTAICAKTDGCNEARWFSLTTRNVNDGQIQGVI

NKLWGVDTNYQSVSKFHVFHDSTNFYGSTGNARGQAVVNISNSAFPILMARNDKNYWLAF

GEKRAWDKNELAYITEAPSIVQPENVTRDTATFNLPFISLGQVGEGKLMVIGNPHYNSIL

RCPNGYSWGGGVNSKGECTLSGDSDDMKHFMQNVLRYLSNDIWQPNTKSIMTVGTNLENV

YFKKAGQVLGNSAPFAFHEDFTGITVKQLTSYGDLNPEEIPLLILNGFEYVTQWSGDPYA

VPLRADTSKPKLTQQDVTDLIAYLNKGGSVLIMENVMSNLKEESASSFVRLLDAAGLSMA

LNKSVVNNDPQGYPDRVRQRRATGIWVYERYPAADGAQPPYTIDPNTGEVTWKYQQDNKP

DDKPKLEVASWQEEVEGKQVTRYAFIDEAEYTTEESLEAAKAKIFEKFPGLQECKDSTYH

YEINCLERRPGTDVPVTGGMYVPRYTQLNLDADTAKAMVQAADLGTNIQRLYQHELYFRT

KGSKGERLNSVDLERLYQNMSVWLWNDTKYRYEEGKEDELGFKTFTEFLNCYANDAYAGG

TKCSADLKKSLVDNNMIYGDGSSKAGMMNPSYPLNYMEKPLTRLMLGRSWWDLNIKVDVE

KYPGSVSAKGESVTENISLYSNPTKWFAGNMQSTGLWAPAQQDVTIKSSASVPVTVTVAL

ADDLTGREKHEVALNRPPRVTKTYTLEANGEVTFKVPYGGLIYIKGDSKDDVSANFTFTG

VVKAPFYKDGEWKNDLDSPAPLGELESASFVYTTPKKNLEASNFTGGVAEFAKDLDTFAS

SMNDFYGRNDEDGKHRMFTYKNLTGHKHRFTNDVQISIGDAHSGYPVMNSSFSTNSTTLP

TTPLNDWLIW
```

>pK1-L3526-2stop (SEQ ID 27)

```
ATGAATAAGAAATTTAAATATAAGAAATCGCTTTTAGCGGCTATTTTAAGCGCAACCCTG

TTAGCCGGTTGTGATGGTGGTGGTTCAGGATCGTCCTCCGATACGCCGTCTGTAGATTCT

GGATCAGGGACTTTGCCGGAAGTGAAACCCGATCCAACACCAACCCCGGAGCCGACACCT

GAGCCGACGCCGGACCCAGAACCTACGCCGGATCCAACACCTGATCCTGAGCCGACACCA

GAACCGGAGCCAGAACCTGTTCCTACGAAAACGGGTTATCTGACCCTGGGCGGAAGCCAG

CGGGTAACTGGTGCTACCTGTAATGGTGAATCCAGCGATGGCTTTACCTTTACGCCAGGC

AATACCGTGAGTTGTGTGGTGGGCAGTACGACCATTGCAACATTCAACACCCAGTCAGAA

GCTGCGCGTAGCCTGCGTGCGGTTGACAAAGTGTCGTTTAGCCTGGAGGACGCGCAGGAG

CTGGCGAATTCTGAAAATAAGAAAACCAACGCCATCTCTCTGGTGACGTCCAGCGACAGT
```

-continued

```
TGCCCCGCAGATGCAGAACAGCTTTGTCTTACTTTCTCGTCAGTGGTTGATCGCGCGCGA

TTTGAAAAACTGTATAAGCAAATTGATCTGGCAACAGACAATTTCAGCAAGCTGGICAAT

GAAGAGGTGGAAAACAATGCTGCGACTGATAAAGCGCCGTCCACCCATACCTCAACGGTA

GTGCCAGTCACGACAGAGGGAACAAAACCGGATCTGAACGCGTCCTTCGTGTCGGCTAAC

GCGGAACAGTTTTATCAGTATCAACCCACTGAAATCATTCTTTCCGAAGGCCAACTGGTG

GATAGCCTGGGGAACGGTGTTGCTGGCGTTGACTACTACACCAATTCAGGCCGTGGCGTA

ACTGACGAAAACGGTAAATTTTCCTTTAGCTGGGGCGAAACCATCTCCTTTGGTATCGAT

ACCTTTGAACTGGGCTCAGTACGTGGCAATAAGTCGACCATTGCGCTGACTGAATTGGGT

GATGAAGTTCGCGGGGCAAATATCGATCAGCTCATTCATCGTTATTCGACGACTGGTCAA

AATAATACTCGTGTTGTTCCGGACGATGTACGCAAGGTCTTTGCCGAATATCCCAACGTG

ATCAACGAGATAATCAATCTTTCGTTATCCAACGGTGCGACGCTGGATGAAGGCGATCAA

AACGTTGTGCTGCCTAACGAATTTATCGAGCAGTTTAAGACGGGTCAGGCCAAAGAGATC

GATACCGCGATTTGTGCGAAAACCGACGGTTGTAACGAGGCTCGCTGGTTCTCGCTGACA

ACGCGCAATGTTAATGACGGCCAGATTCAGGGCGTTATTAACAAGCTGTGGGGCGTGGAT

ACGAACTATCAGTCTGTCAGCAAGTTCCACGTCTTCCATGACTCTACCAACTTCTATGGC

AGCACCGGTAACGCGCGCGGTCAGGCGGTGGTAAATATCTCCAACTCGGCATTCCCGATT

CTGATGGCGCGTAATGATAAAAACTACTGGCTGGCGTTTGGCGAAAAACGCGCCTGGGAT

AAAAATGAGCTGGCGTACATTACGGAAGCGCCTTCCATTGTGCAGCCAGAGAACGTTACG

CGCGATACTGCGACTTTCAACCTGCCGTTTATTTCGCTGGGGCAAGTCGGTGAAGGCAAA

CTGATGGTTATCGGTAACCCGCACTACAACAGCATCCTGCGTTGCCCGAACGGTTACAGT

TGGGGCGGTGGTGTTAATAGTAAAGGTGAGTGTACGCTCAGCGGTGATTCTGATGACATG

AAGCACTTTATGCAGAACGTACTGCGCTACTTGTCAAATGACATCTGGCAGCCAAATACC

AAGAGCATCATGACTGTCGGCACCAACCTGGAGAACGTTTATTTCAAAAAAGCGGGCCAG

GTATTGGGAAATAGTGCACCATTTGCTTTCCATGAGGATTTCACTGGTATCACGGTTAAA

CAGTTGACCAGCTATGGCGATCTGAATCCGGAAGAGATTCCGTTGCTGATCCTCAACGGC

TTTGAATATGTGACTCAGTGGTCTGGCGATCCCTATGCTGTGCCTCTGCGTGCAGATACC

AGCAAACCGAAGCTGACTCAGCAGGATGTGACCGATCTGATCGCTTATCTGAACAAAGGT

GGCTCGGTGCTGATCATGGAAAACGTGATGAGCAATCTTAAGGAAGAGAGCGCGTCCAGT

TTTGTGCGTCTGCTGGATGCCGCGGGTCTGTCAATGGCTCTGAACAAATCGGTGGTGAAC

AACGATCCGCAAGGGTATCCGGATCGCGTTCGTCAGCGTCGCGCGACTGGCATTTGGGTT

TATGAACGTTATCCTGCTGCAGACGGCGCGCAACCGCCGTACACCATCGACCCAAATACA

GGGGAAGTGACCTGGAAATACCAGCAAGACAACAAGCCTGATGACAAGCCGAAACTGGAA

GTTGCGAGCTGGCAGGAGGAAGTTGAGGGCAAACAGGTAACGCGTTATGCCTTTATTGAT

GAAGCGGAATACACAACAGAAGAATCTCTGGAAGCGGCAAAGGCAAAATCTTTGAGAAG

TTTCCTGGGTTACAGGAGTGTAAGGACTCGACTTACCATTACGAGATTAACTGTTTGGAG

CGCCGCCCAGGCACGGATGTTCCGGTAACAGGTGGCATGTATGTTCCGCGCTATACGCAA

CTGAATCTTGACGCCGACACCGCGAAAGCGATGGTGCAGGCGGCGGATTTAGGCACCAAC

ATTCAGCGCCTGTATCAGCATGAGCTTTATTTCCGTACCAAAGGCAGTAAAGGTGAGCGT

CTGAACAGTGTTGATCTGGAACGTCTGTACCAGAACATGTCGGTCTGGCTGTGGAACGAT

ACGAAATATCGTTACGAAGAGGGCAAGGAAGATGAGCTGGGCTTTAAAACGTTCACCGAG

TTCCTGAACTGCTACGCCAATGATGCCTATGCAGGCGGCACCAAGTGCTCCGCAGATCTG
```

-continued

```
AAAAAATCGCTGGTCGATAACAACATGATCTACGGTGACGGTAGCAGCAAAGCGGGCATG

ATGAACCCAAGCTATCCGCTCAACTATATGGAAAAACCGCTGACGCGTCTGATGCTGGGC

CGTTCCTGGTGGGATCTGAACATTAAGGTTGATGTGGAGAAGTACCCAGGATCCGTATCG

GCAAAGGGTGAGAGCGTTACGAAAACATCAGCCTGTACTCGAATCCGACCAAATGGTTT

GCGGGTAACATGCAGTCAACCGGCCTGTGGGCACCGGCCCAGCAGGACGTCACCATTAAG

TCTTCGGCGTCAGTCCCAGTGACTGTTACCGTGGCGCTGGCTGACGACCTGACTGGACGT

GAGAAGCATGAAGTTGCGCTGAACCGTCCGCCAAGAGTGACTAAAACGTATACTCTGGAG

GCTAACGGTGAAGTGACCTTCAAGGTGCCTTATGGTGGTCTGATTTATATCAAGGGCGAC

AGTAAGGATGATGTTTCTGCTAACTTCACCTTTACCGGTGTAGTAAAAGCGCCGTTCTAT

AAAGACGGCGAATGGAAAAACGATCTGGACTCACCGGCGCCGCTGGGCGAGCTGGAGTCT

GCGTCGTTCGTCTATACCACGCCGAAGAAGAACCTTGAGGCCAGCAATTTCACTGGTGGT

GTAGCAGAATTCGCTAAAGATCTGGATACCTTTGCCAGCTCGATGAATGACTTCTACGGT

CGTAATGATGAAGACGGTAAGCACCGGATGTTTACCTATAAAAACTTGACGGGGCACAAG

CATCGTTTCACCAACGATGTGCAGATCTCCATCGGTGATGCGCACTCGGGTTATCCGGTA

ATGAACAGCAGCTTCTCGACGAACAGCACCACGCTGCCGACGACGCCGCTGAACGACTGG

CTGATTTGGCACGAAGTCGGTCATAACGCTGCAGAAACACCGCTGAACGTACCGGGTGCA

ACTGAAGTGGCGAACAACGTGCTGGCGCTGTACATGCAGGATCGCTATCTCGGTAAGATG

AACCGTGTCGCTGACGACATTACCGTCGCGCCGGAATATCTGGACGAGAGCAACGGTCAG

GCCTGGGCGCGCGGCGGTGCGGGTGACCGTCTGCTGATGTACGCACAGTTGAAGGAGTGG

GCAGAGGAAACTTTGATATCAAACAGTGGTATCCAGATGGTGAGCTGCCTAAGTTCTAC

AGCGATCGTAAAGGGATGAAGGGCTGGAACCTGTTCCAGTTGATGCACCGTAAAGCGCGC

GGCGATGATGTTGGTAACAGCACCTTTGGTGGCAAGAATTACTGTGCTGAATCCAATGGT

AACGCTGCCGACACGCTGATGCTGTGTGCATCCTGGGTCGCTCAGGCGGATCTTTCGGAA

TTCTTTAAGAAATGGAATCCGGGTGCAAGTGCTTACCAGTTGCCGGGAGCAACGGAGATG

AGTTTCCAGGGCGGTGTGAGCTCTTCGGCTTACAGCACGCTGGCGTCACTCAAGCTGCCG

AAACCGGAAAAAGGGCCGGAAACCATTAACAAGGTTACCGAGCATAAGATGTCTGCCGAG

TAA

>pK1-L3526-2stop                                              (SEQ ID 28)

MNKKFKYKKSLLAAILSATLLAGCDGGGSGSSSDTPSVDSGSGTLPEVKPDPTPTPEPTP

EPTPDPEPTPDPTPDPEPTPEPEPEPVPTKTGYLTLGGSQRVTGATCNGESSDGFTFTPG

NTVSCVVGSTTIATFNTQSEAARSLRAVDKVSFSLEDAQELANSENKKTNAISLVTSSDS

CPADAEQLCLTFSSVVDRARFEKLYKQIDLATDNESKLVNEEVENNAATDKAPSTHTSTV

VPVTTEGTKPDLNASFVSANAEQFYQYQPTEIILSEGQLVDSLGNGVAGVDYYTNSGRGV

TDENGKFSFSWGETISFGIDTFELGSVRGNKSTIALTELGDEVRGANIDQLIHRYSTTGQ

NNTRVVPDDVRKVFAEYPNVINEIINLSLSNGATLDEGDQNVVLPNEFIEQFKTGQAKEI

DTAICAKTDGCNEARWFSLTTRNVNDGQIQGVINKLWGVDTNYQSVSKFHVPHDSTNFYG

STGNARGQAVVNISNSAFPILMARNDKNYWLAFGEKRAWDKNELAYITEAPSIVQPENVT

RDTATFNLPFISLGQVGEGKLMVIGNPHYNSILRCPNGYSWGGGVNSKGECTLSGDSDDM

KHEMQNVLRYLSNDIWQPNTKSIMTVGTNLENVYFKKAGQVLGNSAPFAFHEDFTGITVK

QLTSYGDLNPEEIPLLILNGFEYVTQWSGDPYAVPLRADTSKPKLTQQDVTDLIAYLNKG
```

```
-continued
GSVLIMENVMSNLKEESASSEVRLLDAAGLSMALNKSVVNNDPQGYPDRVRQRRATGIWV

YERYPAADGAQPPYTIDPNTGEVTWKYQQDNKPDDKPKLEVASWQEEVEGKQVTRYAFID

EAEYTTEESLEAAKAKIFEKFPGLQECKDSTYHYEINCLERRPGTDVPVTGGMYVPRYTQ

LNLDADTAKAMVQAADLGTNIQRLYQHELYFRTKGSKGERLNSVDLERLYQNMSVWLWND

TKYRYEEGKEDELGFKTFTEFLNCYANDAYAGGTKCSADLKKSLVDNNMIYGDGSSKAGM

MNPSYPLNYMEKPLTRLMLGRSWWDLNIKVDVEKYPGSVSAKGESVTENISLYSNPTKWF

AGNMQSTGLWAPAQQDVTIKSSASVPVTVTVALADDLTGREKHEVALNRPPRVTKTYTLE

ANGEVTFKVPYGGLIYIKGDSKDDVSANFTFTGVVKAPFYKDGEWKNDLDSPAPLGELES

ASFVYTTPKKNLEASNFTGGVAEFAKDLDTFASSMNDFYGRNDEDGKHRMFTYKNLTGHK

HRFTNDVQISIGDAHSGYPVMNSSFSTNSTTLPTTPLNDWLIWHEVGHNAAETPLNVPGA

TEVANNVLALYMQDRYLGKMNRVADDITVAPEYLDESNGQAWARGGAGDRLLMYAQLKEW

AEEENFDIKQWYPDGELPKFYSDRKGMKGWNLFQLMHRKARGDDVGNSTFGGKNYCAESNG

NAADTLMLCASWVAQADLSEFFKKWNPGASAYQLPGATEMSFQGGVSSSAYSTLASLKLP

KPEKGPETINKVTEHKMSAE*
```

Preferred orf3526 sequences of the invention match the consensus sequence as recited in SEQ ID NO:54, or are immunogenic fragments thereof. Other preferred orf3526 sequences of the invention match the consensus sequence as recited in SEQ ID NO:55, or are immunogenic fragments thereof. X represents any amino acid. Other preferred orf3526 sequences further contain a sequence motif at those positions that correspond to positions 1304-1308 of SEQ ID NO:8, selected from: XEVGH, XXVGH, XEVGX, HXVGX and XXVGX, wherein in any such sequence motif X is not H or E; or X is not H, E or D; or X is not H, E, D, N, Q or C; or X is a non-polar amino acid, or X is selected from A or G, or X is preferably A. In further embodiments, residues 1-23 or 1-33 of SEQ ID NO:54 or SEQ ID NO:55 are lacking.

```
>consensus_sequence_75%
                                        (SEQ ID NO: 54)
MNKKEKYKKSLLAAILSATLLAGCDGGGSGSSSDTPXVDSGXGXLPEVKP

DPTPXPEPTPEPTPDPEPTPXPTPDPEPTPEPEPEPVPTKTGYLTLGGSQ

RVTGATCNGESSDGFTFTPGXXVXCVXGXXTTIATEBTQSEAARSLRAVX

KVSFSLEDAQELAXSXBKKXNAXSLVTSXBSCPABXEQXCLXFSSVXXXX

RFXXLYKQIDLAXXXFXKLVNEEVENNAATDKAPSTHTSXVVPVTTXGTK

PDLNASEVSANAEQFYQYQPTEIILSEGXLVDSXGXGVXGVBYYTXSGRG

VTXENGXFSFSWGETISEGIDTFELGSVRGNKSTIALTELGDEVRGANID

QLIFIRYSXXGXNBTRVVPDXVRKVFAEYPNVINEIINLSLSNGATLXEG

XQXVXLPNEFIEQFXTGQAKEIDTAICAKTXGCNEARWFSLTTRNVNDGQ

IQGVINKLWGVDXBYXSVXKFHVEHDSTNEYGSTGNARGQAVVNISNAAF

PILMARNDKNYWLAFGEKRAWDKNELAYITEAPSJVZPENVTRDTATENL

PFISLGQVGXGKLMVIGNPHYNSILRCPNGYSWXGGVNXXGZCTLXXDXD

DMKXFMZNVLRYLSBDXWXPBXKXXMTVGTNLXXVYFKXHGQVXGNSAXF

XFHXDFXGIXVXXLXSYGDLBPZEXPLLILNGFEYVTQXGXDPYAXPLRA

DTSKPKLTQQDVTDLIAYLNKGGSVLIMENVMSNLKEESASXFVRLLDAA
```

```
            -continued
GLSMALNKSVVNNDPQGYPBRVRQXRATGIWVYERYPAXDGXXXPYTIDX

XTGEVXWKYQXXNKPDDKPKLEVASWXEXVXGKQXTRYAFIDEAXXXTXX

SLXAAKXKIXXXFPGLXECKDXXYHYEXNCLEXRPGTXVPVTGGMYVPXY

TQLXLXADTAKAMVQAADLGTNIQRLYQHELYERTNGXKGERLXSVDLER

LYQNMSVWLWNXXXYRYEXXKXDELGEKTFTEFLNCYANDAYXXGTXCSA

XLKKSLVDNXMIYGXXSXKAGMMNPSYPLNYMEKPLTRLMLGRSWWDLNI

KVDVEKYPGXVSXXGZXVTEXISLYSNPTKWFAGNMQSTGLWAPAQXEVT

IXSXAXVPVTVTVALADDLTGREKHEVALNRPPXVTKTYXLXAXGXVXFK

VPYGGLIYIKGBSXXBXSAXFTFTGVVKAPFYKDGXWKNXLBSPAPLGEL

ESXXFVYTTPKKNLXASNXTGGXXZFAXDLDTFASSMNDFYGRBXEXGKH

RMFTYKXLTGHKHRFTNDVQISIGDAHSGYPVMNSSFSTNSTTLPTTPLN

DWLIWHEVGHNAAETPLXVPGATEVANNVLALYMQDRYLGKMNRVADDIT

VAPEYLXESNGQAWARGGAGDRLLMYAQLKEWAEKNEDIKXWYPXGXLPX

FYSXREGMKGWNLFQLMHRKARGDXVGXXXFGXXXNYCAESNGNAADTLML

CASWVAQTDLSEFFKKWNPGANAYQLPGAXEMSFEGGVSQSAYXTLAXLX

LPKPZXGPETINXVTEHKMSAE

>consensus_sequence_100%
                                        (SEQ ID NO: 55)
MNKKFKYKKSLLAAILSATLLAGCDGGGSGXSSDTPXXDSGXGXLPXVKP

DPTPXXXXXXXXXXXXXXXXXXXXXXXXXXXPXXXPEXXXXPVTKTGYL

XLGGSXRXTGXXXCNXEXSDGFTFXXGXXVXCVXGXXTTIATEBTQSEAA

RSLRAVXKVSFSLEDAXELAXSXBKKXNAXSLVTXXBSCPABXEQXCLXF

SSVXXXXRFXXLYKQIXLXXXXFXKLVNEEVENNAATDKAPSTHTSXXVP

XTTXGTXPDLNASEVSANAEQXYQYQPXEIIXSEGXLVXSXGXGVXGVBY

YTXXGRGVTXENGXFXFSWGEXXSEGIDTFELGSVRGNKSTIALTELGDE

VRGANIDQUEIRXSXXXXNXXRXVPXXVRXVFAXYPNVINEIINLSLSNG
```

-continued

```
XXLXEGXQXXXXXNXFJEQXXXGQXXEIDTAICXXXXGCNXXRWFSLTXR

NVNXGXIQXVINKLWGVDXXYXSVXKFHVFEIDSTNEYGSTGNARGQAVX

NISNXAFPILMARNDKNYWLAFGEKRAWDKNXLAYITEAPSJVXXENVTR

XTAXENLPFISLGQVGXGKLMVIGNPHYNSILRCPNGYSWXGXVBXXGZC

TXXXDXBDMKXEMZNVLRYLSBXXWXPBXKXXMTVGTNLXXVYFKXXGQV

XGXXAXFXFHXDFXGIXXXXXXSYGBLBPXXXPLLILNGFEYVTQXXXDP

YXXPLRADTSKPKLXQQDVTDLIAYXNKGGXVLIMENVMSNLKEESASXF

VRLLDAAXLSMALNKSVVNXDPQGYPBRXRQXRXXXIWVYERYPXXXXXX

XPYTIBXXTXXVXWKYQXXXKXDXKPKLEVASWXEXVXGXQXXXXAFIDX

AXXXTXXXLXAAKXXIXXXFXGLXXCXBXXYHYEXNCLEXRXGXXVPXTX

XXXXGMXVPXYTQLXLXADTAKAMXQAADXGTNIQRLYQHELYERTXGXX

GERLXXVDLERLYQNXSVWLWNXXXYXYXXXKXDELGEKTFTEFLNCYXN

BAYXXGTXCSXXLKXSLXDNXMIYGXXXXXKAGMMNPXYPLNYMEKPLTR

LMLGRSWWDLNIKVDVEXYPGXVXXXGZXVTZXIXLYSXPTKWFAGNMQS

TGLXAPAXXXVXIXSXXXVXVTVTVAXADDLTGREKHEVXLNRPPXVTKT

YXLXAXXXVXFXVPYGGLIYIKXBSXXXXXSAXFTFXGVVKAPFYKBGXW

XXXXXSPAPLGELESXXFVYTXPKXNLXAXXXSNXXXGXXZFAXXLDTFA

XSMNDFXGRBXXXGXHXMFTXXXLXGHKHRFXNDVQISIGDAHSGYPVMN

SSFSXBSXTLPTXPLNDWLIWHEXGHNAAETPLXVPGATEVANXVLALYM

QDRYLGKMNRVADDITVAPEYLXESNXQAWARGGAGDRLLMYAQLKEWAE

XNFDIXXWYPXGXXLPXFXSXRXGMKGWNLFQLMHRKAXGDXVXXXXFGX

XNYCAESNGNXADXLMLCASWVAQXDLSXFFKKWNPGAXAYQLPGXXEMX

FXXGVXXSAYXTLAXXXLXKPXXGPEXXNXVTEXXMXXE
```

GspK (Orf3515)

gspK general secretion pathway protein is referred to herein as 'orf3515.' 'orf3515' protein from *E. coli* NMEC is disclosed in WO2006/089264 (SEQ IDs 7029 & 7030) is also known as: 'orf3332' from *E. coli* NMEC strain IHE3034, 'c3702' from CFT073 and ecp_3039 from 536.

When used according to the present invention, orf3515 protein may take various forms. Preferred orf3515 sequences have 80% or more identity (e.g. 80%, 85%, 90%, 95%, 96%, 97%, 98%, 99% or more) to SEQ ID NOs 29 and 30. This includes variants (e.g. allelic variants, homologs, orthologs, paralogs, mutants etc).

>orf03515

(SEQ ID 29)

```
ATGATCACCTCACCACCAAAACGCGGAATGGCACTGGTCGTGGTGCTGGT

ATTGCTGGCGGTTATGATGCTGGTGACCATCACGCTTTCCGGGCGGATGC

AGCAACAACTTGGGCGAACGCGCAGCCAGCAGGAGTACCAGCAGGCGCTG

TGGTACAGCGCCAGTGCAGAAAGCCTGGCGCTGAGCGCGCTCAGTCTGAG

CCTGAAAAATGAAAAGCGTGTGCATCTGGCACAACCGTGGGCTTCTGGCC

CGCGTTTTTTCCCACTGCCGCAGGGGCAAATTGCCGTCACTCTGCGTGAC

GCACAGGCCTGCTTTAACCTGAATGCCCTCGCTCAGCCGACGACGGCGTC

GCGTCCGCTCGCGGTACAACAACTGATTGCCCTGATCTCGCGCCTCGATG

TGCCTGCTTATCGGGCCGAACTGATAGCCGAAAGCCTGTGGGAGTTTATT

GACGAAGACCGCAGCGTGCAGACGCGTCTGGGTCGTGAAGACAGCGAGTA

TCTCGCCCGCTCGGTGCCGTTCTACGCCGCTAATCAACCGCTGGCTGATA

TCAGCGAGATGCGCGTGGTGCAGGGAATGGACGCCGGGCTTTATCAAAAA

CTGAAACCGTTGGTCTGTGCGCTGCCGATGGCCCGCCAGCAAATCAACAT

CAATACATTAGATGTCACGCAAAGTGTGATTCTTGAGGCGCTGTTTGACC

CGTGGTTAAGCCCTGTTCAGGCGCGGGCATTATTACAACAACGTCCGGCG

AAGGGCTGGGAAGATGTCGATCAGTTTCTTGCTCAGCCGCTACTTGCAGA

CGTCGATGAGCGTACTAAAAAACAGCTAAAAACCATCCTGAGCGTGGACA

GCAATTACTTCTGGCTGCGTTCAGATATCACCGTGAATGAGATTGAACTG

ACGATGAATTCGTTAATTGTCCGCATGGGCCCACAACACTTTTCTGTTCT

CTGGCATCAGACAGGAGAAAGTGAG
```

>orf03515

(SEQ ID 30)

```
MITSPPKRGMALVVVLVLLAVMMLVTITLSGRMQQQLGRTRSQQEYQQAL

WYSASAESLALSALSLSLKNEKRVHLAQPWASGPRFFPLPQGQIAVTLRD

AQACFNLNALAQPTTASRPLAVQQLIALISRLDVPAYRAELIAESLWEFI

DEDRSVQTRLGREDSEYLARSVPFYAANQPLADISEMRVVQGMDAGLYQK

LKPLVCALPMARQQININTLDVTQSVILEALFDPWLSPVQARALLQQRPA

KGWEDVDQFLAQPLLADVDERTKKQLKTILSVDSNYFWLRSDITVNEIEL

TMNSLIVRMGPQHFSVLWHQTGESE
```

Particular compositions of the invention will comprise a combination of (i) bacterial Ig-like domain protein (orf405B) having the amino acid sequence set forth in SEQ ID NO:2 or a protein having at least 80% similarity thereto, and (ii) putative Lipoprotein (orf3526) having the amino acid sequence set forth in SEQ ID NO:8 or a protein having at least 80% similarity thereto.

Other particular compositions of the invention will further comprise (iii) upec1232 having the amino acid sequence set forth in SEQ ID NO:4 or a protein having at least 80% similarity thereto.

More particularly the immunogenic components of a composition of the invention will consist essentially of (i) bacterial Ig-like domain protein (orf405B) having the amino acid sequence set forth in SEQ ID NO:2 or a protein having at least 80% similarity thereto, and (ii) putative Lipoprotein (orf3526) having the amino acid sequence set forth in SEQ ID NO:8 or a protein having at least 80% similarity thereto. The composition can additionally include non-immunogenic components.

Other particular immunogenic components of a composition of the invention will consist essentially of (i) bacterial Ig-like domain protein (orf405B) having the amino acid sequence set forth in SEQ ID NO:2 or a protein having at least 80% similarity thereto, and (ii) putative Lipoprotein (orf3526) having the amino acid sequence set forth in SEQ ID NO:8 or a protein having at least 80% similarity thereto, and (iii) upec1232 having the amino acid sequence set forth in SEQ ID NO:4 or a protein having at least 80% similarity thereto. The composition can additionally include non-immunogenic components.

Particularly, the compositions of the invention may further comprise at least one bacterial toxin. Particularly, the toxin is derived from *E. coli* (i.e., *E. coli* heat labile enterotoxin "LT"), cholera ("CT"), or pertussis ("PT").

The use of detoxified ADP-ribosylating toxins as mucosal adjuvants is described in WO95/17211 and as parenteral adjuvants in WO98/42375.

Particular detoxified LT mutants include LT-K63, LT-R72, and LTR192G. Preferably, the bacterial toxin will be a mutant or modified bacterial toxin. In a preferred embodiment the bacterial toxin is the modified heat-labile toxin of *Escherichia coli* (LTK63).

The use of ADP-ribosylating toxins and detoxified derivatives thereof, particularly LT-K63 and LT-R72, as adjuvants can be found in the following references, each of which is specifically incorporated by reference herein in their entirety: Beignon, et al., "The LTR72 Mutant of Heat-Labile Enterotoxin of *Escherichia coli* Enhances the Ability of Peptide Antigens to Elicit CD4 T Cells and Secrete Gamma Interferon after Coapplication onto Bare Skin", Infection and Immunity (2002) 70(6):3012-3019; Pizza, et al., "Mucosal vaccines: non toxic derivatives of LT and CT as mucosal adjuvants", Vaccine (2001) 19:2534-2541; Pizza, et al., "LTK63 and LTR72, two mucosal adjuvants ready for clinical trials" Int. J. Med. Microbiol (2000) 290(4-5):455-461; Scharton-Kersten et al., "Transcutaneous Immunization with Bacterial ADP-Ribosylating Exotoxins, Subunits and Unrelated Adjuvants", Infection and Immunity (2000) 68(9):5306-5313; Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" Infection and Immunity (1999) 67(12):6270-6280; Partidos et al., "Heat-labile enterotoxin of *Escherichia coli* and its site-directed mutant LTK63 enhance the proliferative and cytotoxic T-cell responses to intranasally co-immunized synthetic peptides", Immunol. Lett. (1999) 67(3):209-216; Peppoloni et al., "Mutants of the *Escherichia coli* heat-labile enterotoxin as safe and strong adjuvants for intranasal delivery of vaccines", Vaccines (2003) 2(2):285-293; and Pine et al., (2002) "Intranasal immunization with influenza vaccine and a detoxified mutant of heat labile enterotoxin from *Escherichia coli* (LTK63)" J. Control Release (2002) 85(1-3):263-270. Numerical reference for amino acid substitutions is preferably based on the alignments of the A and B subunits of ADP-ribosylating toxins set forth in Domenighini et al., Mol. Microbiol (1995) 15(6):1165-1167, specifically incorporated herein by reference in its entirety.

Thus, in the context of the invention, the word "toxin" is intended to mean toxins that have been detoxified such that they are no longer toxic to humans, or a toxin subunit or fragment thereof that is substantially devoid of toxic activity in humans.

Other detoxified toxins include the B subunit from *E. coli* labile toxin (LT), the amino terminal domain of the anthrax lethal factor (LF), *P. aeruginosa* exotoxin A, adenylate cyclase A from B. Pertussis, a derived or mutant from a toxin which is a family of the ABS family, for example, the cholera toxin (CT), the Bordatella Pertussis toxin (PT) as well as the recently identified subtilase cytotoxins. (Paton et al, J Exp Med 2004, Vol 200 pp 35-46).

The labile toxin (LT) of *E. coil* consists of two subunits, a pentameric B subunit and a monomeric A subunit. The A subunit is responsible for toxicity, whilst the B subunit is responsible for transport into the cell. LT binds the G M1 ganglioside receptor.

A derivative of *E. coli* heat-labile toxin with equal or greater the 90% homology has greater than 90% homology at the amino acid level. In another embodiment the protein has equal or greater than 95% homology, for example 96, 97, 98 or 99%. For example, amino acid deletions may be made that do not affect function. In a further embodiment, a derivative is still able to bind the G M1 ganglioside receptor.

Thus, particular compositions of the invention include combinations of at least two, at least three, at least four or five *E. coli* antigens selected from the group consisting of orf405B, upec1232, orf3526, orf3515 and LTK63. Particular compositions of the invention include no more than two, no more than three, no more than four or no more than five antigens selected from the group consisting of orf405B, upec1232, orf3526, orf3515 and LTK63. Yet more particularly, compositions of the invention consist of, or consist essentially of, a combination of two, three, four or five antigens selected from the group consisting of orf405B, upec1232, orf3526, orf3515 and LTK63. Particular combinations include the following *E. coli* antigen(s)/immunogenic components:

Orf405B+orf3526
Orf405B+upec1232+orf3526
Orf405B+upec1232+orf3526+orf3515
Orf405B+orf3526+LTK63
Orf405B+upec1232+orf3526+LTK63
Orf405B+upec1232+orf3526+orf3515+LTK63

Antigen orf3526 comprises a zinc binding motif which encompasses amino acids at positions 1304-1308 (HEVGH underlined in SEQ ID 8) with reference to SEQ ID 8. Since this zinc binding motif may be associated with toxicity, orf3526 polypeptides which lack or have reduced zinc binding activity are particularly useful in combinations of the present invention. Preferably, zinc binding activity of a mutant orf3526 protein is either reduced by or reduced to at least 50%, at least 45%, at least 40%, at least 35%, at least 30%, at least 25%, at least 20%, at least 15%, at least 10% or at least 5% relative to or compared to wild-type orf3526. Zinc binding can be determined by atomic absorption and other assays will be known to one skilled in the art. Thus, mutations in the zinc binding motif are useful in reducing zinc binding and associated toxicity. For example, mutations in the zinc binding motif from wild-type HEVGH to AEVGH can reduce zinc binding to about 43% or more particularly, mutations from wild-type to AAVGA can reduce zinc binding to around 5%. Surprisingly an orf3526 mutant which comprises the AAVGA sequence has the added advantage that it co-elutes with native orf3526 and is present in only two isoforms (a monomer and truncated form) meaning that the efficiency of purification is simplified and significantly improved in comparison with other mutants tested. Compositions of the invention may comprise orf3526 mutants comprising a sequence motif selected from XEVGH, XXVGH, XEVGX, HXVGX or XXVGX, wherein in any such sequence motif X is not H or E; or X is not H, E or D; or X is not H, E, D, N, Q or C; or X is a non-polar amino acid, or X is selected from A or G, or X is preferably A.

Advantageously, vaccine combinations of the present invention may be used in combination with a Group B Streptococcus vaccine to prevent most cases of neonatal meningitis. Thus, in certain embodiments, the combinations of the invention may include: (i) one or more further, non *E. coli*, polypeptides that elicit antibody responses against Group B Streptococcal (GBS) proteins; (ii) a capsular saccharide from Group B Streptococcus; and/or (iii) one or more further immunogens that elicit antibody responses that recognise epitopes on non-GBS organisms. In other embodiments, the immunogenic combinations of the present invention are administered separately at substantially the same time as a GBS vaccine.

Particular GBS polypeptides include: 'GBS80' (SAG0645) a cell wall surface anchor family protein (see GI: 22533660); 'GBS1523' (SAN1518; SpbI), a cell wall surface anchor family protein (see GI: 77408651); 'GBS104' (SAG0649) (see GI: 22533664); 'GBS67' (SAG1408), a cell wall surface anchor family protein (see GI: 22534437); 'GBS59', a pilus backbone protein encoded by pathogenicity island 2a (BP-2a); 'GBS3' (SAG2603; BibA), a pathogenicity protein (see GI:22535109); 'SAN1485', a cell wall surface anchor family protein '(see GI: 77408233); 'GBS147' (SAG0416), a putative protease (see GI: GI:22533435); 'GBS328' (SAG1333) a 5'-nucleotidase family protein' (see GI: 22534359).

Immunogenic Compositions and Medicaments

The Polypeptides described above are useful as active ingredients (immunogens) in immunogenic compositions of the invention, and such compositions may be useful as vaccines.

Immunogenic compositions will be pharmaceutically acceptable. They will usually include components in addition to the antigens e.g. they typically include one or more pharmaceutical carrier(s), excipient(s) and/or adjuvant(s). Thorough discussions of vaccine adjuvants are available in refs. 6 and 7.

Compositions will generally be administered to a mammal in aqueous form. Prior to administration, however, the composition may have been in a non-aqueous form. For instance, although some vaccines are manufactured in aqueous form, then filled and distributed and administered also in aqueous form, other vaccines are lyophilised during manufacture and are reconstituted into an aqueous form at the time of use. Thus a composition of the invention may be dried, such as a lyophilised formulation.

The composition may include preservatives such as thiomersal or 2-phenoxyethanol. It is preferred, however, that the vaccine should be substantially free from (i.e. less than 5 μg/ml) mercurial material e.g. thiomersal-free. Vaccines containing no mercury are more preferred. Preservative-free vaccines are particularly preferred.

To improve thermal stability, a composition may include a temperature protective agent.

To control tonicity, it is preferred to include a physiological salt, such as a sodium salt. Sodium chloride (NaCl) is preferred, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human vaccines are typically administered in a dosage volume of about 0.5 ml, although a half dose (i.e. about 0.25 ml) may be administered to children.

In certain embodiments the vaccine composition will comprise one or more pharmaceutically acceptable carriers, diluents and/or adjuvants. Adjuvants which may be used in compositions of the invention include, but are not limited to:

mineral salts, such as aluminium salts and calcium salts, including hydroxides (e.g. oxyhydroxides), phosphates (e.g. hydroxyphosphates, orthophosphates) and sulphates, etc. [e.g. see chapters 8 & 9 of ref. 8];

oil-in-water emulsions, such as squalene-water emulsions, including MF59 (5% Squalene, 0.5% Tween 80, and 0.5% Span 85, formulated into submicron particles using a microfluidizer) [Chapter 10 of ref. 6, see also ref. 9-10, chapter 10 of ref. 11 and chapter 12 of ref. 12], complete Freund's adjuvant (CFA) and incomplete Freund's adjuvant (1FA);

saponin formulations [chapter 22 of ref. 6], such as QS21 [13] and ISCOMs [chapter 23 of ref. 6];

virosomes and virus-like particles (VLPs) [14-15];

bacterial or microbial derivatives, such as non-toxic derivatives of enterobacterial lipopolysaccharide (LPS), Lipid A derivatives [16, 17], immunostimulatory oligonucleotides [18-19], such as IC-31™ [20] (deoxynucleotide comprising 26-mer sequence 5'-(IC)$_{13}$-3' (SEQ ID NO:56) and polycationic polymer peptide comprising 11-mer amino acid sequence KLKLLLLLKLK (SEQ ID NO:57)) and ADP-ribosylating toxins and detoxified derivatives thereof [21-22];

human immunomodulators, including cytokines, such as interleukins (e.g. IL-1, IL-2, IL-4, IL-5, IL-6, IL-7, IL-12 [23, 24], interferons (e.g. interferon-γ), macrophage colony stimulating factor, and tumor necrosis factor;

bioadhesives and mucoadhesives, such as chitosan and derivatives thereof, esterified hyaluronic acid microspheres [25] or mucoadhesives, such as cross-linked derivatives of poly(acrylic acid), polyvinyl alcohol, polyvinyl pyrollidone, polysaccharides and carboxymethylcellulos [26];

microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.);

liposomes [Chapters 13 & 14 of ref. 6, ref. 27-28];

polyoxyethylene ethers and polyoxyethylene esters [29];

PCPP formulations [30 and 31];

muramyl peptides, including N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE); and imidazoquinolone compounds, including Imiquamod and its homologues (e.g. "Resiquimod 3M") [32 and 33].

The invention may also comprise combinations of one or more of the adjuvants identified above. For example, the following adjuvant compositions may be used in the invention: (1) a saponin and an oil-in-water emulsion [34]; (2) a saponin (e.g. QS21)+a non-toxic LPS derivative (e.g. 3dMPL) [35]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [36]; (5) combinations of 3dMPL with, for example, QS21 and/or oil-in-water emulsions [37]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 6.

The use of an aluminium hydroxide and/or aluminium phosphate adjuvant is useful, particularly in children, and antigens are generally adsorbed to these salts. Squalene-in-water emulsions are also preferred, particularly in the elderly. Useful adjuvant combinations include combinations of Th1 and Th2 adjuvants such as CpG & alum or resiquimod & alum. A combination of aluminium phosphate and 3dMPL may be used.

The compositions of the invention may elicit both a cell mediated immune response as well as a humoral immune response.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-(3), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

A composition may include a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

Infections can affect various areas of the body and so the compositions of the invention may be prepared in various forms. For example, the compositions may be prepared for parenteral administration as injectables, either as liquid solutions or suspensions. Solid forms suitable for solution in, or suspension in, liquid vehicles prior to injection can also be prepared (e.g. a lyophilised composition or a sprayfreeze dried composition). The composition may be prepared for topical administration e.g. as an ointment, cream or powder. The composition may be formulated for administration using a 'vaccine patch' or plaster. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Delivery methods including parenteral injection (e.g., subcutaneous, intraperitoneal, intravenous, intramuscular, or interstitial injection) and rectal, oral (e.g., tablet, spray), vaginal, topical, transdermal are disclosed in WO 99/27961, transcutaneous methods in WO02/074244 and WO02/064162, intranasal in WO03/028760. Other routes of administration include ocular, aural, and pulmonary or other mucosal administration.

Particularly the compositions of the present invention may be administered via a systemic route or a mucosal route or a transdermal route or it may be administered directly into a specific tissue. As used herein, the term "transdermal delivery" includes intradermal (e.g., into the dermis or epidermis) and transdermal (e.g. "percutaneous") i.e., delivery by passage of an agent into or through at least a top layer of skin. As used herein, the term "systemic administration" includes but is not limited to any parenteral routes of administration. In particular, parenteral administration includes but is not limited to subcutaneous, intraperitoneal, intravenous, intraarterial, intramuscular, or intrasternal injection, intravenous, intraarterial, or kidney dialytic infusion techniques. Generally, the systemic, parenteral administration is intramuscular injection. As used herein, the term "mucosal administration" includes but is not limited to oral, intranasal, intravaginal, intrarectal, intratracheal, intestinal and ophthalmic administration. Novel direct delivery forms can also include transgenic expression of the combinations of polypeptides in foods, e.g., transgenic expression in a potato.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Pharmaceutically Acceptable Carriers

Compositions of the invention will typically, in addition to the components mentioned above, comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, etc. Additionally, an auxiliary substance, such as a wetting or emulsifying agent, pH buffering substance, and the like, may be present. A thorough discussion of pharmaceutically acceptable components is available in Gennaro (2000) Remington: The Science and Practice of Pharmacy. 20th ed., ISBN: 0683306472. The compositions of the invention may be prepared in various forms (e.g., liquid, lyophilized), as is known in the art.

Methods of Treatment, and Administration of Immunogenic or Vaccine Compositions of the Invention The invention also provides a method for raising an immune response in a subject, particularly a mammal, comprising the step of administering an effective amount of a composition of the invention. The immune response is preferably protective and preferably involves antibodies and/or cell-mediated immunity. The method may raise a booster response.

The invention also provides immunogenic combinations or compositions for use as a medicament e.g. for use in raising an immune response in a subject, such as a mammal.

The invention also provides the use of a combination of polypeptides or a composition of the invention in the manufacture of a medicament for raising an immune response in a subject, such as a mammal.

The invention also provides a delivery device pre-filled with an immunogenic composition of the invention.

By raising an immune response in the subject by these uses and methods, the subject, for example a mammal, can be protected against *E. coli* infection, e.g. more than one *E. coli* pathotype, including ExPEC and non-ExPEC strains. The invention is particularly useful for providing broad protection against pathogenic ExPEC *E. coli*, including intestinal pathotypes such as EPEC, EAEC, EIEC, ETEC and DAEC (Diffuse-adhering *Escherichia coli*) pathotypes. Thus the subject may be protected against diseases including, but not limited to peritonitis, pyelonephritis, cystitis, endocarditis, prostatitis, urinary tract infections (UTIs), meningitis (particularly neonatal meningitis), sepsis (or SIRS), dehydration, pneumonia, diarrhea (infantile, travellers', acute, persistent, etc.), bacillary dysentery, hemolytic uremic syndrome (HUS), pericarditis, bacteriuria, etc.

The subject is preferably a mammal, particularly a human, but by way of non-limiting example, may also be a cow, a pig, a sheep, a horse, a cat or a dog since *E. coli* disease is also problematic in these species. In certain embodiments the subject may be an avian subject such as, for example, a chicken, goose, turkey and the like.

Where the vaccine is for prophylactic use, the human is particularly a child (e.g. a toddler or infant) or a teenager; where the vaccine is for therapeutic use, the human is particularly a teenager or an adult. A vaccine intended for children may also be administered to adults e.g. to assess safety, dosage, immunogenicity, etc.

One way of checking efficacy of therapeutic treatment involves monitoring *E. coli* infection after administration of the compositions of the invention. One way of checking efficacy of prophylactic treatment involves monitoring immune responses, systemically (such as monitoring the level of IgG1 and IgG2a production) and/or mucosally (such as monitoring the level of IgA production), against the antigens in the compositions of the invention after administration of the composition. Typically, antigen-specific serum antibody responses are determined post-immunisation but pre-challenge whereas antigen-specific mucosal antibody responses are determined post-immunisation and post-challenge.

Another way of assessing the immunogenicity of the compositions of the present invention is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within antigens.

The efficacy of compositions of the invention can also be determined in vivo by challenging animal models of E. coli infection, e.g., guinea pigs or mice, with the vaccine compositions. A murine model of ExPEC and lethal sepsis is described in reference 38. A cotton rat model is disclosed in ref. 39

Dosage treatment can be a single dose schedule or a multiple dose schedule. In some embodiments, compositions of the invention are administered in combination with an antibiotic treatment regime. In one embodiment, the antibiotic is administered prior to administration of a composition of the invention. In another embodiment, the antibiotic is administered subsequent to the administration of a composition of the invention.

Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines of the invention may be used to treat both children and adults. Thus a human patient may be less than 1 year old, 1-5 years old, 5-15 years old, 15-55 years old, or at least 55 years old. Particular patient groups for receiving the vaccines are the elderly (e.g. ≥50 years old, ≥60 years old, and preferably ≥65 years), the young (e.g. ≤5 years old), hospitalised patients, healthcare workers, armed service and military personnel, travellers, pregnant women, the chronically ill, or immunodeficient patients. The vaccines are not suitable solely for these groups, however, and may be used more generally in a population.

Vaccines of the invention are particularly useful for patients who are expecting a surgical operation, or other hospital in-patients. They are also useful in patients who will be catheterized. They are also useful in adolescent females (e.g. aged 11-18) and in patients with chronic urinary tract infections.

Vaccines of the invention may be administered to patients at substantially the same time as (e.g. during the same medical consultation or visit to a healthcare professional or vaccination centre) or in combination with other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated H. influenzae type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a Streptococcal vaccine such as a Group A Streptococcal vaccine or a Group B Streptococcal vaccine etc.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 40-41, etc.

In some implementations, the term "comprising" refers to the inclusion of the indicated active agent, such as recited polypeptides, as well as inclusion of other active agents, and pharmaceutically acceptable carriers, excipients, emollients, stabilizers, etc., as are known in the pharmaceutical industry. In some implementations, the term "consisting essentially of" refers to a composition, whose only active ingredient is the indicated active ingredient(s), however, other compounds may be included which are for stabilizing, preserving, etc. the formulation, but are not involved directly in the therapeutic effect of the indicated active ingredient. Use of the transitional phrase "consisting essentially" means that the scope of a claim is to be interpreted to encompass the specified materials or steps recited in the claim, and those that do not materially affect the basic and novel characteristic(s) of the claimed invention. See, In re Herz, 537 F.2d 549, 551-52, 190 USPQ 461, 463 (CCPA 1976) (emphasis in the original); see also MPEP § 2111.03. Thus, the term "consisting essentially of" when used in a claim of this invention is not intended to be interpreted to be equivalent to "comprising".

The term "about" in relation to a numerical value x means, for example, x±10%.

"GI" numbering is used herein. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

References to a percentage sequence identity between two amino acid sequences means that, when aligned, that percentage of amino acids are the same (i.e. identical) in comparing the two sequences, relative to the longest of the sequences. This alignment and the percent homology or sequence identity can be determined using software programs known in the art. A preferred alignment is determined by the Smith-Waterman homology search algorithm using an affine gap search with a gap open penalty of 12 and a gap extension penalty of 2, BLOSUM matrix of 62.

While certain embodiments of the present invention have been described and specifically exemplified above, it is not intended that the invention be limited to such embodiments. Various modifications may be made thereto without departing from the scope and spirit of the present invention as set forth in the following claims.

MODES FOR CARRYING OUT THE INVENTION

Example 1

Bacterial Ig-like domain (group 1) protein (orf405), gspK (orf3515), upec-1232, and orf3526, each as more fully described herein, have been expressed, sequenced and purified. Sequences were obtained for the orthologs in various other E. coli strains. Distribution of each of the candidate antigens were determined in most pathogenic strains, specifically NMEC, APEC, UPEC, EHEC, EAEC, EIEC, EPEC, ETEC and AIEC. The presence of each of the antigens is shown in FIGS. 1A and B.

Example 2

Antigens were PCR amplified from the genomic DNA templates, cloned in pET-21b vectors (Novagen) and transformed in DH5α-T1 chemically competent cells for propagation (Invitrogen). BL21 (DE3) chemically competent cells were used for expression. All candidates were cloned and expressed without the signal sequence and as His-tag fusion proteins. Candidates were purified by affinity chromatography.

| Antigen | Homology | Size (kDa) | Solubility | Yield (mg/L of growth) | % Purity |
|---|---|---|---|---|---|
| Orf3526 | IHE3034/RS218/536 | 165 | + | 1.245 mg/L | 90% |
| Orf3515 | All | 31 | + | 16.7 mg/L | 95% |
| 405B | All | 46 | + | 5.3 mg/L | 95% |
| Upec1232 | CFT073 | | + | | 95% |

Example 3

Protection was evaluated in a sepsis animal model. CD1 out bred female mice (5 weeks old) from Charles River Italia were immunized by subcutaneous injections at the $1^{st}$, $21^{st}$ and $35^{th}$ days with 20 µg of recombinant protein in Freund's adjuvant. Positive control was immunized with $10^8$ heat-inactivated bacteria (65° C. for 30 minutes) in 0.15 ml of physiological solution in Freund's adjuvant (Sigma), while negative control was immunized with physiologic solution in Freund's adjuvant. Challenge was done at the $49^{th}$ day with a dose of $10^7$ of fresh bacterial culture/mouse ($LD_{80}$) by intraperitoneal (for strains IHE3034 and CFT073) or intravenous (for strain 536) injection. Heparinised-blood samples were collected from survived mice at 24 hours after challenge to determine bacteremia levels and the mortality was observed for four days after challenge.

| | Sepsis Animal Model | | |
|---|---|---|---|
| Candidate | Survival with vaccination (%) | Survival without vaccination (%) | P value |
| upec-1232 | 15/30 (50) | 3/36 (8) | 0.0002 |
| gspK (orf3515) | 30/110 (27) | 11/116 (9) | 0.0005 |
| 405B (bacterial Ig-like domain (group 1) protein fragment) | 17/63 (26) | 9/66 (13) | 0.07 |
| Orf3526 | 8/8 (100) | 2/8 (25) | — |

Example 3A

Protection was evaluated in a sepsis animal model. CD1 mice were immunized by subcutaneous injections at day 0, 21 and 35 with 20 µg of recombinant protein in Freund's complete adjuvant or alum. Positive control was immunized with $10^8$ heat-inactivated bacteria (65° C. for 30 minutes) in 0.15 ml of physiological solution in Freund's complete adjuvant or alum, while negative control was immunized with physiologic solution in Freund's complete adjuvant or alum. Challenge was done at the $49^{th}$ day with a dose of $10^7$ of fresh bacterial culture/mouse ($LD_{80}$) by intraperitoneal (for strains IHE3034 and CFT073) or intravenous (for strain 536) injection. Heparinised-blood samples were collected from survived mice at 24 hours after challenge to determine bacteremia levels and the mortality was observed for four days after challenge.

Protection Using Freud's Complete Adjuvant:

| | Sepsis Animal Model | | |
|---|---|---|---|
| Candidate | Survival with vaccination (%) | Protection rate | P value |
| upec-1232 | 15/30 (50) | 45% | 0.0002 |
| gspK (orf3515) | 30/110 (27) | 20% | 0.0009 |
| 405B | 25/81 (30) | 18% | 0.029 |
| Orf3526 | 125/149 (84) | 83% | <0.0001 |

Protection Using Alum-Homologous Challenge:

| | Sepsis Animal Model | | |
|---|---|---|---|
| Candidate | Survival with vaccination (%) | Protection rate | P value |
| upec-1232-His | 4/8 (50) | 43% | 0.28 |
| 405B-His | 11/40 (27.5) | 19% | 0.046 |
| Orf3526-native | 7/8 (87.5) | 87.5% | 0.0014 |
| Orf3526-His | 74/102 (72.5) | 70% | <0.0001 |

Protection Using Alum-Heterologous Challenge:

| | Sepsis Animal Model | | |
|---|---|---|---|
| Candidate | Survival with vaccination (%) | Protection rate | P value |
| Orf3526-His | 14/23 (61) | 48% | 0.018 |

Protection rate=((% dead control−% dead immune)/(% dead control))×100

Example 3C

Cross-protection was evaluated in a sepsis animal model by active or passive immunisation. Mice were immunized with antigen 3526-his in alum before challenge (active immunization) or administered anti-3526-his antibodies after challenge (passive immunisation). The sequence of 3526-his is based on the sequence of the native 3526 protein from the NMEC strain IHE3034. Mice were challenged with strains IHE3034, B616, IN1S or 9855/93. % PE (protective efficacy) was calculated as: 1−(% dead vaccinated/% dead control)×100.

| | Active immunisation | | Passive immunisation | |
|---|---|---|---|---|
| Challenge strain | % PE (survival) | P value | % PE (survival) | P value |
| IHE3034 (NMEC) | 70 (74/102) | <0.0001 | 100 (32/32) | <0.0001 |
| B616 (NMEC) | 85 (14/16) | 0.0002 | nd | nd |

-continued

| Challenge strain | Active immunisation | | Passive immunisation | |
|---|---|---|---|---|
| | % PE (survival) | P value | % PE (survival) | P value |
| IN1S (SEPEC) | 50 (23/40) | <0.0001 | 50 (20/32) | 0.0026 |
| 9855/93 (SEPEC) | 35 (11/24) | 0.03 | nd | nd |

The results show that 3526 from ExPEC-NMEC strain IHE3034 confers protection in actively immunized mice against at least three additional ExPEC strains (one NMEC and two SEPEC). The passive immunization experiments confirm cross-protection against at least one additional ExPEC strain (SEPEC).

Example 4

Protection was evaluated in a sepsis animal model according to the following schedule:

| Active immunization | Passive immunization |
|---|---|
| CD1 mice (4 week old) are immunized s.c. 20 μg antigen + Freund's adjuvant; 3 doses at 0, 21, 35 days | Mice or rabbit immune serum is administered i.v. to CD1 mice |
| 14 days after last immunization (11 weeks old mice) mice are infected at a lethal dose ($LD_{80}$) with pathogenic E. coli strains. | 24 h after passive immunization mice are challenged i.p. with IHE3034 strain |

Blood is collected from the tail at 24 hours to evaluate bacteremia
Mortality is monitored for 4 days after the infection and $$\text{Protection rate is calculated as} = \frac{(\% \text{ dead ctrl.} - \% \text{ dead immun})}{\% \text{ dead ctrl.}} \times 100$$

| Candidate | Survival (%) Vacc. | Survival (%) no Vacc. | P value* |
|---|---|---|---|
| Orf3515 | 21/64 (33) | 5/67 (7) | 0.0003 |
| 405B | 17/55 (31) | 7/58 (12) | 0.01 |
| Upec1232 | 8/23 (34) | 2/28 (7) | 0.03 |

Example 5

In order to study the gene distribution, genetic variability and protein expression of antigen orf3526, as well as to evaluate the effective vaccine coverage, we studied three different collections of human and animal isolates including different pathogenic (ExPEC, ETEC, EPEC) and faecal strains. Briefly, Genomic DNA was prepared by culturing bacteria overnight at 37° C. in atmosphere humidified with 5% $CO_2$ in LB (Difco). Chromosomal DNA was prepared from 1.5 mL of culture using the GenElute Bacterial Genomic DNA Kit (Sigma) according to the manufacturer's instructions. DNA concentration was calculated by optical density determination at 260 nm. About 100 ng of chromosomal DNA was used as template for the amplification of antigen orf3526. The amplification enzyme used was the Phusion® DNA Polymerase (Finnzymes). All genes were amplified using primers external to the coding region. Primers were designed in conserved DNA region and the sequences are reported in Table 1. Antigen orf3526 was amplified using primers ECOK1_3385_1 and ECOK1_3385_22. PCR conditions were as follows: 35 cycles of denaturation at 98° C. for 10 s, annealing at 55° C. for 20 s, and elongation at 72° C. for 3 min. PCR products were purified with Agencourt® AMPure® protocol (Beckman Coulter) and sequenced on the capillary sequencer ABI3730x1 DNA Analyzers (Applied Biosystems). Sequences were assembled with Sequencher 4.8 (Gene Codes) and aligned and analyzed using the Vector NT1 Suite 10.

TABLE 1

Primers list used for amplification and sequencing of orf3526 (Orf03343_1 to Orf03343_22 correspond to SEQ ID NOs 32 to 53)

| Orf03343_1 | TGATGCCGTTTTCTTAAGAATGGAGGAA |
| Orf03343_2 | GAGCCAGAACCTGTTCCTA |
| Orf03343_3 | GTAAAGCCATCGCTGGATTCA |
| Orf03343_4 | CCACCTCTTCATTGACCAGC |
| Orf03343_5 | CGGAACAGTTTTATCAGTAT |
| Orf03343_6 | CCCCGCGAACTTCATCAC |
| Orf03343_7 | GCAAGGTCTTTGCCGAGTATC |
| Orf03343_8 | TGATAAAAACTACTGGCTGGC |
| Orf03343_9 | GGTTACCGATAACCATCAG |
| Orf03343_10 | GCAGATACCAGCAAACCGA |
| Orf03343_11 | TCATCACGTTTTCCATGATCAGC |
| Orf03343_12 | GCGGATTTAGGCACCAACATTC |
| Orf03343_13 | GAATGTTGGTGCCTAAATCCGC |
| Orf03343_14 | GTGAACGTTTTAAAGCCCAGCTC |
| Orf03343_15 | AACTATATGGAAAAACCGCTGAC |
| Orf03343_16 | AAAGCGCCGTTCTATAAAGA |
| Orf03343_17 | TTATAGAACGGCGCTTTTAC |
| Orf03343_18 | CATCACCGATGGAGATCTGC |
| Orf03343_19 | AAGATGAACCGTGTCGCTGAC |
| Orf03343_20 | CTGGAACCTGTTCCAGTTGAT |
| Orf03343_21 | ATCAACTGGAACAGGTTCCAG |
| Orf03343_22 | TATTGCTGAAAAACATCAAAAAG |

Elisa Assay orf3526 antigen detection and relative quantification in supernatants (SN) was performed by an antibody-sandwich ELISA targeting orf3526 antigen with rabbit anti-orf3526 antigen polyclonal antibody and revealed by alkaline phosphatase-conjugated anti-rabbit antibody. Briefly, the wells of microtiter plates (Nunc, Maxi Sorp) were coated overnight at 4° C. with 0.22 μm-filtered bacterial supernatant. Unbound SN was washed out twice with a solution of PBS-Tween (0.05%) (PBS-T), and non-specific binding sites were blocked with a PBST-BSA (1%) solution for 1 h at 37° C. The plates were further washed another three times with PBS-T before rabbit anti-orf3526 polyclonal antibody serial dilutions were added to duplicate wells for 1 h 37 min at 37° C. After three washes with PBS-T, alkaline phosphatase-conjugated anti-rabbit polyclonal antibody was added. Subsequently, the microplates were incubated for 1 h at 37° C. and washed three times with PBST, before revelation by adding the enzyme substrate. After a 30-min incubation in the dark at room temperature, the reaction was stopped by adding 50 μl NaOH solution (3N). The plates were read at 405 nm in a microplate reader (TECAN).

Overall, ECOK1_3385 gene was present and expressed in more than 80% of the 417 strains analyzed, with an amino acid sequence identity never below 86%. In conclusion, the results presented here indicate that antigen orf3526 is well represented, conserved and expressed across pathogenic and faecal isolates indicating that this target may be a useful candidate for a broadly protective vaccine against E. coli (FIGS. 2A, 2B, and 2C).

Phylogenetic Reconstruction

Phylogenetic tree of 217 amino acid sequences of orf3526 antigen was computed using MEGA v.4 (ref Tamura K, Dudley J, Nei M, Kumar S (2007) MEGA4: Molecular Evolutionary Genetics Analysis (MEGA) software version 4.0. Mol Biol Evol 24: 1596-1599.) using the Neighbor Joining algorithm from distance matrices between protein sequences computed using the Maximum Composite Likelihood (ref. Tamura K, Nei M, Kumar S (2004) Prospects for inferring very large phylogenies by using the neighbor-joining method. Proc Natl Acad Sci USA 101: 11030-11035.) (FIGS. 3A-3D).

Example 6

Orf3526 is Protective in an Avian Model

Figure 4:
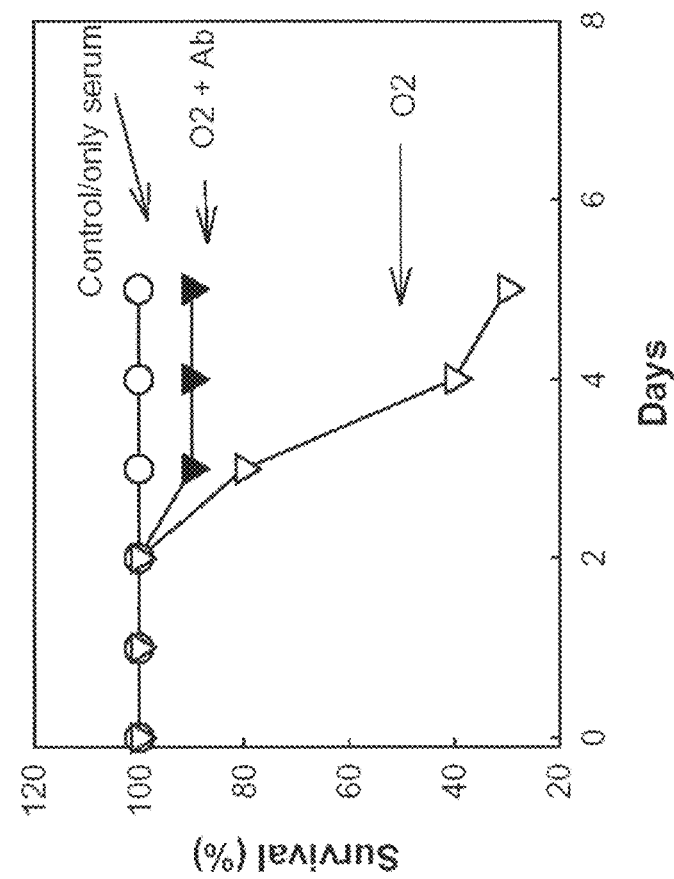
FIG. 4: Antibodies to antigen orf3526 were found to protect in passive immunization in an avian (chicken) model of sepsis.

Three day old chicks (Bar-On) were challenged i.p. with $5 \times 10^6$ of E. coli O2 strain 1772, in two injections of 0.2 ml each, 3 hours apart. Antibodies (anti-orf3526), 0.15 ml, were applied s.c. (neck) 20 min after the first injection. Antibodies to antigen orf3526 were found to protect in passive immunization in a chicken model of sepsis (FIG. 4).

Example 7

The purpose of this experiment was to evaluate the protective ability of conserved antigen orf3526 with and without LTK63 against diarrheal disease in piglets, caused by intestinal pathogenic K88 E. coli (ETEC).

Two studies were carried out:
1. 11NAHLW1019v: Production of Protein orf3526 Antiserum by Hyperimmunization (Phase I), Antiserum Oral Administration Pre-Challenge in Piglets (Phase II)
2. 11NAHLW1020v: ExPEC Antiserum Administration with Challenge Evaluation of orf3526 Protein The first experiment has been designed to generate antisera for the orf3526 protein with and without LTK63 in CD/CD swine followed by a pilot administration with minimum and maximum doses as well as controls to immunologically naive piglets to assess preliminary efficacy of anti-sera type products in the challenge model.

The second experiment is a randomized, blinded trial designed to evaluate the orf3526 protein given in the form of an anti-sera to immunologically naive piglets followed by oral K88 E. coli challenge.

The following material was utilised:
Purified recombinant orf3526 Protein
Purified recombinant orf3526 Protein+LTK63
Monoclonal Antibody to orf3526 for stability testing
Challenge K88 challenge culture (lot no. TBD) was thawed at room temperature (~23 degrees C.); pooled together, diluted 1:2 with sterile Peptone Buffer, 2.0 ml and re-dispensed into 3 ml cryovials and frozen <−60 degrees C. A Post-freeze Viability Count was performed in accordance to SO 6.001, to establish the amount of antigen being administered.

At the time of farrowing, each piglet had the date and time of farrowing recorded on the Farrowing/Challenge Form. The piglets were ear tagged prior to processing, due to the need for the piglets' identification number in recording time and date of birth. Piglets were allowed to suckle ad libitum. Within 6 hours (+/−2 hours) of birth, piglets were weighed. Immediately following processing, piglets meeting the Post-inclusion Removal/Withdrawal criteria were utilized for challenge study.

The diluted and re-dispensed K88 Challenge Culture (lot no. TBD) was thawed at room temperature (~23 degrees C.) and 2.0 ml administered orally to each piglet. Following challenge, piglets were placed back on the gilt.

The treatment outcome for Phase I was assessed by antibody titres to protein orf3526 in the sera collected from hyperimmunized pigs. The treatment outcome for Phase II was assessed by which group has the maximum protection from 2 doses of antisera orally pre-challenge; determined by the mortality/morbidity information gathered from clinical observations and necropsy results.

Example 8

Orf3526 Protection in a Murine Model of Intestinal Tract Colonization by Intragastric Infection With ETEC Strain GL53-K88:

Mice received streptomycin (5 g/liter) in their drinking water (enriched with 6.7% fructose) 48 to 24 h prior to infection to eradicate normal resident bacteria flora. Following this, mice were infected by oral lavage with 109 CFU of a suspension of GL53 strain in a final volume of 400 ul. To reduce the effect of stomach acidity on the bacterial organism, bicarbonate was administered intragastrically 15 minutes prior to bacterial inoculation. 24 hours following infection, mice were euthanized and segments of ileum (2 cm) were harvested and homogenized. Serial dilutions of GL53, resistant to Kanamycin, are plated onto LB agar plates enriched with antibiotic. To confirm that the recovered bacteria were the inoculum strain, bacterial colonies are tested by PCR using primers encoding for LT holotoxin. To test the protective effect of antigen orf3526, mice were immunized intranasally on days 1, 7, 21, and 35 with antigen (20 ug) used alone or in combination with LTR72 as mucosal adjuvant (ratio 1:10). On day 49, mice were infected by oral lavage with 109 CFU of GL53 strain.

Figure 5:
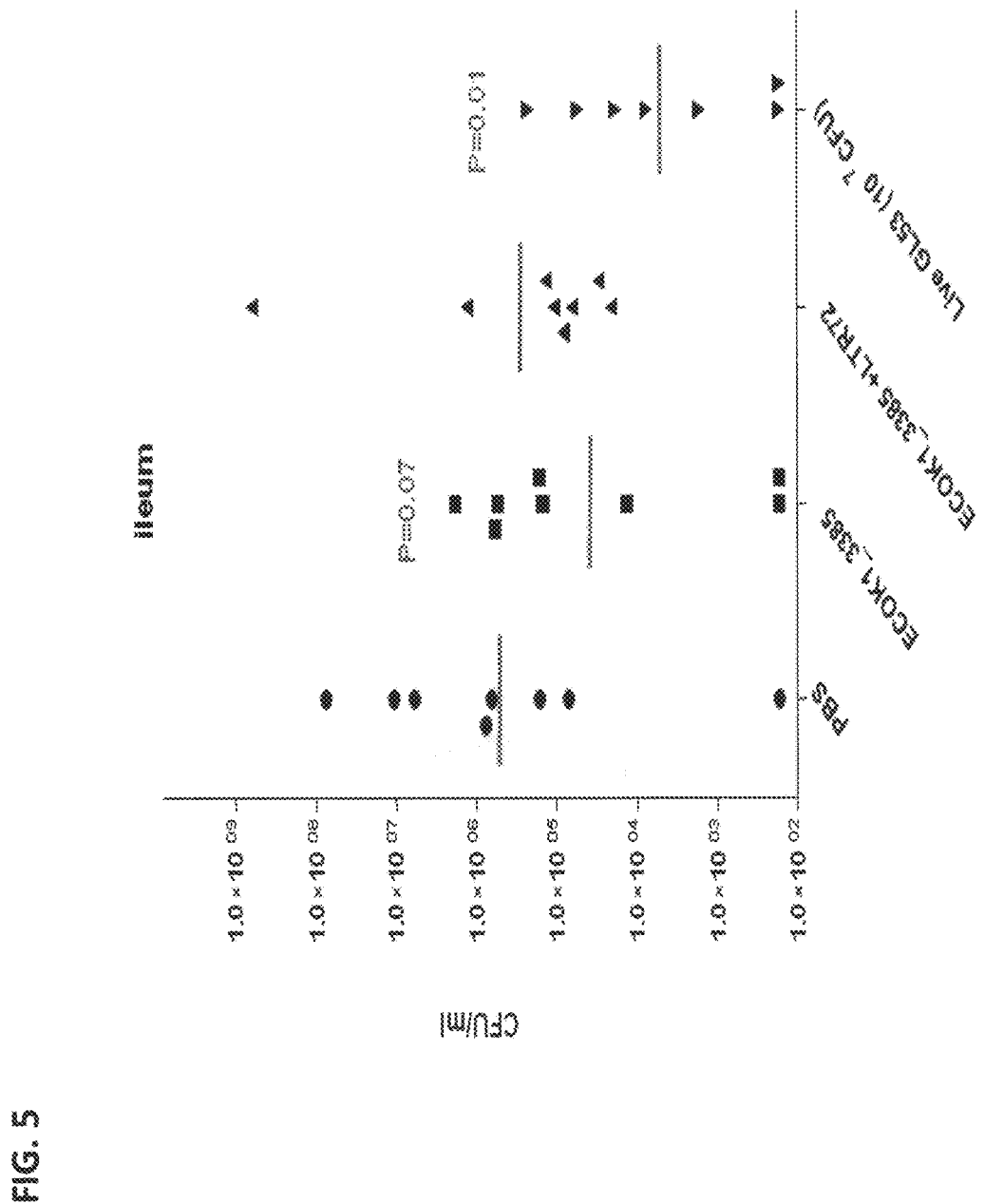
FIG. 5: Intranasal immunization with antigen orf3526 (ECOK1_3385) reduced colonization in ileum tract following challenge with ETEC strain GL53.

As shown in FIG. 5, intranasal immunization with antigen orf3526 reduced colonization in ileum tract following challenge with ETEC strain GL53. Thus, orf3526 is able to protect against challenge with the UPEC strain 536 in an UTI murine model.

Example 9

Antigen orf3526 was prepared and administered as previously described in combination with FCA, IC31, alum, MF59 or alone or in combination. Antigen orf3526 remained protective when administered with a variety of adjuvants:

| Candidates | animal model | | |
|---|---|---|---|
| | % survival immun. | % survival ctrl. | protection |
| pK1-3526 + FCA | 8/8 | 2/8 | 100 |
| pK1-3526 + IC31 | 7/8 | 1/8 | 86 |
| pK1-3526 + alum | 7/8 | 2/8 | 83 |
| pK1-3526 + MF59 | 6/8 | 0/8 | 75 |
| pK1-3526 + alum/IC31 | 8/8 | 2/8 | 100 |
| pK1-3526 + MF59/IC31 | 7/8 | 2/8 | 83 |
| pK1-3526ΔG + FCA | 10/10 | 1/10 | 100 |
| pK1-3526ΔGΔP + FCA | 9/10 | 1/10 | 89 |

Example 10

The Protective Effect of Antigens 405B and Upec1232 were Determined Using a UTI Model of Infection in Mice:

The bacteria used to infect the mice were grown in filter-sterilized human urine and were passaged three times.

The bacteria were incubated at 37° C., shaken at 200 rounds/min overnight, and centrifuged at 6,500×g for 10 min. The pellet was then suspended in phosphate-buffered saline (PBS) to a concentration of approximately 1010 CFU/ml.

Figure 6:
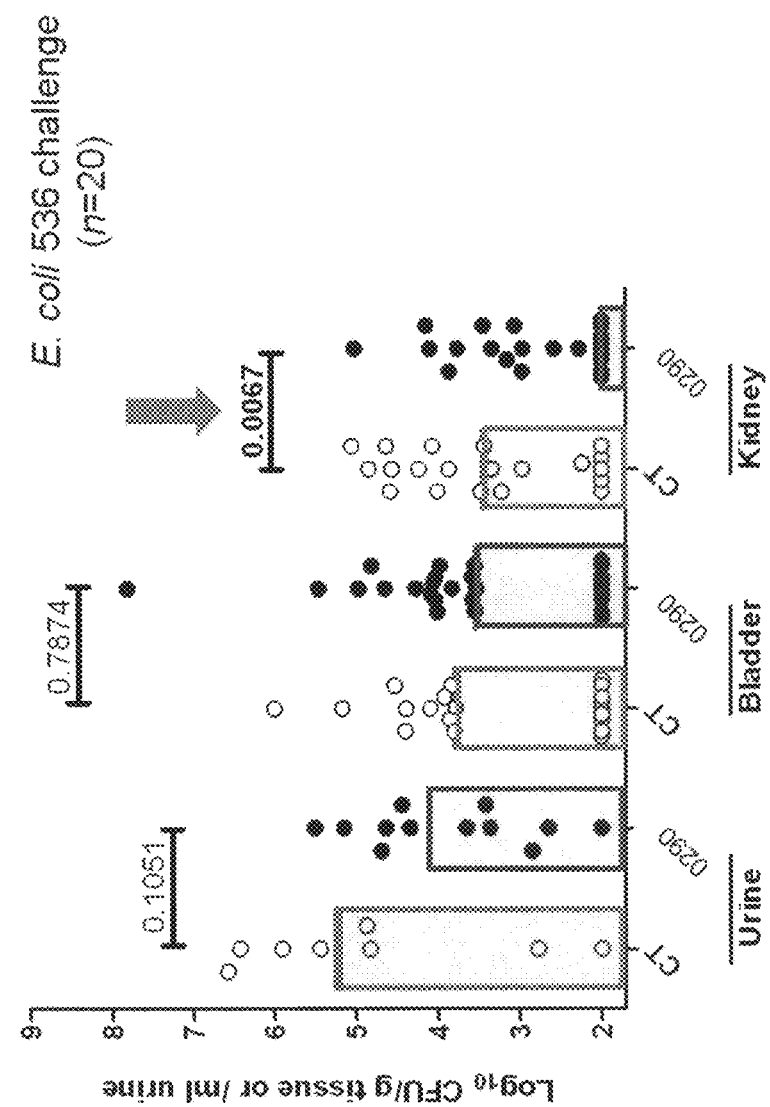
FIG. 6: Antigen 405B (ECOK1_0290) prevents kidney colonisation in a UTI model of infection.
Figure 7:
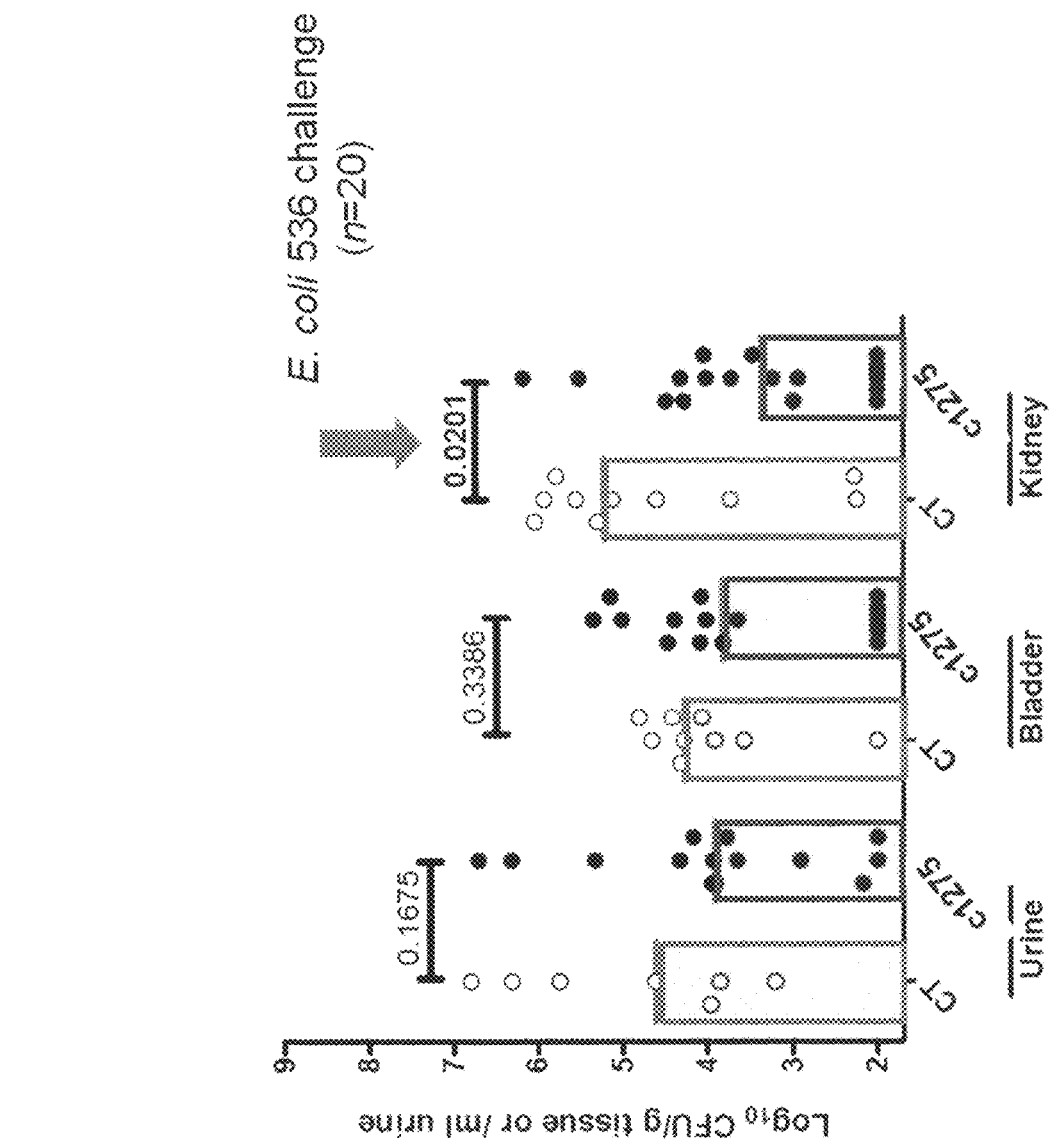
FIG. 7: Antigen upec1232 (c1275) prevents kidney colonisation in a UTI model of infection.

Mice were anesthetized by intraperitoneal administration of 0.08 ml of a mixture of Hypnorm (fentanyl citrate, 0.315 mg/ml; fluanisone, 10 mg/ml) and Stesolid (diazepam, 5 mg/ml) at a ratio of 5:1.5. Anesthetized mice were inoculated transurethrally with the bacterial suspension (*E. coli* 536) by use of plastic catheters. 0.05 ml of bacterial suspension was injected in the bladder over 5 s in order to avoid vesicoureteral reflux (12, 18). The catheter was removed immediately after inoculation. Urine from each mouse was collected in Eppendorf tubes by gentle compression of the abdomen, and the mice were killed by cervical dislocation. The organs were removed aseptically, the bladders were cut off near the urethra, and the kidneys were removed by blunt dissection to avoid bleeding. The organs were placed in cryotubes (Nunc 363452) containing a 750-µl suspension of collagenase (500 U/ml; Sigma C9891) and were stored at −80° C. Prior to homogenization, the infected organs were incubated for 1.5 h at room temperature and were then homogenized manually with inoculating loops and a whirl mixer. Bacteria from the inoculum, bacteria that were recovered from the urine samples and bacteria from either the bladder or one of the kidneys were measured. The results, illustrated in FIGS. 6 and 7 respectively, demonstrate that antigens 405B and upec1232 prevent kidney colonisation in a UTI model of infection.

Example 11

Mutants/Variants of Orf3526

Bacteria with one of each of three constructs expressing his-tagged variants of orf3526 were cultured in 30 ml of medium and induced to express the orf3526 variant at 25° C. (orf3526 without the leader peptide (3526), orf3526 with the N-terminus removed through the gly-ser linker or gly-ser region (ΔG3526), and orf3526 with the N-terminus removed through the proline rich region (ΔG3526)). The bacteria were harvested and lysed by sonication. The soluble fractions were isolated and loaded on an IMAC column. The column was washed three times with 20 mM imidazole buffer. The orf3526 variants were then eluted with three washes of 500 mM imidazole buffer. Removal of the N-terminus of orf3526 through the gly-ser linker or gly-ser region significantly increased solubility and yield of purified protein. The yield obtained was estimated by Bradford assay to be as follows: 0.18 mg of 3526 and 2.34 mg ΔG3526.

Example 12

Mutants/Variants of Orf3526

Figure 8:
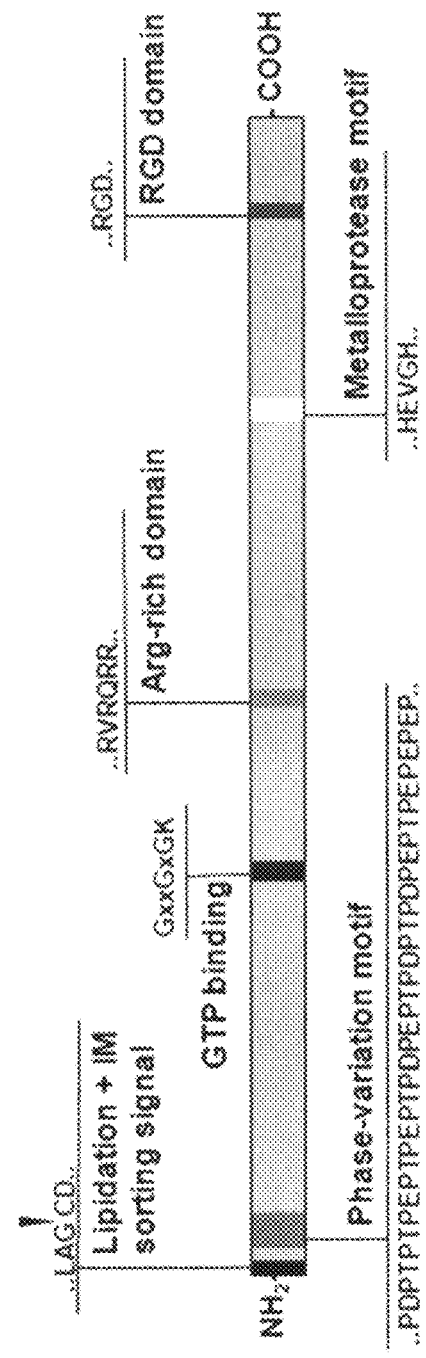
FIG. 8: Analysis of the orf3526 sequence revealed several conserved motifs.
Figure 10:
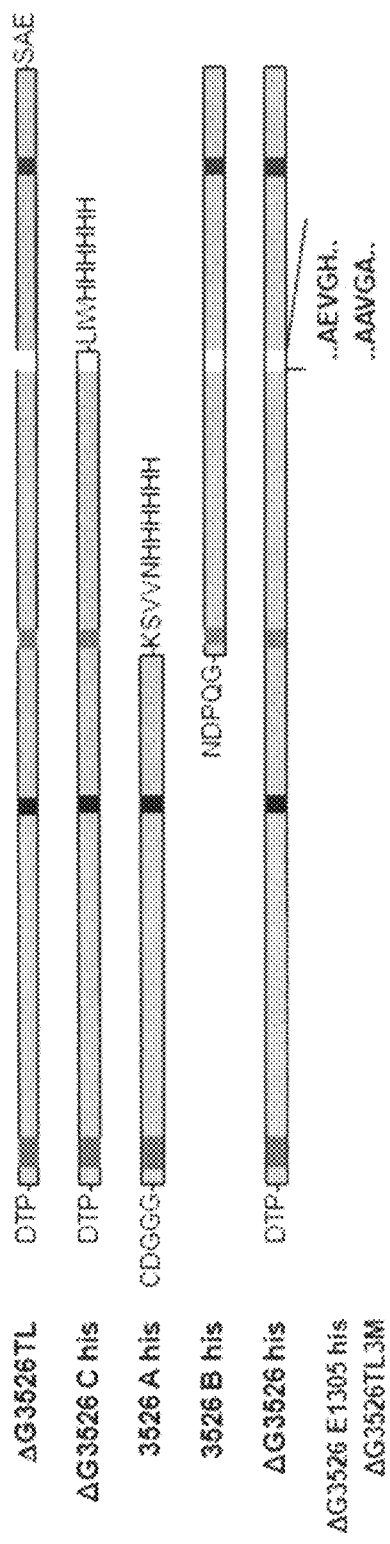
FIG. 10: Cartoon illustrating the seven mutants/variants of orf3526 utilised.

Although the function of orf3526 is not known, analysis of the orf3526 sequence revealed several conserved motifs, most notably a zinc binding motif, possibly part of a metallo-protease function, and an imperfect GTP binding motif (FIG. 8). Native orf3526 is a potential lipoprotein, also secreted into the culture supernatant. Sequence alignments studies show that the protein has homology to AcfD (accessory colonization factor) from *Vibrio cholera*. Native orf3526 is constitutively expressed and secreted by a Type 2 secretion system (T2SS). Seven mutants/variants of orf3526 were prepared as illustrated in FIG. 10.

Zinc content of the various orf3526 derivatives was determined by atomic absorption spectroscopy. Results, illustrated in FIG. 11, suggest the presence of a single zinc ion per protein molecule. The unexpected low zinc content of 3526 B his, actually containing the zinc binding motif, could be explained by misfolding of this truncated derivative, while the single amino acid exchange in the E1305 mutant apparently is not sufficient to completely abolish zinc binding (red boxes).

A purified triple mutant orf3526 (DG3526TL) protein was prepared wherein the amino acids at positions H1304, E1305 and H1308 according to SEQ ID 8 were substituted by another amino acid, specifically H1304A, E1305A and H1308A. Surprisingly, zinc affinity is almost completely lost in the DG3526TL triple mutant which comprised mutations in the zinc binding motif at amino acids 1304, 1305 and 1308 of SEQ ID 8 from the amino acid sequence HEVGH to <u>AAVA</u>.

Figure 9A:
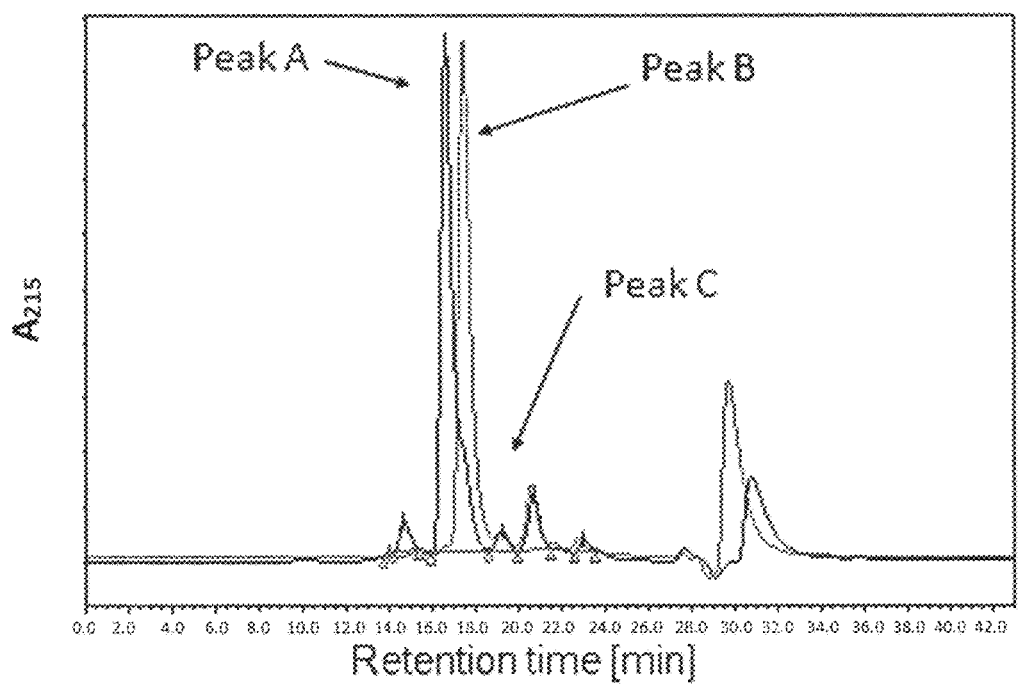
FIG. 9A: Isoforms of DG3526TL were separated by SE-HPLC on a Tosoh G3000SWx1 column. The fraction that binds to butyl Sepharose appears less compact in SEC and forms peak A, while the form that binds to butyl Sepharose forms peak B. Peak C corresponds to an N-terminally truncated form.
Figure 9B:
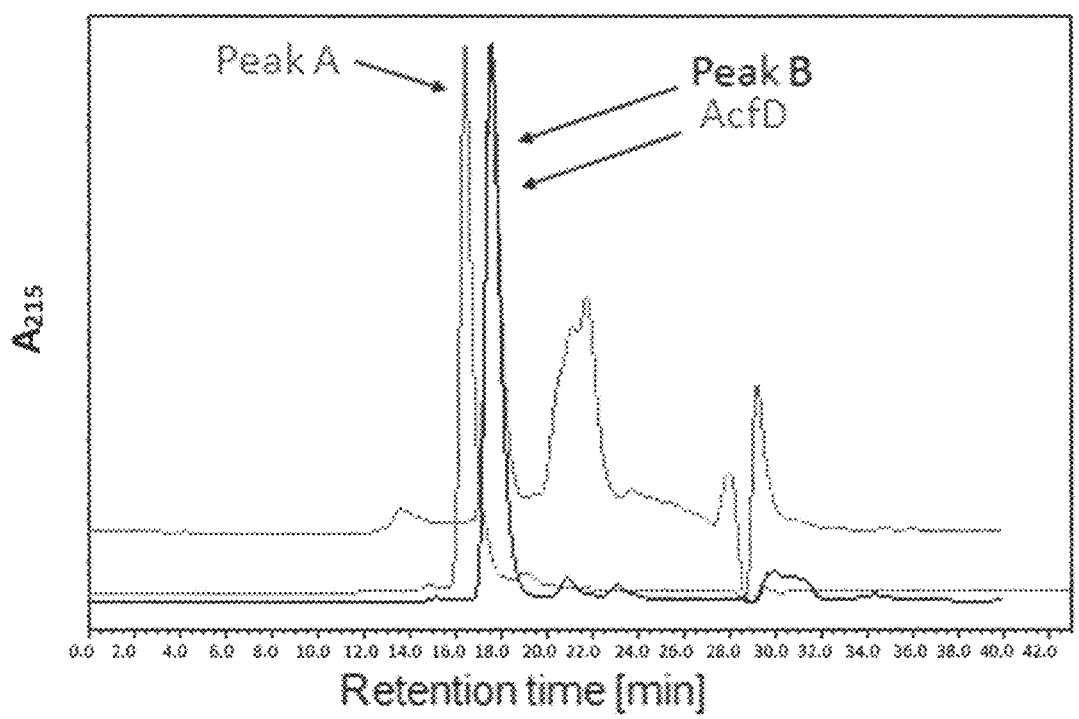
FIG. 9B: To evaluate possible functional differences between DG3526TL and native 3526, the latter was purified from culture supernatant of ExPEC IHE3034. Running 3526 along with the isoforms of DG3526TL reveals that the native form coelutes with peak B, suggesting that native 3526 is i) compact and ii) a monomer.

To allow functional and structural characterization, the soluble tagless recombinant protein DG3526TL (164 KDa) was purified by CaptoQ and butyl Sepharose chromatography. SE-HPLC/MALLS analysis revealed that DG3526TL exists in two isoforms (peaks A and B in FIG. 9*a*) and one truncated form (peak C in FIG. 9*a*). The isoforms can be separated on butyl Sepharose. However, without stabilization by glycerol, conversion of one form into the other was observed over time (FIGS. 9(*a*) and 9(*b*)). Thus, the triple mutant isoform is further advantageous in terms of purification.

The amino acid sequence of the triple mutant TL3M is:

```
>orf03526 Triple Mutant
                                              (SEQ ID 31)
MNKKFKYKKSLLAAILSATLLAGCDGGGSGSSSDTPSVDSGSGTLPEVKP

DPTPTPEPTPEPTPDPEPTPDPTPDPEPTPEPEPEPVPTKTGYLTLGGSQ

RVTGATCNGESSDGFTFTPGNTVSCVVGSTTIATENTQSEAARSLRAVDK

VSFSLEDAQELANSENKKTNAISLVTSSDSCPADAEQLCLTESSVVDRAR

FEKLYKQIDLATDNESKLVNEEVENNAATDKAPSTHTSTVVPVTTEGTKP

DLNASEVSANAEQFYQYQPTEIILSEGQLVDSLGNGVAGVDYYTNSGRGV

TDENGKFSFSWGETISEGIDTFELGSVRGNKSTIALTELGDEVRGANIDQ

LIHRYSTTGQNNTRVVPDDVRKVFAEYPNVINEIINLSLSNGATLDEGDQ

NVVLPNEFIEQFKTGQAKEIDTAICAKTDGCNEARWFSLTTRNVNDGQIQ

GVINKLWGVDTNYQSVSKFHVEHDSTNEYGSTGNARGQAVVNISNSAFPI

LMARNDKNYWLAFGEKRAWDKNELAYITEAPSIVQPENVTRDTATENLPF

ISLGQVGEGKLMVIGNPHYNSILRCPNGYSWGGGVNSKGECTLSGDSDDM

KHFMQNVLRYLSNDIWQPNTKSIMTVGINLENVYFKKAGQVLGNSAPFAF

HEDFTGITVKQLTSYGDLNPEEIPLLILNGFEYVTQWSGDPYAVPLRADT

SKPKLTQQDVTDLIAYLNKGGSVLIMENVMSNLKEESASSEVRLLDAAGL

SMALNKSVVNNDPQGYPDRVRQRRATGIWVYERYPAADGAQPPYTIDPNT

GEVTWKYQQDNKPDDKPKLEVASWQEEVEGKQVTRYAFIDEAEYTTEESL

EAAKAKIFEKFPGLQECKDSTYHYEINCLERRPGTDVPVTGGMYVPRYTQ

LNLDADTAKAMVQAADLGTNIQRLYQHELYERTKGSKGERLNSVDLERLY

QNMSVWLWNDTKYRYEEGKEDELGFKTFTEFLNCYANDAYAGGTKCSADL

KKSLVDNNMIYGDGSSKAGMMNPSYPLNYMEKPLTRLMLGRSWWDLNIKV

DVEKYPGSVSAKGESVTENISLYSNPTKWFAGNMQSTGLWAPAQQDVTIK
```

-continued

SSASVPVTVTVALADDLTGREKHEVALNRPPRVTKTYTLEANGEVTEKVP

YGGLIYIKGDSKDDVSANFTFTGVVKAPFYKDGEWKNDLDSPAPLGELES

ASFVYTTPKKNLEASNFTGGVAEFAKDLDTFASSMNDFYGRNDEDGKHRM

FTYKNLTGHKHRFTNDVQISIGDAHSGYPVMNSSFSTNSTTLPTTPLNDW

LIWAAVGANAAETPLNVPGATEVANNVLALYMQDRYLGKMNRVADDITVA

PEYLDESNGQAWARGGAGDRLLMYAQLKEWAEENFDIKQWYPDGELPKEY

SDRKGMKGWNLFQLMHRKARGDDVGNSTEGGKNYCAESNGNAADTLMLCA

SWVAQADLSEFFKKWNPGASAYQLPGATEMSFQGGVSSSAYSTLASLKLP

KPEKGPETINKVTEHKMSAE

Example 13

Antigen Combinations

His-tagged antigens were combined and administered with alum. The protection rate was calculated:

| Antigen(s) | Protection rate |
|---|---|
| Orf3526 (2 µg) | 61% |
| Orf3526 (2 µg) + 405B (10 µg) + upec-1232 (10 µg) | 87.5% |

Example 14

Antigen Combinations

Antigens were combined and administered with alum. Survival and protection rate were calculated following challenge with either IHE3034 (NMEC) or 9855/93 (SEPEC) ExPEC strains.

| | IHE3034 challenge | | 9855/93 challenge | |
|---|---|---|---|---|
| Antigen(s) | Survival with vaccination | Protection rate | Survival with vaccination | Protection rate |
| Orf3526 (2 µg) | 57/88 (64%) | 61% | n/a | n/a |
| Orf3526 (2 µg) + 405B (10 µg) + upec-1232 (10 µg) | 7/8 (87.5%) | 87.5% | n/a | n/a |
| Orf3526 (10 µg) | 11/16 (68%) | 63% | 14/23 (61%) | 48% |
| (Orf3526 (10 µg) + 405B (10 µg) + upec-1232 (10 µg) | 7/8 (87.5%) | 87.5% | n/a | n/a |
| Orf3526C (0.2 µg) | 7/16 (44%) | 44% | n/a | n/a |
| Orf3526C (0.2 µg) + 405B (20 µg) | 5/8 (62.5%) | 62.5% | n/a | n/a |

Example 15

Protective Efficacy of 3625 in the Intestinal Colonization Model

Figure 14B:
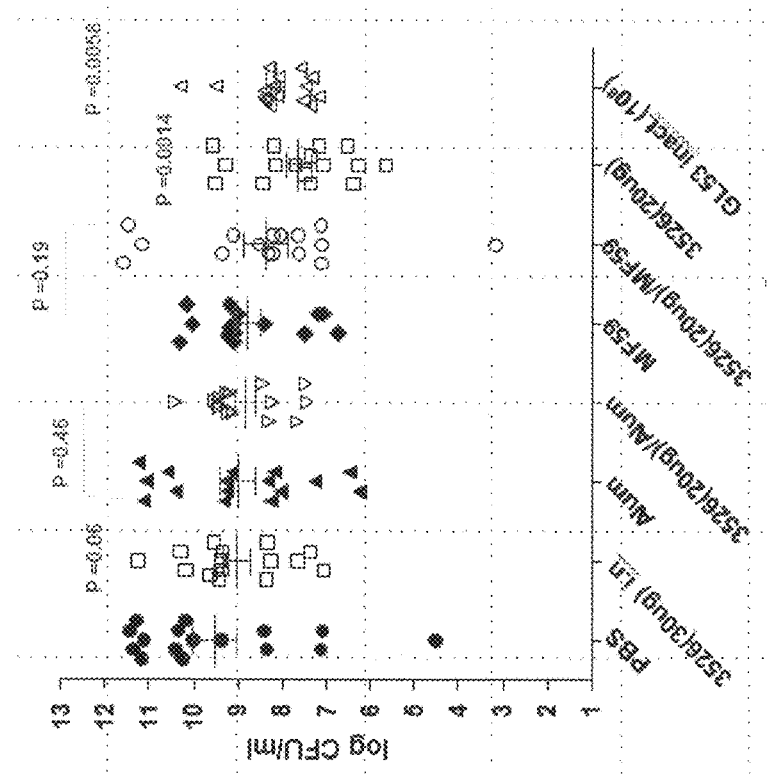
FIG. 14: Bacterial titres were significantly reduced after immunisation with 3526+alum, or after immunisation on days 0, 21, and 35 with 3526+MF59, compared to adjuvant alone (FIG. 14A). The results are confirmed in an experiment were mice were immunised on days 0 and 21 only (FIG. 14B).
Figure 14A:
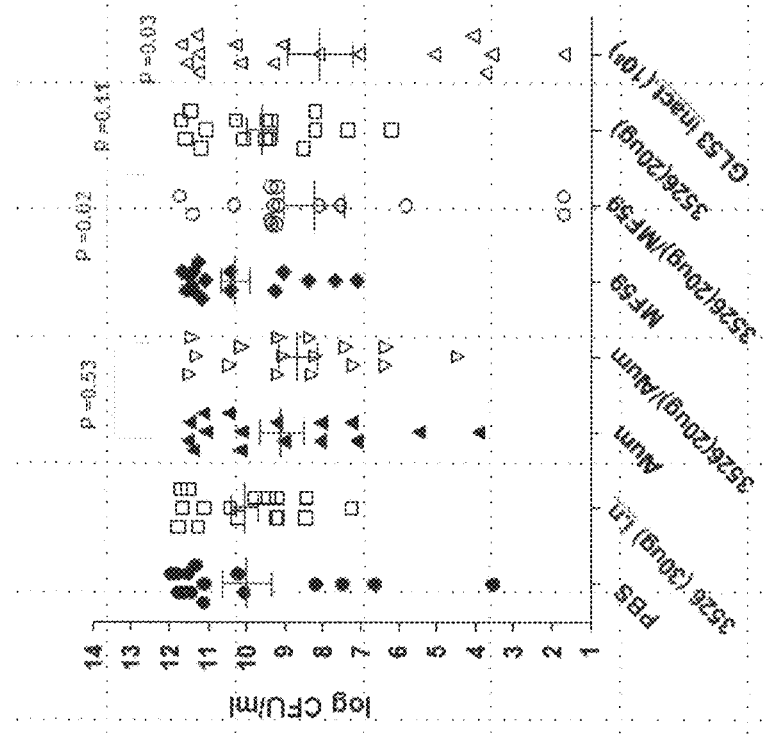

Mice were immunized via the intramuscular route with the 3526 antigen with alum or MF59, on days 0, 21 and 35. Mice were challenged with GL53 (ETEC) on day 48 and bacterial titres were evaluated in the caecum. FIG. 14(a) shows that bacterial titres were significantly reduced after immunisation with 3526+alum, or after immunisation with 3526+MF59, compared to adjuvant alone. The results are confirmed in an experiment were mice were immunised on days 0 and 21 only (FIG. 14(b)).

Example 16

Figure 15:
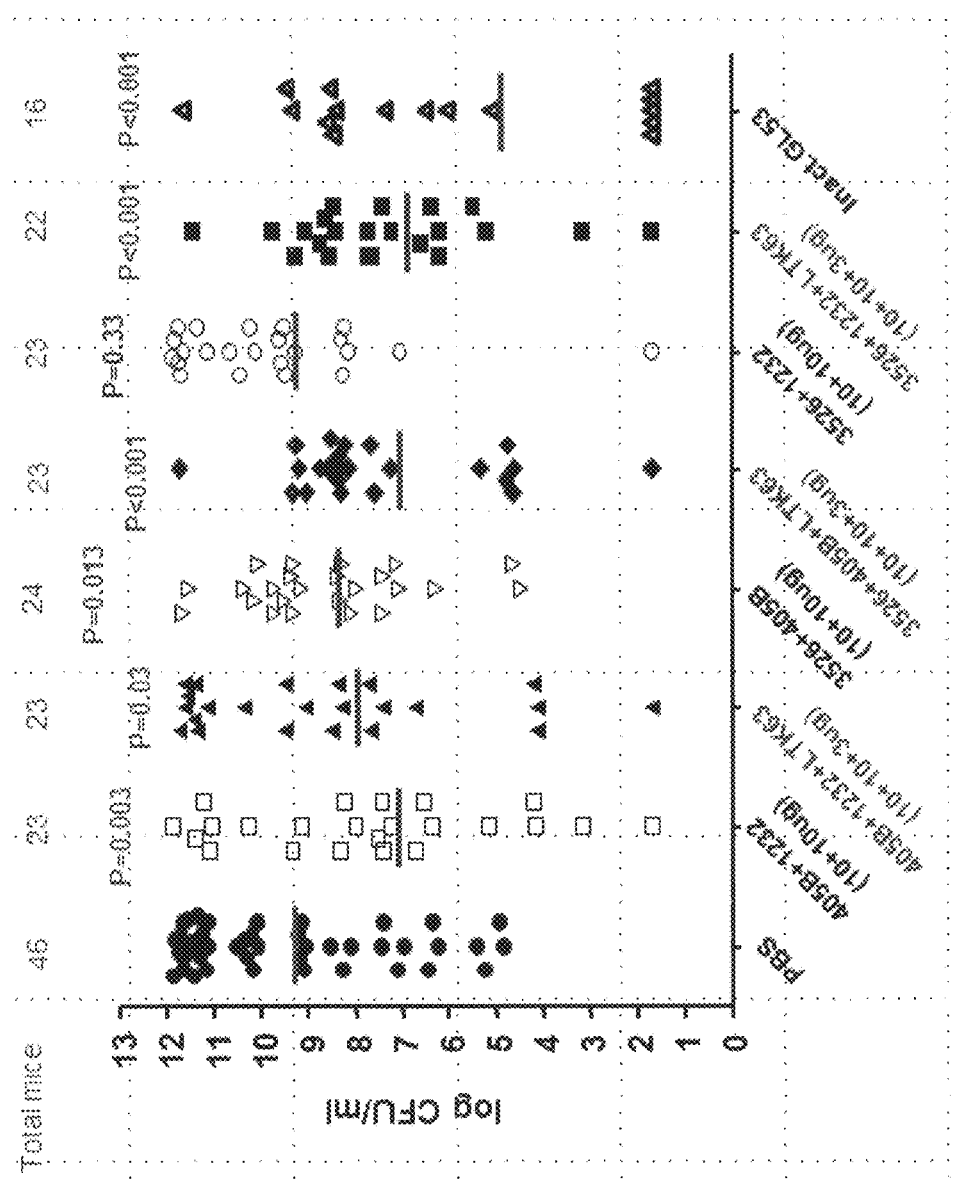
FIG. 15: 405B+3526+LTK63 and 3526+1232+LTK63 significantly reduces intestinal colonization by GL53 in the caecum, compared to LTK63 alone.

Protective Efficacy of Antigen Combinations in the Intestinal Colonization Model Mice were immunized with different combinations of antigens 405B, 1232 and 3526, with or without LTK63 (FIG. 15), on days 1, 21 and 35. Mice were challenged with GL53 (ETEC) and bacterial titres were evaluated in the caecum. The results show that 405B+3526+LTK63 and 3526+1232+LTK63 significantly reduces intestinal colonization by GL53 in the caecum, compared to LTK63 alone.

Example 17

Protective Efficacy of Isoforms A, B, and C of 3526.

Mice were immunized with isoform A alone, isoform B alone, or a combination of isoforms A, B and C. Mice were challenged with IHE3034 and bacterial titres were evaluated. The results show that isoform B alone or combined with isoforms A and C confers greatest protective efficacy.

| 3526-His isoforms | Immunization dose | Survival | PE |
|---|---|---|---|
| [peak A] pur_131 | 20 ug | 44 (7/16) | 36 |
| [peak B] pur_131 | 20 ug | 69 (11/16) | 64.5 |
| [peak A, B, C] pur_131 | 20 ug | 62.5 (5/8) | 75 |
| [peak A, B, C] pur_131 | 5 ug | 87.5 (7/8) | 86 |
| [peak A] pur_131 | 5 ug | 37.5 (3/8) | 28.5 |
| [peak B] pur_131 | 5 ug | 87.5 (7/8) | 86 |

ADDITIONAL REFERENCES

[1] Bodanszky (1993) *Principles of Peptide Synthesis* (ISBN: 0387564314).
[2] Fields et al. (1997) Meth Enzymol 289: Solid-Phase Peptide Synthesis. ISBN: 0121821900.
[3] Chan & White (2000) *Fmoc Solid Phase Peptide Synthesis*. ISBN: 0199637245.
[4] Kullmann (1987) *Enzymatic Peptide Synthesis*. ISBN: 0849368413.
[5] Ibba (1996) *Biotechnol Genet Eng Rev* 13:197-216.
[6] *Vaccine Design: The Subunit and Adjuvant Approach* (eds. Powell & Newman) Plenum Press 1995 (ISBN 0-306-44867-X).
[7] Vaccine Adjuvants: Preparation Methods and Research Protocols (Volume 42 of Methods in Molecular Medicine series). ISBN: 1-59259-083-7. Ed. O'Hagan.
[8] *Vaccine Design* (1995) eds. Powell & Newman. ISBN: 030644867X. Plenum.
[9] WO90/14837.
[10] Podda (2001) *Vaccine* 19: 2673-2680.
[11] *Vaccine Design: The Subunit and Adjuvant Approach* (eds. Powell & Newman) Plenum Press 1995 (ISBN 0-306-44867-X).
[12] Vaccine Adjuvants: Preparation Methods and Research Protocols (Volume 42 of Methods in Molecular Medicine series). ISBN: 1-59259-083-7. Ed. O'Hagan.

[13] U.S. Pat. No. 5,057,540.
[14] Niikura et al. (2002) *Virology* 293:273-280.
[15] Gluck et al. (2002) *Vaccine* 20:B10-B16.
[16] Meraldi et al. (2003) *Vaccine* 21:2485-2491.
[17] Pajak et al. (2003) *Vaccine* 21:836-842.
[18] Krieg (2003) *Nature Medicine* 9:831-835.
[19] U.S. Pat. No. 6,429,199.
[20] Schellack et al. (2006) *Vaccine* 24:5461-72.
[21] Johnson et al. (1999) *Bioorg Med Chem Lett* 9:2273-2278.
[22] Pine et al. (2002) *J Control Release* 85:263-270.
[23] WO99/40936.
[24] WO99/44636.
[25] Singh et al] (2001) *J Cont Release* 70:267-276.
[26] WO99/27960.
[27] U.S. Pat. No. 6,090,406.
[28] EP-A-0626169.
[29] WO99/52549.
[30] Andrianov et al. (1998) *Biomaterials* 19:109-115.
[31] Payne et al. (1998) Adv Drug Delivery Review 31:185-196.
[32] Stanley (2002) *Clin Exp Dermatol* 27:571-577.
[33] Jones (2003) *Curr Opin Investig Drugs* 4:214-218.
[34] WO99/11241.
[35] WO94/00153.
[36] WO98/57659.
[37] European patent applications 0835318, 0735898 and 0761231.
[38] Durant et al. (2007) *Infect Immun* 75:1916-25.
[39] WO02/081653.
[40] Gennaro (2000) *Remington: The Science and Practice of Pharmacy*. 20th edition, ISBN: 0683306472.
[41] *PCR (Introduction to Biotechniques Series)*, 2nd ed. (Newton & Graham eds., 1997, Springer Verlag).

What is claimed:

1. A polypeptide comprising:
   (i) a mutant amino acid sequence comprising at least 15 amino acids wherein one or more of the amino acids at position 1304, 1305, 1306, 1307 and 1308 numbered with reference to SEQ ID NO: 8 are substituted by another amino acid;
   (ii) the amino acid sequence SEQ ID NO: 31; or
   (iii) an immunogenic fragment of (i) comprising at least 15 amino acids, which includes mutations at positions 1304, 1305 and 1308 numbered with reference to SEQ ID NO: 8 or an immunogenic fragment of (ii) comprising at least 15 amino acids which includes the amino acids at positions 1304, 1305 and 1308 numbered with reference to SEQ ID NO: 31.

2. The polypeptide of claim 1, wherein the zinc binding activity of the polypeptide is reduced by at least 50% relative to a wild-type orf3526 polypeptide, SEQ ID NO:8.

3. The polypeptide of claim 1, wherein the polypeptide has a zinc content which is at least 50% lower than the content of an equivalent amount of a wild-type orf3526 polypeptide, SEQ ID NO:8 or the polypeptide is substantially free of zinc.

4. The polypeptide of claim 1, wherein the polypeptide is an immunogenic fragment of SEQ ID NO: 31 comprising amino acid residues 24-1520, or residues 34-1520, of the sequence set forth in SEQ ID NO: 31.

5. The polypeptide of claim 1, wherein the polypeptide is lipidated.

6. The polypeptide of claim 4, wherein the polypeptide is lipidated at an N-terminal cysteine.

* * * * *

SEQUENCE LISTING

<160> NUMBER OF SEQ ID NOS: 57

<210> SEQ ID NO 1
<211> LENGTH: 1242
<212> TYPE: DNA
<213> ORGANISM: Escherichia coli

<400> SEQUENCE: 1

```
gttgctgatg gtcagcaagc ctacacgctg acactgacag cggtggactc cgagggtaat      60
ccggtgacgg gagaagccag ccgcctgcga cttgttccgc aagacactaa tggtgtaacc     120
gttggtgcca tttcggaaat aaaaccaggg gtttacagcg ccacggtttc ttcgacccgt     180
gccggaaacg ttgttgtgcg tgccttcagc gagcagtatc agctgggcac attacaacaa     240
acgctgaagt tgttgccgg gccgcttgat gcagcacatt cgtccatcac actgaatcct     300
gataaaccgg tggttggcgg tacagttacg gcaatctgga cggcaaaaga tgctaatgac     360
aaccctgtaa ctggcctcaa tccggatgca ccgtcattat cgggcgcagc tgctgctggt     420
tctacggcat caggctggac ggataatggc gacgggacct ggactgcgca gatttctctc     480
ggcactacgg cgggtgaatt agacgttatg ccgaagctca atgggcagga cgcggcagca     540
aatgcggcaa aagtaaccgt ggtggctgat gcattatctt caaaccagtc gaaagtctct     600
gtcgcagaag atcacgtaaa agccggtgaa agcacaaccg taacgctggt ggcgaaagat     660
gcgcatggca acgctatcag tggtctttcg ttgtcggcaa gtttgacggg gaccgcctct     720
gaaggggcga ccgtttccag ttggaccgaa aaaggtgacg gttcctatgt tgctacgtta     780
actacaggcg gaaagacggg cgagcttcgt gtcatgccgc tcttcaacgg ccagcctgca     840
gccaccgaag ccgcgcagct gactgttatt gccggagaga tgtcatcagc gaactctacg     900
cttgttgcgg acaataaaac tccaacggtt aaaacgacga cggaactcac cttcaccatg     960
aaggatgcgt acgggaatcc ggtcaccggg ctgaagccag atgcaccagt gtttagtggt    1020
gccgccagca cggggagtga gcgtccttca gcaggaaact ggacagagaa aggtaatggg    1080
gtctacgtgt cgaccttaac gctgggatct gccgcgggtc agttgtctgt gatgccgcga    1140
gtgaacggcc aaaatgccgt tgctcagcca ctggtgctga atgttgcagg tgacgcatct    1200
aaggctgaga ttcgtgatat gacagtgaag gttaataacc aa                       1242
```

<210> SEQ ID NO 2
<211> LENGTH: 414
<212> TYPE: PRT
<213> ORGANISM: Escherichia coli

<400> SEQUENCE: 2

```
Val Ala Asp Gly Gln Gln Ala Tyr Thr Leu Thr Leu Thr Ala Val Asp
1               5                   10                  15

Ser Glu Gly Asn Pro Val Thr Gly Glu Ala Ser Arg Leu Arg Leu Val
            20                  25                  30

Pro Gln Asp Thr Asn Gly Val Thr Val Gly Ala Ile Ser Glu Ile Lys
        35                  40                  45

Pro Gly Val Tyr Ser Ala Thr Val Ser Ser Thr Arg Ala Gly Asn Val
    50                  55                  60

Val Val Arg Ala Phe Ser Glu Gln Tyr Gln Leu Gly Thr Leu Gln Gln
65                  70                  75                  80

Thr Leu Lys Phe Val Ala Gly Pro Leu Asp Ala Ala His Ser Ile
                85                  90                  95

Thr Leu Asn Pro Asp Lys Pro Val Val Gly Thr Val Thr Ala Ile
                100                 105                 110

Trp Thr Ala Lys Asp Ala Asn Asp Asn Pro Val Thr Gly Leu Asn Pro
                115                 120                 125

Asp Ala Pro Ser Leu Ser Gly Ala Ala Ala Gly Ser Thr Ala Ser
130                 135                 140

Gly Trp Thr Asp Asn Gly Asp Gly Thr Trp Thr Ala Gln Ile Ser Leu
145                 150                 155                 160

Gly Thr Thr Ala Gly Glu Leu Asp Val Met Pro Lys Leu Asn Gly Gln
                165                 170                 175

Asp Ala Ala Ala Asn Ala Ala Lys Val Thr Val Val Asp Ala Leu
                180                 185                 190

Ser Ser Asn Gln Ser Lys Val Ser Val Ala Glu Asp His Val Lys Ala
                195                 200                 205

Gly Glu Ser Thr Thr Val Thr Leu Val Ala Lys Asp Ala His Gly Asn
210                 215                 220

Ala Ile Ser Gly Leu Ser Leu Ser Ala Ser Leu Thr Gly Thr Ala Ser
225                 230                 235                 240

Glu Gly Ala Thr Val Ser Ser Trp Thr Glu Lys Gly Asp Gly Ser Tyr
                245                 250                 255

Val Ala Thr Leu Thr Thr Gly Gly Lys Thr Gly Glu Leu Arg Val Met
                260                 265                 270

Pro Leu Phe Asn Gly Gln Pro Ala Ala Thr Glu Ala Ala Gln Leu Thr
                275                 280                 285

Val Ile Ala Gly Glu Met Ser Ser Ala Asn Ser Thr Leu Val Ala Asp
                290                 295                 300

Asn Lys Thr Pro Thr Val Lys Thr Thr Thr Glu Leu Thr Phe Thr Met
305                 310                 315                 320

Lys Asp Ala Tyr Gly Asn Pro Val Thr Gly Leu Lys Pro Asp Ala Pro
                325                 330                 335

Val Phe Ser Gly Ala Ala Ser Thr Gly Ser Arg Pro Ser Ala Gly
                340                 345                 350

Asn Trp Thr Glu Lys Gly Asn Gly Val Tyr Val Ser Thr Leu Thr Leu
                355                 360                 365

Gly Ser Ala Ala Gly Gln Leu Ser Val Met Pro Arg Val Asn Gly Gln
                370                 375                 380

Asn Ala Val Ala Gln Pro Leu Val Leu Asn Val Ala Gly Asp Ala Ser
385                 390                 395                 400

Lys Ala Glu Ile Arg Asp Met Thr Val Lys Val Asn Asn Gln
```

<210> SEQ ID NO 3
<211> LENGTH: 453
<212> TYPE: DNA
<213> ORGANISM: Escherichia coli

<400> SEQUENCE: 3

```
atgattcacc tgttcaaaac ctgcatgatt accgccttca ttctggggtt aacgtggtct      60
gccccactcc gggcacagga tcaacgttac atcagtatac gcaatacaga tacgatatgg     120
ctcccgggaa atatttgtgc ttaccagttc cggctggata atggcggaaa cgatgaagga     180
tttggccccc tcaccatcac tctgcaactc aaagacaaat atggtcagac gctggtgacc     240
agaaaaatgg aaacggaagc ctttggtgac agtaatgcca cgcgaaccac agacgcattt     300
ctggaaacgg agtgcgtgga aaatgtcgcc acaaccgaaa tcattaaagc aactgaagaa     360
agtaacggcc atcgtgtcag tctgccgtta tcggttttcg atccccagga ctaccatcca     420
ctgctgatta ccgtttccgg aaaaaacgtt aac                                   453
```

<210> SEQ ID NO 4
<211> LENGTH: 151
<212> TYPE: PRT
<213> ORGANISM: Escherichia coli

<400> SEQUENCE: 4

```
Met Ile His Leu Phe Lys Thr Cys Met Ile Thr Ala Phe Ile Leu Gly
1               5                   10                  15
Leu Thr Trp Ser Ala Pro Leu Arg Ala Gln Asp Gln Arg Tyr Ile Ser
            20                  25                  30
Ile Arg Asn Thr Asp Thr Ile Trp Leu Pro Gly Asn Ile Cys Ala Tyr
        35                  40                  45
Gln Phe Arg Leu Asp Asn Gly Gly Asn Asp Glu Gly Phe Gly Pro Leu
    50                  55                  60
Thr Ile Thr Leu Gln Leu Lys Asp Lys Tyr Gly Gln Thr Leu Val Thr
65                  70                  75                  80
Arg Lys Met Glu Thr Glu Ala Phe Gly Asp Ser Asn Ala Thr Arg Thr
                85                  90                  95
Thr Asp Ala Phe Leu Glu Thr Glu Cys Val Glu Asn Val Ala Thr Thr
            100                 105                 110
Glu Ile Ile Lys Ala Thr Glu Glu Ser Asn Gly His Arg Val Ser Leu
        115                 120                 125
Pro Leu Ser Val Phe Asp Pro Gln Asp Tyr His Pro Leu Leu Ile Thr
    130                 135                 140
Val Ser Gly Lys Asn Val Asn
145                 150
```

<210> SEQ ID NO 5
<211> LENGTH: 378
<212> TYPE: DNA
<213> ORGANISM: Escherichia coli

<400> SEQUENCE: 5

```
caggatcaac gttacatcag tatacgcaat acagatacga tatggctccc gggaaatatt      60
tgtgcttacc agttccggct ggataatggc ggaaacgatg aaggatttgg ccccctcacc     120
atcactctgc aactcaaaga caaatatggt cagacgctgg tgaccagaaa aatggaaacg     180
gaagcctttg gtgacagtaa tgccacgcga accacagacg catttctgga aacggagtgc     240
```

```
gtggaaaatg tcgccacaac cgaaatcatt aaagcaactg aagaaagtaa cggccatcgt      300
gtcagtctgc cgttatcggt tttcgatccc caggactacc atccactgct gattaccgtt      360
tccggaaaaa acgttaac                                                    378
```

<210> SEQ ID NO 6
<211> LENGTH: 126
<212> TYPE: PRT
<213> ORGANISM: Escherichia coli

<400> SEQUENCE: 6

```
Gln Asp Gln Arg Tyr Ile Ser Ile Arg Asn Thr Asp Thr Ile Trp Leu
1               5                   10                  15

Pro Gly Asn Ile Cys Ala Tyr Gln Phe Arg Leu Asp Asn Gly Gly Asn
            20                  25                  30

Asp Glu Gly Phe Gly Pro Leu Thr Ile Thr Leu Gln Leu Lys Asp Lys
        35                  40                  45

Tyr Gly Gln Thr Leu Val Thr Arg Lys Met Glu Thr Glu Ala Phe Gly
    50                  55                  60

Asp Ser Asn Ala Thr Arg Thr Thr Asp Ala Phe Leu Glu Thr Glu Cys
65                  70                  75                  80

Val Glu Asn Val Ala Thr Thr Glu Ile Ile Lys Ala Thr Glu Glu Ser
                85                  90                  95

Asn Gly His Arg Val Ser Leu Pro Leu Ser Val Phe Asp Pro Gln Asp
            100                 105                 110

Tyr His Pro Leu Leu Ile Thr Val Ser Gly Lys Asn Val Asn
        115                 120                 125
```

<210> SEQ ID NO 7
<211> LENGTH: 4560
<212> TYPE: DNA
<213> ORGANISM: Escherichia coli

<400> SEQUENCE: 7

```
atgaataaga aatttaaata taagaaatcg cttttagcgg ctattttaag cgcaaccctg       60
ttagccggtt gtgatggtgg tggttcagga tcgtcctccg atacgccgtc tgtagattct      120
ggatcaggga cttttgccgga agtgaaaccc gatccaacac caaccccgga gccgacacct     180
gagccgacgc cggacccaga acctacgccg gatccaacac ctgatcctga ccgacaccca     240
gaaccggagc cagaacctgt tcctacgaaa acgggttatc tgaccctggg cggaagccag     300
cgggtaactg tgctacctg taatggtgaa tccagcgatg ctttaccctt tacgccaggc     360
aataccgtga gttgtgtggt gggcagtacg accattgcaa cattcaacac ccagtcagaa     420
gctgcgcgta gcctgcgtgc ggttgacaaa gtgtcgttta gcctggagga cgcgcaggag     480
ctggcgaatt ctgaaaataa gaaaaccaac gccatctctc tggtgacgtc cagcgacagt     540
tgccccgcag atgcagaaca gctttgtctt actttctcgt cagtggttga tcgcgcgcga     600
tttgaaaaac tgtataagca aattgatctg gcaacagaca atttcagcaa gctggtcaat     660
gaagaggtgg aaaacaatgc tgcgactgat aaagcgccgt ccacccatac ctcaacggta     720
gtgccagtca cgacagaggg aacaaaaccg gatctgaacg cgtccttcgt gtcggctaac     780
gcggaacagt tttatcagta tcaacccact gaaatcattc tttccgaagg ccaactggtg     840
gatagcctgg ggaacggtgt tgctggcgtt gactactaca ccaattcagg ccgtggcgta     900
actgacgaaa acggtaaatt ttcctttagc tggggcgaaa ccatctcctt tggtatcgat     960
```

```
acctttgaac tgggctcagt acgtggcaat aagtcgacca ttgcgctgac tgaattgggt    1020
gatgaagttc gcggggcaaa tatcgatcag ctcattcatc gttattcgac gactggtcaa    1080
aataatactc gtgttgttcc ggacgatgta cgcaaggtct ttgccgaata tcccaacgtg    1140
atcaacgaga taatcaatct ttcgttatcc aacggtgcga cgctggatga aggcgatcaa    1200
aacgttgtgc tgcctaacga atttatcgag cagtttaaga cgggtcaggc caaagagatc    1260
gataccgcga tttgtgcgaa aaccgacggt tgtaacgagg ctcgctggtt ctcgctgaca    1320
acgcgcaatg ttaatgacgg ccagattcag ggcgttatta caagctgtg gggcgtggat     1380 acgaactatc agtctgtcag caagttccac gtcttccatg actctaccaa cttctatggc    1440
agcaccggta acgcgcgcgg tcaggcggtg gtaaatatct ccaactcggc attcccgatt    1500
ctgatggcgc gtaatgataa aaactactgg ctggcgtttg gcgaaaaacg cgcctgggat    1560
aaaaatgagc tggcgtacat tacggaagcg ccttccattg tgcagccaga gaacgttacg    1620
cgcgatactg cgactttcaa cctgccgttt atttcgctgg ggcaagtcgg tgaaggcaaa    1680
ctgatggtta tcggtaaccc gcactacaac agcatcctgc gttgcccgaa cggttacagt    1740
tggggcggtg gtgttaatag taaaggtgag tgtacgctca gcggtgattc tgatgacatg    1800 aagcactta tgcagaacgt actgcgctac ttgtcaaatg acatctggca gccaaatacc     1860
aagagcatca tgactgtcgg caccaacctg gagaacgttt atttcaaaaa agcgggccag    1920
gtattgggaa atagtgcacc atttgctttc catgaggatt tcactggtat cacggttaaa    1980
cagttgacca gctatggcga tctgaatccg gaagagattc cgttgctgat cctcaacggc    2040
tttgaatatg tgactcagtg gtctggcgat ccctatgctg tgcctctgcg tgcagatacc    2100
agcaaaccga gctgactca gcaggatgtg accgatctga tcgcttatct gaacaaaggt     2160
ggctcggtgc tgatcatgga aaacgtgatg agcaatctta aggaagagag cgcgtccagt    2220
tttgtgcgtc tgctggatgc cgcgggtctg tcaatggctc tgaacaaatc ggtggtgaac    2280
aacgatccgc aagggtatcc ggatcgcgtt cgtcagcgtc gcgcgactgg catttgggtt    2340
tatgaacgtt atcctgctgc agacggcgcg caaccgccgt acaccatcga cccaaataca    2400
ggggaagtga cctggaaata ccagcaagac aacaagcctg atgacaagcc gaaactggaa    2460
gttgcgagct ggcaggagga agttgagggc aaacaggtaa cgcgttatgc ctttattgat    2520
gaagcggaat acacaacaga agaatctctg gaagcggcaa aggcaaaaat ctttgagaag    2580
tttcctgggt tacaggagtg taaggactcg acttaccatt acgagattaa ctgtttggag    2640
cgccgcccag gcacggatgt tccggtaaca ggtggcatgt atgttccgcg ctatacgcaa    2700
ctgaatcttg acgccgacac cgcgaaagcg atggtgcagg cggcggattt aggcaccaac    2760
attcagcgcc tgtatcagca tgagctttat ttccgtacca aaggcagtaa aggtgagcgt    2820
ctgaacagtg ttgatctgga acgtctgtac cagaacatgt cggtctggct gtggaacgat    2880
acgaaatatc gttacgaaga gggcaaggaa gatgagctgg gctttaaaac gttcaccgag    2940
ttcctgaact gctacgccaa tgatgcctat gcaggcggca ccaagtgctc cgcagatctg    3000
aaaaaatcgc tggtcgataa caacatgatc tacggtgacg gtagcagcaa agcgggcatg    3060
atgaacccaa gctatccgct caactatatg gaaaaaccgc tgacgcgtct gatgctgggc    3120
cgttcctggt gggatctgaa cattaaggtt gatgtggaga agtacccagg atccgtatcg    3180
gcaaagggtg agagcgttac ggaaaacatc agcctgtact cgaatccgac caaatggttt    3240
gcgggtaaca tgcagtcaac cggcctgtgg gcaccggccc agcaggacgt caccattaag    3300
tcttcggcgt cagtcccagt gactgttacc gtggcgctgg ctgacgacct gactggacgt    3360
```

-continued

```
gagaagcatg aagttgcgct gaaccgtccg ccaagagtga ctaaaacgta tactctggag    3420
gctaacggtg aagtgacctt caaggtgcct tatggtggtc tgatttatat caagggcgac    3480
agtaaggatg atgtttctgc taacttcacc tttaccggtg tagtaaaagc gccgttctat    3540
aaagacggcg aatggaaaaa cgatctggac tcaccggcgc cgctgggcga gctggagtct    3600
gcgtcgttcg tctataccac gccgaagaag aaccttgagg ccagcaattt cactggtggt    3660
gtagcagaat cgctaaaga tctggatacc tttgccagct cgatgaatga cttctacggt    3720
cgtaatgatg aagacggtaa gcaccggatg tttacctata aaaacttgac ggggcacaag    3780
catcgtttca ccaacgatgt gcagatctcc atcggtgatg cgcactcggg ttatccggta    3840
atgaacagca gcttctcgac gaacagcacc acgctgccga cgacgccgct gaacgactgg    3900
ctgatttggc acgaagtcgg tcataacgct gcagaaacac cgctgaacgt accgggtgca    3960
actgaagtgg cgaacaacgt gctggcgctg tacatgcagg atcgctatct cggtaagatg    4020
aaccgtgtcg ctgacgacat taccgtcgcg ccggaatatc tggacgagag caacggtcag    4080
gcctgggcgc gcggcggtgc gggtgaccgt ctgctgatgt acgcacagtt gaaggagtgg    4140
gcagaggaaa actttgatat caaacagtgg tatccagatg gtgagctgcc taagttctac    4200
agcgatcgta aagggatgaa gggctggaac ctgttccagt tgatgcaccg taaagcgcgc    4260
ggcgatgatg ttggtaacag caccctttggt ggcaagaatt actgtgctga atccaatggt    4320
aacgctgccg acacgctgat gctgtgtgca tcctgggtcg ctcaggcgga tctttcggaa    4380
ttctttaaga aatggaatcc gggtgcaagt gcttaccagt tgccgggagc aacggagatg    4440
agtttccagg gcggtgtgag ctcttcggct tacagcacgc tggcgtcact caagctgccg    4500
aaaccggaaa aagggccgga accattaac aaggttaccg agcataagat gtctgccgag    4560
```

<210> SEQ ID NO 8
<211> LENGTH: 1520
<212> TYPE: PRT
<213> ORGANISM: Escherichia coli

<400> SEQUENCE: 8

```
Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
                20                  25                  30

Ser Asp Thr Pro Ser Val Asp Ser Gly Ser Gly Thr Leu Pro Glu Val
                35                  40                  45

Lys Pro Asp Pro Thr Pro Thr Pro Glu Pro Thr Glu Pro Thr Pro
            50                  55                  60

Asp Pro Glu Pro Thr Pro Asp Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Val Thr Gly Ala Thr Cys Asn Gly Glu Ser Ser
                100                 105                 110

Asp Gly Phe Thr Phe Thr Pro Gly Asn Thr Val Ser Cys Val Val Gly
                115                 120                 125

Ser Thr Thr Ile Ala Thr Phe Asn Thr Gln Ser Glu Ala Ala Arg Ser
                130                 135                 140

Leu Arg Ala Val Asp Lys Val Ser Phe Ser Leu Glu Asp Ala Gln Glu
145                 150                 155                 160
```

-continued

```
Leu Ala Asn Ser Glu Asn Lys Lys Thr Asn Ala Ile Ser Leu Val Thr
            165                 170                 175
Ser Ser Asp Ser Cys Pro Ala Asp Ala Glu Gln Leu Cys Leu Thr Phe
            180                 185                 190
Ser Ser Val Val Asp Arg Ala Arg Phe Glu Lys Leu Tyr Lys Gln Ile
            195                 200                 205
Asp Leu Ala Thr Asp Asn Phe Ser Lys Leu Val Asn Glu Glu Val Glu
        210                 215                 220
Asn Asn Ala Ala Thr Asp Lys Ala Pro Ser His Thr Ser Thr Val
225                 230                 235                 240
Val Pro Val Thr Thr Glu Gly Thr Lys Pro Asp Leu Asn Ala Ser Phe
            245                 250                 255
Val Ser Ala Asn Ala Glu Gln Phe Tyr Gln Tyr Gln Pro Thr Glu Ile
            260                 265                 270
Ile Leu Ser Glu Gly Gln Leu Val Asp Ser Leu Gly Asn Gly Val Ala
        275                 280                 285
Gly Val Asp Tyr Tyr Thr Asn Ser Gly Arg Gly Val Thr Asp Glu Asn
        290                 295                 300
Gly Lys Phe Ser Phe Ser Trp Gly Glu Thr Ile Ser Phe Gly Ile Asp
305                 310                 315                 320
Thr Phe Glu Leu Gly Ser Val Arg Gly Asn Lys Ser Thr Ile Ala Leu
            325                 330                 335
Thr Glu Leu Gly Asp Glu Val Arg Gly Ala Asn Ile Asp Gln Leu Ile
            340                 345                 350
His Arg Tyr Ser Thr Thr Gly Gln Asn Asn Thr Arg Val Val Pro Asp
            355                 360                 365
Asp Val Arg Lys Val Phe Ala Glu Tyr Pro Asn Val Ile Asn Glu Ile
        370                 375                 380
Ile Asn Leu Ser Leu Ser Asn Gly Ala Thr Leu Asp Glu Gly Asp Gln
385                 390                 395                 400
Asn Val Val Leu Pro Asn Glu Phe Ile Glu Gln Phe Lys Thr Gly Gln
            405                 410                 415
Ala Lys Glu Ile Asp Thr Ala Ile Cys Ala Lys Thr Asp Gly Cys Asn
            420                 425                 430
Glu Ala Arg Trp Phe Ser Leu Thr Thr Arg Asn Val Asn Asp Gly Gln
            435                 440                 445
Ile Gln Gly Val Ile Asn Lys Leu Trp Gly Val Asp Thr Asn Tyr Gln
        450                 455                 460
Ser Val Ser Lys Phe His Val Phe His Asp Ser Thr Asn Phe Tyr Gly
465                 470                 475                 480
Ser Thr Gly Asn Ala Arg Gly Gln Ala Val Val Asn Ile Ser Asn Ser
            485                 490                 495
Ala Phe Pro Ile Leu Met Ala Arg Asn Asp Lys Asn Tyr Trp Leu Ala
            500                 505                 510
Phe Gly Glu Lys Arg Ala Trp Asp Lys Asn Glu Leu Ala Tyr Ile Thr
            515                 520                 525
Glu Ala Pro Ser Ile Val Gln Pro Glu Asn Val Thr Arg Asp Thr Ala
        530                 535                 540
Thr Phe Asn Leu Pro Phe Ile Ser Leu Gly Gln Val Gly Glu Gly Lys
545                 550                 555                 560
Leu Met Val Ile Gly Asn Pro His Tyr Asn Ser Ile Leu Arg Cys Pro
            565                 570                 575
Asn Gly Tyr Ser Trp Gly Gly Gly Val Asn Ser Lys Gly Glu Cys Thr
```

```
            580             585             590
Leu Ser Gly Asp Ser Asp Met Lys His Phe Met Gln Asn Val Leu
        595             600             605

Arg Tyr Leu Ser Asn Asp Ile Trp Gln Pro Asn Thr Lys Ser Ile Met
        610             615             620

Thr Val Gly Thr Asn Leu Glu Asn Val Tyr Phe Lys Lys Ala Gly Gln
625             630             635             640

Val Leu Gly Asn Ser Ala Pro Phe Ala Phe His Glu Asp Phe Thr Gly
            645             650             655

Ile Thr Val Lys Gln Leu Thr Ser Tyr Gly Asp Leu Asn Pro Glu Glu
            660             665             670

Ile Pro Leu Leu Ile Leu Asn Gly Phe Glu Tyr Val Thr Gln Trp Ser
            675             680             685

Gly Asp Pro Tyr Ala Val Pro Leu Arg Ala Asp Thr Ser Lys Pro Lys
        690             695             700

Leu Thr Gln Gln Asp Val Thr Asp Leu Ile Ala Tyr Leu Asn Lys Gly
705             710             715             720

Gly Ser Val Leu Ile Met Glu Asn Val Met Ser Asn Leu Lys Glu Glu
            725             730             735

Ser Ala Ser Ser Phe Val Arg Leu Leu Asp Ala Ala Gly Leu Ser Met
            740             745             750

Ala Leu Asn Lys Ser Val Val Asn Asn Asp Pro Gln Gly Tyr Pro Asp
            755             760             765

Arg Val Arg Gln Arg Arg Ala Thr Gly Ile Trp Val Tyr Glu Arg Tyr
        770             775             780

Pro Ala Ala Asp Gly Ala Gln Pro Pro Tyr Thr Ile Asp Pro Asn Thr
785             790             795             800

Gly Glu Val Thr Trp Lys Tyr Gln Gln Asp Asn Lys Pro Asp Asp Lys
            805             810             815

Pro Lys Leu Glu Val Ala Ser Trp Gln Glu Glu Val Glu Gly Lys Gln
            820             825             830

Val Thr Arg Tyr Ala Phe Ile Asp Glu Ala Glu Tyr Thr Thr Glu Glu
            835             840             845

Ser Leu Glu Ala Ala Lys Ala Lys Ile Phe Glu Lys Phe Pro Gly Leu
            850             855             860

Gln Glu Cys Lys Asp Ser Thr Tyr His Tyr Glu Ile Asn Cys Leu Glu
865             870             875             880

Arg Arg Pro Gly Thr Asp Val Pro Val Thr Gly Gly Met Tyr Val Pro
            885             890             895

Arg Tyr Thr Gln Leu Asn Leu Asp Ala Asp Thr Ala Lys Ala Met Val
            900             905             910

Gln Ala Ala Asp Leu Gly Thr Asn Ile Gln Arg Leu Tyr Gln His Glu
            915             920             925

Leu Tyr Phe Arg Thr Lys Gly Ser Lys Gly Glu Arg Leu Asn Ser Val
        930             935             940

Asp Leu Glu Arg Leu Tyr Gln Asn Met Ser Val Trp Leu Trp Asn Asp
945             950             955             960

Thr Lys Tyr Arg Tyr Glu Glu Gly Lys Glu Asp Glu Leu Gly Phe Lys
            965             970             975

Thr Phe Thr Glu Phe Leu Asn Cys Tyr Ala Asn Asp Ala Tyr Ala Gly
            980             985             990

Gly Thr Lys Cys Ser Ala Asp Leu Lys Lys Ser Leu Val Asp Asn Asn
        995             1000            1005
```

-continued

```
Met Ile Tyr Gly Asp Gly Ser Ser Lys Ala Gly Met Met Asn Pro Ser
    1010                1015                1020

Tyr Pro Leu Asn Tyr Met Glu Lys Pro Leu Thr Arg Leu Met Leu Gly
1025                1030                1035                1040

Arg Ser Trp Trp Asp Leu Asn Ile Lys Val Asp Val Glu Lys Tyr Pro
                1045                1050                1055

Gly Ser Val Ser Ala Lys Gly Glu Ser Val Thr Glu Asn Ile Ser Leu
                1060                1065                1070

Tyr Ser Asn Pro Thr Lys Trp Phe Ala Gly Asn Met Gln Ser Thr Gly
            1075                1080                1085

Leu Trp Ala Pro Ala Gln Gln Asp Val Thr Ile Lys Ser Ala Ser
    1090                1095                1100

Val Pro Val Thr Val Thr Val Ala Leu Ala Asp Asp Leu Thr Gly Arg
1105                1110                1115                1120

Glu Lys His Glu Val Ala Leu Asn Arg Pro Pro Arg Val Thr Lys Thr
                1125                1130                1135

Tyr Thr Leu Glu Ala Asn Gly Glu Val Thr Phe Lys Val Pro Tyr Gly
            1140                1145                1150

Gly Leu Ile Tyr Ile Lys Gly Asp Ser Lys Asp Val Ser Ala Asn
    1155                1160                1165

Phe Thr Phe Thr Gly Val Val Lys Ala Pro Tyr Lys Asp Gly Glu
    1170                1175                1180

Trp Lys Asn Asp Leu Asp Ser Pro Ala Pro Leu Gly Glu Leu Glu Ser
1185                1190                1195                1200

Ala Ser Phe Val Tyr Thr Thr Pro Lys Lys Asn Leu Glu Ala Ser Asn
                1205                1210                1215

Phe Thr Gly Gly Val Ala Glu Phe Ala Lys Asp Leu Asp Thr Phe Ala
                1220                1225                1230

Ser Ser Met Asn Asp Phe Tyr Gly Arg Asn Asp Glu Asp Gly Lys His
            1235                1240                1245

Arg Met Phe Thr Tyr Lys Asn Leu Thr Gly His Lys His Arg Phe Thr
    1250                1255                1260

Asn Asp Val Gln Ile Ser Ile Gly Asp Ala His Ser Gly Tyr Pro Val
1265                1270                1275                1280

Met Asn Ser Ser Phe Ser Thr Asn Ser Thr Thr Leu Pro Thr Thr Pro
                1285                1290                1295

Leu Asn Asp Trp Leu Ile Trp His Glu Val Gly His Asn Ala Ala Glu
            1300                1305                1310

Thr Pro Leu Asn Val Pro Gly Ala Thr Glu Val Ala Asn Asn Val Leu
    1315                1320                1325

Ala Leu Tyr Met Gln Asp Arg Tyr Leu Gly Lys Met Asn Arg Val Ala
    1330                1335                1340

Asp Asp Ile Thr Val Ala Pro Glu Tyr Leu Asp Glu Ser Asn Gly Gln
1345                1350                1355                1360

Ala Trp Ala Arg Gly Gly Ala Gly Asp Arg Leu Leu Met Tyr Ala Gln
                1365                1370                1375

Leu Lys Glu Trp Ala Glu Glu Asn Phe Asp Ile Lys Gln Trp Tyr Pro
            1380                1385                1390

Asp Gly Glu Leu Pro Lys Phe Tyr Ser Asp Arg Lys Gly Met Lys Gly
    1395                1400                1405

Trp Asn Leu Phe Gln Leu Met His Arg Lys Ala Arg Gly Asp Asp Val
    1410                1415                1420
```

-continued

```
Gly Asn Ser Thr Phe Gly Gly Lys Asn Tyr Cys Ala Glu Ser Asn Gly
1425                1430                1435                1440

Asn Ala Ala Asp Thr Leu Met Leu Cys Ala Ser Trp Val Ala Gln Ala
            1445                1450                1455

Asp Leu Ser Glu Phe Phe Lys Lys Trp Asn Pro Gly Ala Ser Ala Tyr
        1460                1465                1470

Gln Leu Pro Gly Ala Thr Glu Met Ser Phe Gln Gly Val Ser Ser
    1475                1480                1485

Ser Ala Tyr Ser Thr Leu Ala Ser Leu Lys Leu Pro Lys Pro Glu Lys
            1490                1495                1500

Gly Pro Glu Thr Ile Asn Lys Val Thr Glu His Lys Met Ser Ala Glu
1505                1510                1515                1520

<210> SEQ ID NO 9
<211> LENGTH: 2214
<212> TYPE: DNA
<213> ORGANISM: Escherichia coli

<400> SEQUENCE: 9
tgtgatggtg gtggttcagg atcgtcctcc gatacgccgt ctgtagattc tggatcaggg      60
actttgccgg aagtgaaacc cgatccaaca ccaaccccgg agccgacacc tgagccgacg     120
ccggacccag aacctacgcc ggatccaaca cctgatcctg agccgacacc agaaccggag     180
ccagaacctg ttcctacgaa aacgggttat ctgaccctgg cggaagcca gcgggtaact      240 ggtgctacct gtaatggtga atccagcgat ggctttacct ttacgccagg caataccgtg     300
agttgtgtgg tgggcagtac gaccattgca acattcaaca cccagtcaga agctgcgcgt     360
agcctgcgtg cggttgacaa agtgtcgttt agcctggagg acgcgcagga gctggcgaat     420
tctgaaaata gaaaaccaa cgccatctct ctggtgacgt ccagcgacag ttgccccgca      480
gatgcagaac agctttgtct tactttctcg tcagtggttg atcgcgcgcg atttgaaaaa     540
ctgtataagc aaattgatct ggcaacagac aatttcagca agctggtcaa tgaagaggtg     600
gaaaacaatg ctgcgactga taaagcgccg tccacccata cctcaacggt agtgccagtc     660
acgacagagg aacaaaaacc ggatctgaac gcgtccttcg tgtcggctaa cgcggaacag     720
ttttatcagt atcaacccac tgaaatcatt ctttccgaag ccaactggt ggatagcctg      780 gggaacggtg ttgctggcgt tgactactac accaattcag ccgtggcgt aactgacgaa      840 aacggtaaat tttcctttag ctggggcgaa accatctcct ttggtatcga tacctttgaa     900
ctgggctcag tacgtggcaa taagtcgacc attgcgctga ctgaattggg tgatgaagtt     960 cgcgggcaa atatcgatca gctcattcat cgttattcga cgactggtca aataatact     1020 cgtgttgttc cggacgatgt acgcaaggtc tttgccgaat atcccaacgt gatcaacgag    1080
ataatcaatc tttcgttatc caacggtgcg acgctggatg aaggcgatca aaacgttgtg    1140
ctgcctaacg aatttatcga gcagtttaag acgggtcagg ccaaagagat cgataccgcg    1200
atttgtgcga aaaccgacgg ttgtaacgag gctcgctggt tctcgctgac aacgcgcaat    1260
gttaatgacg gccagattca gggcgttatt aacaagctgt ggggcgtgga tacgaactat    1320
cagtctgtca gcaagttcca cgtcttccat gactctacca acttctatgg cagcaccggt    1380
aacgcgcgcg gtcaggcggt ggtaaatatc tccaactcgg cattcccgat tctgatggcg    1440
cgtaatgata aaaactactg gctggcgttt ggcgaaaaac gcgcctggga taaaaatgag    1500
ctggcgtaca ttacggaagc gccttccatt gtgcagccag agaacgttac gcgcgatact    1560
gcgactttca acctgccgtt tatttcgctg ggcaagtcg gtgaaggcaa actgatggtt    1620
```

-continued

```
atcggtaacc cgcactacaa cagcatcctg cgttgcccga acggttacag ttggggcggt   1680
ggtgttaata gtaaaggtga gtgtacgctc agcggtgatt ctgatgacat gaagcacttt   1740
atgcagaacg tactgcgcta cttgtcaaat gacatctggc agccaaatac caagagcatc   1800
atgactgtcg gcaccaacct ggagaacgtt tatttcaaaa aagcgggcca ggtattggga   1860
aatagtgcac catttgcttt ccatgaggat ttcactggta tcacggttaa acagttgacc   1920
agctatggcg atctgaatcc ggaagagatt ccgttgctga tcctcaacgg ctttgaatat   1980
gtgactcagt ggtctggcga tccctatgct gtgcctctgc gtgcagatac cagcaaaccg   2040
aagctgactc agcaggatgt gaccgatctg atcgcttatc tgaacaaagg tggctcggtg   2100
ctgatcatgg aaaacgtgat gagcaatctt aaggaagaga gcgcgtccag ttttgtgcgt   2160
ctgctggatg ccgcgggtct gtcaatggct ctgaacaaat cggtggtgaa caac         2214
```

<210> SEQ ID NO 10
<211> LENGTH: 738
<212> TYPE: PRT
<213> ORGANISM: Escherichia coli

<400> SEQUENCE: 10

```
Cys Asp Gly Gly Gly Ser Gly Ser Ser Ser Asp Thr Pro Ser Val Asp
1               5                   10                  15

Ser Gly Ser Gly Thr Leu Pro Glu Val Lys Pro Asp Pro Thr Pro Thr
            20                  25                  30

Pro Glu Pro Thr Pro Glu Pro Thr Pro Asp Pro Glu Pro Thr Pro Asp
        35                  40                  45

Pro Thr Pro Asp Pro Glu Pro Thr Pro Glu Pro Glu Pro Glu Pro Val
    50                  55                  60

Pro Thr Lys Thr Gly Tyr Leu Thr Leu Gly Gly Ser Gln Arg Val Thr
65                  70                  75                  80

Gly Ala Thr Cys Asn Gly Glu Ser Ser Asp Gly Phe Thr Phe Thr Pro
                85                  90                  95

Gly Asn Thr Val Ser Cys Val Val Gly Ser Thr Thr Ile Ala Thr Phe
            100                 105                 110

Asn Thr Gln Ser Glu Ala Ala Arg Ser Leu Arg Ala Val Asp Lys Val
        115                 120                 125

Ser Phe Ser Leu Glu Asp Ala Gln Glu Leu Ala Asn Ser Glu Asn Lys
    130                 135                 140

Lys Thr Asn Ala Ile Ser Leu Val Thr Ser Ser Asp Ser Cys Pro Ala
145                 150                 155                 160

Asp Ala Glu Gln Leu Cys Leu Thr Phe Ser Ser Val Val Asp Arg Ala
                165                 170                 175

Arg Phe Glu Lys Leu Tyr Lys Gln Ile Asp Leu Ala Thr Asp Asn Phe
            180                 185                 190

Ser Lys Leu Val Asn Glu Val Glu Asn Asn Ala Ala Thr Asp Lys
        195                 200                 205

Ala Pro Ser Thr His Thr Ser Thr Val Val Pro Val Thr Thr Glu Gly
    210                 215                 220

Thr Lys Pro Asp Leu Asn Ala Ser Phe Val Ser Ala Asn Ala Glu Gln
225                 230                 235                 240

Phe Tyr Gln Tyr Gln Pro Thr Glu Ile Ile Leu Ser Glu Gly Gln Leu
                245                 250                 255

Val Asp Ser Leu Gly Asn Gly Val Ala Gly Val Asp Tyr Tyr Thr Asn
            260                 265                 270
```

```
Ser Gly Arg Gly Val Thr Asp Glu Asn Gly Lys Phe Ser Phe Ser Trp
    275                 280                 285

Gly Glu Thr Ile Ser Phe Gly Ile Asp Thr Phe Glu Leu Gly Ser Val
    290                 295                 300

Arg Gly Asn Lys Ser Thr Ile Ala Leu Thr Glu Leu Gly Asp Glu Val
305                 310                 315                 320

Arg Gly Ala Asn Ile Asp Gln Leu Ile His Arg Tyr Ser Thr Thr Gly
                325                 330                 335

Gln Asn Asn Thr Arg Val Val Pro Asp Asp Val Arg Lys Val Phe Ala
                340                 345                 350

Glu Tyr Pro Asn Val Ile Asn Glu Ile Ile Asn Leu Ser Leu Ser Asn
                355                 360                 365

Gly Ala Thr Leu Asp Glu Gly Asp Gln Asn Val Val Leu Pro Asn Glu
            370                 375                 380

Phe Ile Glu Gln Phe Lys Thr Gly Gln Ala Lys Glu Ile Asp Thr Ala
385                 390                 395                 400

Ile Cys Ala Lys Thr Asp Gly Cys Asn Glu Ala Arg Trp Phe Ser Leu
                405                 410                 415

Thr Thr Arg Asn Val Asn Asp Gly Gln Ile Gln Gly Val Ile Asn Lys
                420                 425                 430

Leu Trp Gly Val Asp Thr Asn Tyr Gln Ser Val Ser Lys Phe His Val
            435                 440                 445

Phe His Asp Ser Thr Asn Phe Tyr Gly Ser Thr Gly Asn Ala Arg Gly
            450                 455                 460

Gln Ala Val Val Asn Ile Ser Asn Ser Ala Phe Pro Ile Leu Met Ala
465                 470                 475                 480

Arg Asn Asp Lys Asn Tyr Trp Leu Ala Phe Gly Glu Lys Arg Ala Trp
                485                 490                 495

Asp Lys Asn Glu Leu Ala Tyr Ile Thr Glu Ala Pro Ser Ile Val Gln
            500                 505                 510

Pro Glu Asn Val Thr Arg Asp Thr Ala Thr Phe Asn Leu Pro Phe Ile
            515                 520                 525

Ser Leu Gly Gln Val Gly Glu Gly Lys Leu Met Val Ile Gly Asn Pro
            530                 535                 540

His Tyr Asn Ser Ile Leu Arg Cys Pro Asn Gly Tyr Ser Trp Gly Gly
545                 550                 555                 560

Gly Val Asn Ser Lys Gly Glu Cys Thr Leu Ser Gly Asp Ser Asp Asp
                565                 570                 575

Met Lys His Phe Met Gln Asn Val Leu Arg Tyr Leu Ser Asn Asp Ile
                580                 585                 590

Trp Gln Pro Asn Thr Lys Ser Ile Met Thr Val Gly Thr Asn Leu Glu
            595                 600                 605

Asn Val Tyr Phe Lys Lys Ala Gly Gln Val Leu Gly Asn Ser Ala Pro
            610                 615                 620

Phe Ala Phe His Glu Asp Phe Thr Gly Ile Thr Val Lys Gln Leu Thr
625                 630                 635                 640

Ser Tyr Gly Asp Leu Asn Pro Glu Glu Ile Pro Leu Leu Ile Leu Asn
                645                 650                 655

Gly Phe Glu Tyr Val Thr Gln Trp Ser Gly Asp Pro Tyr Ala Val Pro
            660                 665                 670

Leu Arg Ala Asp Thr Ser Lys Pro Lys Leu Thr Gln Gln Asp Val Thr
            675                 680                 685
```

```
        Asp Leu Ile Ala Tyr Leu Asn Lys Gly Gly Ser Val Leu Ile Met Glu
            690                 695                 700

Asn Val Met Ser Asn Leu Lys Glu Glu Ser Ala Ser Ser Phe Val Arg
        705                 710                 715                 720

Leu Leu Asp Ala Ala Gly Leu Ser Met Ala Leu Asn Lys Ser Val Val
                        725                 730                 735

Asn Asn

<210> SEQ ID NO 11
<211> LENGTH: 2277
<212> TYPE: DNA
<213> ORGANISM: Escherichia coli

<400> SEQUENCE: 11
gatccgcaag ggtatccgga tcgcgttcgt cagcgtcgcg cgactggcat ttgggtttat      60
gaacgttatc ctgctgcaga cggcgcgcaa ccgccgtaca ccatcgaccc aaatacaggg    120
gaagtgacct ggaaatacca gcaagacaac aagcctgatg acaagccgaa actggaagtt    180
gcgagctggc aggaggaagt tgagggcaaa caggtaacgc gttatgcctt tattgatgaa    240
gcggaataca caacagaaga atctctggaa gcggcaaagg caaaaatctt tgagaagttt    300
cctgggttac aggagtgtaa ggactcgact taccattacg agattaactg tttggagcgc    360
cgcccaggca cggatgttcc ggtaacaggt ggcatgtatg ttccgcgcta tacgcaactg    420
aatcttgacg ccgacaccgc gaaagcgatg gtgcaggcgg cggatttagg caccaacatt    480
cagcgcctgt atcagcatga gctttatttc cgtaccaaag gcagtaaagg tgagcgtctg    540
aacagtgttg atctggaacg tctgtaccag aacatgtcgg tctggctgtg aacgatacg    600 aaatatcgtt acgaagaggg caaggaagat gagctgggct taaaacgtt caccgagttc    660 ctgaactgct acgccaatga tgcctatgca ggcggcacca agtgctccgc agatctgaaa    720
aaatcgctgg tcgataacaa catgatctac ggtgacggta gcagcaaagc gggcatgatg    780
aacccaagct atccgctcaa ctatatggaa aaaccgctga cgcgtctgat gctgggccgt    840
tcctggtggg atctgaacat taaggttgat gtggagaagt acccaggatc cgtatcggca    900
aagggtgaga gcgttacgga aaacatcagc ctgtactcga atccgaccaa atggtttgcg    960
ggtaacatgc agtcaaccgg cctgtgggca ccggcccagc aggacgtcac cattaagtct   1020
tcggcgtcag tcccagtgac tgttaccgtg gcgctggctg acgacctgac tggacgtgag   1080
aagcatgaag ttgcgctgaa ccgtccgcca agagtgacta aaacgtatac tctggaggct   1140
aacggtgaag tgaccttcaa ggtgccttat ggtggtctga tttatatcaa gggcgacagt   1200
aaggatgatg tttctgctaa cttcaccttt accggtgtag taaaagcgcc gttctataaa   1260
gacggcgaat ggaaaaacga tctggactca ccggcgccgc tgggcgagct ggagtctgcg   1320
tcgttcgtct ataccacgcc gaagaagaac cttgaggcca gcaatttcac tggtggtgta   1380
gcagaattcg ctaaagatct ggatacccttt gccagctcga tgaatgactt ctacggtcgt   1440
aatgatgaag acggtaagca ccggatgtttt acctataaaa acttgacggg gcacaagcat   1500
cgtttcacca acgatgtgca gatctccatc ggtgatgcgc actcgggtta tccggtaatg   1560
aacagcagct tctcgacgaa cagcaccacg ctgccgacga cgccgctgaa cgactggctg   1620
atttggcacg aagtcggtca taacgctgca gaaacaccgc tgaacgtacc gggtgcaact   1680
gaagtggcga caacgtgct ggcgctgtac atgcaggatc gctatctcgg taagatgaac   1740
cgtgtcgctg acgacattac cgtcgcgccg gaatatctgg acgagagcaa cggtcaggcc   1800
```

```
tgggcgcgcg gcggtgcggg tgaccgtctg ctgatgtacg cacagttgaa ggagtgggca    1860
gaggaaaact ttgatatcaa acagtggtat ccagatggtg agctgcctaa gttctacagc    1920
gatcgtaaag ggatgaaggg ctggaacctg ttccagttga tgcaccgtaa agcgcgcggc    1980
gatgatgttg gtaacagcac ctttggtggc aagaattact gtgctgaatc caatggtaac    2040
gctgccgaca cgctgatgct gtgtgcatcc tgggtcgctc aggcggatct ttcggaattc    2100
tttaagaaat ggaatccggg tgcaagtgct taccagttgc cgggagcaac ggagatgagt    2160
ttccagggcg gtgtgagctc ttcggcttac agcacgctgg cgtcactcaa gctgccgaaa    2220
ccggaaaaag ggccggaaac cattaacaag gttaccgagc ataagatgtc tgccgag      2277
```

<210> SEQ ID NO 12
<211> LENGTH: 759
<212> TYPE: PRT
<213> ORGANISM: Escherichia coli

<400> SEQUENCE: 12

```
Asp Pro Gln Gly Tyr Pro Asp Arg Val Arg Gln Arg Ala Thr Gly
1               5                   10                  15

Ile Trp Val Tyr Glu Arg Tyr Pro Ala Ala Asp Gly Ala Gln Pro Pro
            20                  25                  30

Tyr Thr Ile Asp Pro Asn Thr Gly Glu Val Thr Trp Lys Tyr Gln Gln
        35                  40                  45

Asp Asn Lys Pro Asp Asp Lys Pro Lys Leu Glu Val Ala Ser Trp Gln
    50                  55                  60

Glu Glu Val Glu Gly Lys Gln Val Thr Arg Tyr Ala Phe Ile Asp Glu
65                  70                  75                  80

Ala Glu Tyr Thr Thr Glu Glu Ser Leu Glu Ala Ala Lys Ala Lys Ile
                85                  90                  95

Phe Glu Lys Phe Pro Gly Leu Gln Glu Cys Lys Asp Ser Thr Tyr His
            100                 105                 110

Tyr Glu Ile Asn Cys Leu Glu Arg Arg Pro Gly Thr Asp Val Pro Val
        115                 120                 125

Thr Gly Gly Met Tyr Val Pro Arg Tyr Thr Gln Leu Asn Leu Asp Ala
    130                 135                 140

Asp Thr Ala Lys Ala Met Val Gln Ala Ala Asp Leu Gly Thr Asn Ile
145                 150                 155                 160

Gln Arg Leu Tyr Gln His Glu Leu Tyr Phe Arg Thr Lys Gly Ser Lys
                165                 170                 175

Gly Glu Arg Leu Asn Ser Val Asp Leu Glu Arg Leu Tyr Gln Asn Met
            180                 185                 190

Ser Val Trp Leu Trp Asn Asp Thr Lys Tyr Arg Tyr Glu Glu Gly Lys
        195                 200                 205

Glu Asp Glu Leu Gly Phe Lys Thr Phe Thr Glu Phe Leu Asn Cys Tyr
    210                 215                 220

Ala Asn Asp Ala Tyr Ala Gly Gly Thr Lys Cys Ser Ala Asp Leu Lys
225                 230                 235                 240

Lys Ser Leu Val Asp Asn Asn Met Ile Tyr Gly Asp Gly Ser Ser Lys
                245                 250                 255

Ala Gly Met Met Asn Pro Ser Tyr Pro Leu Asn Tyr Met Glu Lys Pro
            260                 265                 270

Leu Thr Arg Leu Met Leu Gly Arg Ser Trp Trp Asp Leu Asn Ile Lys
        275                 280                 285

Val Asp Val Glu Lys Tyr Pro Gly Ser Val Ser Ala Lys Gly Glu Ser
```

```
              290                 295                 300
Val Thr Glu Asn Ile Ser Leu Tyr Ser Asn Pro Thr Lys Trp Phe Ala
305                 310                 315                 320

Gly Asn Met Gln Ser Thr Gly Leu Trp Ala Pro Ala Gln Gln Asp Val
                325                 330                 335

Thr Ile Lys Ser Ser Ala Ser Val Pro Val Thr Val Thr Val Ala Leu
                340                 345                 350

Ala Asp Asp Leu Thr Gly Arg Glu Lys His Glu Val Ala Leu Asn Arg
                355                 360                 365

Pro Pro Arg Val Thr Lys Thr Tyr Thr Leu Glu Ala Asn Gly Glu Val
370                 375                 380

Thr Phe Lys Val Pro Tyr Gly Gly Leu Ile Tyr Ile Lys Gly Asp Ser
385                 390                 395                 400

Lys Asp Asp Val Ser Ala Asn Phe Thr Phe Thr Gly Val Val Lys Ala
                405                 410                 415

Pro Phe Tyr Lys Asp Gly Glu Trp Lys Asn Asp Leu Asp Ser Pro Ala
                420                 425                 430

Pro Leu Gly Glu Leu Glu Ser Ala Ser Phe Val Tyr Thr Thr Pro Lys
                435                 440                 445

Lys Asn Leu Glu Ala Ser Asn Phe Thr Gly Gly Val Ala Glu Phe Ala
                450                 455                 460

Lys Asp Leu Asp Thr Phe Ala Ser Ser Met Asn Asp Phe Tyr Gly Arg
465                 470                 475                 480

Asn Asp Glu Asp Gly Lys His Arg Met Phe Thr Tyr Lys Asn Leu Thr
                485                 490                 495

Gly His Lys His Arg Phe Thr Asn Asp Val Gln Ile Ser Ile Gly Asp
                500                 505                 510

Ala His Ser Gly Tyr Pro Val Met Asn Ser Ser Phe Ser Thr Asn Ser
                515                 520                 525

Thr Thr Leu Pro Thr Thr Pro Leu Asn Asp Trp Leu Ile Trp His Glu
                530                 535                 540

Val Gly His Asn Ala Ala Glu Thr Pro Leu Asn Val Pro Gly Ala Thr
545                 550                 555                 560

Glu Val Ala Asn Asn Val Leu Ala Leu Tyr Met Gln Asp Arg Tyr Leu
                565                 570                 575

Gly Lys Met Asn Arg Val Ala Asp Ile Thr Val Ala Pro Glu Tyr
                580                 585                 590

Leu Asp Glu Ser Asn Gly Gln Ala Trp Ala Arg Gly Gly Ala Gly Asp
                595                 600                 605

Arg Leu Leu Met Tyr Ala Gln Leu Lys Glu Trp Ala Glu Asn Phe
610                 615                 620

Asp Ile Lys Gln Trp Tyr Pro Asp Gly Glu Leu Pro Lys Phe Tyr Ser
625                 630                 635                 640

Asp Arg Lys Gly Met Lys Gly Trp Asn Leu Phe Gln Leu Met His Arg
                645                 650                 655

Lys Ala Arg Gly Asp Asp Val Gly Asn Ser Thr Phe Gly Gly Lys Asn
                660                 665                 670

Tyr Cys Ala Glu Ser Asn Gly Asn Ala Ala Asp Thr Leu Met Leu Cys
                675                 680                 685

Ala Ser Trp Val Ala Gln Ala Asp Leu Ser Glu Phe Phe Lys Lys Trp
                690                 695                 700

Asn Pro Gly Ala Ser Ala Tyr Gln Leu Pro Gly Ala Thr Glu Met Ser
705                 710                 715                 720
```

Phe Gln Gly Gly Val Ser Ser Ser Ala Tyr Ser Thr Leu Ala Ser Leu
                725                 730                 735

Lys Leu Pro Lys Pro Glu Lys Gly Pro Glu Thr Ile Asn Lys Val Thr
            740                 745                 750

Glu His Lys Met Ser Ala Glu
        755

<210> SEQ ID NO 13
<211> LENGTH: 4461
<212> TYPE: DNA
<213> ORGANISM: Escherichia coli

<400> SEQUENCE: 13

| | | | | | |
|---|---|---|---|---|---|
| gatacgccgt | ctgtagattc | tggatcaggg | actttgccgg | aagtgaaacc | cgatccaaca | 60 |
| ccaaccccgg | agccgacacc | tgagccgacg | ccggaccccag | aacctacgcc | ggatccaaca | 120 |
| cctgatcctg | agccgacacc | agaaccggag | ccagaacctg | ttcctacgaa | acgggttat | 180 |
| ctgaccctgg | gcggaagcca | gcgggtaact | ggtgctacct | gtaatggtga | atccagcgat | 240 |
| ggctttacct | ttacgccagg | caataccgtg | agttgtgtgg | tgggcagtac | gaccattgca | 300 |
| acattcaaca | cccagtcaga | agctgcgcgt | agcctgcgtg | cggttgacaa | agtgtcgttt | 360 |
| agcctggagg | acgcgcagga | gctggcgaat | tctgaaaata | agaaaaccaa | cgccatctct | 420 |
| ctggtgacgt | ccagcgacag | ttgccccgca | gatgcagaac | agctttgtct | tactttctcg | 480 |
| tcagtggttg | atcgcgcgcg | atttgaaaaa | ctgtataagc | aaattgatct | ggcaacagac | 540 |
| aatttcagca | agctggtcaa | tgaagaggtg | aaaacaatg | ctgcgactga | taaagcgccg | 600 |
| tccaccccata | cctcaacggt | agtgccagtc | acgacagagg | gaacaaaacc | ggatctgaac | 660 |
| gcgtccttcg | tgtcggctaa | cgcggaacag | ttttatcagt | atcaacccac | tgaaatcatt | 720 |
| cttttccgaag | gccaactggt | ggatagcctg | gggaacggtg | ttgctggcgt | tgactactac | 780 |
| accaattcag | gccgtggcgt | aactgacgaa | acggtaaat | tttccttag | ctggggcgaa | 840 |
| accatctcct | ttggtatcga | tacctttgaa | ctgggctcag | tacgtggcaa | taagtcgacc | 900 |
| attgcgctga | ctgaattggg | tgatgaagtt | cgcggggcaa | atatcgatca | gctcattcat | 960 |
| cgttattcga | cgactggtca | aaataatact | cgtgttgttc | cggacgatgt | acgcaaggtc | 1020 |
| tttgccgaat | atcccaacgt | gatcaacgag | ataatcaatc | tttcgttatc | caacggtgcg | 1080 |
| acgctggatg | aaggcgatca | aaacgttgtg | ctgcctaacg | aatttatcga | gcagtttaag | 1140 |
| acgggtcagg | ccaaagagat | cgataccgcg | atttgtgcga | aaaccgacgg | ttgtaacgag | 1200 |
| gctcgctggt | tctcgctgac | aacgcgcaat | gttaatgacg | gccagattca | gggcgttatt | 1260 |
| aacaagctgt | ggggcgtgga | tacgaactat | cagtctgtca | gcaagttcca | cgtcttccat | 1320 |
| gactctacca | acttctatgg | cagcaccggt | aacgcgcgcg | gtcaggcggt | ggtaaatatc | 1380 |
| tccaactcgg | cattcccgat | tctgatggcg | cgtaatgata | aaaactactg | gctggcgttt | 1440 |
| ggcgaaaaac | gcgcctggga | taaaaatgag | ctggcgtaca | ttacggaagc | gccttccatt | 1500 |
| gtgcagccag | agaacgttac | gcgcgatact | gcgactttca | acctgccgtt | tatttcgctg | 1560 |
| gggcaagtcg | gtgaaggcaa | actgatggtt | atcggtaacc | cgcactacaa | cagcatcctg | 1620 |
| cgttgcccga | acggttacag | ttggggcggt | ggtgttaata | gtaaaggtga | gtgtacgctc | 1680 |
| agcggtgatt | ctgatgacat | gaagcacttt | atgcagaacg | tactgcgcta | cttgtcaaat | 1740 |
| gacatctggc | agccaaatac | caagagcatc | atgactgtcg | gcaccaacct | ggagaacgtt | 1800 |
| tatttcaaaa | aagcgggcca | ggtattggga | aatagtgcac | catttgcttt | ccatgaggat | 1860 |

```
ttcactggta tcacggttaa acagttgacc agctatggcg atctgaatcc ggaagagatt   1920
ccgttgctga tcctcaacgg ctttgaatat gtgactcagt ggtctggcga tccctatgct   1980
gtgcctctgc gtgcagatac cagcaaaccg aagctgactc agcaggatgt gaccgatctg   2040
atcgcttatc tgaacaaagg tggctcggtg ctgatcatgg aaaacgtgat gagcaatctt   2100
aaggaagaga gcgcgtccag ttttgtgcgt ctgctggatg ccgcgggtct gtcaatggct   2160
ctgaacaaat cggtggtgaa caacgatccg caagggtatc cggatcgcgt tcgtcagcgt   2220
cgcgcgactg gcatttgggt ttatgaacgt tatcctgctg cagacggcgc gcaaccgccg   2280
tacaccatcg acccaaatac aggggaagtg acctggaaat accagcaaga caacaagcct   2340
gatgacaagc cgaaactgga agttgcgagc tggcaggagg aagttgaggg caaacaggta   2400
acgcgttatg cctttattga tgaagcggaa tacacaacag aagaatctct ggaagcggca   2460
aaggcaaaaa tctttgagaa gtttcctggg ttacaggagt gtaaggactc gacttaccat   2520
tacgagatta actgtttgga gcgccgccca ggcacggatt tccggtaac aggtggcatg   2580 tatgttccgc gctatacgca actgaatctt gacgccgaca ccgcgaaagc gatggtgcag   2640
gcggcggatt taggcaccaa cattcagcgc ctgtatcagc atgagcttta tttccgtacc   2700
aaaggcagta aggtgagcg tctgaacagt gttgatctgg aacgtctgta ccagaacatg   2760
tcggtctggc tgtggaacga tacgaaatat cgttacgaag agggcaagga agatgagctg   2820
ggctttaaaa cgttcaccga gttcctgaac tgctacgcca atgatgccta tgcaggcggc   2880
accaagtgct ccgcagatct gaaaaaatcg ctggtcgata caacatgat ctacggtgac    2940 ggtagcagca aagcgggcat gatgaaccca agctatccgc tcaactatat ggaaaaaccg   3000
ctgacgcgtc tgatgctggg ccgttcctgg tgggatctga acattaaggt tgatgtggag   3060
aagtacccag gatccgtatc ggcaaagggt gagagcgtta cggaaaacat cagcctgtac   3120
tcgaatccga ccaaatggtt tgcgggtaac atgcagtcaa ccggcctgtg ggcaccggcc   3180
cagcaggacg tcaccattaa gtcttcggcg tcagtcccag tgactgttac cgtggcgctg   3240
gctgacgacc tgactggacg tgagaagcat gaagttgcgc tgaaccgtcc gccaagagtg   3300
actaaaacgt atactctgga ggctaacggt gaagtgacct tcaaggtgcc ttatggtggt   3360
ctgatttata tcaagggcga cagtaaggat gatgtttctg ctaacttcac ctttaccggt   3420
gtagtaaaag cgccgttcta taagacggc gaatggaaaa acgatctgga ctcaccggcg   3480
ccgctgggcg agctggagtc tgcgtcgttc gtctatacca cgccgaagaa gaaccttgag   3540
gccagcaatt tcactggtgg tgtagcagaa ttcgctaaag atctggatac ctttgccagc   3600
tcgatgaatg acttctacgg tcgtaatgat gaagacggta agcaccggat gtttacctat   3660
aaaaacttga cggggcacaa gcatcgtttc accaacgatg tgcagatctc catcggtgat   3720
gcgcactcgg ttatccggt aatgaacagc agcttctcga cgaacagcac cacgctgccg   3780
acgacgccgc tgaacgactg gctgatttgg cacgaagtcg gtcataacgc tgcagaaaca   3840
ccgctgaacg taccgggtgc aactgaagtg gcgaacaacg tgctggcgct gtacatgcag   3900
gatcgctatc tcggtaagat gaaccgtgtc gctgacgaca ttaccgtcgc gccggaatat   3960
ctggacgaga gcaacggtca ggcctggcg cgcggcggtg cgggtgaccg tctgctgatg   4020
tacgcacagt tgaaggagtg ggcagaggaa aactttgata tcaaacagtg gtatccagat   4080
ggtgagctgc ctaagttcta cagcgatcgt aaagggatga agggctggaa cctgttccag   4140
ttgatgcacc gtaaagcgcg cggcgatgat gttggtaaca gcacctttgg tggcaagaat   4200
```

-continued

```
tactgtgctg aatccaatgg taacgctgcc gacacgctga tgctgtgtgc atcctgggtc    4260
gctcaggcgg atctttcgga attcttaag aaatggaatc cgggtgcaag tgcttaccag     4320
ttgccgggag caacggagat gagtttccag ggcggtgtga gctcttcggc ttacagcacg    4380
ctggcgtcac tcaagctgcc gaaaccggaa aagggccgg aaaccattaa caaggttacc     4440
gagcataaga tgtctgccga g                                              4461
```

<210> SEQ ID NO 14
<211> LENGTH: 1487
<212> TYPE: PRT
<213> ORGANISM: Escherichia coli

<400> SEQUENCE: 14

```
Asp Thr Pro Ser Val Asp Ser Gly Ser Gly Thr Leu Pro Glu Val Lys
1               5                   10                  15

Pro Asp Pro Thr Pro Thr Pro Glu Pro Thr Pro Glu Pro Thr Pro Asp
                20                  25                  30

Pro Glu Pro Thr Pro Asp Pro Thr Pro Asp Pro Glu Pro Thr Pro Glu
            35                  40                  45

Pro Glu Pro Glu Pro Val Pro Thr Lys Thr Gly Tyr Leu Thr Leu Gly
        50                  55                  60

Gly Ser Gln Arg Val Thr Gly Ala Thr Cys Asn Gly Glu Ser Ser Asp
65                  70                  75                  80

Gly Phe Thr Phe Thr Pro Gly Asn Thr Val Ser Cys Val Val Gly Ser
                85                  90                  95

Thr Thr Ile Ala Thr Phe Asn Thr Gln Ser Glu Ala Ala Arg Ser Leu
            100                 105                 110

Arg Ala Val Asp Lys Val Ser Phe Ser Leu Glu Asp Ala Gln Glu Leu
        115                 120                 125

Ala Asn Ser Glu Asn Lys Lys Thr Asn Ala Ile Ser Leu Val Thr Ser
130                 135                 140

Ser Asp Ser Cys Pro Ala Asp Ala Glu Gln Leu Cys Leu Thr Phe Ser
145                 150                 155                 160

Ser Val Val Asp Arg Ala Arg Phe Glu Lys Leu Tyr Lys Gln Ile Asp
                165                 170                 175

Leu Ala Thr Asp Asn Phe Ser Lys Leu Val Asn Glu Val Glu Asn
            180                 185                 190

Asn Ala Ala Thr Asp Lys Ala Pro Ser Thr His Thr Ser Thr Val Val
        195                 200                 205

Pro Val Thr Thr Glu Gly Thr Lys Pro Asp Leu Asn Ala Ser Phe Val
    210                 215                 220

Ser Ala Asn Ala Glu Gln Phe Tyr Gln Tyr Gln Pro Thr Glu Ile Ile
225                 230                 235                 240

Leu Ser Glu Gly Gln Leu Val Asp Ser Leu Gly Asn Gly Val Ala Gly
                245                 250                 255

Val Asp Tyr Tyr Thr Asn Ser Gly Arg Gly Val Thr Asp Glu Asn Gly
            260                 265                 270

Lys Phe Ser Phe Ser Trp Gly Glu Thr Ile Ser Phe Gly Ile Asp Thr
        275                 280                 285

Phe Glu Leu Gly Ser Val Arg Gly Asn Lys Ser Thr Ile Ala Leu Thr
    290                 295                 300

Glu Leu Gly Asp Glu Val Arg Gly Ala Asn Ile Asp Gln Leu Ile His
305                 310                 315                 320

Arg Tyr Ser Thr Thr Gly Gln Asn Asn Thr Arg Val Val Pro Asp Asp
```

-continued

```
                325                 330                 335
Val Arg Lys Val Phe Ala Glu Tyr Pro Asn Val Ile Asn Glu Ile Ile
            340                 345                 350
Asn Leu Ser Leu Ser Asn Gly Ala Thr Leu Asp Glu Gly Asp Gln Asn
        355                 360                 365
Val Val Leu Pro Asn Glu Phe Ile Glu Gln Phe Lys Thr Gly Gln Ala
    370                 375                 380
Lys Glu Ile Asp Thr Ala Ile Cys Ala Lys Thr Asp Gly Cys Asn Glu
385                 390                 395                 400
Ala Arg Trp Phe Ser Leu Thr Thr Arg Asn Val Asn Asp Gly Gln Ile
                405                 410                 415
Gln Gly Val Ile Asn Lys Leu Trp Gly Val Asp Thr Asn Tyr Gln Ser
            420                 425                 430
Val Ser Lys Phe His Val Phe His Asp Ser Thr Asn Phe Tyr Gly Ser
        435                 440                 445
Thr Gly Asn Ala Arg Gly Gln Ala Val Val Asn Ile Ser Asn Ser Ala
    450                 455                 460
Phe Pro Ile Leu Met Ala Arg Asn Asp Lys Asn Tyr Trp Leu Ala Phe
465                 470                 475                 480
Gly Glu Lys Arg Ala Trp Asp Lys Asn Glu Leu Ala Tyr Ile Thr Glu
                485                 490                 495
Ala Pro Ser Ile Val Gln Pro Glu Asn Val Thr Arg Asp Thr Ala Thr
            500                 505                 510
Phe Asn Leu Pro Phe Ile Ser Leu Gly Gln Val Gly Glu Gly Lys Leu
        515                 520                 525
Met Val Ile Gly Asn Pro His Tyr Asn Ser Ile Leu Arg Cys Pro Asn
    530                 535                 540
Gly Tyr Ser Trp Gly Gly Val Asn Ser Lys Gly Glu Cys Thr Leu
545                 550                 555                 560
Ser Gly Asp Ser Asp Met Lys His Phe Met Gln Asn Val Leu Arg
                565                 570                 575
Tyr Leu Ser Asn Asp Ile Trp Gln Pro Asn Thr Lys Ser Ile Met Thr
            580                 585                 590
Val Gly Thr Asn Leu Glu Asn Val Tyr Phe Lys Lys Ala Gly Gln Val
        595                 600                 605
Leu Gly Asn Ser Ala Pro Phe Ala Phe His Glu Asp Phe Thr Gly Ile
    610                 615                 620
Thr Val Lys Gln Leu Thr Ser Tyr Gly Asp Leu Asn Pro Glu Glu Ile
625                 630                 635                 640
Pro Leu Leu Ile Leu Asn Gly Phe Glu Tyr Val Thr Gln Trp Ser Gly
                645                 650                 655
Asp Pro Tyr Ala Val Pro Leu Arg Ala Asp Thr Ser Lys Pro Lys Leu
            660                 665                 670
Thr Gln Gln Asp Val Thr Asp Leu Ile Ala Tyr Leu Asn Lys Gly Gly
        675                 680                 685
Ser Val Leu Ile Met Glu Asn Val Met Ser Asn Leu Lys Glu Glu Ser
    690                 695                 700
Ala Ser Ser Phe Val Arg Leu Leu Asp Ala Ala Gly Leu Ser Met Ala
705                 710                 715                 720
Leu Asn Lys Ser Val Val Asn Asn Asp Pro Gln Gly Tyr Pro Asp Arg
                725                 730                 735
Val Arg Gln Arg Arg Ala Thr Gly Ile Trp Val Tyr Glu Arg Tyr Pro
            740                 745                 750
```

-continued

Ala Ala Asp Gly Ala Gln Pro Pro Tyr Thr Ile Asp Pro Asn Thr Gly
            755                 760                 765

Glu Val Thr Trp Lys Tyr Gln Gln Asp Asn Lys Pro Asp Lys Pro
    770                 775                 780

Lys Leu Glu Val Ala Ser Trp Gln Glu Val Glu Gly Lys Gln Val
785                 790                 795                 800

Thr Arg Tyr Ala Phe Ile Asp Glu Ala Glu Tyr Thr Thr Glu Ser
                805                 810                 815

Leu Glu Ala Ala Lys Ala Lys Ile Phe Glu Lys Phe Pro Gly Leu Gln
                820                 825                 830

Glu Cys Lys Asp Ser Thr Tyr His Tyr Glu Ile Asn Cys Leu Glu Arg
    835                 840                 845

Arg Pro Gly Thr Asp Val Pro Val Thr Gly Gly Met Tyr Val Pro Arg
    850                 855                 860

Tyr Thr Gln Leu Asn Leu Asp Ala Asp Thr Ala Lys Ala Met Val Gln
865                 870                 875                 880

Ala Ala Asp Leu Gly Thr Asn Ile Gln Arg Leu Tyr Gln His Glu Leu
                885                 890                 895

Tyr Phe Arg Thr Lys Gly Ser Lys Gly Glu Arg Leu Asn Ser Val Asp
                900                 905                 910

Leu Glu Arg Leu Tyr Gln Asn Met Ser Val Trp Leu Trp Asn Asp Thr
    915                 920                 925

Lys Tyr Arg Tyr Glu Glu Gly Lys Glu Asp Glu Leu Gly Phe Lys Thr
    930                 935                 940

Phe Thr Glu Phe Leu Asn Cys Tyr Ala Asn Asp Ala Tyr Ala Gly Gly
945                 950                 955                 960

Thr Lys Cys Ser Ala Asp Leu Lys Lys Ser Leu Val Asp Asn Asn Met
                965                 970                 975

Ile Tyr Gly Asp Gly Ser Ser Lys Ala Gly Met Met Asn Pro Ser Tyr
                980                 985                 990

Pro Leu Asn Tyr Met Glu Lys Pro Leu Thr Arg Leu Met Leu Gly Arg
    995                 1000                1005

Ser Trp Trp Asp Leu Asn Ile Lys Val Asp Val Glu Lys Tyr Pro Gly
    1010                1015                1020

Ser Val Ser Ala Lys Gly Glu Ser Val Thr Glu Asn Ile Ser Leu Tyr
1025                1030                1035                1040

Ser Asn Pro Thr Lys Trp Phe Ala Gly Asn Met Gln Ser Thr Gly Leu
                1045                1050                1055

Trp Ala Pro Ala Gln Gln Asp Val Thr Ile Lys Ser Ser Ala Ser Val
                1060                1065                1070

Pro Val Thr Val Thr Val Ala Leu Ala Asp Asp Leu Thr Gly Arg Glu
    1075                1080                1085

Lys His Glu Val Ala Leu Asn Arg Pro Pro Arg Val Thr Lys Thr Tyr
    1090                1095                1100

Thr Leu Glu Ala Asn Gly Glu Val Thr Phe Lys Val Pro Tyr Gly Gly
1105                1110                1115                1120

Leu Ile Tyr Ile Lys Gly Asp Ser Lys Asp Asp Val Ser Ala Asn Phe
                1125                1130                1135

Thr Phe Thr Gly Val Val Lys Ala Pro Phe Tyr Lys Asp Gly Glu Trp
                1140                1145                1150

Lys Asn Asp Leu Asp Ser Pro Ala Pro Leu Gly Glu Leu Glu Ser Ala
                1155                1160                1165

Ser Phe Val Tyr Thr Thr Pro Lys Lys Asn Leu Glu Ala Ser Asn Phe
1170            1175                1180

Thr Gly Gly Val Ala Glu Phe Ala Lys Asp Leu Asp Thr Phe Ala Ser
1185            1190                1195                1200

Ser Met Asn Asp Phe Tyr Gly Arg Asn Asp Glu Asp Gly Lys His Arg
        1205                1210                1215

Met Phe Thr Tyr Lys Asn Leu Thr Gly His Lys His Arg Phe Thr Asn
        1220                1225                1230

Asp Val Gln Ile Ser Ile Gly Asp Ala His Ser Gly Tyr Pro Val Met
        1235                1240                1245

Asn Ser Ser Phe Ser Thr Asn Ser Thr Thr Leu Pro Thr Thr Pro Leu
1250            1255                1260

Asn Asp Trp Leu Ile Trp His Glu Val Gly His Asn Ala Ala Glu Thr
1265            1270                1275                1280

Pro Leu Asn Val Pro Gly Ala Thr Glu Val Ala Asn Asn Val Leu Ala
                1285                1290                1295

Leu Tyr Met Gln Asp Arg Tyr Leu Gly Lys Met Asn Arg Val Ala Asp
                1300                1305                1310

Asp Ile Thr Val Ala Pro Glu Tyr Leu Asp Glu Ser Asn Gly Gln Ala
            1315                1320                1325

Trp Ala Arg Gly Gly Ala Gly Asp Arg Leu Leu Met Tyr Ala Gln Leu
            1330                1335                1340

Lys Glu Trp Ala Glu Glu Asn Phe Asp Ile Lys Gln Trp Tyr Pro Asp
1345            1350                1355                1360

Gly Glu Leu Pro Lys Phe Tyr Ser Asp Arg Lys Gly Met Lys Gly Trp
                1365                1370                1375

Asn Leu Phe Gln Leu Met His Arg Lys Ala Arg Gly Asp Asp Val Gly
            1380                1385                1390

Asn Ser Thr Phe Gly Gly Lys Asn Tyr Cys Ala Glu Ser Asn Gly Asn
            1395                1400                1405

Ala Ala Asp Thr Leu Met Leu Cys Ala Ser Trp Val Ala Gln Ala Asp
        1410                1415                1420

Leu Ser Glu Phe Phe Lys Lys Trp Asn Pro Gly Ala Ser Ala Tyr Gln
1425            1430                1435                1440

Leu Pro Gly Ala Thr Glu Met Ser Phe Gln Gly Gly Val Ser Ser Ser
            1445                1450                1455

Ala Tyr Ser Thr Leu Ala Ser Leu Lys Leu Pro Lys Pro Glu Lys Gly
            1460                1465                1470

Pro Glu Thr Ile Asn Lys Val Thr Glu His Lys Met Ser Ala Glu
        1475                1480                1485

<210> SEQ ID NO 15
<211> LENGTH: 4293
<212> TYPE: DNA
<213> ORGANISM: Escherichia coli

<400> SEQUENCE: 15
aaaacgggtt atctgaccct gggcggaagc cagcgggtaa ctggtgctac ctgtaatggt    60
gaatccagcg atggctttac ctttacgcca ggcaataccg tgagttgtgt ggtgggcagt   120
acgaccattg caacattcaa cacccagtca gaagctgcgc gtagcctgcg tgcggttgac   180
aaagtgtcgt ttagcctgga ggacgcgcag gagctggcga attctgaaaa taagaaaacc   240
aacgccatct ctctggtgac gtccagcgac agttgccccg cagatgcaga acagctttgt   300
cttactttct cgtcagtggt tgatcgcgcg cgatttgaaa aactgtataa gcaaattgat   360

```
ctggcaacag acaatttcag caagctggtc aatgaagagg tggaaaacaa tgctgcgact    420
gataaagcgc cgtccaccca tacctcaacg gtagtgccag tcacgacaga gggaacaaaa    480
ccggatctga acgcgtcctt cgtgtcggct aacgcggaac agttttatca gtatcaaccc    540
actgaaatca ttctttccga aggccaactg gtggatagcc tggggaacgg tgttgctggc    600
gttgactact acaccaattc aggccgtggc gtaactgacg aaaacggtaa atttccttt     660
agctggggcg aaaccatctc ctttggtatc gatacctttg aactgggctc agtacgtggc    720
aataagtcga ccattgcgct gactgaattg ggtgatgaag ttcgcggggc aaatatcgat    780
cagctcattc atcgttattc gacgactggt caaaataata ctcgtgttgt tccggacgat    840
gtacgcaagg tctttgccga atatcccaac gtgatcaacg agataatcaa tctttcgtta    900
tccaacggtg cgacgctgga tgaaggcgat caaaacgttg tgctgcctaa cgaatttatc    960
gagcagttta gacgggtca ggccaaagag atcgataccg cgatttgtgc gaaaaccgac    1020
ggttgtaacg aggctcgctg gttctcgctg acaacgcgca atgttaatga cggccagatt    1080
cagggcgtta ttaacaagct gtggggcgtg gatacgaact atcagtctgt cagcaagttc    1140
cacgtcttcc atgactctac caacttctat ggcagcaccg gtaacgcgcg cggtcaggcg    1200
gtggtaaata tctccaactc ggcattcccg attctgatgg cgcgtaatga taaaaactac    1260
tggctggcgt ttggcgaaaa acgcgcctgg gataaaaatg agctggcgta cattacggaa    1320
gcgccttcca ttgtgcagcc agagaacgtt acgcgcgata ctgcgacttt caacctgccg    1380
tttatttcgc tggggcaagt cggtgaaggc aaactgatgg ttatcggtaa cccgcactac    1440
aacagcatcc tgcgttgccc gaacggttac agttggggcg gtggtgttaa tagtaaaggt    1500
gagtgtacgc tcagcggtga ttctgatgac atgaagcact ttatgcagaa cgtactgcgc    1560
tacttgtcaa atgacatctg gcagccaaat accaagagca tcatgactgt cggcaccaac    1620
ctggagaacg tttatttcaa aaaagcgggc caggtattgg gaaatagtgc accatttgct    1680
ttccatgagg atttcactgg tatcacggtt aaacagttga ccagctatgg cgatctgaat    1740
ccggaagaga ttccgttgct gatcctcaac ggctttgaat atgtgactca gtggtctggc    1800
gatccctatg ctgtgcctct gcgtgcagat accagcaaac cgaagctgac tcagcaggat    1860
gtgaccgatc tgatcgctta tctgaacaaa ggtggctcgg tgctgatcat ggaaaacgtg    1920
atgagcaatc ttaaggaaga gagcgcgtcc agttttgtgc gtctgctgga tgccgcgggt    1980
ctgtcaatgg ctctgaacaa atcggtggtg aacaacgatc cgcaagggta tccggatcgc    2040
gttcgtcagc gtcgcgcgac tggcatttgg gtttatgaac gttatcctgc tgcagacggc    2100
gcgcaaccgc cgtacaccat cgacccaaat acagggaag tgacctggaa ataccagcaa    2160
gacaacaagc ctgatgacaa gccgaaactg gaagttgcga gctggcagga ggaagttgag    2220
ggcaaacagg taacgcgtta tgcctttatt gatgaagcgg aatacacaac agaagaatct    2280
ctggaagcgc aaaggcaaa atctttgag agtttcctg ggttacagga gtgtaaggac    2340
tcgacttacc attacgagat taactgtttg gagcgccgcc caggcacgga tgttccggta    2400
acaggtggca tgtatgttcc gcgctatacg caactgaatc ttgacgccga caccgcgaaa    2460
gcgatggtgc aggcggcgga tttaggcacc aacattcagc gcctgtatca gcatgagctt    2520
tatttccgta ccaaaggcag taaaggtgag cgtctgaaca tgttgatctg gaacgtctg    2580
taccagaaca tgtcggtctg gctgtggaac gatacgaaat atcgttacga agagggcaag    2640
gaagatgagc tgggctttaa aacgttcacc gagttcctga actgctacgc caatgatgcc    2700
```

```
tatgcaggcg gcaccaagtg ctccgcagat ctgaaaaaat cgctggtcga taacaacatg      2760
atctacggtg acggtagcag caaagcgggc atgatgaacc caagctatcc gctcaactat      2820
atggaaaaac cgctgacgcg tctgatgctg ggccgttcct ggtgggatct gaacattaag      2880
gttgatgtgg agaagtaccc aggatccgta tcggcaaagg gtgagagcgt tacgaaaaac      2940
atcagcctgt actcgaatcc gaccaaatgg tttgcgggta acatgcagtc aaccggcctg      3000
tgggcaccgg cccagcagga cgtcaccatt aagtcttcgg cgtcagtccc agtgactgtt      3060
accgtggcgc tggctgacga cctgactgga cgtgagaagc atgaagttgc gctgaaccgt      3120
ccgccaagag tgactaaaaac gtatactctg gaggctaacg tgaagtgac cttcaaggtg      3180 ccttatggtg gtctgattta tcaagggc gacagtaagg atgatgtttc tgctaacttc      3240
acctttaccg gtgtagtaaa agcgccgttc tataaagacg gcgaatggaa aaacgatctg      3300
gactcaccgg cgccgctggg cgagctggag tctgcgtcgt tcgtctatac cacgccgaag      3360
aagaaccttg aggccagcaa tttcactggt ggtgtagcag aattcgctaa agatctggat      3420
accttgtcca gctcgatgaa tgacttctac ggtcgtaatg atgaagacgg taagcaccgg      3480
atgtttacct ataaaaactt gacggggcac aagcatcgtt tcaccaacga tgtgcagatc      3540
tccatcggtg atgcgcactc gggttatccg gtaatgaaca gcagcttctc gacgaacagc      3600
accacgctgc cgacgacgcc gctgaacgac tggctgatt ggcacgaagt cggtcataac      3660
gctgcagaaa caccgctgaa cgtaccgggt gcaactgaag tggcgaacaa cgtgctggcg      3720
ctgtacatgc aggatcgcta tctcggtaag atgaaccgtg tcgctgacga cattaccgtc      3780
gcgccggaat atctggacga gagcaacggt caggcctggg cgcgcggcgg tgcgggtgac      3840
cgtctgctga tgtacgcaca gttgaaggag tgggcagagg aaaactttga tatcaaacag      3900
tggtatccag atggtgagct gcctaagttc tacagcgatc gtaaagggat gaagggctgg      3960
aacctgttcc agttgatgca ccgtaaagcg cgcggcgatg atgttggtaa cagcacctt      4020 ggtggcaaga attactgtgc tgaatccaat ggtaacgctg ccgacacgct gatgctgtgt      4080
gcatcctggg tcgctcaggc ggatcttttcg gaattctta agaaatggaa tccgggtgca      4140
agtgcttacc agttgccggg agcaacggag atgagtttcc agggcggtgt gagctcttcg      4200
gcttacagca cgctggcgtc actcaagctg ccgaaaccgg aaaaagggcc ggaaaccatt      4260
aacaaggtta ccgagcataa gatgtctgcc gag                                  4293
```

<210> SEQ ID NO 16
<211> LENGTH: 1431
<212> TYPE: PRT
<213> ORGANISM: Escherichia coli

<400> SEQUENCE: 16

Lys Thr Gly Tyr Leu Thr Leu Gly Gly Ser Gln Arg Val Thr Gly Ala
1               5                   10                  15

Thr Cys Asn Gly Glu Ser Ser Asp Gly Phe Thr Phe Thr Pro Gly Asn
            20                  25                  30

Thr Val Ser Cys Val Val Gly Ser Thr Thr Ile Ala Thr Phe Asn Thr
        35                  40                  45

Gln Ser Glu Ala Ala Arg Ser Leu Arg Ala Val Asp Lys Val Ser Phe
    50                  55                  60

Ser Leu Glu Asp Ala Gln Glu Leu Ala Asn Ser Glu Asn Lys Lys Thr
65                  70                  75                  80

Asn Ala Ile Ser Leu Val Thr Ser Ser Asp Ser Cys Pro Ala Asp Ala
                85                  90                  95

```
Glu Gln Leu Cys Leu Thr Phe Ser Ser Val Val Asp Arg Ala Arg Phe
                100                 105                 110

Glu Lys Leu Tyr Lys Gln Ile Asp Leu Ala Thr Asp Asn Phe Ser Lys
            115                 120                 125

Leu Val Asn Glu Glu Val Glu Asn Asn Ala Ala Thr Asp Lys Ala Pro
        130                 135                 140

Ser Thr His Thr Ser Thr Val Val Pro Val Thr Thr Glu Gly Thr Lys
145                 150                 155                 160

Pro Asp Leu Asn Ala Ser Phe Val Ser Ala Asn Ala Glu Gln Phe Tyr
                165                 170                 175

Gln Tyr Gln Pro Thr Glu Ile Ile Leu Ser Glu Gly Gln Leu Val Asp
            180                 185                 190

Ser Leu Gly Asn Gly Val Ala Gly Val Asp Tyr Tyr Thr Asn Ser Gly
        195                 200                 205

Arg Gly Val Thr Asp Glu Asn Gly Lys Phe Ser Phe Ser Trp Gly Glu
    210                 215                 220

Thr Ile Ser Phe Gly Ile Asp Thr Phe Glu Leu Gly Ser Val Arg Gly
225                 230                 235                 240

Asn Lys Ser Thr Ile Ala Leu Thr Glu Leu Gly Asp Glu Val Arg Gly
                245                 250                 255

Ala Asn Ile Asp Gln Leu Ile His Arg Tyr Ser Thr Thr Gly Gln Asn
            260                 265                 270

Asn Thr Arg Val Val Pro Asp Val Arg Lys Val Phe Ala Glu Tyr
        275                 280                 285

Pro Asn Val Ile Asn Glu Ile Ile Asn Leu Ser Leu Ser Asn Gly Ala
        290                 295                 300

Thr Leu Asp Glu Gly Asp Gln Asn Val Val Leu Pro Asn Glu Phe Ile
305                 310                 315                 320

Glu Gln Phe Lys Thr Gly Gln Ala Lys Glu Ile Asp Thr Ala Ile Cys
                325                 330                 335

Ala Lys Thr Asp Gly Cys Asn Glu Ala Arg Trp Phe Ser Leu Thr Thr
            340                 345                 350

Arg Asn Val Asn Asp Gly Gln Ile Gln Gly Val Ile Asn Lys Leu Trp
        355                 360                 365

Gly Val Asp Thr Asn Tyr Gln Ser Val Ser Lys Phe His Val Phe His
    370                 375                 380

Asp Ser Thr Asn Phe Tyr Gly Ser Thr Gly Asn Ala Arg Gly Gln Ala
385                 390                 395                 400

Val Val Asn Ile Ser Asn Ser Ala Phe Pro Ile Leu Met Ala Arg Asn
                405                 410                 415

Asp Lys Asn Tyr Trp Leu Ala Phe Gly Glu Lys Arg Ala Trp Asp Lys
            420                 425                 430

Asn Glu Leu Ala Tyr Ile Thr Glu Ala Pro Ser Ile Val Gln Pro Glu
        435                 440                 445

Asn Val Thr Arg Asp Thr Ala Thr Phe Asn Leu Pro Phe Ile Ser Leu
    450                 455                 460

Gly Gln Val Gly Glu Gly Lys Leu Met Val Ile Gly Asn Pro His Tyr
465                 470                 475                 480

Asn Ser Ile Leu Arg Cys Pro Asn Gly Tyr Ser Trp Gly Gly Val
                485                 490                 495

Asn Ser Lys Gly Glu Cys Thr Leu Ser Gly Asp Ser Asp Met Lys
            500                 505                 510
```

```
His Phe Met Gln Asn Val Leu Arg Tyr Leu Ser Asn Asp Ile Trp Gln
            515                 520                 525

Pro Asn Thr Lys Ser Ile Met Thr Val Gly Thr Asn Leu Glu Asn Val
530                 535                 540

Tyr Phe Lys Lys Ala Gly Gln Val Leu Gly Asn Ser Ala Pro Phe Ala
545                 550                 555                 560

Phe His Glu Asp Phe Thr Gly Ile Thr Val Lys Gln Leu Thr Ser Tyr
                    565                 570                 575

Gly Asp Leu Asn Pro Glu Glu Ile Pro Leu Leu Ile Leu Asn Gly Phe
                580                 585                 590

Glu Tyr Val Thr Gln Trp Ser Gly Asp Pro Tyr Ala Val Pro Leu Arg
            595                 600                 605

Ala Asp Thr Ser Lys Pro Lys Leu Thr Gln Gln Asp Val Thr Asp Leu
        610                 615                 620

Ile Ala Tyr Leu Asn Lys Gly Gly Ser Val Leu Ile Met Glu Asn Val
625                 630                 635                 640

Met Ser Asn Leu Lys Glu Glu Ser Ala Ser Phe Val Arg Leu Leu
                    645                 650                 655

Asp Ala Ala Gly Leu Ser Met Ala Leu Asn Lys Ser Val Val Asn Asn
                660                 665                 670

Asp Pro Gln Gly Tyr Pro Asp Arg Val Arg Gln Arg Ala Thr Gly
            675                 680                 685

Ile Trp Val Tyr Glu Arg Tyr Pro Ala Ala Asp Gly Ala Gln Pro Pro
            690                 695                 700

Tyr Thr Ile Asp Pro Asn Thr Gly Glu Val Thr Trp Lys Tyr Gln Gln
705                 710                 715                 720

Asp Asn Lys Pro Asp Asp Lys Pro Lys Leu Glu Val Ala Ser Trp Gln
                    725                 730                 735

Glu Glu Val Glu Gly Lys Gln Val Thr Arg Tyr Ala Phe Ile Asp Glu
                740                 745                 750

Ala Glu Tyr Thr Thr Glu Glu Ser Leu Glu Ala Ala Lys Ala Lys Ile
            755                 760                 765

Phe Glu Lys Phe Pro Gly Leu Gln Glu Cys Lys Asp Ser Thr Tyr His
770                 775                 780

Tyr Glu Ile Asn Cys Leu Glu Arg Arg Pro Gly Thr Asp Val Pro Val
785                 790                 795                 800

Thr Gly Gly Met Tyr Val Pro Arg Tyr Thr Gln Leu Asn Leu Asp Ala
                    805                 810                 815

Asp Thr Ala Lys Ala Met Val Gln Ala Ala Asp Leu Gly Thr Asn Ile
                820                 825                 830

Gln Arg Leu Tyr Gln His Glu Leu Tyr Phe Arg Thr Lys Gly Ser Lys
            835                 840                 845

Gly Glu Arg Leu Asn Ser Val Asp Leu Glu Arg Leu Tyr Gln Asn Met
        850                 855                 860

Ser Val Trp Leu Trp Asn Asp Thr Lys Tyr Arg Tyr Glu Glu Gly Lys
865                 870                 875                 880

Glu Asp Glu Leu Gly Phe Lys Thr Phe Thr Glu Phe Leu Asn Cys Tyr
                    885                 890                 895

Ala Asn Asp Ala Tyr Ala Gly Gly Thr Lys Cys Ser Ala Asp Leu Lys
                900                 905                 910

Lys Ser Leu Val Asp Asn Asn Met Ile Tyr Gly Asp Gly Ser Ser Lys
            915                 920                 925

Ala Gly Met Met Asn Pro Ser Tyr Pro Leu Asn Tyr Met Glu Lys Pro
```

```
                  930              935              940
Leu Thr Arg Leu Met Leu Gly Arg Ser Trp Trp Asp Leu Asn Ile Lys
945                  950              955              960

Val Asp Val Glu Lys Tyr Pro Gly Ser Val Ala Lys Gly Glu Ser
                965              970              975

Val Thr Glu Asn Ile Ser Leu Tyr Ser Asn Pro Thr Lys Trp Phe Ala
                980              985              990

Gly Asn Met Gln Ser Thr Gly Leu Trp Ala Pro Ala Gln Gln Asp Val
                995              1000             1005

Thr Ile Lys Ser Ser Ala Ser Val Pro Val Thr Val Thr Val Ala Leu
                1010             1015             1020

Ala Asp Asp Leu Thr Gly Arg Glu Lys His Glu Val Ala Leu Asn Arg
1025             1030             1035             1040

Pro Pro Arg Val Thr Lys Thr Tyr Thr Leu Glu Ala Asn Gly Glu Val
                1045             1050             1055

Thr Phe Lys Val Pro Tyr Gly Gly Leu Ile Tyr Ile Lys Gly Asp Ser
                1060             1065             1070

Lys Asp Asp Val Ser Ala Asn Phe Thr Phe Thr Gly Val Val Lys Ala
                1075             1080             1085

Pro Phe Tyr Lys Asp Gly Glu Trp Lys Asn Asp Leu Asp Ser Pro Ala
                1090             1095             1100

Pro Leu Gly Glu Leu Glu Ser Ala Ser Phe Val Tyr Thr Thr Pro Lys
1105             1110             1115             1120

Lys Asn Leu Glu Ala Ser Asn Phe Thr Gly Gly Val Ala Glu Phe Ala
                1125             1130             1135

Lys Asp Leu Asp Thr Phe Ala Ser Ser Met Asn Asp Phe Tyr Gly Arg
                1140             1145             1150

Asn Asp Glu Asp Gly Lys His Arg Met Phe Thr Tyr Lys Asn Leu Thr
                1155             1160             1165

Gly His Lys His Arg Phe Thr Asn Asp Val Gln Ile Ser Ile Gly Asp
                1170             1175             1180

Ala His Ser Gly Tyr Pro Val Met Asn Ser Ser Phe Ser Thr Asn Ser
1185             1190             1195             1200

Thr Thr Leu Pro Thr Thr Pro Leu Asn Asp Trp Leu Ile Trp His Glu
                1205             1210             1215

Val Gly His Asn Ala Ala Glu Thr Pro Leu Asn Val Pro Gly Ala Thr
                1220             1225             1230

Glu Val Ala Asn Asn Val Leu Ala Leu Tyr Met Gln Asp Arg Tyr Leu
                1235             1240             1245

Gly Lys Met Asn Arg Val Ala Asp Asp Ile Thr Val Ala Pro Glu Tyr
                1250             1255             1260

Leu Asp Glu Ser Asn Gly Gln Ala Trp Ala Arg Gly Gly Ala Gly Asp
1265             1270             1275             1280

Arg Leu Leu Met Tyr Ala Gln Leu Lys Glu Trp Ala Glu Glu Asn Phe
                1285             1290             1295

Asp Ile Lys Gln Trp Tyr Pro Asp Gly Glu Leu Pro Lys Phe Tyr Ser
                1300             1305             1310

Asp Arg Lys Gly Met Lys Gly Trp Asn Leu Phe Gln Leu Met His Arg
                1315             1320             1325

Lys Ala Arg Gly Asp Asp Val Gly Asn Ser Thr Phe Gly Gly Lys Asn
                1330             1335             1340

Tyr Cys Ala Glu Ser Asn Gly Asn Ala Ala Asp Thr Leu Met Leu Cys
1345             1350             1355             1360
```

Ala Ser Trp Val Ala Gln Ala Asp Leu Ser Glu Phe Phe Lys Lys Trp
            1365                1370                1375

Asn Pro Gly Ala Ser Ala Tyr Gln Leu Pro Gly Ala Thr Glu Met Ser
        1380                1385                1390

Phe Gln Gly Gly Val Ser Ser Ala Tyr Ser Thr Leu Ala Ser Leu
        1395                1400            1405

Lys Leu Pro Lys Pro Glu Lys Gly Pro Glu Thr Ile Asn Lys Val Thr
    1410                1415                1420

Glu His Lys Met Ser Ala Glu
1425                1430

<210> SEQ ID NO 17
<211> LENGTH: 4491
<212> TYPE: DNA
<213> ORGANISM: Escherichia coli

<400> SEQUENCE: 17

| | | | | | | |
|---|---|---|---|---|---|---|
| tgtgatggtg | gtggttcagg | atcgtcctcc | gatacgccgt | ctgtagattc | tggatcaggg | 60 |
| actttgccgg | aagtgaaacc | cgatccaaca | ccaaccccgg | agccgacacc | tgagccgacg | 120 |
| ccggacccag | aacctacgcc | ggatccaaca | cctgatcctg | agccgacacc | agaaccggag | 180 |
| ccagaacctg | ttcctacgaa | acgggttat | ctgaccctgg | gcggaagcca | gcgggtaact | 240 |
| ggtgctacct | gtaatggtga | atccagcgat | ggctttacct | ttacgccagg | caataccgtg | 300 |
| agttgtgtgg | tgggcagtac | gaccattgca | acattcaaca | cccagtcaga | agctgcgcgt | 360 |
| agcctgcgtg | cggttgacaa | agtgtcgttt | agcctggagg | acgcgcagga | gctggcgaat | 420 |
| tctgaaaata | gaaaaccaa | cgccatctct | ctggtgacgt | ccagcgacag | ttgccccgca | 480 |
| gatgcagaac | agctttgtct | tactttctcg | tcagtggttg | atcgcgcgcg | atttgaaaaa | 540 |
| ctgtataagc | aaattgatct | ggcaacagac | aatttcagca | agctggtcaa | tgaagaggtg | 600 |
| gaaaacaatg | ctgcgactga | taaagcgccg | tccaccccata | cctcaacggt | agtgccagtc | 660 |
| acgacagagg | gaacaaaacc | ggatctgaac | gcgtccttcg | tgtcggctaa | cgcggaacag | 720 |
| ttttatcagt | atcaacccac | tgaaatcatt | ctttccgaag | ccaactggt | ggatagcctg | 780 |
| gggaacggtg | ttgctggcgt | tgactactac | accaattcag | gccgtggcgt | aactgacgaa | 840 |
| aacggtaaat | tttcctttag | ctggggcgaa | accatctcct | tggtatcga | tacctttgaa | 900 |
| ctgggctcag | tacgtggcaa | taagtcgacc | attgcgctga | ctgaattggg | tgatgaagtt | 960 |
| cgcggggcaa | atatcgatca | gctcattcat | cgttattcga | cgactggtca | aaataatact | 1020 |
| cgtgttgttc | cggacgatgt | acgcaaggtc | tttgccgaat | atcccaacgt | gatcaacgag | 1080 |
| ataatcaatc | tttcgttatc | caacggtgcg | acgctggatg | aaggcgatca | aaacgttgtg | 1140 |
| ctgcctaacg | aatttatcga | gcagtttaag | acgggtcagg | ccaaagagat | cgataccgcg | 1200 |
| atttgtgcga | aaaccgacgg | ttgtaacgag | gctcgctggt | tctcgctgac | aacgcgcaat | 1260 |
| gttaatgacg | gccagattca | gggcgttatt | aacaagctgt | ggggcgtgga | tacgaactat | 1320 |
| cagtctgtca | gcaagttcca | cgtcttccat | gactctacca | acttctatgg | cagcaccggt | 1380 |
| aacgcgcgcg | gtcaggcggt | ggtaaatatc | tccaactcgg | cattcccgat | tctgatggcg | 1440 |
| cgtaatgata | aaaactactg | gctggcgttt | ggcgaaaaac | gcgcctggga | taaaaatgag | 1500 |
| ctggcgtaca | ttacggaagc | gccttccatt | gtgcagccag | agaacgttac | gcgcgatact | 1560 |
| gcgactttca | acctgccgtt | tatttcgctg | ggcaagtcg | gtgaaggcaa | actgatggtt | 1620 |
| atcggtaacc | cgcactacaa | cagcatcctg | cgttgcccga | acggttacag | ttgggcggt | 1680 |

```
ggtgttaata gtaaaggtga gtgtacgctc agcggtgatt ctgatgacat gaagcacttt   1740
atgcagaacg tactgcgcta cttgtcaaat gacatctggc agccaaatac caagagcatc   1800
atgactgtcg gcaccaacct ggagaacgtt tatttcaaaa agcgggcca ggtattggga    1860
aatagtgcac catttgcttt ccatgaggat ttcactggta tcacggttaa acagttgacc   1920
agctatggcg atctgaatcc ggaagagatt ccgttgctga tcctcaacgg ctttgaatat   1980
gtgactcagt ggtctggcga tccctatgct gtgcctctgc gtgcagatac cagcaaaccg   2040
aagctgactc agcaggatgt gaccgatctg atcgcttatc tgaacaaagg tggctcggtg   2100
ctgatcatgg aaaacgtgat gagcaatctt aaggaagaga gcgcgtccag ttttgtgcgt   2160
ctgctggatg ccgcgggtct gtcaatggct ctgaacaaat cggtggtgaa caacgatccg   2220
caagggtatc cggatcgcgt tcgtcagcgt cgcgcgactg gcatttgggt ttatgaacgt   2280
tatcctgctg cagacggcgc gcaaccgccg tacaccatcg acccaaatac aggggaagtg   2340
acctggaaat accagcaaga caacaagcct gatgacaagc cgaaactgga agttgcgagc   2400
tggcaggagg aagttgaggg caaacaggta acgcgttatg cctttattga tgaagcggaa   2460
tacacaacag aagaatctct ggaagcggca aaggcaaaaa tctttgagaa gtttcctggg   2520
ttacaggagt gtaaggactc gacttaccat tacgagatta actgtttgga gcgccgccca   2580
ggcacggatg ttccggtaac aggtggcatg tatgttccgc gctatacgca actgaatctt   2640
gacgccgaca ccgcgaaagc gatggtgcag gcggcggatt taggcaccaa cattcagcgc   2700
ctgtatcagc atgagcttta tttccgtacc aaaggcagta aggtgagcg tctgaacagt    2760
gttgatctgg aacgtctgta ccagaacatg tcggtctggc tgtggaacga tacgaaatat   2820
cgttacgaag agggcaagga agatgagctg ggctttaaaa cgttcaccga gttcctgaac   2880
tgctacgcca atgatgccta tgcaggcggc accaagtgct ccgcagatct gaaaaaatcg   2940
ctggtcgata caacatgat ctacggtgac ggtagcagca agcgggcat gatgaaccca     3000
agctatccgc tcaactatat ggaaaaaccg ctgacgcgtc tgatgctggg ccgttcctgg   3060
tgggatctga acattaaggt tgatgtggag aagtacccag gatccgtatc ggcaaagggt   3120
gagagcgtta cggaaaacat cagcctgtac tcgaatccga ccaaatggtt tgcgggtaac   3180
atgcagtcaa ccggcctgtg ggcaccggcc cagcaggacg tcaccattaa gtcttcggcg   3240
tcagtcccag tgactgttac cgtggcgctg gctgacgacc tgactggacg tgagaagcat   3300
gaagttgcgc tgaaccgtcc gccaagagtg actaaaacgt atactctgga ggctaacggt   3360
gaagtgacct tcaaggtgcc ttatggtggt ctgatttata tcaagggcga cagtaaggat   3420
gatgtttctg ctaacttcac ctttaccggt gtagtaaaag cgccgttcta taaagacggc   3480
gaatggaaaa acgatctgga ctcaccgcg ccgctgggcg agctggagtc tgcgtcgttc    3540
gtctatacca cgccgaagaa gaaccttgag gccagcaatt tcactggtgg tgtagcagaa   3600
ttcgctaaag atctggatac cttttgccagc tcgatgaatg acttctacgg tcgtaatgat  3660
gaagacggta agcaccggat gtttacctat aaaaacttga cggggcacaa gcatcgtttc   3720
accaacgatg tgcagatctc catcggtgat gcgcactcgg ttatccggt aatgaacagc    3780
agcttctcga cgaacagcac cacgctgccg acgacgccgc tgaacgactg gctgatttgg   3840
cacgaagtcg gtcataacgc tgcagaaaca ccgctgaacg taccgggtgc aactgaagtg   3900
gcgaacaacg tgctggcgct gtacatgcag gatcgctatc tcggtaagat gaaccgtgtc   3960
gctgacgaca ttaccgtcgc gccggaatat ctggacgaga gcaacggtca ggcctgggcg   4020
```

-continued

```
cgcggcggtg cgggtgaccg tctgctgatg tacgcacagt tgaaggagtg ggcagaggaa    4080
aactttgata tcaaacagtg gtatccagat ggtgagctgc ctaagttcta cagcgatcgt    4140
aaagggatga agggctggaa cctgttccag ttgatgcacc gtaaagcgcg cggcgatgat    4200
gttggtaaca gcacctttgg tggcaagaat tactgtgctg aatccaatgg taacgctgcc    4260
gacacgctga tgctgtgtgc atcctgggtc gctcaggcgg atctttcgga attctttaag    4320
aaatggaatc cgggtgcaag tgcttaccag ttgccgggag caacggagat gagtttccag    4380
ggcggtgtga gctcttcggc ttacagcacg ctggcgtcac tcaagctgcc gaaaccggaa    4440
aaagggccgg aaaccattaa caaggttacc gagcataaga tgtctgccga g             4491
```

<210> SEQ ID NO 18
<211> LENGTH: 1497
<212> TYPE: PRT
<213> ORGANISM: Escherichia coli

<400> SEQUENCE: 18

```
Cys Asp Gly Gly Gly Ser Gly Ser Ser Ser Asp Thr Pro Ser Val Asp
1               5                   10                  15

Ser Gly Ser Gly Thr Leu Pro Glu Val Lys Pro Asp Pro Thr Pro Thr
            20                  25                  30

Pro Glu Pro Thr Pro Glu Pro Thr Pro Asp Pro Glu Pro Thr Pro Asp
        35                  40                  45

Pro Thr Pro Asp Pro Glu Pro Thr Pro Glu Pro Glu Pro Glu Pro Val
    50                  55                  60

Pro Thr Lys Thr Gly Tyr Leu Thr Leu Gly Gly Ser Gln Arg Val Thr
65                  70                  75                  80

Gly Ala Thr Cys Asn Gly Glu Ser Ser Asp Gly Phe Thr Phe Thr Pro
                85                  90                  95

Gly Asn Thr Val Ser Cys Val Val Gly Ser Thr Thr Ile Ala Thr Phe
            100                 105                 110

Asn Thr Gln Ser Glu Ala Ala Arg Ser Leu Arg Ala Val Asp Lys Val
        115                 120                 125

Ser Phe Ser Leu Glu Asp Ala Gln Glu Leu Ala Asn Ser Glu Asn Lys
    130                 135                 140

Lys Thr Asn Ala Ile Ser Leu Val Thr Ser Ser Asp Ser Cys Pro Ala
145                 150                 155                 160

Asp Ala Glu Gln Leu Cys Leu Thr Phe Ser Val Val Asp Arg Ala
                165                 170                 175

Arg Phe Glu Lys Leu Tyr Lys Gln Ile Asp Leu Ala Thr Asp Asn Phe
            180                 185                 190

Ser Lys Leu Val Asn Glu Glu Val Glu Asn Asn Ala Ala Thr Asp Lys
        195                 200                 205

Ala Pro Ser Thr His Thr Ser Thr Val Val Pro Val Thr Thr Glu Gly
    210                 215                 220

Thr Lys Pro Asp Leu Asn Ala Ser Phe Val Ser Ala Asn Ala Glu Gln
225                 230                 235                 240

Phe Tyr Gln Tyr Gln Pro Thr Glu Ile Ile Leu Ser Glu Gly Gln Leu
                245                 250                 255

Val Asp Ser Leu Gly Asn Gly Val Ala Gly Val Asp Tyr Tyr Thr Asn
            260                 265                 270

Ser Gly Arg Gly Val Thr Asp Glu Asn Gly Lys Phe Ser Phe Ser Trp
        275                 280                 285

Gly Glu Thr Ile Ser Phe Gly Ile Asp Thr Phe Glu Leu Gly Ser Val
```

```
                290              295              300
    Arg Gly Asn Lys Ser Thr Ile Ala Leu Thr Glu Leu Gly Asp Glu Val
    305              310              315              320

Arg Gly Ala Asn Ile Asp Gln Leu Ile His Arg Tyr Ser Thr Thr Gly
                     325              330              335

Gln Asn Asn Thr Arg Val Val Pro Asp Val Arg Lys Val Phe Ala
                 340              345              350

Glu Tyr Pro Asn Val Ile Asn Glu Ile Ile Asn Leu Ser Leu Ser Asn
                 355              360              365

Gly Ala Thr Leu Asp Glu Gly Asp Gln Asn Val Val Leu Pro Asn Glu
                 370              375              380

Phe Ile Glu Gln Phe Lys Thr Gly Gln Ala Lys Glu Ile Asp Thr Ala
    385              390              395              400

Ile Cys Ala Lys Thr Asp Gly Cys Asn Glu Ala Arg Trp Phe Ser Leu
                     405              410              415

Thr Thr Arg Asn Val Asn Asp Gly Gln Ile Gln Gly Val Ile Asn Lys
                     420              425              430

Leu Trp Gly Val Asp Thr Asn Tyr Gln Ser Val Ser Lys Phe His Val
                 435              440              445

Phe His Asp Ser Thr Asn Phe Tyr Gly Ser Thr Gly Asn Ala Arg Gly
                 450              455              460

Gln Ala Val Val Asn Ile Ser Asn Ser Ala Phe Pro Ile Leu Met Ala
    465              470              475              480

Arg Asn Asp Lys Asn Tyr Trp Leu Ala Phe Gly Glu Lys Arg Ala Trp
                     485              490              495

Asp Lys Asn Glu Leu Ala Tyr Ile Thr Glu Ala Pro Ser Ile Val Gln
                 500              505              510

Pro Glu Asn Val Thr Arg Asp Thr Ala Thr Phe Asn Leu Pro Phe Ile
                 515              520              525

Ser Leu Gly Gln Val Gly Glu Gly Lys Leu Met Val Ile Gly Asn Pro
    530              535              540

His Tyr Asn Ser Ile Leu Arg Cys Pro Asn Gly Tyr Ser Trp Gly Gly
    545              550              555              560

Gly Val Asn Ser Lys Gly Glu Cys Thr Leu Ser Gly Asp Ser Asp Asp
                     565              570              575

Met Lys His Phe Met Gln Asn Val Leu Arg Tyr Leu Ser Asn Asp Ile
                 580              585              590

Trp Gln Pro Asn Thr Lys Ser Ile Met Thr Val Gly Thr Asn Leu Glu
                 595              600              605

Asn Val Tyr Phe Lys Lys Ala Gly Gln Val Leu Gly Asn Ser Ala Pro
    610              615              620

Phe Ala Phe His Glu Asp Phe Thr Gly Ile Thr Val Lys Gln Leu Thr
    625              630              635              640

Ser Tyr Gly Asp Leu Asn Pro Glu Glu Ile Pro Leu Leu Ile Leu Asn
                     645              650              655

Gly Phe Glu Tyr Val Thr Gln Trp Ser Gly Asp Pro Tyr Ala Val Pro
                 660              665              670

Leu Arg Ala Asp Thr Ser Lys Pro Lys Leu Thr Gln Gln Asp Val Thr
                 675              680              685

Asp Leu Ile Ala Tyr Leu Asn Lys Gly Gly Ser Val Leu Ile Met Glu
                 690              695              700

Asn Val Met Ser Asn Leu Lys Glu Glu Ser Ala Ser Ser Phe Val Arg
    705              710              715              720
```

```
Leu Leu Asp Ala Ala Gly Leu Ser Met Ala Leu Asn Lys Ser Val Val
            725                 730                 735

Asn Asn Asp Pro Gln Gly Tyr Pro Asp Arg Val Arg Gln Arg Arg Ala
        740                 745                 750

Thr Gly Ile Trp Val Tyr Glu Arg Tyr Pro Ala Ala Asp Gly Ala Gln
            755                 760                 765

Pro Pro Tyr Thr Ile Asp Pro Asn Thr Gly Glu Val Thr Trp Lys Tyr
770                 775                 780

Gln Gln Asp Asn Lys Pro Asp Asp Lys Pro Lys Leu Glu Val Ala Ser
785                 790                 795                 800

Trp Gln Glu Glu Val Glu Gly Lys Gln Val Thr Arg Tyr Ala Phe Ile
            805                 810                 815

Asp Glu Ala Glu Tyr Thr Thr Glu Glu Ser Leu Glu Ala Ala Lys Ala
            820                 825                 830

Lys Ile Phe Glu Lys Phe Pro Gly Leu Gln Glu Cys Lys Asp Ser Thr
            835                 840                 845

Tyr His Tyr Glu Ile Asn Cys Leu Glu Arg Arg Pro Gly Thr Asp Val
            850                 855                 860

Pro Val Thr Gly Gly Met Tyr Val Pro Arg Tyr Thr Gln Leu Asn Leu
865                 870                 875                 880

Asp Ala Asp Thr Ala Lys Ala Met Val Gln Ala Ala Asp Leu Gly Thr
                885                 890                 895

Asn Ile Gln Arg Leu Tyr Gln His Glu Leu Tyr Phe Arg Thr Lys Gly
            900                 905                 910

Ser Lys Gly Glu Arg Leu Asn Ser Val Asp Leu Glu Arg Leu Tyr Gln
            915                 920                 925

Asn Met Ser Val Trp Leu Trp Asn Asp Thr Lys Tyr Arg Tyr Glu Glu
930                 935                 940

Gly Lys Glu Asp Glu Leu Gly Phe Lys Thr Phe Thr Glu Phe Leu Asn
945                 950                 955                 960

Cys Tyr Ala Asn Asp Ala Tyr Ala Gly Gly Thr Lys Cys Ser Ala Asp
                965                 970                 975

Leu Lys Lys Ser Leu Val Asp Asn Asn Met Ile Tyr Gly Asp Gly Ser
            980                 985                 990

Ser Lys Ala Gly Met Met Asn Pro Ser Tyr Pro Leu Asn Tyr Met Glu
            995                 1000                1005

Lys Pro Leu Thr Arg Leu Met Leu Gly Arg Ser Trp Trp Asp Leu Asn
    1010                1015                1020

Ile Lys Val Asp Val Glu Lys Tyr Pro Gly Ser Val Ser Ala Lys Gly
1025                1030                1035                1040

Glu Ser Val Thr Glu Asn Ile Ser Leu Tyr Ser Asn Pro Thr Lys Trp
                1045                1050                1055

Phe Ala Gly Asn Met Gln Ser Thr Gly Leu Trp Ala Pro Ala Gln Gln
                1060                1065                1070

Asp Val Thr Ile Lys Ser Ser Ala Ser Val Pro Val Thr Val Thr Val
            1075                1080                1085

Ala Leu Ala Asp Asp Leu Thr Gly Arg Glu Lys His Glu Val Ala Leu
1090                1095                1100

Asn Arg Pro Pro Arg Val Thr Lys Thr Tyr Thr Leu Glu Ala Asn Gly
1105                1110                1115                1120

Glu Val Thr Phe Lys Val Pro Tyr Gly Gly Leu Ile Tyr Ile Lys Gly
            1125                1130                1135
```

-continued

```
Asp Ser Lys Asp Asp Val Ser Ala Asn Phe Thr Phe Thr Gly Val Val
        1140                1145                1150

Lys Ala Pro Phe Tyr Lys Asp Gly Glu Trp Lys Asn Asp Leu Asp Ser
    1155                1160                1165

Pro Ala Pro Leu Gly Glu Leu Glu Ser Ala Ser Phe Val Tyr Thr Thr
    1170                1175                1180

Pro Lys Lys Asn Leu Glu Ala Ser Asn Phe Thr Gly Val Ala Glu
1185                1190                1195                1200

Phe Ala Lys Asp Leu Asp Thr Phe Ala Ser Ser Met Asn Asp Phe Tyr
                1205                1210                1215

Gly Arg Asn Asp Glu Asp Gly Lys His Arg Met Phe Thr Tyr Lys Asn
            1220                1225                1230

Leu Thr Gly His Lys His Arg Phe Thr Asn Asp Val Gln Ile Ser Ile
            1235                1240                1245

Gly Asp Ala His Ser Gly Tyr Pro Val Met Asn Ser Ser Phe Ser Thr
        1250                1255                1260

Asn Ser Thr Thr Leu Pro Thr Thr Pro Leu Asn Asp Trp Leu Ile Trp
1265                1270                1275                1280

His Glu Val Gly His Asn Ala Ala Glu Thr Pro Leu Asn Val Pro Gly
                1285                1290                1295

Ala Thr Glu Val Ala Asn Asn Val Leu Ala Leu Tyr Met Gln Asp Arg
            1300                1305                1310

Tyr Leu Gly Lys Met Asn Arg Val Ala Asp Ile Thr Val Ala Pro
            1315                1320                1325

Glu Tyr Leu Asp Glu Ser Asn Gly Gln Ala Trp Ala Arg Gly Gly Ala
        1330                1335                1340

Gly Asp Arg Leu Leu Met Tyr Ala Gln Leu Lys Glu Trp Ala Glu Glu
1345                1350                1355                1360

Asn Phe Asp Ile Lys Gln Trp Tyr Pro Asp Gly Glu Leu Pro Lys Phe
                1365                1370                1375

Tyr Ser Asp Arg Lys Gly Met Lys Gly Trp Asn Leu Phe Gln Leu Met
            1380                1385                1390

His Arg Lys Ala Arg Gly Asp Asp Val Gly Asn Ser Thr Phe Gly Gly
            1395                1400                1405

Lys Asn Tyr Cys Ala Glu Ser Asn Gly Asn Ala Ala Asp Thr Leu Met
    1410                1415                1420

Leu Cys Ala Ser Trp Val Ala Gln Ala Asp Leu Ser Glu Phe Phe Lys
1425                1430                1435                1440

Lys Trp Asn Pro Gly Ala Ser Ala Tyr Gln Leu Pro Gly Ala Thr Glu
                1445                1450                1455

Met Ser Phe Gln Gly Gly Val Ser Ser Ser Ala Tyr Ser Thr Leu Ala
            1460                1465                1470

Ser Leu Lys Leu Pro Lys Pro Glu Lys Gly Pro Glu Thr Ile Asn Lys
    1475                1480                1485

Val Thr Glu His Lys Met Ser Ala Glu
    1490                1495

<210> SEQ ID NO 19
<211> LENGTH: 4491
<212> TYPE: DNA
<213> ORGANISM: Escherichia coli

<400> SEQUENCE: 19
tgtgatggtg gtggttcagg atcgtcctcc gatacgccgt ctgtagattc tggatcaggg     60
```

```
actttgccgg aagtgaaacc cgatccaaca ccaaccccgg agccgacacc tgagccgacg    120
ccggacccag aacctacgcc ggatccaaca cctgatcctg agccgacacc agaaccggag    180
ccagaacctg ttcctacgaa aacgggttat ctgaccctgg gcggaagcca gcgggtaact    240
ggtgctacct gtaatggtga atccagcgat ggctttacct ttacgccagg caataccgtg    300
agttgtgtgg tgggcagtac gaccattgca acattcaaca cccagtcaga agctgcgcgt    360
agcctgcgtg cggttgacaa agtgtcgttt agcctggagg acgcgcagga gctgcgaat    420 tctgaaaata agaaaaccaa cgccatctct ctggtgacgt ccagcgacag ttgccccgca    480
gatgcagaac agctttgtct tactttctcg tcagtggttg atcgcgcgcg atttgaaaaa    540
ctgtataagc aaattgatct ggcaacagac aatttcagca agctggtcaa tgaagaggtg    600
gaaaacaatg ctgcgactga taaagcgccg tccacccata cctcaacggt agtgccagtc    660
acgacagagg gaacaaaacc ggatctgaac gcgtccttcg tgtcggctaa cgcggaacag    720
ttttatcagt atcaacccac tgaaatcatt cttccgaag gccaactggt ggatagcctg    780
gggaacggtg ttgctggcgt tgactactac accaattcag gccgtggcgt aactgacgaa    840
aacggtaaat tttccttag ctggggcgaa accatctcct ttggtatcga tacctttgaa    900
ctgggctcag tacgtggcaa taagtcgacc attgcgctga ctgaattggg tgatgaagtt    960
cgcggggcaa atatcgatca gctcattcat cgttattcga cgactggtca aaataatact   1020
cgtgttgttc cggacgatgt acgcaaggtc tttgccgaat atcccaacgt gatcaacgag   1080
ataatcaatc tttcgttatc caacggtgcg acgctggatg aaggcgatca aacgttgtg   1140 ctgcctaacg aatttatcga gcagtttaag acgggtcagg ccaaagagat cgataccgcg   1200
atttgtgcga aaccgacgg ttgtaacgag gctcgctggt tctcgctgac aacgcgcaat   1260
gttaatgacg gccagattca gggcgttatt aacaagctgt ggggcgtgga tacgaactat   1320
cagtctgtca gcaagttcca cgtcttccat gactctacca acttctatgg cagcaccggt   1380
aacgcgcgcg tcaggcggt ggtaaatatc tccaactcgg cattcccgat tctgatggcg   1440
cgtaatgata aaaactactg ctggcgtttt ggcgaaaaac gcgcctggga taaaaatgag   1500
ctggcgtaca ttacggaagc gccttccatt gtgcagccag agaacgttac gcgcgatact   1560
gcgactttca acctgccgtt tatttcgctg ggcaagtcg gtgaaggcaa actgatggtt   1620
atcggtaacc cgcactacaa cagcatcctg cgttgcccga acggttacag ttggggcggt   1680
ggtgttaata gtaaaggtga gtgtacgctc agcggtgatt ctgatgacat gaagcacttt   1740
atgcagaacg tactgcgcta cttgtcaaat gacatctggc agccaaatac caagagcatc   1800
atgactgtcg gcaccaacct ggagaacgtt tatttcaaaa agcgggcca ggtattggga   1860 aatagtgcac catttgcttt ccatgaggat ttcactggta tcacggttaa acagttgacc   1920
agctatggcg atctgaatcc ggaagagatt ccgttgctga tcctcaacgg ctttgaatat   1980
gtgactcagt ggtctggcga tcccatgct gtgcctctgc gtgcagatac cagcaaaccg   2040
aagctgactc agcaggatgt gaccgatctg atcgcttatc tgaacaaagg tggctcggtg   2100
ctgatcatgg aaaacgtgat gagcaatctt aaggaagaga gcgcgtccag ttttgtgcgt   2160
ctgctggatt ccgcgggtct gtcaatggct ctgaacaaat cggtggtgaa caacgatccg   2220
caagggtatc cggatcgcgt tcgtcagcgt cgcgcgactg gcatttgggt ttatgaacgt   2280
tatcctgctg cagacggcgc gcaaccgccg tacaccatcg acccaaatac aggggaagtg   2340
acctggaaat accagcaaga caacaagcct gatgacaagc cgaaactgga agttgcgagc   2400
tggcaggagg aagttgaggg caaacaggta acgcgttatg cctttattga tgaagcggaa   2460
```

```
tacacaacag aagaatctct ggaagcggca aaggcaaaaa tctttgagaa gtttcctggg   2520
ttacaggagt gtaaggactc gacttaccat tacgagatta actgtttgga gcgccgccca   2580
ggcacggatg ttccggtaac aggtggcatg tatgttccgc gctatacgca actgaatctt   2640
gacgccgaca ccgcgaaagc gatggtgcag gcggcggatt taggcaccaa cattcagcgc   2700
ctgtatcagc atgagcttta tttccgtacc aaaggcagta aaggtgagcg tctgaacagt   2760
gttgatctgg aacgtctgta ccagaacatg tcggtctggc tgtggaacga tacgaaatat   2820
cgttacgaag agggcaagga agatgagctg gctttaaaaa cgttcaccga gttcctgaac   2880
tgctacgcca atgatgccta tgcaggcggc accaagtgct ccgcagatct gaaaaaatcg   2940
ctggtcgata caacatgat ctacggtgac ggtagcagca aagcgggcat gatgaaccca   3000
agctatccgc tcaactatat ggaaaaaccg ctgacgcgtc tgatgctggg ccgttcctgg   3060
tgggatctga acattaaggt tgatgtggag aagtacccag gatccgtatc ggcaaagggt   3120
gagagcgtta cggaaaacat cagcctgtac tcgaatccga ccaaatggtt tgcgggtaac   3180
atgcagtcaa ccggcctgtg ggcaccggcc cagcaggacg tcaccattaa gtcttcggcg   3240
tcagtcccag tgactgttac cgtggcgctg gctgacgacc tgactggacg tgagaagcat   3300
gaagttgcgc tgaaccgtcc gccaagagtg actaaaacgt atactctgga ggctaacggt   3360
gaagtgacct tcaaggtgcc ttatggtggt ctgatttata tcaagggcga cagtaaggat   3420
gatgtttctg ctaacttcac ctttaccggt gtagtaaaag cgccgttcta taagacggc   3480 gaatggaaaa acgatctgga ctcaccggcg ccgctgggcg agctggagtc tgcgtcgttc   3540
gtctatacca cgccgaagaa gaaccttgag gccagcaatt tcactggtgg tgtagcagaa   3600
ttcgctaaag atctggatac ctttgccagc tcgatgaatg acttctacgg tcgtaatgat   3660
gaagacggta agcaccggat gtttacctat aaaaacttga cggggcacaa gcatcgtttc   3720
accaacgatg tgcagatctc catcggtgat gcgcactcgg gttatccggt aatgaacagc   3780
agcttctcga cgaacagcac cacgctgccg acgacgccgc tgaacgactg gctgatttgg   3840
cacgcagtcg gtcataacgc tgcagaaaca ccgctgaacg taccgggtgc aactgaagtg   3900
gcgaacaacg tgctggcgct gtacatgcag gatcgctatc tcggtaagat gaaccgtgtc   3960
gctgacgaca ttaccgtcgc gccggaatat ctggacgaga caacggtca ggcctgggcg   4020 cgcggcggtg cgggtgaccg tctgctgatg tacgcacagt tgaaggagtg ggcagaggaa   4080
aactttgata tcaaacagtg gtatccagat ggtgagctgc ctaagttcta cagcgatcgt   4140
aaagggatga agggctggaa cctgttccag ttgatgcacc gtaaagcgcg cggcgatgat   4200
gttggtaaca gcacctttgg tgcaagaat tactgtgctg aatccaatgg taacgctgcc   4260
gacacgctga tgctgtgtgc atcctgggtc gctcaggcgg atctttcgga attctttaag   4320
aaatggaatc cgggtgcaag tgcttaccag ttgccgggag caacggagat gagtttccag   4380
ggcggtgtga gctcttcggc ttacagcacg ctggcgtcac tcaagctgcc gaaaccggaa   4440
aaagggccgg aaaccattaa caaggttacc gagcataaga tgtctgccga g            4491
```

<210> SEQ ID NO 20
<211> LENGTH: 1497
<212> TYPE: PRT
<213> ORGANISM: Escherichia coli

<400> SEQUENCE: 20

```
Cys Asp Gly Gly Gly Ser Gly Ser Ser Ser Asp Thr Pro Ser Val Asp
1               5                   10                  15
```

```
Ser Gly Ser Gly Thr Leu Pro Glu Val Lys Pro Asp Pro Thr Pro Thr
            20                  25                  30

Pro Glu Pro Thr Pro Glu Pro Thr Pro Asp Pro Glu Pro Thr Pro Asp
        35                  40                  45

Pro Thr Pro Asp Pro Glu Pro Thr Pro Glu Pro Glu Pro Glu Pro Val
50                  55                  60

Pro Thr Lys Thr Gly Tyr Leu Thr Leu Gly Gly Ser Gln Arg Val Thr
65                      70                  75                  80

Gly Ala Thr Cys Asn Gly Glu Ser Ser Asp Gly Phe Thr Phe Thr Pro
                85                  90                  95

Gly Asn Thr Val Ser Cys Val Val Gly Ser Thr Thr Ile Ala Thr Phe
                100                 105                 110

Asn Thr Gln Ser Glu Ala Ala Arg Ser Leu Arg Ala Val Asp Lys Val
            115                 120                 125

Ser Phe Ser Leu Glu Asp Ala Gln Glu Leu Ala Asn Ser Glu Asn Lys
    130                 135                 140

Lys Thr Asn Ala Ile Ser Leu Val Thr Ser Ser Asp Ser Cys Pro Ala
145                 150                 155                 160

Asp Ala Glu Gln Leu Cys Leu Thr Phe Ser Ser Val Val Asp Arg Ala
                165                 170                 175

Arg Phe Glu Lys Leu Tyr Lys Gln Ile Asp Leu Ala Thr Asp Asn Phe
            180                 185                 190

Ser Lys Leu Val Asn Glu Glu Val Glu Asn Asn Ala Ala Thr Asp Lys
        195                 200                 205

Ala Pro Ser Thr His Thr Ser Thr Val Val Pro Val Thr Thr Glu Gly
    210                 215                 220

Thr Lys Pro Asp Leu Asn Ala Ser Phe Val Ser Ala Asn Ala Glu Gln
225                 230                 235                 240

Phe Tyr Gln Tyr Gln Pro Thr Glu Ile Ile Leu Ser Glu Gly Gln Leu
                245                 250                 255

Val Asp Ser Leu Gly Asn Gly Val Ala Gly Val Asp Tyr Tyr Thr Asn
            260                 265                 270

Ser Gly Arg Gly Val Thr Asp Glu Asn Gly Lys Phe Ser Phe Ser Trp
        275                 280                 285

Gly Glu Thr Ile Ser Phe Gly Ile Asp Thr Phe Glu Leu Gly Ser Val
    290                 295                 300

Arg Gly Asn Lys Ser Thr Ile Ala Leu Thr Glu Leu Gly Asp Glu Val
305                 310                 315                 320

Arg Gly Ala Asn Ile Asp Gln Leu Ile His Arg Tyr Ser Thr Thr Gly
                325                 330                 335

Gln Asn Asn Thr Arg Val Val Pro Asp Val Arg Lys Val Phe Ala
            340                 345                 350

Glu Tyr Pro Asn Val Ile Asn Glu Ile Asn Leu Ser Leu Ser Asn
        355                 360                 365

Gly Ala Thr Leu Asp Glu Gly Asp Gln Asn Val Val Leu Pro Asn Glu
    370                 375                 380

Phe Ile Glu Gln Phe Lys Thr Gly Gln Ala Lys Glu Ile Asp Thr Ala
385                 390                 395                 400

Ile Cys Ala Lys Thr Asp Gly Cys Asn Glu Ala Arg Trp Phe Ser Leu
                405                 410                 415

Thr Thr Arg Asn Val Asn Asp Gly Gln Ile Gln Gly Val Ile Asn Lys
            420                 425                 430
```

```
Leu Trp Gly Val Asp Thr Asn Tyr Gln Ser Val Ser Lys Phe His Val
            435                 440                 445
Phe His Asp Ser Thr Asn Phe Tyr Gly Ser Thr Gly Asn Ala Arg Gly
450                 455                 460
Gln Ala Val Val Asn Ile Ser Asn Ser Ala Phe Pro Ile Leu Met Ala
465                 470                 475                 480
Arg Asn Asp Lys Asn Tyr Trp Leu Ala Phe Gly Lys Arg Ala Trp
                485                 490                 495
Asp Lys Asn Glu Leu Ala Tyr Ile Thr Glu Ala Pro Ser Ile Val Gln
            500                 505                 510
Pro Glu Asn Val Thr Arg Asp Thr Ala Thr Phe Asn Leu Pro Phe Ile
            515                 520                 525
Ser Leu Gly Gln Val Gly Glu Gly Lys Leu Met Val Ile Gly Asn Pro
530                 535                 540
His Tyr Asn Ser Ile Leu Arg Cys Pro Asn Gly Tyr Ser Trp Gly Gly
545                 550                 555                 560
Gly Val Asn Ser Lys Gly Glu Cys Thr Leu Ser Gly Asp Ser Asp
                565                 570                 575
Met Lys His Phe Met Gln Asn Val Leu Arg Tyr Leu Ser Asn Asp Ile
            580                 585                 590
Trp Gln Pro Asn Thr Lys Ser Ile Met Thr Val Gly Thr Asn Leu Glu
            595                 600                 605
Asn Val Tyr Phe Lys Lys Ala Gly Gln Val Leu Gly Asn Ser Ala Pro
            610                 615                 620
Phe Ala Phe His Glu Asp Phe Thr Gly Ile Thr Val Lys Gln Leu Thr
625                 630                 635                 640
Ser Tyr Gly Asp Leu Asn Pro Glu Glu Ile Pro Leu Leu Ile Leu Asn
                645                 650                 655
Gly Phe Glu Tyr Val Thr Gln Trp Ser Gly Asp Pro Tyr Ala Val Pro
                660                 665                 670
Leu Arg Ala Asp Thr Ser Lys Pro Lys Leu Thr Gln Gln Asp Val Thr
            675                 680                 685
Asp Leu Ile Ala Tyr Leu Asn Lys Gly Gly Ser Val Leu Ile Met Glu
            690                 695                 700
Asn Val Met Ser Asn Leu Lys Glu Glu Ser Ala Ser Ser Phe Val Arg
705                 710                 715                 720
Leu Leu Asp Ala Ala Gly Leu Ser Met Ala Leu Asn Lys Ser Val Val
                725                 730                 735
Asn Asn Asp Pro Gln Gly Tyr Pro Asp Arg Val Arg Gln Arg Ala
                740                 745                 750
Thr Gly Ile Trp Val Tyr Glu Arg Tyr Pro Ala Ala Asp Gly Ala Gln
            755                 760                 765
Pro Pro Tyr Thr Ile Asp Pro Asn Thr Gly Glu Val Thr Trp Lys Tyr
770                 775                 780
Gln Gln Asp Asn Lys Pro Asp Lys Pro Lys Leu Glu Val Ala Ser
785                 790                 795                 800
Trp Gln Glu Glu Val Glu Gly Lys Gln Val Thr Arg Tyr Ala Phe Ile
                805                 810                 815
Asp Glu Ala Glu Tyr Thr Thr Glu Glu Ser Leu Glu Ala Ala Lys Ala
            820                 825                 830
Lys Ile Phe Glu Lys Phe Pro Gly Leu Gln Glu Cys Lys Asp Ser Thr
            835                 840                 845
Tyr His Tyr Glu Ile Asn Cys Leu Glu Arg Arg Pro Gly Thr Asp Val
```

-continued

```
            850                 855                 860
Pro Val Thr Gly Gly Met Tyr Val Pro Arg Tyr Thr Gln Leu Asn Leu
865                 870                 875                 880

Asp Ala Asp Thr Ala Lys Ala Met Val Gln Ala Asp Leu Gly Thr
                885                 890                 895

Asn Ile Gln Arg Leu Tyr Gln His Glu Leu Tyr Phe Arg Thr Lys Gly
                900                 905                 910

Ser Lys Gly Glu Arg Leu Asn Ser Val Asp Leu Glu Arg Leu Tyr Gln
            915                 920                 925

Asn Met Ser Val Trp Leu Trp Asn Asp Thr Lys Tyr Arg Tyr Glu Glu
            930                 935                 940

Gly Lys Glu Asp Glu Leu Gly Phe Lys Thr Phe Thr Glu Phe Leu Asn
945                 950                 955                 960

Cys Tyr Ala Asn Asp Ala Tyr Ala Gly Gly Thr Lys Cys Ser Ala Asp
                965                 970                 975

Leu Lys Lys Ser Leu Val Asp Asn Met Ile Tyr Gly Asp Gly Ser
                980                 985                 990

Ser Lys Ala Gly Met Met Asn Pro Ser Tyr Pro Leu Asn Tyr Met Glu
            995                 1000                1005

Lys Pro Leu Thr Arg Leu Met Leu Gly Arg Ser Trp Trp Asp Leu Asn
    1010                1015                1020

Ile Lys Val Asp Val Glu Lys Tyr Pro Gly Ser Val Ser Ala Lys Gly
1025                1030                1035                1040

Glu Ser Val Thr Glu Asn Ile Ser Leu Tyr Ser Asn Pro Thr Lys Trp
                1045                1050                1055

Phe Ala Gly Asn Met Gln Ser Thr Gly Leu Trp Ala Pro Ala Gln Gln
                1060                1065                1070

Asp Val Thr Ile Lys Ser Ser Ala Ser Val Pro Val Thr Val Thr Val
                1075                1080                1085

Ala Leu Ala Asp Asp Leu Thr Gly Arg Glu Lys His Glu Val Ala Leu
    1090                1095                1100

Asn Arg Pro Pro Arg Val Thr Lys Thr Tyr Thr Leu Glu Ala Asn Gly
1105                1110                1115                1120

Glu Val Thr Phe Lys Val Pro Tyr Gly Gly Leu Ile Tyr Ile Lys Gly
                1125                1130                1135

Asp Ser Lys Asp Val Ser Ala Asn Phe Thr Phe Thr Gly Val Val
                1140                1145                1150

Lys Ala Pro Phe Tyr Lys Asp Gly Glu Trp Lys Asn Asp Leu Asp Ser
    1155                1160                1165

Pro Ala Pro Leu Gly Glu Leu Glu Ser Ala Ser Phe Val Tyr Thr Thr
    1170                1175                1180

Pro Lys Lys Asn Leu Glu Ala Ser Asn Phe Thr Gly Gly Val Ala Glu
1185                1190                1195                1200

Phe Ala Lys Asp Leu Asp Thr Phe Ala Ser Ser Met Asn Asp Phe Tyr
                1205                1210                1215

Gly Arg Asn Asp Glu Asp Gly Lys His Arg Met Phe Thr Tyr Lys Asn
                1220                1225                1230

Leu Thr Gly His Lys His Arg Phe Thr Asn Asp Val Gln Ile Ser Ile
                1235                1240                1245

Gly Asp Ala His Ser Gly Tyr Pro Val Met Asn Ser Ser Phe Ser Thr
    1250                1255                1260

Asn Ser Thr Thr Leu Pro Thr Pro Leu Asn Asp Trp Leu Ile Trp
1265                1270                1275                1280
```

His Ala Val Gly His Asn Ala Ala Glu Thr Pro Leu Asn Val Pro Gly
            1285                1290                1295

Ala Thr Glu Val Ala Asn Asn Val Leu Ala Leu Tyr Met Gln Asp Arg
        1300                1305                1310

Tyr Leu Gly Lys Met Asn Arg Val Ala Asp Asp Ile Thr Val Ala Pro
        1315                1320                1325

Glu Tyr Leu Asp Glu Ser Asn Gly Gln Ala Trp Ala Arg Gly Gly Ala
        1330                1335                1340

Gly Asp Arg Leu Leu Met Tyr Ala Gln Leu Lys Glu Trp Ala Glu Glu
1345                1350                1355                1360

Asn Phe Asp Ile Lys Gln Trp Tyr Pro Asp Gly Glu Leu Pro Lys Phe
            1365                1370                1375

Tyr Ser Asp Arg Lys Gly Met Lys Gly Trp Asn Leu Phe Gln Leu Met
        1380                1385                1390

His Arg Lys Ala Arg Gly Asp Asp Val Gly Asn Ser Thr Phe Gly Gly
        1395                1400                1405

Lys Asn Tyr Cys Ala Glu Ser Asn Gly Asn Ala Ala Asp Thr Leu Met
        1410                1415                1420

Leu Cys Ala Ser Trp Val Ala Gln Ala Asp Leu Ser Glu Phe Phe Lys
1425                1430                1435                1440

Lys Trp Asn Pro Gly Ala Ser Ala Tyr Gln Leu Pro Gly Ala Thr Glu
            1445                1450                1455

Met Ser Phe Gln Gly Gly Val Ser Ser Ser Ala Tyr Ser Thr Leu Ala
        1460                1465                1470

Ser Leu Lys Leu Pro Lys Pro Glu Lys Gly Pro Glu Thr Ile Asn Lys
        1475                1480                1485

Val Thr Glu His Lys Met Ser Ala Glu
        1490                1495

<210> SEQ ID NO 21
<211> LENGTH: 4491
<212> TYPE: DNA
<213> ORGANISM: Escherichia coli

<400> SEQUENCE: 21
tgtgatggtg gtggttcagg atcgtcctcc gatacgccgt ctgtagattc tggatcaggg      60
actttgccgg aagtgaaacc cgatccaaca ccaaccccgg agccgacacc tgagccgacg     120
ccggacccag aacctacgcc ggatccaaca cctgatcctg agccgacacc agaaccggag     180
ccagaacctg ttcctacgaa aacgggttat ctgaccctgg cggaagcca gcgggtaact      240 ggtgctacct gtaatggtga atccagcgat ggctttacct ttacgccagg caataccgtg     300
agttgtgtgg tgggcagtac gaccattgca acattcaaca cccagtcaga agctgcgcgt     360
agcctgcgtg cggttgacaa agtgtcgttt agcctggagg acgcgcagga gctggcgaat     420
tctgaaaata gaaaaccaa cgccatctct ctggtgacgt ccagcgacag ttgccccgca     480
gatgcagaac agctttgtct tactttctcg tcagtggttg atcgcgcgcg atttgaaaaa     540
ctgtataagc aaattgatct ggcaacagac aatttcagca agctggtcaa tgaagaggtg     600
gaaaacaatg ctgcgactga taaagcgccg tccaccccata cctcaacggt agtgccagtc     660
acgacagagg gaacaaaacc ggatctgaac gcgtccttcg tgtcggctaa cgcggaacag     720
ttttatcagt atcaacccac tgaaatcatt ctttccgaag ccaactggt ggatagcctg     780 gggaacggtg ttgctggcgt tgactactac accaattcag ccgtggcgt aactgacgaa     840

```
aacggtaaat tttcctttag ctggggcgaa accatctcct ttggtatcga tacctttgaa    900
ctgggctcag tacgtggcaa taagtcgacc attgcgctga ctgaatgggt tgatgaagtt    960
cgcggggcaa atatcgatca gctcattcat cgttattcga cgactggtca aaataatact   1020
cgtgttgttc cggacgatgt acgcaaggtc tttgccgaat atcccaacgt gatcaacgag   1080
ataatcaatc tttcgttatc caacggtgcg acgctggatg aaggcgatca aaacgttgtg   1140
ctgcctaacg aatttatcga gcagtttaag acgggtcagg ccaaagagat cgataccgcg   1200
atttgtgcga aaccgacgg ttgtaacgag gctcgctggt tctcgctgac aacgcgcaat   1260
gttaatgacg gccagattca gggcgttatt aacaagctgt ggggcgtgga tacgaactat   1320
cagtctgtca gcaagttcca cgtcttccat gactctacca acttctatgg cagcaccggt   1380
aacgcgcgcg tcaggcggt ggtaaatatc tccaactcgg cattcccgat tctgatggcg   1440
cgtaatgata aaactactg gctggcgttt ggcgaaaaac gcgcctggga taaaaatgag   1500
ctggcgtaca ttacggaagc gccttccatt gtgcagccag agaacgttac gcgcgatact   1560
gcgactttca acctgccgtt tatttcgctg ggcaagtcg gtgaaggcaa actgatggtt   1620
atcggtaacc cgcactacaa cagcatcctg cgttgcccga acggttacag ttggggcggt   1680
ggtgttaata gtaaaggtga gtgtacgctc agcggtgatt ctgatgacat gaagcacttt   1740
atgcagaacg tactgcgcta cttgtcaaat gacatctggc agccaaatac caagagcatc   1800
atgactgtcg gcaccaacct ggagaacgtt tatttcaaaa agcgggcca ggtattggga   1860
aatagtgcac catttgcttt ccatgaggat ttcactggta tcacggttaa acagttgacc   1920
agctatggcg atctgaatcc ggaagagatt ccgttgctga tcctcaacgg ctttgaatat   1980
gtgactcagt ggtctggcga tccctatgct gtgcctctgc gtgcagatac cagcaaaccg   2040
aagctgactc agcaggatgt gaccgatctg atcgcttatc tgaacaaagg tggctcggtg   2100
ctgatcatgg aaaacgtgat gagcaatctt aaggaagaga gcgcgtccag ttttgtgcgt   2160
ctgctggatg ccgcgggtct gtcaatggct ctgaacaaat cggtggtgaa caacgatccg   2220
caagggtatc cggatcgcgt tcgtcagcgt cgcgcgactg gcatttgggt ttatgaacgt   2280
tatcctgctg cagacggcgc gcaaccgccg tacaccatcg acccaaatac aggggaagtg   2340
acctggaaat accagcaaga caacaagcct gatgacaagc cgaaactgga agttgcgagc   2400
tggcaggagg aagttgaggg caaacaggta acgcgttatg cctttattga tgaagcggaa   2460
tacacaacag aagaatctct ggaagcggca aaggcaaaaa tctttgagaa gtttcctggg   2520
ttacaggagt gtaaggactc gacttaccat tacgagatta actgtttgga gcgccgccca   2580
ggcacggatg ttccggtaac aggtggcatg tatgttccgc gctatacgca actgaatctt   2640
gacgccgaca ccgcgaaagc gatggtgcag gcggcggatt taggcaccaa cattcagcgc   2700
ctgtatcagc atgagcttta tttccgtacc aaaggcagta aggtgagcg tctgaacagt   2760
gttgatctgg aacgtctgta ccagaacatg tcggtctggc tgtggaacga tacgaaaatat   2820
cgttacgaag agggcaagga agatgagctg ggctttaaaa cgttcaccga gttcctgaac   2880
tgctacgcca atgatgccta tgcaggcggc accaagtgct ccgcagatct gaaaaaatcg   2940
ctggtcgata caacatgat ctacggtgac ggtagcagca agcgggcat gatgaaccca   3000
agctatccgc tcaactatat ggaaaaaccg ctgacgcgtc tgatgctggg ccgttcctgg   3060
tgggatctga acattaaggt tgatgtggag aagtacccag atccgtatc ggcaaagggt   3120
gagagcgtta cggaaaacat cagcctgtac tcgaatccga ccaaatggtt tgcgggtaac   3180
atgcagtcaa ccggcctgtg ggcaccggcc cagcaggacg tcaccattaa gtcttcggcg   3240
```

-continued

```
tcagtcccag tgactgttac cgtggcgctg gctgacgacc tgactggacg tgagaagcat    3300
gaagttgcgc tgaaccgtcc gccaagagtg actaaaacgt atactctgga ggctaacggt    3360
gaagtgacct tcaaggtgcc ttatggtggt ctgatttata tcaagggcga cagtaaggat    3420
gatgtttctg ctaacttcac ctttaccggt gtagtaaaag cgccgttcta taagacggc    3480
gaatggaaaa acgatctgga ctcaccggcg ccgctgggcg agctggagtc tgcgtcgttc    3540
gtctatacca cgccgaagaa gaaccttgag gccagcaatt tcactggtgg tgtagcagaa    3600
ttcgctaaag atctggatac ctttgccagc tcgatgaatg acttctacgg tcgtaatgat    3660
gaagacggta agcaccggat gtttacctat aaaaacttga cggggcacaa gcatcgtttc    3720
accaacgatg tgcagatctc catcggtgat gcgcactcgg ttatccggt aatgaacagc     3780
agcttctcga cgaacagcac cacgctgccg acgacgccgc tgaacgactg gctgatttgg    3840
cacgaagtcg gtcataacgc tgcagaaaca ccgctgaacg taccgggtgc aactgaagtg    3900
gcgaacaacg tgctggcgct gtacatgcag gatcgctatc tcggtaagat gaaccgtgtc    3960
gctgacgaca ttaccgtcgc gccggaatat ctggacgaga gcaacggtca ggcctgggcg    4020
cgcggcggtg cgggtgaccg tctgctgatg tacgcacagt tgaaggagtg gcagaggaa     4080
aactttgata tcaaacagtg gtatccagat ggtgagctgc ctaagttcta cagcgatcgt    4140
aaagggatga agggctggaa cctgttccag ttgatgcacc gtaaagcgcg cggcgctgat    4200
gttggtaaca gcacctttgg tggcaagaat tactgtgctg aatccaatgg taacgctgcc    4260
gacacgctga tgctgtgtgc atcctgggtc gctcaggcgg atctttcgga attcttaag     4320
aaatggaatc cgggtgcaag tgcttaccag ttgccgggag caacggagat gagtttccag    4380
ggcggtgtga gctcttcggc ttacagcacg ctggcgtcac tcaagctgcc gaaaccggaa    4440
aaagggccgg aaaccattaa caaggttacc gagcataaga tgtctgccga g             4491
```

<210> SEQ ID NO 22
<211> LENGTH: 1497
<212> TYPE: PRT
<213> ORGANISM: Escherichia coli

<400> SEQUENCE: 22

```
Cys Asp Gly Gly Gly Ser Gly Ser Ser Asp Thr Pro Ser Val Asp
1               5                   10                  15

Ser Gly Ser Gly Thr Leu Pro Glu Val Lys Pro Asp Pro Thr Pro Thr
                20                  25                  30

Pro Glu Pro Thr Pro Glu Pro Thr Pro Asp Glu Pro Thr Pro Asp
            35                  40                  45

Pro Thr Pro Asp Pro Glu Pro Thr Pro Glu Pro Glu Pro Val
        50                  55                  60

Pro Thr Lys Thr Gly Tyr Leu Thr Leu Gly Gly Ser Gln Arg Val Thr
65                  70                  75                  80

Gly Ala Thr Cys Asn Gly Glu Ser Asp Gly Phe Thr Phe Thr Pro
                85                  90                  95

Gly Asn Thr Val Ser Cys Val Val Gly Ser Thr Thr Ile Ala Thr Phe
            100                 105                 110

Asn Thr Gln Ser Glu Ala Ala Arg Ser Leu Arg Ala Val Asp Lys Val
        115                 120                 125

Ser Phe Ser Leu Glu Asp Ala Gln Glu Leu Ala Asn Ser Glu Asn Lys
    130                 135                 140

Lys Thr Asn Ala Ile Ser Leu Val Thr Ser Ser Asp Ser Cys Pro Ala
```

```
                145                 150                 155                 160
Asp Ala Glu Gln Leu Cys Leu Thr Phe Ser Ser Val Val Asp Arg Ala
                    165                 170                 175

Arg Phe Glu Lys Leu Tyr Lys Gln Ile Asp Leu Ala Thr Asp Asn Phe
                180                 185                 190

Ser Lys Leu Val Asn Glu Glu Val Glu Asn Asn Ala Ala Thr Asp Lys
                    195                 200                 205

Ala Pro Ser Thr His Thr Ser Thr Val Val Pro Val Thr Thr Glu Gly
                210                 215                 220

Thr Lys Pro Asp Leu Asn Ala Ser Phe Val Ser Ala Asn Ala Glu Gln
225                 230                 235                 240

Phe Tyr Gln Tyr Gln Pro Thr Glu Ile Ile Leu Ser Glu Gly Gln Leu
                    245                 250                 255

Val Asp Ser Leu Gly Asn Gly Val Ala Gly Val Asp Tyr Tyr Thr Asn
                260                 265                 270

Ser Gly Arg Gly Val Thr Asp Glu Asn Gly Lys Phe Ser Phe Ser Trp
                    275                 280                 285

Gly Glu Thr Ile Ser Phe Gly Ile Asp Thr Phe Glu Leu Gly Ser Val
                290                 295                 300

Arg Gly Asn Lys Ser Thr Ile Ala Leu Thr Glu Leu Gly Asp Glu Val
305                 310                 315                 320

Arg Gly Ala Asn Ile Asp Gln Leu Ile His Arg Tyr Ser Thr Thr Gly
                    325                 330                 335

Gln Asn Asn Thr Arg Val Val Pro Asp Asp Val Arg Lys Val Phe Ala
                340                 345                 350

Glu Tyr Pro Asn Val Ile Asn Glu Ile Ile Asn Leu Ser Leu Ser Asn
                    355                 360                 365

Gly Ala Thr Leu Asp Glu Gly Asp Gln Asn Val Val Leu Pro Asn Glu
                370                 375                 380

Phe Ile Glu Gln Phe Lys Thr Gly Gln Ala Lys Glu Ile Asp Thr Ala
385                 390                 395                 400

Ile Cys Ala Lys Thr Asp Gly Cys Asn Glu Ala Arg Trp Phe Ser Leu
                    405                 410                 415

Thr Thr Arg Asn Val Asn Asp Gly Gln Ile Gln Gly Val Ile Asn Lys
                420                 425                 430

Leu Trp Gly Val Asp Thr Asn Tyr Gln Ser Val Ser Lys Phe His Val
                    435                 440                 445

Phe His Asp Ser Thr Asn Phe Tyr Gly Ser Thr Gly Asn Ala Arg Gly
                450                 455                 460

Gln Ala Val Val Asn Ile Ser Asn Ser Ala Phe Pro Ile Leu Met Ala
465                 470                 475                 480

Arg Asn Asp Lys Asn Tyr Trp Leu Ala Phe Gly Glu Lys Arg Ala Trp
                    485                 490                 495

Asp Lys Asn Glu Leu Ala Tyr Ile Thr Glu Ala Pro Ser Ile Val Gln
                500                 505                 510

Pro Glu Asn Val Thr Arg Asp Thr Ala Thr Phe Asn Leu Pro Phe Ile
                    515                 520                 525

Ser Leu Gly Gln Val Gly Glu Gly Lys Leu Met Val Ile Gly Asn Pro
                530                 535                 540

His Tyr Asn Ser Ile Leu Arg Cys Pro Asn Gly Tyr Ser Trp Gly Gly
545                 550                 555                 560

Gly Val Asn Ser Lys Gly Glu Cys Thr Leu Ser Gly Asp Ser Asp Asp
                    565                 570                 575
```

```
-continued

Met Lys His Phe Met Gln Asn Val Leu Arg Tyr Leu Ser Asn Asp Ile
            580                 585                 590

Trp Gln Pro Asn Thr Lys Ser Ile Met Thr Val Gly Thr Asn Leu Glu
            595                 600                 605

Asn Val Tyr Phe Lys Lys Ala Gly Gln Val Leu Gly Asn Ser Ala Pro
            610                 615                 620

Phe Ala Phe His Glu Asp Phe Thr Gly Ile Thr Val Lys Gln Leu Thr
625                 630                 635                 640

Ser Tyr Gly Asp Leu Asn Pro Glu Glu Ile Pro Leu Leu Ile Leu Asn
                645                 650                 655

Gly Phe Glu Tyr Val Thr Gln Trp Ser Gly Asp Pro Tyr Ala Val Pro
                660                 665                 670

Leu Arg Ala Asp Thr Ser Lys Pro Lys Leu Thr Gln Gln Asp Val Thr
                675                 680                 685

Asp Leu Ile Ala Tyr Leu Asn Lys Gly Gly Ser Val Leu Ile Met Glu
            690                 695                 700

Asn Val Met Ser Asn Leu Lys Glu Glu Ser Ala Ser Ser Phe Val Arg
705                 710                 715                 720

Leu Leu Asp Ala Ala Gly Leu Ser Met Ala Leu Asn Lys Ser Val Val
                725                 730                 735

Asn Asn Asp Pro Gln Gly Tyr Pro Asp Arg Val Arg Gln Arg Arg Ala
                740                 745                 750

Thr Gly Ile Trp Val Tyr Glu Arg Tyr Pro Ala Ala Asp Gly Ala Gln
                755                 760                 765

Pro Pro Tyr Thr Ile Asp Pro Asn Thr Gly Glu Val Thr Trp Lys Tyr
            770                 775                 780

Gln Gln Asp Asn Lys Pro Asp Asp Lys Pro Lys Leu Glu Val Ala Ser
785                 790                 795                 800

Trp Gln Glu Glu Val Glu Gly Lys Gln Val Thr Arg Tyr Ala Phe Ile
                805                 810                 815

Asp Glu Ala Glu Tyr Thr Thr Glu Glu Ser Leu Glu Ala Ala Lys Ala
                820                 825                 830

Lys Ile Phe Glu Lys Phe Pro Gly Leu Gln Glu Cys Lys Asp Ser Thr
            835                 840                 845

Tyr His Tyr Glu Ile Asn Cys Leu Glu Arg Arg Pro Gly Thr Asp Val
            850                 855                 860

Pro Val Thr Gly Gly Met Tyr Val Pro Arg Tyr Thr Gln Leu Asn Leu
865                 870                 875                 880

Asp Ala Asp Thr Ala Lys Ala Met Val Gln Ala Ala Asp Leu Gly Thr
                885                 890                 895

Asn Ile Gln Arg Leu Tyr Gln His Glu Leu Tyr Phe Arg Thr Lys Gly
            900                 905                 910

Ser Lys Gly Glu Arg Leu Asn Ser Val Asp Leu Glu Arg Leu Tyr Gln
            915                 920                 925

Asn Met Ser Val Trp Leu Trp Asn Asp Thr Lys Tyr Arg Tyr Glu Glu
            930                 935                 940

Gly Lys Glu Asp Glu Leu Gly Phe Lys Thr Phe Thr Glu Phe Leu Asn
945                 950                 955                 960

Cys Tyr Ala Asn Asp Ala Tyr Ala Gly Gly Thr Lys Cys Ser Ala Asp
                965                 970                 975

Leu Lys Lys Ser Leu Val Asp Asn Asn Met Ile Tyr Gly Asp Gly Ser
            980                 985                 990
```

```
Ser Lys Ala Gly Met Met Asn Pro Ser Tyr Pro Leu Asn Tyr Met Glu
            995                 1000                1005

Lys Pro Leu Thr Arg Leu Met Leu Gly Arg Ser Trp Trp Asp Leu Asn
        1010                1015                1020

Ile Lys Val Asp Val Glu Lys Tyr Pro Gly Ser Val Ser Ala Lys Gly
1025                1030                1035                1040

Glu Ser Val Thr Glu Asn Ile Ser Leu Tyr Ser Asn Pro Thr Lys Trp
            1045                1050                1055

Phe Ala Gly Asn Met Gln Ser Thr Gly Leu Trp Ala Pro Ala Gln Gln
        1060                1065                1070

Asp Val Thr Ile Lys Ser Ser Ala Ser Val Pro Val Thr Val Thr Val
            1075                1080                1085

Ala Leu Ala Asp Asp Leu Thr Gly Arg Glu Lys His Glu Val Ala Leu
        1090                1095                1100

Asn Arg Pro Pro Arg Val Thr Lys Thr Tyr Thr Leu Glu Ala Asn Gly
1105                1110                1115                1120

Glu Val Thr Phe Lys Val Pro Tyr Gly Gly Leu Ile Tyr Ile Lys Gly
            1125                1130                1135

Asp Ser Lys Asp Asp Val Ser Ala Asn Phe Thr Phe Thr Gly Val Val
            1140                1145                1150

Lys Ala Pro Phe Tyr Lys Asp Gly Glu Trp Lys Asn Asp Leu Asp Ser
        1155                1160                1165

Pro Ala Pro Leu Gly Glu Leu Glu Ser Ala Ser Phe Val Tyr Thr Thr
        1170                1175                1180

Pro Lys Lys Asn Leu Glu Ala Ser Asn Phe Thr Gly Gly Val Ala Glu
1185                1190                1195                1200

Phe Ala Lys Asp Leu Asp Thr Phe Ala Ser Ser Met Asn Asp Phe Tyr
            1205                1210                1215

Gly Arg Asn Asp Glu Asp Gly Lys His Arg Met Phe Thr Tyr Lys Asn
            1220                1225                1230

Leu Thr Gly His Lys His Arg Phe Thr Asn Asp Val Gln Ile Ser Ile
        1235                1240                1245

Gly Asp Ala His Ser Gly Tyr Pro Val Met Asn Ser Ser Phe Ser Thr
    1250                1255                1260

Asn Ser Thr Thr Leu Pro Thr Thr Pro Leu Asn Asp Trp Leu Ile Trp
1265                1270                1275                1280

His Glu Val Gly His Asn Ala Ala Glu Thr Pro Leu Asn Val Pro Gly
            1285                1290                1295

Ala Thr Glu Val Ala Asn Asn Val Leu Ala Leu Tyr Met Gln Asp Arg
        1300                1305                1310

Tyr Leu Gly Lys Met Asn Arg Val Ala Asp Asp Ile Thr Val Ala Pro
        1315                1320                1325

Glu Tyr Leu Asp Glu Ser Asn Gly Gln Ala Trp Ala Arg Gly Gly Ala
    1330                1335                1340

Gly Asp Arg Leu Leu Met Tyr Ala Gln Leu Lys Glu Trp Ala Glu Glu
1345                1350                1355                1360

Asn Phe Asp Ile Lys Gln Trp Tyr Pro Asp Gly Glu Leu Pro Lys Phe
        1365                1370                1375

Tyr Ser Asp Arg Lys Gly Met Lys Gly Trp Asn Leu Phe Gln Leu Met
        1380                1385                1390

His Arg Lys Ala Arg Gly Ala Asp Val Gly Asn Ser Thr Phe Gly Gly
        1395                1400                1405

Lys Asn Tyr Cys Ala Glu Ser Asn Gly Asn Ala Ala Asp Thr Leu Met
```

```
                1410               1415               1420
Leu Cys Ala Ser Trp Val Ala Gln Ala Asp Leu Ser Glu Phe Phe Lys
1425               1430               1435               1440

Lys Trp Asn Pro Gly Ala Ser Ala Tyr Gln Leu Pro Gly Ala Thr Glu
            1445               1450               1455

Met Ser Phe Gln Gly Gly Val Ser Ser Ala Tyr Ser Thr Leu Ala
            1460               1465               1470

Ser Leu Lys Leu Pro Lys Pro Glu Lys Gly Pro Glu Thr Ile Asn Lys
        1475               1480               1485

Val Thr Glu His Lys Met Ser Ala Glu
    1490               1495

<210> SEQ ID NO 23
<211> LENGTH: 2184
<212> TYPE: DNA
<213> ORGANISM: Escherichia coli

<400> SEQUENCE: 23
gatacgccgt ctgtagattc tggatcaggg actttgccgg aagtgaaacc cgatccaaca      60
ccaaccccgg agccgacacc tgagccgacg ccggacccag aacctacgcc ggatccaaca     120
cctgatcctg agccgacacc agaaccggag ccagaacctg ttcctacgaa acgggttat     180 ctgaccctgg cggaagcca gcgggtaact ggtgctacct gtaatggtga atccagcgat     240
ggctttacct ttacgccagg caataccgtg agttgtgtgg tgggcagtac gaccattgca     300
acattcaaca cccagtcaga agctgcgcgt agcctgcgtg cggttgacaa agtgtcgttt     360
agcctggagg acgcgcagga gctggcgaat tctgaaaata agaaaaccaa cgccatctct     420
ctggtgacgt ccagcgacag ttgccccgca gatgcagaac agctttgtct tactttctcg     480
tcagtggttg atcgcgcgcg atttgaaaaa ctgtataagc aaattgatct ggcaacagac     540
aatttcagca agctggtcaa tgaagaggtg gaaaacaatg ctgcgactga taaagcgccg     600
tccacccata cctcaacggt agtgccagtc acgacagagg gaacaaaacc ggatctgaac     660
gcgtccttcg tgtcggctaa cgcggaacag ttttatcagt atcaacccac tgaaatcatt     720 cttctccgaag gccaactggt ggatagcctg ggaacggttg ttgctggcgt tgactactac     780
accaattcag gccgtggcgt aactgacgaa acggtaaat tttcctttag ctggggcgaa     840
accatctcct ttggtatcga tacctttgaa ctgggctcag tacgtggcaa taagtcgacc     900
attgcgctga ctgaattggg tgatgaagtt cgcggggcaa atatcgatca gctcattcat     960
cgttattcga cgactggtca aataatact cgtgttgttc cggacgatgt acgcaaggtc    1020
tttgccgaat atcccaacgt gatcaacgag ataatcaatc tttcgttatc caacggtgcg    1080
acgctggatt aaggcgatca aaacgttgtg ctgcctaacg aatttatcga gcagtttaag    1140
acgggtcagg ccaaagagat cgataccgcg atttgtgcga aaccgacgg ttgtaacgag    1200 gctcgctggt tctcgctgac aacgcgcaat gttaatgacg ccagattca gggcgttatt    1260 aacaagctgt ggggcgtgga tacgaactat cagtctgtca gcaagttcca cgtcttccat    1320
gactctacca acttctatgg cagcaccggt aacgcgcgcg tcaggcggt ggtaaatatc    1380 tccaactcgg cattcccgat tctgatggcg cgtaatgata aaaactactg gctggcgttt    1440
ggcgaaaaac gcgcctggga taaaaatgag ctggcgtaca ttacggaagc gccttccatt    1500
gtgcagccag agaacgttac gcgcgatact gcgactttca acctgccgtt tatttcgctg    1560
gggcaagtcg gtgaaggcaa actgatggtt atcggtaacc cgcactacaa cagcatcctg    1620
```

-continued

```
cgttgcccga acggttacag ttggggcggt ggtgttaata gtaaaggtga gtgtacgctc    1680
agcggtgatt ctgatgacat gaagcacttt atgcagaacg tactgcgcta cttgtcaaat    1740
gacatctggc agccaaatac caagagcatc atgactgtcg gcaccaacct ggagaacgtt    1800
tatttcaaaa aagcgggcca ggtattggga aatagtgcac catttgcttt ccatgaggat    1860
ttcactggta tcacggttaa acagttgacc agctatggcg atctgaatcc ggaagagatt    1920
ccgttgctga tcctcaacgg ctttgaatat gtgactcagt ggtctggcga tccctatgct    1980
gtgcctctgc gtgcagatac cagcaaaccg aagctgactc agcaggatgt gaccgatctg    2040
atcgcttatc tgaacaaagg tggctcggtg ctgatcatgg aaaacgtgat gagcaatctt    2100
aaggaagaga gcgcgtccag tttttgtgcgt ctgctggatg ccgcgggtct gtcaatggct    2160
ctgaacaaat cggtggtgaa caac                                            2184
```

<210> SEQ ID NO 24
<211> LENGTH: 728
<212> TYPE: PRT
<213> ORGANISM: Escherichia coli

<400> SEQUENCE: 24

```
Asp Thr Pro Ser Val Asp Ser Gly Ser Gly Thr Leu Pro Glu Val Lys
1               5                   10                  15

Pro Asp Pro Thr Pro Thr Pro Glu Pro Thr Pro Glu Pro Thr Pro Asp
            20                  25                  30

Pro Glu Pro Thr Pro Asp Pro Thr Pro Asp Pro Glu Pro Thr Pro Glu
        35                  40                  45

Pro Glu Pro Glu Pro Val Pro Thr Lys Thr Gly Tyr Leu Thr Leu Gly
    50                  55                  60

Gly Ser Gln Arg Val Thr Gly Ala Thr Cys Asn Gly Glu Ser Ser Asp
65                  70                  75                  80

Gly Phe Thr Phe Thr Pro Gly Asn Thr Val Ser Cys Val Val Gly Ser
                85                  90                  95

Thr Thr Ile Ala Thr Phe Asn Thr Gln Ser Glu Ala Ala Arg Ser Leu
            100                 105                 110

Arg Ala Val Asp Lys Val Ser Phe Ser Leu Glu Asp Ala Gln Glu Leu
        115                 120                 125

Ala Asn Ser Glu Asn Lys Lys Thr Asn Ala Ile Ser Leu Val Thr Ser
    130                 135                 140

Ser Asp Ser Cys Pro Ala Asp Ala Glu Gln Leu Cys Leu Thr Phe Ser
145                 150                 155                 160

Ser Val Val Asp Arg Ala Arg Phe Glu Lys Leu Tyr Lys Gln Ile Asp
                165                 170                 175

Leu Ala Thr Asp Asn Phe Ser Lys Leu Val Asn Glu Glu Val Glu Asn
            180                 185                 190

Asn Ala Ala Thr Asp Lys Ala Pro Ser Thr His Thr Ser Thr Val Val
        195                 200                 205

Pro Val Thr Thr Glu Gly Thr Lys Pro Asp Leu Asn Ala Ser Phe Val
    210                 215                 220

Ser Ala Asn Ala Glu Gln Phe Tyr Gln Tyr Gln Pro Thr Glu Ile Ile
225                 230                 235                 240

Leu Ser Glu Gly Gln Leu Val Asp Ser Leu Gly Asn Gly Val Ala Gly
                245                 250                 255

Val Asp Tyr Tyr Thr Asn Ser Gly Arg Gly Val Thr Asp Glu Asn Gly
            260                 265                 270
```

```
Lys Phe Ser Phe Ser Trp Gly Glu Thr Ile Ser Phe Gly Ile Asp Thr
            275                 280                 285

Phe Glu Leu Gly Ser Val Arg Gly Asn Lys Ser Thr Ile Ala Leu Thr
        290                 295                 300

Glu Leu Gly Asp Glu Val Arg Gly Ala Asn Ile Asp Gln Leu Ile His
305                 310                 315                 320

Arg Tyr Ser Thr Thr Gly Gln Asn Asn Thr Arg Val Val Pro Asp Asp
                325                 330                 335

Val Arg Lys Val Phe Ala Glu Tyr Pro Asn Val Ile Asn Glu Ile Ile
            340                 345                 350

Asn Leu Ser Leu Ser Asn Gly Ala Thr Leu Asp Glu Gly Asp Gln Asn
        355                 360                 365

Val Val Leu Pro Asn Glu Phe Ile Glu Gln Phe Lys Thr Gly Gln Ala
    370                 375                 380

Lys Glu Ile Asp Thr Ala Ile Cys Ala Lys Thr Asp Gly Cys Asn Glu
385                 390                 395                 400

Ala Arg Trp Phe Ser Leu Thr Thr Arg Asn Val Asn Asp Gly Gln Ile
                405                 410                 415

Gln Gly Val Ile Asn Lys Leu Trp Gly Val Asp Thr Asn Tyr Gln Ser
            420                 425                 430

Val Ser Lys Phe His Val Phe His Asp Ser Thr Asn Phe Tyr Gly Ser
        435                 440                 445

Thr Gly Asn Ala Arg Gly Gln Ala Val Val Asn Ile Ser Asn Ser Ala
    450                 455                 460

Phe Pro Ile Leu Met Ala Arg Asn Asp Lys Asn Tyr Trp Leu Ala Phe
465                 470                 475                 480

Gly Glu Lys Arg Ala Trp Asp Lys Asn Glu Leu Ala Tyr Ile Thr Glu
                485                 490                 495

Ala Pro Ser Ile Val Gln Pro Glu Asn Val Thr Arg Asp Thr Ala Thr
            500                 505                 510

Phe Asn Leu Pro Phe Ile Ser Leu Gly Gln Val Gly Glu Gly Lys Leu
        515                 520                 525

Met Val Ile Gly Asn Pro His Tyr Asn Ser Ile Leu Arg Cys Pro Asn
    530                 535                 540

Gly Tyr Ser Trp Gly Gly Val Asn Ser Lys Gly Glu Cys Thr Leu
545                 550                 555                 560

Ser Gly Asp Ser Asp Met Lys His Phe Met Gln Asn Val Leu Arg
                565                 570                 575

Tyr Leu Ser Asn Asp Ile Trp Gln Pro Asn Thr Lys Ser Ile Met Thr
            580                 585                 590

Val Gly Thr Asn Leu Glu Asn Val Tyr Phe Lys Lys Ala Gly Gln Val
        595                 600                 605

Leu Gly Asn Ser Ala Pro Phe Ala Phe His Glu Asp Phe Thr Gly Ile
    610                 615                 620

Thr Val Lys Gln Leu Thr Ser Tyr Gly Asp Leu Asn Pro Glu Ile
625                 630                 635                 640

Pro Leu Leu Ile Leu Asn Gly Phe Glu Tyr Val Thr Gln Trp Ser Gly
                645                 650                 655

Asp Pro Tyr Ala Val Pro Leu Arg Ala Asp Thr Ser Lys Pro Lys Leu
            660                 665                 670

Thr Gln Gln Asp Val Thr Asp Leu Ile Ala Tyr Leu Asn Lys Gly Gly
        675                 680                 685

Ser Val Leu Ile Met Glu Asn Val Met Ser Asn Leu Lys Glu Glu Ser
```

```
                      690                 695                 700
Ala Ser Ser Phe Val Arg Leu Leu Asp Ala Ala Gly Leu Ser Met Ala
705                 710                 715                 720

Leu Asn Lys Ser Val Val Asn Asn
            725
```

<210> SEQ ID NO 25
<211> LENGTH: 3810
<212> TYPE: DNA
<213> ORGANISM: Escherichia coli

<400> SEQUENCE: 25

```
gatacgccgt ctgtagattc tggatcaggg actttgccgg aagtgaaacc cgatccaaca    60
ccaaccccgg agccgacacc tgagccgacg ccggacccag aacctacgcc ggatccaaca   120
cctgatcctg agccgacacc agaaccggag ccagaacctg ttcctacgaa aacgggttat   180
ctgaccctgg cggaagcca gcgggtaact ggtgctacct gtaatggtga atccagcgat   240
ggctttacct ttacgccagg caataccgtg agttgtgtgg tgggcagtac gaccattgca   300
acattcaaca cccagtcaga agctgcgcgt agcctgcgtg cggttgacaa agtgtcgttt   360
agcctggagg acgcgcagga gctggcgaat tctgaaaata agaaaaccaa cgccatctct   420
ctggtgacgt ccagcgacag ttgccccgca gatgcagaac agctttgtct tactttctcg   480
tcagtggttg atcgcgcgcg atttgaaaaa ctgtataagc aaattgatct ggcaacagac   540
aatttcagca agctggtcaa tgaagaggtg aaaacaatg ctgcgactga taaagcgccg   600
tccacccata cctcaacggt agtgccagtc acgacagagg gaacaaaacc ggatctgaac   660
gcgtccttcg tgtcggctaa cgcggaacag ttttatcagt atcaacccac tgaaatcatt   720
ctttccgaag ccaactggt ggatagcctg gggaacggtg ttgctggcgt tgactactac   780
accaattcag gccgtggcgt aactgacgaa aacggtaaat tttccttag ctggggcgaa   840
accatctcct tggtatcga tacctttgaa ctgggctcag tacgtggcaa taagtcgacc   900
attgcgctga ctgaattggg tgatgaagtt cgcggggcaa atatcgatca gctcattcat   960
cgttattcga cgactggtca aaataatact cgtgttgttc cggacgatgt acgcaaggtc  1020
tttgccgaat atcccaacgt gatcaacgag ataatcaatc tttcgttatc caacggtgcg  1080
acgctggatg aaggcgatca aaacgttgtg ctgcctaacg aatttatcga gcagtttaag  1140
acgggtcagg ccaaagagat cgataccgcg atttgtgcga aaaccgacgg ttgtaacgag  1200
gctcgctggt tctcgctgac aacgcgcaat gttaatgacg ccagattca gggcgttatt  1260
aacaagctgt ggggcgtgga tacgaactat cagtctgtca gcaagttcca cgtcttccat  1320
gactctacca acttctatgg cagcaccggt aacgcgcgcg tcaggcggt ggtaaatatc  1380
tccaactcgg cattcccgat tctgatggcg cgtaatgata aaaactactg gctggcgttt  1440
ggcgaaaaac gcgcctggga taaaaatgag ctggcgtaca ttacgaagc gccttccatt  1500
gtgcagccag agaacgttac gcgcgatact gcgactttca acctgccgtt tatttcgctg  1560
gggcaagtcg gtgaaggcaa actgatggtt atcggtaacc cgcactacaa cagcatcctg  1620
cgttgcccga acggttacag ttggggcggt ggtgttaata gtaaaggtga gtgtacgctc  1680
agcggtgatt ctgatgacat gaagcacttt atgcagaacg tactgcgcta cttgtcaaat  1740
gacatctggc agccaaatac caagagcatc atgactgtcg gcaccaacct ggagaacgtt  1800
tatttcaaaa aagcgggcca ggtattggga aatagtgcac catttgcttt ccatgaggat  1860
ttcactggta tcacggttaa acagttgacc agctatggcg atctgaatcc ggaagagatt  1920
```

```
ccgttgctga tcctcaacgg ctttgaatat gtgactcagt ggtctggcga tccctatgct    1980
gtgcctctgc gtgcagatac cagcaaaccg aagctgactc agcaggatgt gaccgatctg    2040
atcgcttatc tgaacaaagg tggctcggtg ctgatcatgg aaaacgtgat gagcaatctt    2100
aaggaagaga gcgcgtccag ttttgtgcgt ctgctggatg ccgcgggtct gtcaatggct    2160
ctgaacaaat cggtggtgaa caacgatccg caagggtatc cggatcgcgt tcgtcagcgt    2220
cgcgcgactg gcatttgggt ttatgaacgt tatcctgctg cagacggcgc gcaaccgccg    2280
tacaccatcg acccaaatac aggggaagtg acctggaaat accagcaaga caacaagcct    2340
gatgacaagc cgaaactgga agttgcgagc tggcaggagg aagttgaggg caaacaggta    2400
acgcgttatg cctttattga tgaagcggaa tacacaacag aagaatctct ggaagcggca    2460
aaggcaaaaa tctttgagaa gtttcctggg ttacaggagt gtaaggactc gacttaccat    2520
tacgagatta actgtttgga gcgccgccca ggcacggatg ttccggtaac aggtggcatg    2580
tatgttccgc gctatacgca actgaatctt gacgccgaca ccgcgaaagc gatggtgcag    2640
gcggcggatt taggcaccaa cattcagcgc ctgtatcagc atgagcttta tttccgtacc    2700
aaaggcagta aggtgagcg tctgaacagt gttgatctgg aacgtctgta ccagaacatg    2760
tcggtctggc tgtggaacga tacgaaatat cgttacgaag agggcaagga agatgagctg    2820
ggctttaaaa cgttcaccga gttcctgaac tgctacgcca atgatgccta tgcaggcggc    2880
accaagtgct ccgcagatct gaaaaaatcg ctggtcgata caacatgat ctacggtgac     2940
ggtagcagca aagcgggcat gatgaaccca agctatccgc tcaactatat ggaaaaaccg    3000
ctgacgcgtc tgatgctggg ccgttcctgg tgggatctga acattaaggt tgatgtggag    3060
aagtacccag gatccgtatc ggcaaagggt gagagcgtta cggaaaacat cagcctgtac    3120
tcgaatccga ccaaatggtt tgcgggtaac atgcagtcaa ccggcctgtg ggcaccggcc    3180
cagcaggacg tcaccattaa gtcttcggcg tcagtcccag tgactgttac cgtggcgctg    3240
gctgacgacc tgactggacg tgagaagcat gaagttgcgc tgaaccgtcc gccaagagtg    3300
actaaaacgt atactctgga ggctaacggt gaagtgacct tcaaggtgcc ttatggtggt    3360
ctgatttata tcaagggcga cagtaaggat gatgtttctg ctaacttcac ctttaccggt    3420
gtagtaaaag cgccgttcta taaagacggc gaatggaaaa acgatctgga ctcaccggcg    3480
ccgctgggcg agctggagtc tgcgtcgttc gtctatacca cgccgaagaa gaaccttgag    3540
gccagcaatt tcactggtgg tgtagcagaa ttcgctaaag atctggatac ctttgccagc    3600
tcgatgaatg acttctacgg tcgtaatgat gaagacggta gcaccggat gtttacctat    3660
aaaaacttga cggggcacaa gcatcgtttc accaacgatg tgcagatctc catcggtgat    3720
gcgcactcgg ttatccggt aatgaacagc agcttctcga cgaacagcac cacgctgccg    3780
acgacgccgc tgaacgactg gctgatttgg                                     3810
```

<210> SEQ ID NO 26
<211> LENGTH: 1270
<212> TYPE: PRT
<213> ORGANISM: Escherichia coli

<400> SEQUENCE: 26

Asp Thr Pro Ser Val Asp Ser Gly Ser Gly Thr Leu Pro Glu Val Lys
1               5                   10                  15

Pro Asp Pro Thr Pro Thr Pro Glu Pro Thr Pro Glu Pro Thr Pro Asp
            20                  25                  30

```
Pro Glu Pro Thr Pro Asp Pro Thr Pro Asp Pro Glu Pro Thr Pro Glu
         35                  40                  45
Pro Glu Pro Glu Pro Val Pro Thr Lys Thr Gly Tyr Leu Thr Leu Gly
 50                  55                  60
Gly Ser Gln Arg Val Thr Gly Ala Thr Cys Asn Gly Glu Ser Ser Asp
 65                  70                  75                  80
Gly Phe Thr Phe Thr Pro Gly Asn Thr Val Ser Cys Val Val Gly Ser
                     85                  90                  95
Thr Thr Ile Ala Thr Phe Asn Thr Gln Ser Glu Ala Ala Arg Ser Leu
             100                 105                 110
Arg Ala Val Asp Lys Val Ser Phe Ser Leu Glu Asp Ala Gln Glu Leu
             115                 120                 125
Ala Asn Ser Glu Asn Lys Lys Thr Asn Ala Ile Ser Leu Val Thr Ser
 130                 135                 140
Ser Asp Ser Cys Pro Ala Asp Ala Glu Gln Leu Cys Leu Thr Phe Ser
 145                 150                 155                 160
Ser Val Val Asp Arg Ala Arg Phe Glu Lys Leu Tyr Lys Gln Ile Asp
                 165                 170                 175
Leu Ala Thr Asp Asn Phe Ser Lys Leu Val Asn Glu Glu Val Glu Asn
             180                 185                 190
Asn Ala Ala Thr Asp Lys Ala Pro Ser Thr His Thr Ser Thr Val Val
             195                 200                 205
Pro Val Thr Thr Glu Gly Thr Lys Pro Asp Leu Asn Ala Ser Phe Val
         210                 215                 220
Ser Ala Asn Ala Glu Gln Phe Tyr Gln Tyr Gln Pro Thr Glu Ile Ile
 225                 230                 235                 240
Leu Ser Glu Gly Gln Leu Val Asp Ser Leu Gly Asn Gly Val Ala Gly
                 245                 250                 255
Val Asp Tyr Tyr Thr Asn Ser Arg Gly Val Thr Asp Glu Asn Gly
                 260                 265                 270
Lys Phe Ser Phe Ser Trp Gly Glu Thr Ile Ser Phe Gly Ile Asp Thr
                 275                 280                 285
Phe Glu Leu Gly Ser Val Arg Gly Asn Lys Ser Thr Ile Ala Leu Thr
         290                 295                 300
Glu Leu Gly Asp Glu Val Arg Gly Ala Asn Ile Asp Gln Leu Ile His
 305                 310                 315                 320
Arg Tyr Ser Thr Thr Gly Gln Asn Asn Thr Arg Val Val Pro Asp Asp
                 325                 330                 335
Val Arg Lys Val Phe Ala Glu Tyr Pro Asn Val Ile Asn Glu Ile Ile
                 340                 345                 350
Asn Leu Ser Leu Ser Asn Gly Ala Thr Leu Asp Glu Gly Asp Gln Asn
                 355                 360                 365
Val Val Leu Pro Asn Glu Phe Ile Glu Gln Phe Lys Thr Gly Gln Ala
         370                 375                 380
Lys Glu Ile Asp Thr Ala Ile Cys Ala Lys Thr Asp Gly Cys Asn Glu
 385                 390                 395                 400
Ala Arg Trp Phe Ser Leu Thr Thr Arg Asn Val Asn Asp Gly Gln Ile
                 405                 410                 415
Gln Gly Val Ile Asn Lys Leu Trp Gly Val Asp Thr Asn Tyr Gln Ser
                 420                 425                 430
Val Ser Lys Phe His Val Phe His Asp Ser Thr Asn Phe Tyr Gly Ser
                 435                 440                 445
Thr Gly Asn Ala Arg Gly Gln Ala Val Val Asn Ile Ser Asn Ser Ala
```

```
            450                 455                 460
Phe Pro Ile Leu Met Ala Arg Asn Asp Lys Asn Tyr Trp Leu Ala Phe
465                 470                 475                 480

Gly Glu Lys Arg Ala Trp Asp Lys Asn Glu Leu Ala Tyr Ile Thr Glu
                485                 490                 495

Ala Pro Ser Ile Val Gln Pro Glu Asn Val Thr Arg Asp Thr Ala Thr
                500                 505                 510

Phe Asn Leu Pro Phe Ile Ser Leu Gly Gln Val Gly Glu Gly Lys Leu
            515                 520                 525

Met Val Ile Gly Asn Pro His Tyr Asn Ser Ile Leu Arg Cys Pro Asn
        530                 535                 540

Gly Tyr Ser Trp Gly Gly Val Asn Ser Lys Gly Glu Cys Thr Leu
545                 550                 555                 560

Ser Gly Asp Ser Asp Asp Met Lys His Phe Met Gln Asn Val Leu Arg
                565                 570                 575

Tyr Leu Ser Asn Asp Ile Trp Gln Pro Asn Thr Lys Ser Ile Met Thr
                580                 585                 590

Val Gly Thr Asn Leu Glu Asn Val Tyr Phe Lys Lys Ala Gly Gln Val
            595                 600                 605

Leu Gly Asn Ser Ala Pro Phe Ala Phe His Glu Asp Phe Thr Gly Ile
        610                 615                 620

Thr Val Lys Gln Leu Thr Ser Tyr Gly Asp Leu Asn Pro Glu Ile
625                 630                 635                 640

Pro Leu Leu Ile Leu Asn Gly Phe Glu Tyr Val Thr Gln Trp Ser Gly
                645                 650                 655

Asp Pro Tyr Ala Val Pro Leu Arg Ala Asp Thr Ser Lys Pro Lys Leu
                660                 665                 670

Thr Gln Gln Asp Val Thr Asp Leu Ile Ala Tyr Leu Asn Lys Gly Gly
            675                 680                 685

Ser Val Leu Ile Met Glu Asn Val Met Ser Asn Leu Lys Glu Glu Ser
        690                 695                 700

Ala Ser Ser Phe Val Arg Leu Leu Asp Ala Ala Gly Leu Ser Met Ala
705                 710                 715                 720

Leu Asn Lys Ser Val Val Asn Asn Asp Pro Gln Gly Tyr Pro Asp Arg
                725                 730                 735

Val Arg Gln Arg Arg Ala Thr Gly Ile Trp Val Tyr Glu Arg Tyr Pro
                740                 745                 750

Ala Ala Asp Gly Ala Gln Pro Pro Tyr Thr Ile Asp Pro Asn Thr Gly
            755                 760                 765

Glu Val Thr Trp Lys Tyr Gln Gln Asp Asn Lys Pro Asp Asp Lys Pro
        770                 775                 780

Lys Leu Glu Val Ala Ser Trp Gln Glu Val Glu Gly Lys Gln Val
785                 790                 795                 800

Thr Arg Tyr Ala Phe Ile Asp Glu Ala Glu Tyr Thr Thr Glu Glu Ser
                805                 810                 815

Leu Glu Ala Ala Lys Ala Lys Ile Phe Glu Lys Phe Pro Gly Leu Gln
                820                 825                 830

Glu Cys Lys Asp Ser Thr Tyr His Tyr Glu Ile Asn Cys Leu Glu Arg
            835                 840                 845

Arg Pro Gly Thr Asp Val Pro Val Thr Gly Gly Met Tyr Val Pro Arg
        850                 855                 860

Tyr Thr Gln Leu Asn Leu Asp Ala Asp Thr Ala Lys Ala Met Val Gln
865                 870                 875                 880
```

```
Ala Ala Asp Leu Gly Thr Asn Ile Gln Arg Leu Tyr Gln His Glu Leu
            885                 890                 895

Tyr Phe Arg Thr Lys Gly Ser Lys Gly Glu Arg Leu Asn Ser Val Asp
            900                 905                 910

Leu Glu Arg Leu Tyr Gln Asn Met Ser Val Trp Leu Trp Asn Asp Thr
            915                 920                 925

Lys Tyr Arg Tyr Glu Glu Gly Lys Glu Asp Glu Leu Gly Phe Lys Thr
            930                 935                 940

Phe Thr Glu Phe Leu Asn Cys Tyr Ala Asn Asp Ala Tyr Ala Gly Gly
945                 950                 955                 960

Thr Lys Cys Ser Ala Asp Leu Lys Lys Ser Leu Val Asp Asn Asn Met
            965                 970                 975

Ile Tyr Gly Asp Gly Ser Ser Lys Ala Gly Met Met Asn Pro Ser Tyr
            980                 985                 990

Pro Leu Asn Tyr Met Glu Lys Pro Leu Thr Arg Leu Met Leu Gly Arg
            995                 1000                1005

Ser Trp Trp Asp Leu Asn Ile Lys Val Asp Val Glu Lys Tyr Pro Gly
            1010                1015                1020

Ser Val Ser Ala Lys Gly Glu Ser Val Thr Glu Asn Ile Ser Leu Tyr
1025                1030                1035                1040

Ser Asn Pro Thr Lys Trp Phe Ala Gly Asn Met Gln Ser Thr Gly Leu
            1045                1050                1055

Trp Ala Pro Ala Gln Gln Asp Val Thr Ile Lys Ser Ser Ala Ser Val
            1060                1065                1070

Pro Val Thr Val Thr Val Ala Leu Ala Asp Asp Leu Thr Gly Arg Glu
            1075                1080                1085

Lys His Glu Val Ala Leu Asn Arg Pro Pro Arg Val Thr Lys Thr Tyr
            1090                1095                1100

Thr Leu Glu Ala Asn Gly Glu Val Thr Phe Lys Val Pro Tyr Gly Gly
1105                1110                1115                1120

Leu Ile Tyr Ile Lys Gly Asp Ser Lys Asp Asp Val Ser Ala Asn Phe
            1125                1130                1135

Thr Phe Thr Gly Val Val Lys Ala Pro Phe Tyr Lys Asp Gly Glu Trp
            1140                1145                1150

Lys Asn Asp Leu Asp Ser Pro Ala Pro Leu Gly Glu Leu Glu Ser Ala
            1155                1160                1165

Ser Phe Val Tyr Thr Thr Pro Lys Lys Asn Leu Glu Ala Ser Asn Phe
            1170                1175                1180

Thr Gly Gly Val Ala Glu Phe Ala Lys Asp Leu Asp Thr Phe Ala Ser
1185                1190                1195                1200

Ser Met Asn Asp Phe Tyr Gly Arg Asn Asp Glu Asp Gly Lys His Arg
            1205                1210                1215

Met Phe Thr Tyr Lys Asn Leu Thr Gly His Lys His Arg Phe Thr Asn
            1220                1225                1230

Asp Val Gln Ile Ser Ile Gly Asp Ala His Ser Gly Tyr Pro Val Met
            1235                1240                1245

Asn Ser Ser Phe Ser Thr Asn Ser Thr Thr Leu Pro Thr Thr Pro Leu
            1250                1255                1260

Asn Asp Trp Leu Ile Trp
1265                1270

<210> SEQ ID NO 27
<211> LENGTH: 4563
```

<212> TYPE: DNA
<213> ORGANISM: Escherichia coli

<400> SEQUENCE: 27

```
atgaataaga aatttaaata taagaaatcg cttttagcgg ctattttaag cgcaaccctg      60
ttagccggtt gtgatggtgg tggttcagga tcgtcctccg atacgccgtc tgtagattct     120
ggatcaggga ctttgccgga agtgaaaccc gatccaacac caaccccgga gccgacacct     180
gagccgacgc cggacccaga acctacgccg atccaacac ctgatcctga gccgacacca      240
gaaccggagc cagaacctgt tcctacgaaa acgggttatc tgaccctggg cggaagccag     300
cgggtaactg gtgctacctg taatggtgaa tccagcgatg gctttacctt tacgccaggc     360
ataccgtga gttgtgtggt gggcagtacg accattgcaa cattcaacac ccagtcagaa      420
gctgcgcgta gcctgcgtgc ggttgacaaa gtgtcgttta gcctggagga cgcgcaggag     480
ctggcgaatt ctgaaaataa gaaaaccaac gccatctctc tggtgacgtc cagcgacagt     540
tgccccgcag atgcagaaca gctttgtctt actttctcgt cagtggttga tcgcgcgcga     600
tttgaaaaac tgtataagca aattgatctg gcaacagaca atttcagcaa gctggtcaat     660
gaagaggtgg aaaacaatgc tgcgactgat aaagcgccgt ccacccatac ctcaacggta     720
gtgccagtca cgacagaggg aacaaaaccg gatctgaacg cgtccttcgt gtcggctaac     780
gcggaacagt tttatcagta tcaacccact gaaatcattc tttccgaagg ccaactggtg     840
gatagcctgg ggaacggtgt tgctggcgtt gactactaca ccaattcagg ccgtggcgta     900
actgacgaaa acggtaaatt ttcctttagc tggggcgaaa ccatctcctt tggtatcgat     960
acctttgaac tgggctcagt acgtggcaat aagtcgacca ttgcgctgac tgaattgggt    1020
gatgaagttc gcggggcaaa tatcgatcag ctcattcatc gttattcgac gactggtcaa    1080
aataatactc gtgttgttcc ggacgatgta cgcaaggtct tgccgaata tcccaacgtg     1140
atcaacgaga taatcaatct ttcgttatcc aacggtgcga cgctggatga aggcgatcaa    1200
aacgttgtgc tgcctaacga atttatcgag cagtttaaga cgggtcaggc caaagagatc    1260
gataccgcga tttgtgcgaa aaccgacggt tgtaacgagg ctcgctggtt ctcgctgaca    1320
acgcgcaatg ttaatgacgg ccagattcag ggcgttatta caagctgtg gggcgtggat    1380
acgaactatc agtctgtcag caagttccac gtcttccatg actctaccaa cttctatggc    1440
agcaccggta acgcgcgcgg tcaggcggtg gtaaatatct ccaactcggc attcccgatt    1500
ctgatggcgc gtaatgataa aaactactgg ctggcgtttg cgaaaaacg cgcctgggat    1560
aaaaatgagc tggcgtacat tacggaagcg ccttccattg tgcagccaga gaacgttacg    1620
cgcgatactg cgactttcaa cctgccgttt atttcgctgg ggcaagtcgg tgaaggcaaa    1680
ctgatggtta tcggtaaccc gcactacaac agcatcctgc gttgcccgaa cggttacagt    1740
tggggcggtg gtgttaatag taaaggtgag tgtacgctca gcggtgattc tgatgacatg    1800
aagcacttta tgcagaacgt actgcgctac ttgtcaaatg acatctggca gccaaatacc    1860
aagagcatca tgactgtcgg caccaacctg gagaacgttt atttcaaaaa agcgggccag    1920
gtattgggaa atagtgcacc atttgctttc catgaggatt tcactggtat cacggttaaa    1980
cagttgacca gctatggcga tctgaatccg gaagagattc gttgctgat cctcaacggc     2040
tttgaatatg tgactcagtg gtctggcgat ccctatgctg tgcctctgcg tgcagatacc    2100
agcaaaccga gctgactca gcaggatgtg accgatctga tcgcttatct gaacaaaggt     2160
ggctcggtgc tgatcatgga aaacgtgatg agcaatctta aggaagagag cgcgtccagt    2220
```

```
tttgtgcgtc tgctggatgc cgcgggtctg tcaatggctc tgaacaaatc ggtggtgaac    2280
aacgatccgc aagggtatcc ggatcgcgtt cgtcagcgtc gcgcgactgg catttgggtt    2340
tatgaacgtt atcctgctgc agacggcgcg caaccgccgt acaccatcga cccaaataca    2400
ggggaagtga cctggaaata ccagcaagac aacaagcctg atgacaagcc gaaactggaa    2460
gttgcgagct ggcaggagga agttgagggc aaacaggtaa cgcgttatgc ctttattgat    2520
gaagcggaat acacaacaga gaatctctg gaagcggcaa aggcaaaaat ctttgagaag    2580
tttcctgggt tacaggagtg taaggactcg acttaccatt acgagattaa ctgtttggag    2640
cgccgcccag gcacggatgt tccggtaaca ggtggcatgt atgttccgcg ctatacgcaa    2700
ctgaatcttg acgccgacac cgcgaaagcg atggtgcagg cggcggattt aggcaccaac    2760
attcagcgcc tgtatcagca tgagctttat ttccgtacca aaggcagtaa aggtgagcgt    2820
ctgaacagtg ttgatctgga acgtctgtac cagaacatgt cggtctggct gtggaacgat    2880
acgaaatatc gttacgaaga gggcaaggaa gatgagctgg gctttaaaac gttcaccgag    2940
ttcctgaact gctacgccaa tgatgcctat gcaggcggca ccaagtgctc cgcagatctg    3000
aaaaaatcgc tggtcgataa caacatgatc tacggtgacg gtagcagcaa agcgggcatg    3060
atgaacccaa gctatccgct caactatatg gaaaaaccgc tgacgcgtct gatgctgggc    3120
cgttcctggt gggatctgaa cattaaggtt gatgtggaga agtacccagg atccgtatcg    3180
gcaaagggtg agagcgttac ggaaaacatc agcctgtact cgaatccgac caaatggttt    3240
gcgggtaaca tgcagtcaac cggcctgtgg gcaccggccc agcaggacgt caccattaag    3300
tcttcggcgt cagtcccagt gactgttacc gtggcgctgg ctgacgacct gactggacgt    3360
gagaagcatg aagttgcgct gaaccgtccg ccaagagtga ctaaaacgta tactctggag    3420
gctaacggta aagtgacctt caaggtgcct tatggtggtc tgatttatat caagggcgac    3480
agtaaggatg atgtttctgc taacttcacc tttaccggtg tagtaaaagc gccgttctat    3540
aaagacggcg aatggaaaaa cgatctggac tcaccggcgc cgctgggcga gctggagtct    3600
gcgtcgttcg tctataccac gccgaagaag aaccttgagg ccagcaattt cactggtggt    3660
gtagcagaat cgctaaaga tctggatacc tttgccagct cgatgaatga cttctacggt    3720
cgtaatgatg aagacggtaa gcaccggatg tttacctata aaaacttgac ggggcacaag    3780
catcgtttca ccaacgatgt gcagatctcc atcggtgatg cgcactcggg ttatccggta    3840
atgaacagca gcttctcgac gaacagcacc acgctgccga cgacgccgct gaacgactgg    3900
ctgatttggc acgaagtcgg tcataacgct gcagaaacac cgctgaacgt accgggtgca    3960
actgaagtgg cgaacaacgt gctggcgctg tacatgcagg atcgctatct cggtaagatg    4020
aaccgtgtcg ctgacgacat taccgtcgcg ccggaatatc tggacgagag caacggtcag    4080
gcctgggcgc gcggcggtgc gggtgaccgt ctgctgatgt acgcacagtt gaaggagtgg    4140
gcagaggaaa actttgatat caaacagtgg tatccagatg gtgagctgcc taagttctac    4200
agcgatcgta aagggatgaa gggctggaac ctgttccagt tgatgcaccg taaagcgcgc    4260
ggcgatgatg ttggtaacag cacctttggt ggcaagaatt actgtgctga atccaatggt    4320
aacgctgccg acacgctgat gctgtgtgca tcctgggtcg ctcaggcgga tctttcggaa    4380
ttctttaaga aatggaatcc gggtgcaagt gcttaccagt tgccgggagc aacggagatg    4440
agtttccagg gcggtgtgag ctcttcggct tacagcacgc tggcgtcact caagctgccg    4500
aaaccggaaa aagggccgga aaccattaac aaggttaccg agcataagat gtctgccgag    4560
taa                                                                  4563
```

-continued

```
<210> SEQ ID NO 28
<211> LENGTH: 1520
<212> TYPE: PRT
<213> ORGANISM: Escherichia coli

<400> SEQUENCE: 28
```

| | | | | | | | | | | | | | | |
|---|---|---|---|---|---|---|---|---|---|---|---|---|---|---|
| Met | Asn | Lys | Lys | Phe | Lys | Tyr | Lys | Lys | Ser | Leu | Leu | Ala | Ala | Ile | Leu |
| 1 | | | | 5 | | | | | 10 | | | | | 15 | |

| Ser | Ala | Thr | Leu | Leu | Ala | Gly | Cys | Asp | Gly | Gly | Ser | Gly | Ser | Ser |
|---|---|---|---|---|---|---|---|---|---|---|---|---|---|---|
| | | | 20 | | | | | 25 | | | | | 30 | |

| Ser | Asp | Thr | Pro | Ser | Val | Asp | Ser | Gly | Ser | Gly | Thr | Leu | Pro | Glu | Val |
|---|---|---|---|---|---|---|---|---|---|---|---|---|---|---|---|
| | | | 35 | | | | | 40 | | | | | 45 | | |

| Lys | Pro | Asp | Pro | Thr | Pro | Thr | Pro | Glu | Pro | Thr | Pro | Glu | Pro | Thr | Pro |
|---|---|---|---|---|---|---|---|---|---|---|---|---|---|---|---|
| | 50 | | | | | 55 | | | | | 60 | | | | |

| Asp | Pro | Glu | Pro | Thr | Pro | Asp | Pro | Thr | Pro | Asp | Pro | Glu | Pro | Thr | Pro |
|---|---|---|---|---|---|---|---|---|---|---|---|---|---|---|---|
| 65 | | | | | 70 | | | | | 75 | | | | | 80 |

| Glu | Pro | Glu | Pro | Glu | Pro | Val | Pro | Thr | Lys | Thr | Gly | Tyr | Leu | Thr | Leu |
|---|---|---|---|---|---|---|---|---|---|---|---|---|---|---|---|
| | | | | 85 | | | | | 90 | | | | | 95 | |

| Gly | Gly | Ser | Gln | Arg | Val | Thr | Gly | Ala | Thr | Cys | Asn | Gly | Glu | Ser | Ser |
|---|---|---|---|---|---|---|---|---|---|---|---|---|---|---|---|
| | | | 100 | | | | | 105 | | | | | 110 | | |

| Asp | Gly | Phe | Thr | Phe | Thr | Pro | Gly | Asn | Thr | Val | Ser | Cys | Val | Val | Gly |
|---|---|---|---|---|---|---|---|---|---|---|---|---|---|---|---|
| | | | 115 | | | | | 120 | | | | | 125 | | |

| Ser | Thr | Thr | Ile | Ala | Thr | Phe | Asn | Thr | Gln | Ser | Glu | Ala | Ala | Arg | Ser |
|---|---|---|---|---|---|---|---|---|---|---|---|---|---|---|---|
| | | 130 | | | | | 135 | | | | | 140 | | | |

| Leu | Arg | Ala | Val | Asp | Lys | Val | Ser | Phe | Ser | Leu | Glu | Asp | Ala | Gln | Glu |
|---|---|---|---|---|---|---|---|---|---|---|---|---|---|---|---|
| 145 | | | | | 150 | | | | | 155 | | | | | 160 |

| Leu | Ala | Asn | Ser | Glu | Asn | Lys | Lys | Thr | Asn | Ala | Ile | Ser | Leu | Val | Thr |
|---|---|---|---|---|---|---|---|---|---|---|---|---|---|---|---|
| | | | | 165 | | | | | 170 | | | | | 175 | |

| Ser | Ser | Asp | Ser | Cys | Pro | Ala | Asp | Ala | Glu | Gln | Leu | Cys | Leu | Thr | Phe |
|---|---|---|---|---|---|---|---|---|---|---|---|---|---|---|---|
| | | | 180 | | | | | 185 | | | | | 190 | | |

| Ser | Ser | Val | Val | Asp | Arg | Ala | Arg | Phe | Glu | Lys | Leu | Tyr | Lys | Gln | Ile |
|---|---|---|---|---|---|---|---|---|---|---|---|---|---|---|---|
| | | | 195 | | | | | 200 | | | | | 205 | | |

| Asp | Leu | Ala | Thr | Asp | Asn | Phe | Ser | Lys | Leu | Val | Asn | Glu | Glu | Val | Glu |
|---|---|---|---|---|---|---|---|---|---|---|---|---|---|---|---|
| | 210 | | | | | 215 | | | | | 220 | | | | |

| Asn | Asn | Ala | Ala | Thr | Asp | Lys | Ala | Pro | Ser | Thr | His | Thr | Ser | Thr | Val |
|---|---|---|---|---|---|---|---|---|---|---|---|---|---|---|---|
| 225 | | | | | 230 | | | | | 235 | | | | | 240 |

| Val | Pro | Val | Thr | Thr | Glu | Gly | Thr | Lys | Pro | Asp | Leu | Asn | Ala | Ser | Phe |
|---|---|---|---|---|---|---|---|---|---|---|---|---|---|---|---|
| | | | | 245 | | | | | 250 | | | | | 255 | |

| Val | Ser | Ala | Asn | Ala | Glu | Gln | Phe | Tyr | Gln | Tyr | Gln | Pro | Thr | Glu | Ile |
|---|---|---|---|---|---|---|---|---|---|---|---|---|---|---|---|
| | | | 260 | | | | | 265 | | | | | 270 | | |

| Ile | Leu | Ser | Glu | Gly | Gln | Leu | Val | Asp | Ser | Leu | Gly | Asn | Gly | Val | Ala |
|---|---|---|---|---|---|---|---|---|---|---|---|---|---|---|---|
| | | | 275 | | | | | 280 | | | | | 285 | | |

| Gly | Val | Asp | Tyr | Tyr | Thr | Asn | Ser | Gly | Arg | Gly | Val | Thr | Asp | Glu | Asn |
|---|---|---|---|---|---|---|---|---|---|---|---|---|---|---|---|
| | 290 | | | | | 295 | | | | | 300 | | | | |

| Gly | Lys | Phe | Ser | Phe | Ser | Trp | Gly | Glu | Thr | Ile | Ser | Phe | Gly | Ile | Asp |
|---|---|---|---|---|---|---|---|---|---|---|---|---|---|---|---|
| 305 | | | | | 310 | | | | | 315 | | | | | 320 |

| Thr | Phe | Glu | Leu | Gly | Ser | Val | Arg | Gly | Asn | Lys | Ser | Thr | Ile | Ala | Leu |
|---|---|---|---|---|---|---|---|---|---|---|---|---|---|---|---|
| | | | | 325 | | | | | 330 | | | | | 335 | |

| Thr | Glu | Leu | Gly | Asp | Glu | Val | Arg | Gly | Ala | Asn | Ile | Asp | Gln | Leu | Ile |
|---|---|---|---|---|---|---|---|---|---|---|---|---|---|---|---|
| | | | 340 | | | | | 345 | | | | | 350 | | |

| His | Arg | Tyr | Ser | Thr | Thr | Gly | Gln | Asn | Asn | Thr | Arg | Val | Val | Pro | Asp |
|---|---|---|---|---|---|---|---|---|---|---|---|---|---|---|---|
| | | | 355 | | | | | 360 | | | | | 365 | | |

| Asp | Val | Arg | Lys | Val | Phe | Ala | Glu | Tyr | Pro | Asn | Val | Ile | Asn | Glu | Ile |

```
            370                 375                 380
Ile Asn Leu Ser Leu Ser Asn Gly Ala Thr Leu Asp Glu Gly Asp Gln
385                 390                 395                 400

Asn Val Val Leu Pro Asn Glu Phe Ile Glu Gln Phe Lys Thr Gly Gln
                405                 410                 415

Ala Lys Glu Ile Asp Thr Ala Ile Cys Ala Lys Thr Asp Gly Cys Asn
                420                 425                 430

Glu Ala Arg Trp Phe Ser Leu Thr Thr Arg Asn Val Asn Asp Gly Gln
                435                 440                 445

Ile Gln Gly Val Ile Asn Lys Leu Trp Gly Val Asp Thr Asn Tyr Gln
                450                 455                 460

Ser Val Ser Lys Phe His Val Phe His Asp Ser Thr Asn Phe Tyr Gly
465                 470                 475                 480

Ser Thr Gly Asn Ala Arg Gly Gln Ala Val Val Asn Ile Ser Asn Ser
                485                 490                 495

Ala Phe Pro Ile Leu Met Ala Arg Asn Asp Lys Asn Tyr Trp Leu Ala
                500                 505                 510

Phe Gly Glu Lys Arg Ala Trp Asp Lys Asn Glu Leu Ala Tyr Ile Thr
                515                 520                 525

Glu Ala Pro Ser Ile Val Gln Pro Glu Asn Val Thr Arg Asp Thr Ala
                530                 535                 540

Thr Phe Asn Leu Pro Phe Ile Ser Leu Gly Gln Val Gly Glu Gly Lys
545                 550                 555                 560

Leu Met Val Ile Gly Asn Pro His Tyr Asn Ser Ile Leu Arg Cys Pro
                565                 570                 575

Asn Gly Tyr Ser Trp Gly Gly Val Asn Ser Lys Gly Glu Cys Thr
                580                 585                 590

Leu Ser Gly Asp Ser Asp Met Lys His Phe Met Gln Asn Val Leu
                595                 600                 605

Arg Tyr Leu Ser Asn Asp Ile Trp Gln Pro Asn Thr Lys Ser Ile Met
                610                 615                 620

Thr Val Gly Thr Asn Leu Glu Asn Val Tyr Phe Lys Lys Ala Gly Gln
625                 630                 635                 640

Val Leu Gly Asn Ser Ala Pro Phe Ala Phe His Glu Asp Phe Thr Gly
                645                 650                 655

Ile Thr Val Lys Gln Leu Thr Ser Tyr Gly Asp Leu Asn Pro Glu Glu
                660                 665                 670

Ile Pro Leu Leu Ile Leu Asn Gly Phe Glu Tyr Val Thr Gln Trp Ser
                675                 680                 685

Gly Asp Pro Tyr Ala Val Pro Leu Arg Ala Asp Thr Ser Lys Pro Lys
                690                 695                 700

Leu Thr Gln Gln Asp Val Thr Asp Leu Ile Ala Tyr Leu Asn Lys Gly
705                 710                 715                 720

Gly Ser Val Leu Ile Met Glu Asn Val Met Ser Asn Leu Lys Glu Glu
                725                 730                 735

Ser Ala Ser Ser Phe Val Arg Leu Leu Asp Ala Ala Gly Leu Ser Met
                740                 745                 750

Ala Leu Asn Lys Ser Val Val Asn Asn Asp Pro Gln Gly Tyr Pro Asp
                755                 760                 765

Arg Val Arg Gln Arg Ala Thr Gly Ile Trp Val Tyr Glu Arg Tyr
                770                 775                 780

Pro Ala Ala Asp Gly Ala Gln Pro Pro Tyr Thr Ile Asp Pro Asn Thr
785                 790                 795                 800
```

```
Gly Glu Val Thr Trp Lys Tyr Gln Gln Asp Asn Lys Pro Asp Asp Lys
                805                 810                 815

Pro Lys Leu Glu Val Ala Ser Trp Gln Glu Val Glu Gly Lys Gln
            820                 825                 830

Val Thr Arg Tyr Ala Phe Ile Asp Glu Ala Glu Tyr Thr Thr Glu Glu
            835                 840                 845

Ser Leu Glu Ala Ala Lys Ala Lys Ile Phe Glu Lys Phe Pro Gly Leu
    850                 855                 860

Gln Glu Cys Lys Asp Ser Thr Tyr His Tyr Glu Ile Asn Cys Leu Glu
865                 870                 875                 880

Arg Arg Pro Gly Thr Asp Val Pro Val Thr Gly Gly Met Tyr Val Pro
                885                 890                 895

Arg Tyr Thr Gln Leu Asn Leu Asp Ala Asp Thr Ala Lys Ala Met Val
            900                 905                 910

Gln Ala Ala Asp Leu Gly Thr Asn Ile Gln Arg Leu Tyr Gln His Glu
            915                 920                 925

Leu Tyr Phe Arg Thr Lys Gly Ser Lys Gly Glu Arg Leu Asn Ser Val
    930                 935                 940

Asp Leu Glu Arg Leu Tyr Gln Asn Met Ser Val Trp Leu Trp Asn Asp
945                 950                 955                 960

Thr Lys Tyr Arg Tyr Glu Glu Gly Lys Glu Asp Glu Leu Gly Phe Lys
                965                 970                 975

Thr Phe Thr Glu Phe Leu Asn Cys Tyr Ala Asn Asp Ala Tyr Ala Gly
            980                 985                 990

Gly Thr Lys Cys Ser Ala Asp Leu Lys Lys Ser Leu Val Asp Asn Asn
            995                 1000                1005

Met Ile Tyr Gly Asp Gly Ser Ser Lys Ala Gly Met Met Asn Pro Ser
    1010                1015                1020

Tyr Pro Leu Asn Tyr Met Glu Lys Pro Leu Thr Arg Leu Met Leu Gly
1025                1030                1035                1040

Arg Ser Trp Trp Asp Leu Asn Ile Lys Val Asp Val Glu Lys Tyr Pro
                1045                1050                1055

Gly Ser Val Ser Ala Lys Gly Glu Ser Val Thr Glu Asn Ile Ser Leu
            1060                1065                1070

Tyr Ser Asn Pro Thr Lys Trp Phe Ala Gly Asn Met Gln Ser Thr Gly
            1075                1080                1085

Leu Trp Ala Pro Ala Gln Gln Asp Val Thr Ile Lys Ser Ser Ala Ser
    1090                1095                1100

Val Pro Val Thr Val Thr Val Ala Leu Ala Asp Asp Leu Thr Gly Arg
1105                1110                1115                1120

Glu Lys His Glu Val Ala Leu Asn Arg Pro Pro Arg Val Thr Lys Thr
                1125                1130                1135

Tyr Thr Leu Glu Ala Asn Gly Glu Val Thr Phe Lys Val Pro Tyr Gly
            1140                1145                1150

Gly Leu Ile Tyr Ile Lys Gly Asp Ser Lys Asp Val Ser Ala Asn
            1155                1160                1165

Phe Thr Phe Thr Gly Val Val Lys Ala Pro Tyr Lys Asp Gly Glu
    1170                1175                1180

Trp Lys Asn Asp Leu Asp Ser Pro Ala Pro Leu Gly Glu Leu Glu Ser
1185                1190                1195                1200

Ala Ser Phe Val Tyr Thr Thr Pro Lys Lys Asn Leu Glu Ala Ser Asn
            1205                1210                1215
```

Phe Thr Gly Gly Val Ala Glu Phe Ala Lys Asp Leu Asp Thr Phe Ala
                1220                1225                1230

Ser Ser Met Asn Asp Phe Tyr Gly Arg Asn Asp Glu Asp Gly Lys His
        1235                1240                1245

Arg Met Phe Thr Tyr Lys Asn Leu Thr Gly His Lys His Arg Phe Thr
    1250                1255                1260

Asn Asp Val Gln Ile Ser Ile Gly Asp Ala His Ser Gly Tyr Pro Val
1265                1270                1275                1280

Met Asn Ser Ser Phe Ser Thr Asn Ser Thr Thr Leu Pro Thr Thr Pro
            1285                1290                1295

Leu Asn Asp Trp Leu Ile Trp His Glu Val Gly His Asn Ala Ala Glu
            1300                1305                1310

Thr Pro Leu Asn Val Pro Gly Ala Thr Glu Val Ala Asn Asn Val Leu
        1315                1320                1325

Ala Leu Tyr Met Gln Asp Arg Tyr Leu Gly Lys Met Asn Arg Val Ala
        1330                1335                1340

Asp Asp Ile Thr Val Ala Pro Glu Tyr Leu Asp Glu Ser Asn Gly Gln
1345                1350                1355                1360

Ala Trp Ala Arg Gly Gly Ala Gly Asp Arg Leu Leu Met Tyr Ala Gln
            1365                1370                1375

Leu Lys Glu Trp Ala Glu Glu Asn Phe Asp Ile Lys Gln Trp Tyr Pro
            1380                1385                1390

Asp Gly Glu Leu Pro Lys Phe Tyr Ser Asp Arg Lys Gly Met Lys Gly
        1395                1400                1405

Trp Asn Leu Phe Gln Leu Met His Arg Lys Ala Arg Gly Asp Asp Val
    1410                1415                1420

Gly Asn Ser Thr Phe Gly Gly Lys Asn Tyr Cys Ala Glu Ser Asn Gly
1425                1430                1435                1440

Asn Ala Ala Asp Thr Leu Met Leu Cys Ala Ser Trp Val Ala Gln Ala
            1445                1450                1455

Asp Leu Ser Glu Phe Phe Lys Lys Trp Asn Pro Gly Ala Ser Ala Tyr
        1460                1465                1470

Gln Leu Pro Gly Ala Thr Glu Met Ser Phe Gln Gly Gly Val Ser Ser
        1475                1480                1485

Ser Ala Tyr Ser Thr Leu Ala Ser Leu Lys Leu Pro Lys Pro Glu Lys
        1490                1495                1500

Gly Pro Glu Thr Ile Asn Lys Val Thr Glu His Lys Met Ser Ala Glu
1505                1510                1515                1520

<210> SEQ ID NO 29
<211> LENGTH: 975
<212> TYPE: DNA
<213> ORGANISM: Escherichia coli

<400> SEQUENCE: 29
atgatcacct caccaccaaa acgcggaatg gcactggtcg tggtgctggt attgctggcg      60
gttatgatgc tggtgaccat cacgctttcc gggcggatgc agcaacaact tgggcgaacg     120
cgcagccagc aggagtacca gcaggcgctg tggtacagcg ccagtgcaga aagcctggcg     180
ctgagcgcgc tcagtctgag cctgaaaaat gaaaagcgtg tgcatctggc acaaccgtgg     240
gcttctggcc gcgttttttt cccactgccg caggggcaaa ttgccgtcac tctgcgtgac     300
gcacaggcct gctttaacct gaatgccctc gctcagccga cgacggcgtc gcgtccgctc     360
gcggtacaac aactgattgc cctgatctcg cgcctcgatg tgcctgctta tcgggccgaa     420

```
ctgatagccg aaagcctgtg ggagtttatt gacgaagacc gcagcgtgca gacgcgtctg    480
ggtcgtgaag acagcgagta tctcgcccgc tcggtgccgt tctacgccgc taatcaaccg    540
ctggctgata tcagcgagat gcgcgtggtg cagggaatgg acgccgggct ttatcaaaaa    600
ctgaaaccgt tggtctgtgc gctgccgatg gcccgccagc aaatcaacat caatacatta    660
gatgtcacgc aaagtgtgat tcttgaggcg ctgtttgacc cgtggttaag ccctgttcag    720
gcgcgggcat tattacaaca acgtccggcg aagggctggg aagatgtcga tcagtttctt    780
gctcagccgc tacttgcaga cgtcgatgag cgtactaaaa aacagctaaa aaccatcctg    840
agcgtggaca gcaattactt ctggctgcgt tcagatatca ccgtgaatga gattgaactg    900
acgatgaatt cgttaattgt ccgcatgggc ccacaacact tttctgttct ctggcatcag    960
acaggagaaa gtgag                                                     975
```

<210> SEQ ID NO 30
<211> LENGTH: 325
<212> TYPE: PRT
<213> ORGANISM: Escherichia coli
<400> SEQUENCE: 30

```
Met Ile Thr Ser Pro Pro Lys Arg Gly Met Ala Leu Val Val Leu
1               5                   10                  15

Val Leu Leu Ala Val Met Met Leu Val Thr Ile Thr Leu Ser Gly Arg
                20                  25                  30

Met Gln Gln Gln Leu Gly Arg Thr Arg Ser Gln Gln Glu Tyr Gln Gln
                35                  40                  45

Ala Leu Trp Tyr Ser Ala Ser Ala Glu Ser Leu Ala Leu Ser Ala Leu
            50                  55                  60

Ser Leu Ser Leu Lys Asn Glu Lys Arg Val His Leu Ala Gln Pro Trp
65                  70                  75                  80

Ala Ser Gly Pro Arg Phe Phe Pro Leu Pro Gln Gly Gln Ile Ala Val
                85                  90                  95

Thr Leu Arg Asp Ala Gln Ala Cys Phe Asn Leu Asn Ala Leu Ala Gln
            100                 105                 110

Pro Thr Thr Ala Ser Arg Pro Leu Ala Val Gln Gln Leu Ile Ala Leu
        115                 120                 125

Ile Ser Arg Leu Asp Val Pro Ala Tyr Arg Ala Glu Leu Ile Ala Glu
    130                 135                 140

Ser Leu Trp Glu Phe Ile Asp Glu Asp Arg Ser Val Gln Thr Arg Leu
145                 150                 155                 160

Gly Arg Glu Asp Ser Glu Tyr Leu Ala Arg Ser Val Pro Phe Tyr Ala
                165                 170                 175

Ala Asn Gln Pro Leu Ala Asp Ile Ser Glu Met Arg Val Val Gln Gly
            180                 185                 190

Met Asp Ala Gly Leu Tyr Gln Lys Leu Lys Pro Leu Val Cys Ala Leu
        195                 200                 205

Pro Met Ala Arg Gln Gln Ile Asn Ile Asn Thr Leu Asp Val Thr Gln
    210                 215                 220

Ser Val Ile Leu Glu Ala Leu Phe Asp Pro Trp Leu Ser Pro Val Gln
225                 230                 235                 240

Ala Arg Ala Leu Leu Gln Gln Arg Pro Ala Lys Gly Trp Glu Asp Val
                245                 250                 255

Asp Gln Phe Leu Ala Gln Pro Leu Leu Ala Asp Val Asp Glu Arg Thr
            260                 265                 270
```

```
Lys Lys Gln Leu Lys Thr Ile Leu Ser Val Asp Ser Asn Tyr Phe Trp
            275                 280                 285

Leu Arg Ser Asp Ile Thr Val Asn Glu Ile Glu Leu Thr Met Asn Ser
290                 295                 300

Leu Ile Val Arg Met Gly Pro Gln His Phe Ser Val Leu Trp His Gln
305                 310                 315                 320

Thr Gly Glu Ser Glu
                325

<210> SEQ ID NO 31
<211> LENGTH: 1520
<212> TYPE: PRT
<213> ORGANISM: Escherichia coli

<400> SEQUENCE: 31

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Gly Ser Gly Ser Ser
                20                  25                  30

Ser Asp Thr Pro Ser Val Asp Ser Gly Ser Gly Thr Leu Pro Glu Val
            35                  40                  45

Lys Pro Asp Pro Thr Pro Thr Pro Glu Pro Thr Pro Glu Pro Thr Pro
50                  55                  60

Asp Pro Glu Pro Thr Pro Asp Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Val Thr Gly Ala Thr Cys Asn Gly Glu Ser Ser
                100                 105                 110

Asp Gly Phe Thr Phe Thr Pro Gly Asn Thr Val Ser Cys Val Val Gly
            115                 120                 125

Ser Thr Thr Ile Ala Thr Phe Asn Thr Gln Ser Glu Ala Ala Arg Ser
            130                 135                 140

Leu Arg Ala Val Asp Lys Val Ser Phe Ser Leu Glu Asp Ala Gln Glu
145                 150                 155                 160

Leu Ala Asn Ser Glu Asn Lys Lys Thr Asn Ala Ile Ser Leu Val Thr
                165                 170                 175

Ser Ser Asp Ser Cys Pro Ala Ala Glu Gln Leu Cys Leu Thr Phe
                180                 185                 190

Ser Ser Val Val Asp Arg Ala Arg Phe Glu Lys Leu Tyr Lys Gln Ile
            195                 200                 205

Asp Leu Ala Thr Asp Asn Phe Ser Lys Leu Val Asn Glu Glu Val Glu
210                 215                 220

Asn Asn Ala Ala Thr Asp Lys Ala Pro Ser Thr His Thr Ser Thr Val
225                 230                 235                 240

Val Pro Val Thr Thr Glu Gly Thr Lys Pro Asp Leu Asn Ala Ser Phe
                245                 250                 255

Val Ser Ala Asn Ala Glu Gln Phe Tyr Gln Tyr Gln Pro Thr Glu Ile
            260                 265                 270

Ile Leu Ser Glu Gly Gln Leu Val Asp Ser Leu Gly Asn Gly Val Ala
            275                 280                 285

Gly Val Asp Tyr Tyr Thr Asn Ser Gly Arg Gly Val Thr Asp Glu Asn
290                 295                 300

Gly Lys Phe Ser Phe Ser Trp Gly Glu Thr Ile Ser Phe Gly Ile Asp
305                 310                 315                 320
```

```
Thr Phe Glu Leu Gly Ser Val Arg Gly Asn Lys Ser Thr Ile Ala Leu
            325                 330                 335

Thr Glu Leu Gly Asp Glu Val Arg Gly Ala Asn Ile Asp Gln Leu Ile
            340                 345                 350

His Arg Tyr Ser Thr Thr Gly Gln Asn Asn Thr Arg Val Val Pro Asp
            355                 360                 365

Asp Val Arg Lys Val Phe Ala Glu Tyr Pro Asn Val Ile Asn Glu Ile
            370                 375                 380

Ile Asn Leu Ser Leu Ser Asn Gly Ala Thr Leu Asp Glu Gly Asp Gln
385                 390                 395                 400

Asn Val Val Leu Pro Asn Glu Phe Ile Glu Gln Phe Lys Thr Gly Gln
            405                 410                 415

Ala Lys Glu Ile Asp Thr Ala Ile Cys Ala Lys Thr Asp Gly Cys Asn
            420                 425                 430

Glu Ala Arg Trp Phe Ser Leu Thr Thr Arg Asn Val Asn Asp Gly Gln
            435                 440                 445

Ile Gln Gly Val Ile Asn Lys Leu Trp Gly Val Asp Thr Asn Tyr Gln
            450                 455                 460

Ser Val Ser Lys Phe His Val Phe His Asp Ser Thr Asn Phe Tyr Gly
465                 470                 475                 480

Ser Thr Gly Asn Ala Arg Gly Gln Ala Val Val Asn Ile Ser Asn Ser
            485                 490                 495

Ala Phe Pro Ile Leu Met Ala Arg Asn Asp Lys Asn Tyr Trp Leu Ala
            500                 505                 510

Phe Gly Glu Lys Arg Ala Trp Asp Lys Asn Glu Leu Ala Tyr Ile Thr
            515                 520                 525

Glu Ala Pro Ser Ile Val Gln Pro Glu Asn Val Thr Arg Asp Thr Ala
            530                 535                 540

Thr Phe Asn Leu Pro Phe Ile Ser Leu Gly Gln Val Gly Glu Gly Lys
545                 550                 555                 560

Leu Met Val Ile Gly Asn Pro His Tyr Asn Ser Ile Leu Arg Cys Pro
            565                 570                 575

Asn Gly Tyr Ser Trp Gly Gly Gly Val Asn Ser Lys Gly Glu Cys Thr
            580                 585                 590

Leu Ser Gly Asp Ser Asp Asp Met Lys His Phe Met Gln Asn Val Leu
            595                 600                 605

Arg Tyr Leu Ser Asn Asp Ile Trp Gln Pro Asn Thr Lys Ser Ile Met
            610                 615                 620

Thr Val Gly Thr Asn Leu Glu Asn Val Tyr Phe Lys Lys Ala Gly Gln
625                 630                 635                 640

Val Leu Gly Asn Ser Ala Pro Phe Ala Phe His Glu Asp Phe Thr Gly
            645                 650                 655

Ile Thr Val Lys Gln Leu Thr Ser Tyr Gly Asp Leu Asn Pro Glu Glu
            660                 665                 670

Ile Pro Leu Leu Ile Leu Asn Gly Phe Glu Tyr Val Thr Gln Trp Ser
            675                 680                 685

Gly Asp Pro Tyr Ala Val Pro Leu Arg Ala Asp Thr Ser Lys Pro Lys
            690                 695                 700

Leu Thr Gln Gln Asp Val Thr Asp Leu Ile Ala Tyr Leu Asn Lys Gly
705                 710                 715                 720

Gly Ser Val Leu Ile Met Glu Asn Val Met Ser Asn Leu Lys Glu Glu
            725                 730                 735
```

-continued

Ser Ala Ser Ser Phe Val Arg Leu Leu Asp Ala Ala Gly Leu Ser Met
        740                 745                 750

Ala Leu Asn Lys Ser Val Val Asn Asn Asp Pro Gln Gly Tyr Pro Asp
        755                 760                 765

Arg Val Arg Gln Arg Ala Thr Gly Ile Trp Val Tyr Glu Arg Tyr
770                 775                 780

Pro Ala Ala Asp Gly Ala Gln Pro Pro Tyr Thr Ile Asp Pro Asn Thr
785                 790                 795                 800

Gly Glu Val Thr Trp Lys Tyr Gln Gln Asp Asn Lys Pro Asp Asp Lys
                805                 810                 815

Pro Lys Leu Glu Val Ala Ser Trp Gln Glu Glu Val Glu Gly Lys Gln
                820                 825                 830

Val Thr Arg Tyr Ala Phe Ile Asp Glu Ala Glu Tyr Thr Thr Glu Glu
                835                 840                 845

Ser Leu Glu Ala Ala Lys Ala Lys Ile Phe Glu Lys Phe Pro Gly Leu
                850                 855                 860

Gln Glu Cys Lys Asp Ser Thr Tyr His Tyr Glu Ile Asn Cys Leu Glu
865                 870                 875                 880

Arg Arg Pro Gly Thr Asp Val Pro Val Thr Gly Gly Met Tyr Val Pro
                885                 890                 895

Arg Tyr Thr Gln Leu Asn Leu Asp Ala Asp Thr Ala Lys Ala Met Val
                900                 905                 910

Gln Ala Ala Asp Leu Gly Thr Asn Ile Gln Arg Leu Tyr Gln His Glu
                915                 920                 925

Leu Tyr Phe Arg Thr Lys Gly Ser Lys Gly Glu Arg Leu Asn Ser Val
                930                 935                 940

Asp Leu Glu Arg Leu Tyr Gln Asn Met Ser Val Trp Leu Trp Asn Asp
945                 950                 955                 960

Thr Lys Tyr Arg Tyr Glu Gly Lys Glu Asp Leu Gly Phe Lys
                965                 970                 975

Thr Phe Thr Glu Phe Leu Asn Cys Tyr Ala Asn Asp Ala Tyr Ala Gly
                980                 985                 990

Gly Thr Lys Cys Ser Ala Asp Leu Lys Lys Ser Leu Val Asp Asn Asn
                995                 1000                1005

Met Ile Tyr Gly Asp Gly Ser Ser Lys Ala Gly Met Met Asn Pro Ser
        1010                1015                1020

Tyr Pro Leu Asn Tyr Met Glu Lys Pro Leu Thr Arg Leu Met Leu Gly
1025                1030                1035                1040

Arg Ser Trp Trp Asp Leu Asn Ile Lys Val Asp Val Glu Lys Tyr Pro
                1045                1050                1055

Gly Ser Val Ser Ala Lys Gly Glu Ser Val Thr Glu Asn Ile Ser Leu
                1060                1065                1070

Tyr Ser Asn Pro Thr Lys Trp Phe Ala Gly Asn Met Gln Ser Thr Gly
        1075                1080                1085

Leu Trp Ala Pro Ala Gln Gln Asp Val Thr Ile Lys Ser Ser Ala Ser
        1090                1095                1100

Val Pro Val Thr Val Thr Val Ala Leu Ala Asp Asp Leu Thr Gly Arg
1105                1110                1115                1120

Glu Lys His Glu Val Ala Leu Asn Arg Pro Pro Arg Val Thr Lys Thr
                1125                1130                1135

Tyr Thr Leu Glu Ala Asn Gly Glu Val Thr Phe Lys Val Pro Tyr Gly
                1140                1145                1150

Gly Leu Ile Tyr Ile Lys Gly Asp Ser Lys Asp Asp Val Ser Ala Asn

```
            1155                1160                1165
Phe Thr Phe Thr Gly Val Val Lys Ala Pro Phe Tyr Lys Asp Gly Glu
            1170                1175                1180

Trp Lys Asn Asp Leu Asp Ser Pro Ala Pro Leu Gly Glu Leu Glu Ser
1185                1190                1195                1200

Ala Ser Phe Val Tyr Thr Thr Pro Lys Lys Asn Leu Glu Ala Ser Asn
                1205                1210                1215

Phe Thr Gly Gly Val Ala Glu Phe Ala Lys Asp Leu Asp Thr Phe Ala
                1220                1225                1230

Ser Ser Met Asn Asp Phe Tyr Gly Arg Asn Asp Glu Asp Gly Lys His
                1235                1240                1245

Arg Met Phe Thr Tyr Lys Asn Leu Thr Gly His Lys His Arg Phe Thr
            1250                1255                1260

Asn Asp Val Gln Ile Ser Ile Gly Asp Ala His Ser Gly Tyr Pro Val
1265                1270                1275                1280

Met Asn Ser Ser Phe Ser Thr Asn Ser Thr Thr Leu Pro Thr Thr Pro
                1285                1290                1295

Leu Asn Asp Trp Leu Ile Trp Ala Ala Val Gly Ala Asn Ala Ala Glu
                1300                1305                1310

Thr Pro Leu Asn Val Pro Gly Ala Thr Glu Val Ala Asn Asn Val Leu
            1315                1320                1325

Ala Leu Tyr Met Gln Asp Arg Tyr Leu Gly Lys Met Asn Arg Val Ala
            1330                1335                1340

Asp Asp Ile Thr Val Ala Pro Glu Tyr Leu Asp Glu Ser Asn Gly Gln
1345                1350                1355                1360

Ala Trp Ala Arg Gly Gly Ala Gly Asp Arg Leu Leu Met Tyr Ala Gln
                1365                1370                1375

Leu Lys Glu Trp Ala Glu Glu Asn Phe Asp Ile Lys Gln Trp Tyr Pro
                1380                1385                1390

Asp Gly Glu Leu Pro Lys Phe Tyr Ser Asp Arg Lys Gly Met Lys Gly
            1395                1400                1405

Trp Asn Leu Phe Gln Leu Met His Arg Lys Ala Arg Gly Asp Asp Val
1410                1415                1420

Gly Asn Ser Thr Phe Gly Gly Lys Asn Tyr Cys Ala Glu Ser Asn Gly
1425                1430                1435                1440

Asn Ala Ala Asp Thr Leu Met Leu Cys Ala Ser Trp Val Ala Gln Ala
                1445                1450                1455

Asp Leu Ser Glu Phe Phe Lys Lys Trp Asn Pro Gly Ala Ser Ala Tyr
                1460                1465                1470

Gln Leu Pro Gly Ala Thr Glu Met Ser Phe Gln Gly Val Ser Ser
            1475                1480                1485

Ser Ala Tyr Ser Thr Leu Ala Ser Leu Lys Leu Pro Lys Pro Glu Lys
            1490                1495                1500

Gly Pro Glu Thr Ile Asn Lys Val Thr Glu His Lys Met Ser Ala Glu
1505                1510                1515                1520

<210> SEQ ID NO 32
<211> LENGTH: 28
<212> TYPE: DNA
<213> ORGANISM: Artificial Sequence
<220> FEATURE:
<223> OTHER INFORMATION: Primer

<400> SEQUENCE: 32
tgatgccgtt ttcttaagaa tggaggaa                                        28
```

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
gagccagaac ctgttccta                                                19

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
gtaaagccat cgctggattc a                                             21

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ccacctcttc attgaccagc                                               20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
cggaacagtt ttatcagtat                                               20

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
ccccgcgaac ttcatcac                                                 18

<210> SEQ ID NO 38
<211> LENGTH: 21
<212> TYPE: DNA
<213> ORGANISM: Artificial Sequence
<220> FEATURE:
<223> OTHER INFORMATION: Primer

<400> SEQUENCE: 38
gcaaggtctt tgccgagtat c                                             21

<210> SEQ ID NO 39
<211> LENGTH: 21
<212> TYPE: DNA
<213> ORGANISM: Artificial Sequence
<220> FEATURE:

<223> OTHER INFORMATION: Primer

<400> SEQUENCE: 39
tgataaaaac tactggctgg c                                              21

<210> SEQ ID NO 40
<211> LENGTH: 19
<212> TYPE: DNA
<213> ORGANISM: Artificial Sequence
<220> FEATURE:
<223> OTHER INFORMATION: Primer

<400> SEQUENCE: 40
ggttaccgat aaccatcag                                                 19

<210> SEQ ID NO 41
<211> LENGTH: 19
<212> TYPE: DNA
<213> ORGANISM: Artificial Sequence
<220> FEATURE:
<223> OTHER INFORMATION: Primer

<400> SEQUENCE: 41
gcagatacca gcaaaccga                                                 19

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
tcatcacgtt ttccatgatc agc                                            23

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
gcggatttag gcaccaacat tc                                             22

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
gaatgttggt gcctaaatcc gc                                             22

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
gtgaacgttt taaagcccag ctc                                            23

```
<210> SEQ ID NO 46
<211> LENGTH: 23
<212> TYPE: DNA
<213> ORGANISM: Artificial Sequence
<220> FEATURE:
<223> OTHER INFORMATION: Primer

<400> SEQUENCE: 46
aactatatgg aaaaaccgct gac                                          23

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
aaagcgccgt tctataaaga                                              20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
ttatagaacg gcgcttttac                                              20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
catcaccgat ggagatctgc                                              20

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
aagatgaacc gtgtcgctga c                                            21

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
ctggaacctg ttccagttga t                                            21

<210> SEQ ID NO 52
<211> LENGTH: 21
<212> TYPE: DNA
<213> ORGANISM: Artificial Sequence
<220> FEATURE:
<223> OTHER INFORMATION: Primer
```

```
<400> SEQUENCE: 52
atcaactgga acaggttcca g                                              21

<210> SEQ ID NO 53
<211> LENGTH: 23
<212> TYPE: DNA
<213> ORGANISM: Artificial Sequence
<220> FEATURE:
<223> OTHER INFORMATION: Primer

<400> SEQUENCE: 53
tattgctgaa aaacatcaaa aag                                            23

<210> SEQ ID NO 54
<211> LENGTH: 1521
<212> TYPE: PRT
<213> ORGANISM: Escherichia coli
<220> FEATURE:
<221> NAME/KEY: misc_feature
<222> LOCATION: 37, 42, 44, 55, 71, 121, 122, 124, 127,
      129, 130, 150, 164, 166, 170, 173, 179, 186, 189,
      192, 197, 198, 199, 200, 203, 204, 213, 214, 215,
      217, 240, 247, 279, 284, 286, 289, 296, 303, 307,
      358, 359, 361, 370, 397, 400, 402, 404, 414, 430,
      462, 465, 468, 559, 583, 588, 589, 595, 596, 598,
      603, 616, 618, 621, 623, 624, 632, 633, 638, 643,
      648, 650, 653, 656, 659, 661, 662, 664, 674, 688,
      690, 695, 741, 774, 788, 791, 792, 793, 799, 800,
      805, 810, 811, 826, 828, 830, 834, 844, 845, 846,
      848, 849, 852, 856, 859, 860, 861, 866, 871, 872,
      877, 882, 887, 898, 903, 905, 937, 943, 961, 962,
      963, 968, 969, 971, 992, 993, 996, 1000, 1009, 1014,
      1015, 1017, 1059, 1062, 1063, 1066, 1070, 1096, 1101,
      1103, 1105, 1133, 1139, 1141, 1143, 1145, 1147, 1163,
      1164, 1166, 1169, 1185, 1189, 1202, 1203, 1214, 1218,
      1222, 1223, 1227, 1244, 1246, 1256, 1317, 1356, 1390,
      1394, 1396, 1399, 1403, 1424, 1427, 1428, 1429, 1432,
      1433, 1479, 1493, 1497, 1499, 1505, 1512
<223> OTHER INFORMATION: 'Xaa' is any amino acid
<220> FEATURE:
<221> NAME/KEY: misc_feature
<222> LOCATION: 534
<223> OTHER INFORMATION: 'Xaa' is Ile or Leu

<400> SEQUENCE: 54

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Gly Ser Gly Ser Ser
            20                  25                  30

Ser Asp Thr Pro Xaa Val Asp Ser Gly Xaa Gly Xaa Leu Pro Glu Val
        35                  40                  45

Lys Pro Asp Pro Thr Pro Xaa Pro Glu Pro Thr Pro Glu Pro Thr Pro
    50                  55                  60

Asp Pro Glu Pro Thr Pro Xaa Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Val Thr Gly Ala Thr Cys Asn Gly Glu Ser Ser
            100                 105                 110

Asp Gly Phe Thr Phe Thr Pro Gly Xaa Xaa Val Xaa Cys Val Xaa Gly
        115                 120                 125

Xaa Xaa Thr Thr Ile Ala Thr Phe Asx Thr Gln Ser Glu Ala Ala Arg
    130                 135                 140

Ser Leu Arg Ala Val Xaa Lys Val Ser Phe Ser Leu Glu Asp Ala Gln
145                 150                 155                 160
```

```
Glu Leu Ala Xaa Ser Xaa Asx Lys Lys Xaa Asn Ala Xaa Ser Leu Val
                165             170             175

Thr Ser Xaa Asx Ser Cys Pro Ala Asx Xaa Glu Gln Xaa Cys Leu Xaa
            180             185             190

Phe Ser Ser Val Xaa Xaa Xaa Arg Phe Xaa Xaa Leu Tyr Lys Gln
            195             200             205

Ile Asp Leu Ala Xaa Xaa Xaa Phe Xaa Lys Leu Val Asn Glu Glu Val
    210             215             220

Glu Asn Asn Ala Ala Thr Asp Lys Ala Pro Ser Thr His Thr Ser Xaa
225             230             235             240

Val Val Pro Val Thr Thr Xaa Gly Thr Lys Pro Asp Leu Asn Ala Ser
            245             250             255

Phe Val Ser Ala Asn Ala Glu Gln Phe Tyr Gln Tyr Gln Pro Thr Glu
            260             265             270

Ile Ile Leu Ser Glu Gly Xaa Leu Val Asp Ser Xaa Gly Xaa Gly Val
        275             280             285

Xaa Gly Val Asx Tyr Tyr Thr Xaa Ser Gly Arg Gly Val Thr Xaa Glu
        290             295             300

Asn Gly Xaa Phe Ser Phe Ser Trp Gly Glu Thr Ile Ser Phe Gly Ile
305             310             315             320

Asp Thr Phe Glu Leu Gly Ser Val Arg Gly Asn Lys Ser Thr Ile Ala
            325             330             335

Leu Thr Glu Leu Gly Asp Glu Val Arg Gly Ala Asn Ile Asp Gln Leu
            340             345             350

Ile His Arg Tyr Ser Xaa Xaa Gly Xaa Asn Asx Thr Arg Val Val Pro
            355             360             365

Asp Xaa Val Arg Lys Val Phe Ala Glu Tyr Pro Asn Val Ile Asn Glu
    370             375             380

Ile Ile Asn Leu Ser Leu Ser Asn Gly Ala Thr Leu Xaa Glu Gly Xaa
385             390             395             400

Gln Xaa Val Xaa Leu Pro Asn Glu Phe Ile Glu Gln Phe Xaa Thr Gly
            405             410             415

Gln Ala Lys Glu Ile Asp Thr Ala Ile Cys Ala Lys Thr Xaa Gly Cys
            420             425             430

Asn Glu Ala Arg Trp Phe Ser Leu Thr Thr Arg Asn Val Asn Asp Gly
            435             440             445

Gln Ile Gln Gly Val Ile Asn Lys Leu Trp Gly Val Asp Xaa Asx Tyr
    450             455             460

Xaa Ser Val Xaa Lys Phe His Val Phe His Asp Ser Thr Asn Phe Tyr
465             470             475             480

Gly Ser Thr Gly Asn Ala Arg Gly Gln Ala Val Val Asn Ile Ser Asn
            485             490             495

Ala Ala Phe Pro Ile Leu Met Ala Arg Asn Asp Lys Asn Tyr Trp Leu
            500             505             510

Ala Phe Gly Glu Lys Arg Ala Trp Asp Lys Asn Glu Leu Ala Tyr Ile
            515             520             525

Thr Glu Ala Pro Ser Xaa Val Glx Pro Glu Asn Val Thr Arg Asp Thr
            530             535             540

Ala Thr Phe Asn Leu Pro Phe Ile Ser Leu Gly Gln Val Gly Xaa Gly
545             550             555             560

Lys Leu Met Val Ile Gly Asn Pro His Tyr Asn Ser Ile Leu Arg Cys
            565             570             575
```

```
Pro Asn Gly Tyr Ser Trp Xaa Gly Gly Val Asn Xaa Xaa Gly Glx Cys
                580                 585                 590

Thr Leu Xaa Xaa Asp Xaa Asp Asp Met Lys Xaa Phe Met Glx Asn Val
            595                 600                 605

Leu Arg Tyr Leu Ser Asx Asp Xaa Trp Xaa Pro Asx Xaa Lys Xaa Xaa
        610                 615                 620

Met Thr Val Gly Thr Asn Leu Xaa Xaa Val Tyr Phe Lys Xaa His Gly
625                 630                 635                 640

Gln Val Xaa Gly Asn Ser Ala Xaa Phe Xaa Phe His Xaa Asp Phe Xaa
                645                 650                 655

Gly Ile Xaa Val Xaa Xaa Leu Xaa Ser Tyr Gly Asp Leu Asx Pro Glx
            660                 665                 670

Glu Xaa Pro Leu Leu Ile Leu Asn Gly Phe Glu Tyr Val Thr Gln Xaa
        675                 680                 685

Gly Xaa Asp Pro Tyr Ala Xaa Pro Leu Arg Ala Asp Thr Ser Lys Pro
690                 695                 700

Lys Leu Thr Gln Gln Asp Val Thr Asp Leu Ile Ala Tyr Leu Asn Lys
705                 710                 715                 720

Gly Gly Ser Val Leu Ile Met Glu Asn Val Met Ser Asn Leu Lys Glu
                725                 730                 735

Glu Ser Ala Ser Xaa Phe Val Arg Leu Leu Asp Ala Ala Gly Leu Ser
            740                 745                 750

Met Ala Leu Asn Lys Ser Val Asn Asn Asp Pro Gln Gly Tyr Pro
        755                 760                 765

Asx Arg Val Arg Gln Xaa Arg Ala Thr Gly Ile Trp Val Tyr Glu Arg
770                 775                 780

Tyr Pro Ala Xaa Asp Gly Xaa Xaa Pro Tyr Thr Ile Asp Xaa Xaa
785                 790                 795                 800

Thr Gly Glu Val Xaa Trp Lys Tyr Gln Xaa Xaa Asn Lys Pro Asp Asp
            805                 810                 815

Lys Pro Lys Leu Glu Val Ala Ser Trp Xaa Glu Xaa Val Xaa Gly Lys
        820                 825                 830

Gln Xaa Thr Arg Tyr Ala Phe Ile Asp Glu Ala Xaa Xaa Xaa Thr Xaa
        835                 840                 845

Xaa Ser Leu Xaa Ala Ala Lys Xaa Lys Ile Xaa Xaa Xaa Phe Pro Gly
850                 855                 860

Leu Xaa Glu Cys Lys Asp Xaa Xaa Tyr His Tyr Glu Xaa Asn Cys Leu
865                 870                 875                 880

Glu Xaa Arg Pro Gly Thr Xaa Val Pro Val Thr Gly Gly Met Tyr Val
            885                 890                 895

Pro Xaa Tyr Thr Gln Leu Xaa Leu Xaa Ala Asp Thr Ala Lys Ala Met
        900                 905                 910

Val Gln Ala Ala Asp Leu Gly Thr Asn Ile Gln Arg Leu Tyr Gln His
        915                 920                 925

Glu Leu Tyr Phe Arg Thr Asn Gly Xaa Lys Gly Glu Arg Leu Xaa Ser
        930                 935                 940

Val Asp Leu Glu Arg Leu Tyr Gln Asn Met Ser Val Trp Leu Trp Asn
945                 950                 955                 960

Xaa Xaa Xaa Tyr Arg Tyr Glu Xaa Xaa Lys Xaa Asp Glu Leu Gly Phe
                965                 970                 975

Lys Thr Phe Thr Glu Phe Leu Asn Cys Tyr Ala Asn Asp Ala Tyr Xaa
            980                 985                 990

Xaa Gly Thr Xaa Cys Ser Ala Xaa Leu Lys Lys Ser Leu Val Asp Asn
```

```
                995                 1000                1005
Xaa Met Ile Tyr Gly Xaa Xaa Ser Xaa Lys Ala Gly Met Met Asn Pro
        1010                1015                1020

Ser Tyr Pro Leu Asn Tyr Met Glu Lys Pro Leu Thr Arg Leu Met Leu
1025                1030                1035                1040

Gly Arg Ser Trp Trp Asp Leu Asn Ile Lys Val Asp Val Glu Lys Tyr
            1045                1050                1055

Pro Gly Xaa Val Ser Xaa Xaa Gly Glx Xaa Val Thr Glu Xaa Ile Ser
        1060                1065                1070

Leu Tyr Ser Asn Pro Thr Lys Trp Phe Ala Gly Asn Met Gln Ser Thr
        1075                1080                1085

Gly Leu Trp Ala Pro Ala Gln Xaa Glu Val Thr Ile Xaa Ser Xaa Ala
        1090                1095                1100

Xaa Val Pro Val Thr Val Thr Val Ala Leu Ala Asp Asp Leu Thr Gly
1105                1110                1115                1120

Arg Glu Lys His Glu Val Ala Leu Asn Arg Pro Pro Xaa Val Thr Lys
            1125                1130                1135

Thr Tyr Xaa Leu Xaa Ala Xaa Gly Xaa Val Xaa Phe Lys Val Pro Tyr
        1140                1145                1150

Gly Gly Leu Ile Tyr Ile Lys Gly Asx Ser Xaa Xaa Asx Xaa Ser Ala
        1155                1160                1165

Xaa Phe Thr Phe Thr Gly Val Val Lys Ala Pro Phe Tyr Lys Asp Gly
        1170                1175                1180

Xaa Trp Lys Asn Xaa Leu Asx Ser Pro Ala Pro Leu Gly Glu Leu Glu
1185                1190                1195                1200

Ser Xaa Xaa Phe Val Tyr Thr Thr Pro Lys Lys Asn Leu Xaa Ala Ser
            1205                1210                1215

Asn Xaa Thr Gly Gly Xaa Xaa Glx Phe Ala Xaa Asp Leu Asp Thr Phe
        1220                1225                1230

Ala Ser Ser Met Asn Asp Phe Tyr Gly Arg Asx Xaa Glu Xaa Gly Lys
        1235                1240                1245

His Arg Met Phe Thr Tyr Lys Xaa Leu Thr Gly His Lys His Arg Phe
        1250                1255                1260

Thr Asn Asp Val Gln Ile Ser Ile Gly Asp Ala His Ser Gly Tyr Pro
1265                1270                1275                1280

Val Met Asn Ser Ser Phe Ser Thr Asn Ser Thr Thr Leu Pro Thr Thr
            1285                1290                1295

Pro Leu Asn Asp Trp Leu Ile Trp His Glu Val Gly His Asn Ala Ala
        1300                1305                1310

Glu Thr Pro Leu Xaa Val Pro Gly Ala Thr Glu Val Ala Asn Asn Val
        1315                1320                1325

Leu Ala Leu Tyr Met Gln Asp Arg Tyr Leu Gly Lys Met Asn Arg Val
        1330                1335                1340

Ala Asp Asp Ile Thr Val Ala Pro Glu Tyr Leu Xaa Glu Ser Asn Gly
1345                1350                1355                1360

Gln Ala Trp Ala Arg Gly Gly Ala Gly Asp Arg Leu Leu Met Tyr Ala
            1365                1370                1375

Gln Leu Lys Glu Trp Ala Glu Lys Asn Phe Asp Ile Lys Xaa Trp Tyr
        1380                1385                1390

Pro Xaa Gly Xaa Leu Pro Xaa Phe Tyr Ser Xaa Arg Glu Gly Met Lys
        1395                1400                1405

Gly Trp Asn Leu Phe Gln Leu Met His Arg Lys Ala Arg Gly Asp Xaa
        1410                1415                1420
```

```
Val Gly Xaa Xaa Xaa Phe Gly Xaa Xaa Asn Tyr Cys Ala Glu Ser Asn
1425                1430                1435                1440

Gly Asn Ala Ala Asp Thr Leu Met Leu Cys Ala Ser Trp Val Ala Gln
            1445                1450                1455

Thr Asp Leu Ser Glu Phe Phe Lys Lys Trp Asn Pro Gly Ala Asn Ala
        1460                1465                1470

Tyr Gln Leu Pro Gly Ala Xaa Glu Met Ser Phe Glu Gly Gly Val Ser
    1475                1480                1485

Gln Ser Ala Tyr Xaa Thr Leu Ala Xaa Leu Xaa Leu Pro Lys Pro Glx
    1490                1495                1500

Xaa Gly Pro Glu Thr Ile Asn Xaa Val Thr Glu His Lys Met Ser Ala
1505                1510                1515                1520

Glu
```

<210> SEQ ID NO 55
<211> LENGTH: 1538
<212> TYPE: PRT
<213> ORGANISM: Escherichia coli
<220> FEATURE:
<221> NAME/KEY: misc_feature
<222> LOCATION: 31, 37, 38, 42, 44, 47, 55, 56, 57, 58, 59,
      60, 61, 62, 63, 64, 65, 66, 67, 68, 69, 70, 71, 72,
      73, 74, 75, 76, 77, 78, 79, 80, 81, 83, 84, 85, 88,
      89, 90, 91, 94, 101, 106, 108, 111, 112, 113, 116,
      118, 125, 126, 128, 129, 131, 134, 136, 137, 157,
      167, 171, 173, 177, 180, 185, 186, 193, 196, 199,
      204, 205, 206, 207, 210, 211, 217, 219, 220, 221,
      222, 224, 247, 248, 251, 254, 257, 272, 278, 282,
      286, 289, 291, 293, 296, 303, 304, 310, 314, 316,
      322, 363, 365, 366, 367, 368, 370, 371, 373, 376,
      377, 380, 384, 401, 402, 404, 407, 409, 410, 411,
      412, 413, 415, 420, 421, 422, 425, 426, 434, 435,
      436, 437, 441, 442, 449, 454, 456, 459, 469, 470,
      472, 475, 499, 504, 531, 543, 544, 550, 553, 566,
      590, 592, 595, 596, 601, 602, 603, 605, 610, 622,
      623, 625, 628, 630, 631, 639, 640, 645, 646, 650,
      652, 653, 655, 657, 660, 663, 666, 667, 668, 669,
      670, 671, 679, 680, 681, 695, 696, 697, 701, 702,
      714, 725, 730, 748, 757, 769, 778, 781, 783, 784,
      785, 794, 795, 796, 797, 798, 799, 800, 806, 807,
      809, 810, 812, 817, 818, 819, 821, 823, 833, 835,
      837, 839, 841, 842, 843, 844, 849, 851, 852, 853,
      855, 856, 857, 859, 863, 864, 866, 867, 868, 870,
      873, 874, 876, 878, 879, 884, 889, 891, 893, 894,
      897, 899, 900, 901, 902, 903, 906, 909, 914, 916,
      924, 929, 946, 948, 949, 954, 955, 965, 972, 973,
      974, 976, 978, 979, 980, 982, 998, 1003, 1004, 1007,
      1010, 1011, 1014, 1017, 1020, 1025, 1026, 1027, 1028,
      1029, 1037, 1067, 1071, 1073, 1074, 1075, 1078, 1082,
      1084, 1088, 1103, 1107, 1108, 1109, 1111, 1113, 1115,
      1116, 1117, 1119, 1126, 1139, 1145, 1151, 1153, 1155,
      1156, 1157, 1159, 1161, 1172, 1175, 1176, 1177, 1178,
      1179, 1182, 1186, 1198, 1200, 1201, 1202, 1203, 1204,
      1215, 1216, 1221, 1224, 1227, 1229, 1230, 1231, 1234,
      1235, 1236, 1238, 1239, 1243, 1244, 1250, 1256, 1260,
      1261, 1262, 1264, 1266, 1270, 1271, 1272, 1274, 1281,
      1304, 1307, 1312, 1323, 1333, 1343, 1372, 1376, 1400,
      1405, 1406, 1410, 1412, 1413, 1416, 1418, 1420, 1422,
      1438, 1441, 1443, 1444, 1445, 1446, 1449, 1450, 1460,
      1463, 1474, 1478, 1488, 1495, 1496, 1499, 1501, 1502,
      1505, 1506, 1510, 1514, 1515, 1516, 1518, 1521, 1522,
      1526, 1527, 1529, 1533, 1534, 1536, 1537
<223> OTHER INFORMATION: 'Xaa' is any amino acid
<220> FEATURE:
<221> NAME/KEY: misc_feature
<222> LOCATION: 323, 417, 541
<223> OTHER INFORMATION: 'Xaa' is Ile or Leu

<400> SEQUENCE: 55

Met Asn Lys Lys Phe Lys Tyr Lys Lys Ser Leu Leu Ala Ala Ile Leu

```
1               5                   10                  15
Ser Ala Thr Leu Leu Ala Gly Cys Asp Gly Gly Gly Ser Gly Xaa Ser
            20                  25                  30

Ser Asp Thr Pro Xaa Xaa Asp Ser Gly Xaa Gly Xaa Leu Pro Xaa Val
                35                  40                  45

Lys Pro Asp Pro Thr Pro Xaa Xaa Xaa Xaa Xaa Xaa Xaa Xaa Xaa Xaa
50                      55                  60

Xaa Xaa Xaa Xaa Xaa Xaa Xaa Xaa Xaa Xaa Xaa Xaa Xaa Xaa Xaa Xaa
65                      70                  75                  80

Xaa Pro Xaa Xaa Xaa Pro Glu Xaa Xaa Xaa Xaa Pro Val Xaa Thr Lys
                85                  90                  95

Thr Gly Tyr Leu Xaa Leu Gly Gly Ser Xaa Arg Xaa Thr Gly Xaa Xaa
                100                 105                 110

Xaa Cys Asn Xaa Glu Xaa Ser Asp Gly Phe Thr Phe Xaa Xaa Gly Xaa
                115                 120                 125

Xaa Val Xaa Cys Val Xaa Gly Xaa Xaa Thr Thr Ile Ala Thr Phe Asx
            130                 135                 140

Thr Gln Ser Glu Ala Ala Arg Ser Leu Arg Ala Val Xaa Lys Val Ser
145                     150                 155                 160

Phe Ser Leu Glu Asp Ala Xaa Glu Leu Ala Xaa Ser Xaa Asx Lys Lys
                165                 170                 175

Xaa Asn Ala Xaa Ser Leu Val Thr Xaa Xaa Asx Ser Cys Pro Ala Asx
            180                 185                 190

Xaa Glu Gln Xaa Cys Leu Xaa Phe Ser Ser Val Xaa Xaa Xaa Xaa Arg
                195                 200                 205

Phe Xaa Xaa Leu Tyr Lys Gln Ile Xaa Leu Xaa Xaa Xaa Xaa Phe Xaa
            210                 215                 220

Lys Leu Val Asn Glu Val Glu Asn Asn Ala Ala Thr Asp Lys Ala
225                     230                 235                 240

Pro Ser Thr His Thr Ser Xaa Xaa Val Pro Xaa Thr Thr Xaa Gly Thr
                    245                 250                 255

Xaa Pro Asp Leu Asn Ala Ser Phe Val Ser Ala Asn Ala Glu Gln Xaa
                260                 265                 270

Tyr Gln Tyr Gln Pro Xaa Glu Ile Ile Xaa Ser Glu Gly Xaa Leu Val
                275                 280                 285

Xaa Ser Xaa Gly Xaa Gly Val Xaa Gly Val Asx Tyr Tyr Thr Xaa Xaa
            290                 295                 300

Gly Arg Gly Val Thr Xaa Glu Asn Gly Xaa Phe Xaa Phe Ser Trp Gly
305                     310                 315                 320

Glu Xaa Xaa Ser Phe Gly Ile Asp Thr Phe Glu Leu Gly Ser Val Arg
                325                 330                 335

Gly Asn Lys Ser Thr Ile Ala Leu Thr Glu Leu Gly Asp Glu Val Arg
                340                 345                 350

Gly Ala Asn Ile Asp Gln Leu Ile His Arg Xaa Ser Xaa Xaa Xaa Xaa
                355                 360                 365

Asn Xaa Xaa Arg Xaa Val Pro Xaa Xaa Val Arg Xaa Val Phe Ala Xaa
    370                 375                 380

Tyr Pro Asn Val Ile Asn Glu Ile Ile Asn Leu Ser Leu Ser Asn Gly
385                     390                 395                 400

Xaa Xaa Leu Xaa Glu Gly Xaa Gln Xaa Xaa Xaa Xaa Xaa Asn Xaa Phe
                405                 410                 415

Xaa Glu Gln Xaa Xaa Xaa Gly Gln Xaa Xaa Glu Ile Asp Thr Ala Ile
            420                 425                 430
```

```
Cys Xaa Xaa Xaa Gly Cys Asn Xaa Xaa Arg Trp Phe Ser Leu Thr
        435                 440                 445

Xaa Arg Asn Val Asn Xaa Gly Xaa Ile Gln Xaa Val Ile Asn Lys Leu
450                 455                 460

Trp Gly Val Asp Xaa Xaa Tyr Xaa Ser Val Xaa Lys Phe His Val Phe
465                 470                 475                 480

His Asp Ser Thr Asn Phe Tyr Gly Ser Thr Gly Asn Ala Arg Gly Gln
            485                 490                 495

Ala Val Xaa Asn Ile Ser Asn Xaa Ala Phe Pro Ile Leu Met Ala Arg
            500                 505                 510

Asn Asp Lys Asn Tyr Trp Leu Ala Phe Gly Glu Lys Arg Ala Trp Asp
            515                 520                 525

Lys Asn Xaa Leu Ala Tyr Ile Thr Glu Ala Pro Ser Xaa Val Xaa Xaa
            530                 535                 540

Glu Asn Val Thr Arg Xaa Thr Ala Xaa Phe Asn Leu Pro Phe Ile Ser
545                 550                 555                 560

Leu Gly Gln Val Gly Xaa Gly Lys Leu Met Val Ile Gly Asn Pro His
                565                 570                 575

Tyr Asn Ser Ile Leu Arg Cys Pro Asn Gly Tyr Ser Trp Xaa Gly Xaa
            580                 585                 590

Val Asx Xaa Xaa Gly Glx Cys Thr Xaa Xaa Xaa Asp Xaa Asx Asp Met
            595                 600                 605

Lys Xaa Phe Met Glx Asn Val Leu Arg Tyr Leu Ser Asx Xaa Xaa Trp
            610                 615                 620

Xaa Pro Asx Xaa Lys Xaa Xaa Met Thr Val Gly Thr Asn Leu Xaa Xaa
625                 630                 635                 640

Val Tyr Phe Lys Xaa Xaa Gly Gln Val Xaa Gly Xaa Xaa Ala Xaa Phe
                645                 650                 655

Xaa Phe His Xaa Asp Phe Xaa Gly Ile Xaa Xaa Xaa Xaa Xaa Xaa Ser
            660                 665                 670

Tyr Gly Asx Leu Asx Pro Xaa Xaa Xaa Pro Leu Leu Ile Leu Asn Gly
            675                 680                 685

Phe Glu Tyr Val Thr Gln Xaa Xaa Xaa Asp Pro Tyr Xaa Xaa Pro Leu
            690                 695                 700

Arg Ala Asp Thr Ser Lys Pro Lys Leu Xaa Gln Gln Asp Val Thr Asp
705                 710                 715                 720

Leu Ile Ala Tyr Xaa Asn Lys Gly Gly Xaa Val Leu Ile Met Glu Asn
                725                 730                 735

Val Met Ser Asn Leu Lys Glu Glu Ser Ala Ser Xaa Phe Val Arg Leu
            740                 745                 750

Leu Asp Ala Ala Xaa Leu Ser Met Ala Leu Asn Lys Ser Val Val Asn
            755                 760                 765

Xaa Asp Pro Gln Gly Tyr Pro Asx Arg Xaa Arg Gln Xaa Arg Xaa Xaa
            770                 775                 780

Xaa Ile Trp Val Tyr Glu Arg Tyr Pro Xaa Xaa Xaa Xaa Xaa Xaa Xaa
785                 790                 795                 800

Pro Tyr Thr Ile Asx Xaa Xaa Thr Xaa Xaa Val Xaa Trp Lys Tyr Gln
                805                 810                 815

Xaa Xaa Xaa Lys Xaa Asp Xaa Lys Pro Lys Leu Glu Val Ala Ser Trp
            820                 825                 830

Xaa Glu Xaa Val Xaa Gly Xaa Gln Xaa Xaa Xaa Xaa Ala Phe Ile Asp
            835                 840                 845
```

```
Xaa Ala Xaa Xaa Xaa Thr Xaa Xaa Leu Xaa Ala Ala Lys Xaa Xaa
    850                 855                 860

Ile Xaa Xaa Xaa Phe Xaa Gly Leu Xaa Xaa Cys Xaa Asx Xaa Xaa Tyr
865                 870                 875                 880

His Tyr Glu Xaa Asn Cys Leu Glu Xaa Arg Xaa Gly Xaa Xaa Val Pro
            885                 890                 895

Xaa Thr Xaa Xaa Xaa Xaa Gly Met Xaa Val Pro Xaa Tyr Thr Gln
        900                 905                 910

Leu Xaa Leu Xaa Ala Asp Thr Ala Lys Ala Met Xaa Gln Ala Ala Asp
    915                 920                 925

Xaa Gly Thr Asn Ile Gln Arg Leu Tyr Gln His Glu Leu Tyr Phe Arg
930                 935                 940

Thr Xaa Gly Xaa Xaa Gly Glu Arg Leu Xaa Xaa Val Asp Leu Glu Arg
945                 950                 955                 960

Leu Tyr Gln Asn Xaa Ser Val Trp Leu Trp Asn Xaa Xaa Xaa Tyr Xaa
                965                 970                 975

Tyr Xaa Xaa Xaa Lys Xaa Asp Glu Leu Gly Phe Lys Thr Phe Thr Glu
        980                 985                 990

Phe Leu Asn Cys Tyr Xaa Asn Asx Ala Tyr Xaa Xaa Gly Thr Xaa Cys
            995                 1000                1005

Ser Xaa Xaa Leu Lys Xaa Ser Leu Xaa Asp Asn Xaa Met Ile Tyr Gly
    1010                1015                1020

Xaa Xaa Xaa Xaa Xaa Lys Ala Gly Met Met Asn Pro Xaa Tyr Pro Leu
1025                1030                1035                1040

Asn Tyr Met Glu Lys Pro Leu Thr Arg Leu Met Leu Gly Arg Ser Trp
                1045                1050                1055

Trp Asp Leu Asn Ile Lys Val Asp Val Glu Xaa Tyr Pro Gly Xaa Val
                1060                1065                1070

Xaa Xaa Xaa Gly Glx Xaa Val Thr Glx Xaa Ile Xaa Leu Tyr Ser Xaa
            1075                1080                1085

Pro Thr Lys Trp Phe Ala Gly Asn Met Gln Ser Thr Gly Leu Xaa Ala
    1090                1095                1100

Pro Ala Xaa Xaa Xaa Val Xaa Ile Xaa Ser Xaa Xaa Val Xaa Val
1105                1110                1115                1120

Thr Val Thr Val Ala Xaa Ala Asp Asp Leu Thr Gly Arg Glu Lys His
            1125                1130                1135

Glu Val Xaa Leu Asn Arg Pro Pro Xaa Val Thr Lys Thr Tyr Xaa Leu
        1140                1145                1150

Xaa Ala Xaa Xaa Xaa Val Xaa Phe Xaa Val Pro Tyr Gly Gly Leu Ile
    1155                1160                1165

Tyr Ile Lys Xaa Asx Ser Xaa Xaa Xaa Xaa Ser Ala Xaa Phe Thr
    1170                1175                1180

Phe Xaa Gly Val Val Lys Ala Pro Phe Tyr Lys Asx Gly Xaa Trp Xaa
1185                1190                1195                1200

Xaa Xaa Xaa Xaa Ser Pro Ala Pro Leu Gly Glu Leu Glu Ser Xaa Xaa
            1205                1210                1215

Phe Val Tyr Thr Xaa Pro Lys Xaa Asn Leu Xaa Ala Xaa Xaa Xaa Ser
            1220                1225                1230
```

```
Asn Xaa Xaa Xaa Gly Xaa Xaa Glx Phe Ala Xaa Xaa Leu Asp Thr Phe
        1235                1240                1245

Ala Xaa Ser Met Asn Asp Phe Xaa Gly Arg Asx Xaa Xaa Xaa Gly Xaa
    1250                1255                1260

His Xaa Met Phe Thr Xaa Xaa Xaa Leu Xaa Gly His Lys His Arg Phe
1265            1270                1275                1280

Xaa Asn Asp Val Gln Ile Ser Ile Gly Asp Ala His Ser Gly Tyr Pro
            1285                1290                1295

Val Met Asn Ser Ser Phe Ser Xaa Asx Ser Xaa Thr Leu Pro Thr Xaa
        1300                1305                1310

Pro Leu Asn Asp Trp Leu Ile Trp His Glu Xaa Gly His Asn Ala Ala
        1315                1320                1325

Glu Thr Pro Leu Xaa Val Pro Gly Ala Thr Glu Val Ala Asn Xaa Val
        1330                1335                1340

Leu Ala Leu Tyr Met Gln Asp Arg Tyr Leu Gly Lys Met Asn Arg Val
1345            1350                1355                1360

Ala Asp Asp Ile Thr Val Ala Pro Glu Tyr Leu Xaa Glu Ser Asn Xaa
            1365                1370                1375

Gln Ala Trp Ala Arg Gly Gly Ala Gly Asp Arg Leu Leu Met Tyr Ala
        1380                1385                1390

Gln Leu Lys Glu Trp Ala Glu Xaa Asn Phe Asp Ile Xaa Xaa Trp Tyr
        1395                1400                1405

Pro Xaa Gly Xaa Xaa Leu Pro Xaa Phe Xaa Ser Xaa Arg Xaa Gly Met
        1410                1415                1420

Lys Gly Trp Asn Leu Phe Gln Leu Met His Arg Lys Ala Xaa Gly Asp
1425            1430                1435                1440

Xaa Val Xaa Xaa Xaa Xaa Phe Gly Xaa Xaa Asn Tyr Cys Ala Glu Ser
            1445                1450                1455

Asn Gly Asn Xaa Ala Asp Xaa Leu Met Leu Cys Ala Ser Trp Val Ala
            1460                1465                1470

Gln Xaa Asp Leu Ser Xaa Phe Phe Lys Lys Trp Asn Pro Gly Ala Xaa
        1475                1480                1485

Ala Tyr Gln Leu Pro Gly Xaa Xaa Glu Met Xaa Phe Xaa Xaa Gly Val
    1490                1495                1500

Xaa Xaa Ser Ala Tyr Xaa Thr Leu Ala Xaa Xaa Xaa Leu Xaa Lys Pro
1505            1510                1515                1520

Xaa Xaa Gly Pro Glu Xaa Xaa Asn Xaa Val Thr Glu Xaa Xaa Met Xaa
            1525                1530                1535

Xaa Glu

<210> SEQ ID NO 56
<211> LENGTH: 26
<212> TYPE: DNA
<213> ORGANISM: Artificial Sequence
<220> FEATURE:
<223> OTHER INFORMATION: immunostimulatory oligonucleotide
<220> FEATURE:
<221> NAME/KEY: modified_base
<222> LOCATION: 1, 3, 5, 7, 9, 11, 13, 15, 17, 19, 21, 23, 25
<223> OTHER INFORMATION: 'n' is 'i' (Inosine)

<400> SEQUENCE: 56 ncncncnc ncncncnc ncncnc                                      26

<210> SEQ ID NO 57
<211> LENGTH: 11
<212> TYPE: PRT
```

```
<213> ORGANISM: Artificial Sequence
<220> FEATURE:
<223> OTHER INFORMATION: polycationic oligopeptide

<400> SEQUENCE: 57

Lys Leu Lys Leu Leu Leu Leu Leu Lys Leu Lys
1               5                   10
```